US008367836B2

(12) United States Patent
Xu et al.

(10) Patent No.: US 8,367,836 B2
(45) Date of Patent: Feb. 5, 2013

(54) PYRIDINONE ANTAGONISTS OF ALPHA-4 INTEGRINS

(75) Inventors: Ying-zi Xu, Palo Alto, CA (US); Shendong Yuan, San Ramon, CA (US); David Wone, Newark, CA (US); Andrei Konradi, Burlingame, CA (US)

(73) Assignee: Elan Pharmaceuticals, Inc., South San Francisco, CA (US)

( * ) Notice: Subject to any disclaimer, the term of this patent is extended or adjusted under 35 U.S.C. 154(b) by 77 days.

(21) Appl. No.: 12/768,680

(22) Filed: Apr. 27, 2010

(65) Prior Publication Data

US 2011/0009407 A1 Jan. 13, 2011

Related U.S. Application Data

(60) Provisional application No. 61/172,876, filed on Apr. 27, 2009.

(51) Int. Cl.
*C07D 413/12* (2006.01)
*C07D 401/12* (2006.01)
*C07D 213/02* (2006.01)
*A61K 31/4412* (2006.01)

(52) U.S. Cl. ............... 546/268.1; 544/124; 544/365; 514/237.2; 514/253.02; 514/332

(58) Field of Classification Search ............... None
See application file for complete search history.

(56) References Cited

U.S. PATENT DOCUMENTS

| | | | |
|---|---|---|---|
| 4,018,913 A | 4/1977 | Okamoto et al. |
| 4,018,915 A | 4/1977 | Okamoto et al. |
| 4,036,955 A | 7/1977 | Okamoto et al. |
| 4,041,156 A | 8/1977 | Okamoto et al. |
| 4,046,876 A | 9/1977 | Okamoto et al. |
| 4,055,636 A | 10/1977 | Okamoto et al. |
| 4,055,651 A | 10/1977 | Okamoto et al. |
| 4,070,457 A | 1/1978 | Okamoto et al. |
| 4,073,914 A | 2/1978 | Kikumoto et al. |
| 4,085,057 A | 4/1978 | Masuda et al. |
| 4,096,255 A | 6/1978 | Kikumoto et al. |
| 4,104,392 A | 8/1978 | Okamoto et al. |
| 4,235,871 A | 11/1980 | Papahadjopoulos et al. |
| 4,438,122 A | 3/1984 | Holmwood et al. |
| 4,501,728 A | 2/1985 | Geho et al. |
| 4,505,910 A | 3/1985 | Bagli |
| 4,518,600 A | 5/1985 | Holmwood et al. |
| 4,544,402 A | 10/1985 | Schnurbusch et al. |
| 4,559,345 A | 12/1985 | Gomarasca et al. |
| 4,672,065 A | 6/1987 | Spatz |
| 4,837,028 A | 6/1989 | Allen et al. |
| 4,908,368 A | 3/1990 | Murase et al. |
| 4,959,364 A | 9/1990 | Mueller et al. |
| 4,992,439 A | 2/1991 | Meanwell |
| 5,011,472 A | 4/1991 | Aebischer et al. |
| 5,023,252 A | 6/1991 | Hseih |
| 5,030,644 A | 7/1991 | Baldwin et al. |
| 5,120,734 A | 6/1992 | Klausener et al. |
| 5,238,934 A | 8/1993 | Knuppel et al. |
| 5,278,184 A | 1/1994 | Artico et al. |
| 5,510,332 A | 4/1996 | Kogan et al. |
| 5,580,868 A | 12/1996 | Lunkenheimer et al. |
| 5,770,573 A | 6/1998 | Arrhenius et al. |
| 5,814,643 A | 9/1998 | Duggan et al. |
| 5,861,429 A | 1/1999 | Sato et al. |
| 5,925,644 A | 7/1999 | Jakobi et al. |
| 5,942,504 A | 8/1999 | Grobelny |
| 5,955,491 A | 9/1999 | Sohda et al. |
| 5,962,479 A | 10/1999 | Chen |
| 5,972,946 A | 10/1999 | Murata et al. |
| 6,005,117 A | 12/1999 | Wehner et al. |
| 6,436,904 B1 | 8/2002 | Ashwell et al. |
| 6,479,492 B1 | 11/2002 | Konradi et al. |
| 6,492,372 B1 | 12/2002 | Konradi et al. |
| 6,544,994 B2 | 4/2003 | Rabelink et al. |
| 6,545,003 B1 | 4/2003 | Grant et al. |

(Continued)

FOREIGN PATENT DOCUMENTS

| | | |
|---|---|---|
| AU | 782 616 | 8/2005 |
| CA | 2241149 | 7/1997 |

(Continued)

OTHER PUBLICATIONS

Abraham, et al., "Blockade of Late-phase Airway Responses and Airway Hyperresponsiveness in Allergic Sheep with a Small-molecule Peptide Inhibitor of VLA-4", *Am J Resper Crit Care Med.*, 156:696-703 (1997).

(Continued)

*Primary Examiner* — Joseph K. McKane
*Assistant Examiner* — Nyeemah A Grazier
(74) *Attorney, Agent, or Firm* — Foley & Lardner LLP

(57) ABSTRACT

The present invention provides compounds that are alpha4 integrin antagonists having a structure according to the following formula:

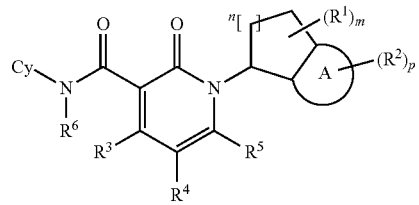

or a tautomer, mixture of tautomers, salt or solvate thereof, wherein Cy, ring A, m, n, p, $R^1$, $R^2$, $R^3$, $R^4$, $R^5$ and $R^6$ are defined in the specification. The invention further provides pharmaceutical compositions including the compounds of the invention as well as methods of making and using the compounds and compositions of the invention, e.g., in the treatment and prevention of various conditions and disorders, such as Crohn's disease and ulcerative colitis.

27 Claims, 63 Drawing Sheets

| | U.S. PATENT DOCUMENTS | | |
|---|---|---|---|
| 6,689,781 | B2 | 2/2004 | Konradi et al. |
| 6,794,506 | B2 | 9/2004 | Konradi et al. |
| 6,903,088 | B2 | 6/2005 | Konradi et al. |
| 6,911,439 | B2 | 6/2005 | Konradi et al. |
| 7,005,433 | B2 | 2/2006 | Konradi et al. |
| 7,008,949 | B2 | 3/2006 | Konradi et al. |
| 7,026,328 | B2 | 4/2006 | Konradi et al. |
| 7,049,306 | B2 | 5/2006 | Konradi et al. |
| 7,135,477 | B2 | 11/2006 | Konradi et al. |
| 7,335,663 | B2 | 2/2008 | Konradi et al. |
| 7,378,529 | B2 | 5/2008 | Konradi et al. |
| 7,427,628 | B2 | 9/2008 | Konradi et al. |
| 7,452,912 | B2 | 11/2008 | Grant et al. |
| 7,968,547 | B2 | 6/2011 | Konradi et al. |
| 7,973,044 | B2 | 7/2011 | Konradi et al. |
| 2005/0203093 | A1 | 9/2005 | Konradi et al. |
| 2005/0261293 | A1 | 11/2005 | Konradi et al. |
| 2006/0013799 | A1 | 1/2006 | Konradi et al. |
| 2007/0099921 | A1 | 5/2007 | Konradi et al. |
| 2007/0129390 | A1 | 6/2007 | Semko et al. |
| 2007/0142416 | A1 | 6/2007 | Semko et al. |
| 2007/0203129 | A1 | 8/2007 | Andersson |
| 2008/0058357 | A1 | 3/2008 | Smith et al. |
| 2010/0113434 | A1 | 5/2010 | Semko et al. |
| 2010/0261715 | A1 | 10/2010 | Semko et al. |

| | FOREIGN PATENT DOCUMENTS | |
|---|---|---|
| CA | 2259224 | 1/1998 |
| CA | 2359115 | 7/2000 |
| DE | 026 55 636 | 6/1977 |
| DE | 195 36 891 | 4/1997 |
| DE | 195 48 709 | 7/1997 |
| DE | 196 54 483 | 1/1998 |
| DE | 197 13 000 | 10/1998 |
| EP | 0 116 494 | 8/1984 |
| EP | 0 147 211 | 7/1985 |
| EP | 0 288 176 | 10/1988 |
| EP | 0 330 506 | 8/1989 |
| EP | 0 526 348 | 2/1993 |
| EP | 0 535 521 | 4/1993 |
| GB | 1500063 | 2/1978 |
| HU | 169926 | 2/1977 |
| JP | 59212480 | 12/1984 |
| WO | WO 91/05038 | 4/1991 |
| WO | WO 92/16549 | 10/1992 |
| WO | WO 93/12809 | 7/1993 |
| WO | WO 93/24154 | 12/1993 |
| WO | WO 96/01644 | 1/1996 |
| WO | WO 96/22966 | 8/1996 |
| WO | WO 96/32383 | 10/1996 |
| WO | WO 97/23451 | 7/1997 |
| WO | WO 97/48726 | 12/1997 |
| WO | WO 98/00395 | 1/1998 |
| WO | WO 98/22430 | 5/1998 |
| WO | WO 98/33783 | 8/1998 |
| WO | WO 98/53814 | 12/1998 |
| WO | WO 98/53817 | 12/1998 |
| WO | WO 99/06390 | 2/1999 |
| WO | WO 99/06391 | 2/1999 |
| WO | WO 99/06431 | 2/1999 |
| WO | WO 99/06432 | 2/1999 |
| WO | WO 99/06433 | 2/1999 |
| WO | WO 99/10312 | 3/1999 |
| WO | WO 99/10313 | 3/1999 |
| WO | WO 99/37605 | 7/1999 |
| WO | WO 99/37618 | 7/1999 |
| WO | WO 99/52898 | 10/1999 |
| WO | WO 00/18759 | 4/2000 |
| WO | WO 00/31067 | 6/2000 |
| WO | WO 00/43369 | 7/2000 |
| WO | WO 00/43371 | 7/2000 |
| WO | WO 00/43372 | 7/2000 |
| WO | WO 02/08201 | 1/2002 |
| WO | WO 03/099231 | 12/2003 |
| WO | WO 03/099809 | 12/2003 |
| WO | WO 2005/111020 | 11/2005 |
| WO | WO 2007/041270 | 4/2007 |
| WO | WO 2007/041324 | 4/2007 |
| WO | WO 2007/101165 | 9/2007 |

OTHER PUBLICATIONS

Abraham, et al. "α4-Integrins Mediate Antigen -induced Late Bronchial Responses and Prolonged Airway Hyperresponsiveness in Sheep", *J. Clin. Invest.*, 93:776-787 (1994).

Advani, et al. "Potential Antineoplastic Agents: N-(2-Benzoxazolyl)amino Acid Esters", *J. of Pharm. Sci.*, 57(10):1693-1696 (1968).

Andersen, et al., "Acute Kidney Graft Rejection", *APMIS*, 102, 23-37 (1994).

Anderson, et al., "Process Development of 5-Fluoro-3-[3-[4-(5-methoxy-4 pyrimidinyl)-1 piperazinyl]propyl]-1*H* -indole Dihydrochloride", *Org Proc Res Devel.*, 1:300-310 (1997).

Balaban, "An Investigation into the Formation of 4(5)-Aminoglyoxalines", *J. Chem. Soc.*, Part 1:1-268-273 (1930).

Banker, et al., "Modern Pharmaceutics, 3ed.", Marcel Dekker, New York, pp. 451 and 596 (1996).

Bao, et al. "Correlation of VLA-4 Integrin Expression with Metastatic Potential in Various Human Tumour Cell Lines", *Diff.*, 52: 239-246 (1993).

Baron, et al. "Surface Expression of α4 Integrin by CD4 T Cells is Required for Their Entry into Brain Parenchyma", *J. Exp. Med.*, 177: 57-68 (1993).

Baron, et al. "The Pathogenesis of Adoptive Murine Autoimmune Diabetes Requires an Interaction between α4-Integrins and Vascular Cell Adhesion Molecule-1", *J. Clin. Invest.*, 93: 1700-1708 (1994).

Belka, et al., "Radiation Induced CNS Toxicity—Molecular and Cellular Mechanism", *Br. J. Cancer*, 85:1233-1239 (2001).

Burkly, et al. "Protection Against Adoptive Transfer of Autoimmune Diabetes Mediated Through Very Late Antigen-4 Integrin", *Diabetes*, 43: 529-534 (1994).

Casanova, et al., PubMed Abstract (*Rev Neurol.*) 28(9):909-915 (1999) (Abstract only).

Chang "Mechanism Underlying the Suppression of Adjuvant-induced Arthritis by 6-mercaptopurine", *Arth. Rheum.*, 20; No. 5, 1135-1141 (1977).

Chapman, et al. "Allergen-induced Airway Hyperreactivity and Eosinophil Accumulation are Temporarily Dissociated in Actively Sensitized Brown Norway Rats", *Am. J. Resp. Crit. Care Med.*, A881 (1997).

Chem Abstract 102:149279 for stucture of JP 59212480 dated Dec. 1984.

Chem. Abstract 102:24642 for structures of EP 116494 dated Aug. 1984.

Chem. Abstract 105:97885 for structure, Marr-Leisy et al., *Coloid and Polymer Sc.*, 263/10,79-8 (1985).

Chem. Abstract 113:130558-1990:530558, also cited as Simchowitz et al., *J. Biol. Chem.*, 265/23, 13457-63 (1990).

Chem. Abstract 114:101454-1991:101454, also cited as Ohta et al., *Heterocycles*, 31/9, 1655-1662 (1990).

Chem. Abstract 125:89352 also cited as HCAPLUS, JP 08100141; Hiroshi et al., (1996).

Chem. Abstract 130:52724 structures for WO 9853814 dated Dec. 1998.

Chem. Abstract 69:676 structures for Jaeger et al., *Chem. Berichte.*, 101/8, 2762-70 (1968).

Chem. Abstract 93:46584, also cited as Ohta et al., *Chem. & Pharmaceutical Bulletin*, 27/12, 2980-7 (1979).

Chen, et al., "Mediation of Sperm-egg Fusion: Evidence that Mouse Eg $\alpha^6 \beta^{11}$ ntegrin is the Receptor for Sperm Fertilinβ", *Chem. Biol.*, 6:1-10 (1999).

Coito, et al., "Blockade of very late antigen-4 integrin binding to fibronectin in allograft recipients: I. Treatment with connecting segment-1 peptides prevents acute rejection by suppressing intragraft mononuclear cell accumulation, endothelial activation, and cytokine expression.", Transplantation, 65:699-706 (1998).

Cybulsky, et al. "Endothelial Expression of a Mononuclear Leukocyte Adhesion Molecule During Atherogenesis", *Science*, 251: 788-791 (1991).

Damasio, et al., "Alzheimer's Disease and Related Dementias", *Cecil Textbook of Medicine*, 20th Ed., vol. 2, pp. 1992-1996 (1996).

Elewaut, et al., "Distinctive Activated Cellular Subsets in Colon from Patients with Crohn's Disease and Ulcerative Colitis", *Scand. J. Gastroenterol.*, 33:743-748 (1998).

Elices, et al. "Expression and Functional Significance of Alternatively Spliced CS1 Fibronectin in Rheumatoid Arthritis Microvasculature", *J. Clin. Invest.*, 93: 405-416 (1994).

Elices, et al. "VCAM-1 on Activated Endothelium Interacts with the Leukocyte Integrin VLA-4 at a Site Distinct from the VLA-4/Fibronectin Binding Site", *Cell*, 60: 577-584 (1990).

Ewenson, et al., "Analogues of Substance P Containing an α-hydroxy, β-amino Acid: Synthesis and Biological Activity", *Eur J Med Chem.*, 26, 435-442 (1991).

Freedman, et al, "Adhesion of Follicular Lymphoma Cells to Lymphoid Germinal Centers—A Potential Mechanism of Tumor Cell Homing Following Autologous Transplantation," *Leukemia and Lymphoma*, 13:47-52 (1994).

Giardina, et al., "Selective κ-Opioid Agonists: Synthesis and Structure-Activity Relationships of Piperidines Incorporating an Oxo-Containing Acyl Group", *J. Med. Chem.*, 37:3482-3491 (1994).

Gonzalez-Amaro et al., Therapeutic Anti-integrin (alpha4 and alphaL) Monoclonal Antibodies: Two-edged swords?, *Immunology*, vol. 116, No. 3, pp. 289-296, (2005).

Gorczynski, et al., "Altered Patterns of Migration of Cytokine-producing T Lymphocytes in Skin-grafted Naïve or Immune Mice Following in vivo Administration of Anti-VCAM-1 or ICAM-1", *Immunology*, 87:573-580 (1996).

Gorczynski, et al., "Manipulation of Skin Graft Rejection in Alloimmune Mice by Anti-VCAM-1:VLA-4 but not Anti-ICAM-1:LFA-1 Monoclonal Antibodies", *Trans Immunol.*, 3:55-61 (1995).

Gordeev, "Combinatorial Approaches to Pharmacophoric Heterocycles: A Solid-Phase Synthesis of 3,1-Benzoxazine-4-ones", *Biotech. and Bioengineering*, 61(1): 13-16 (1998).

Grayson, et al., αdβ2 Integrin Is Expressed on Human Eosinophils and Functions as an Alternative Ligand for Vascular Cell Adhesion Molecule 1 (VCAM-1) *J. Exp. Med.*, 188(11) 2187-2191 (1998).

Hamann, et al. "Role of α4-Integrins in Lymphocyte Homing to Mucosal Tissues in Vivo." *J. Immunology*, 152: 3282-3293 (1994).

Hartman, et. al., "Synthesis and Activity of Novel Nitropyrazines for Use as Hypoxic Cell Radiosensitizers," *J Med. Chem.*, 27:1634-1639 (1984).

Henke, et al. "N-(2-Benzoylphenyl)-L-tyrosine: PPARγ Agonists. 1. Discovery of a Novel Series of Potent Antihyperglycemic and Antihyperlipidemic Agents", *J. Med. Chem.*, 41(25): 5020-5036 (1998).

Hladon, et al. In Vitro Cytostatic activity of Some Amino Acid 4-N-substituted Cytosines, *Arch. Immunol. Ther. Exp.*, 40(2): 145-150 (1992).

Hoeve, et al., "Chiral Tetraalkylmethanes. Two Syntheses of Optically Active Butylethylmethylpropylmethane of Known and High Optical Purity", *J. Org. Chem.*, 45:2754-2763 (1980).

Hoffmann, et al. "N-Pyrimidinylamino Acids. III. N-(oxopyrimidinyl) Derivatives of Neutral Amino Acids", *Z. Chem.* 12(1): 21-22 (1972), Coden: Zeceal (Only Abstract Considered).

Hopewell, et al. "Models of CNS Radiation Damage During Space Flight", *Adv. Space Res.*, 14:433-442 (1994).

Jaeger, et al., "Peptide syntheses with O-Carbamoyltyrosine Derivates", *Chem. Ber.*, 101:2762-2770 (1968) (English abstract) (Only Abstract Considered).

Kascheres et al., Cycloaddition Reactions of Cyclopropenones, 4, Reaction of Some 2-Aminopyridines with Methylphenylcyclopropenone. *J. Org. Chem.*, 41/22, 3546-9 (1976).

Kawaguchi, et al. "VLA-4 Molecules on Tumor Cells Initiate an Adhesive Interaction with VCAM-1 Molecules on Endothelial Cell Surface", *Japanese J. Cancer Res.*, 83: 1304-1316 (1992).

Keszthelyi, et al., "Evidence for a Prolonged Role of $\alpha_4$ integrin Throughout Active Experimental Allergic Encephalomyelitis", *Neurology*, 47:1053-1059 (1996).

Korom, et al., "Blockade of very late antigen-4 integrin binding to fibronectin in allograft recipients. II. Treatment with connecting segment-1 peptides prevents chronic rejection by attenuating arteriosclerotic development and suppressing intragraft T cell and macrophage activation.", *Transplantation*, 65:854-859 (1998).

Kroneld, et al., "Expression of the Mucosal Lymphocyte Integrin αE β7 and its Ligand E-cadherin in Salivary Glands of Patients with Sjögren's Syndrome", *Scan. J. Rheumatol.*, 27:215-218 (1998).

Kung et al. "Involvement of IL-5 in a Murine Model of Allergic Pulmonary Inflammation: Prophylactic and Therapeutic Effect of an Anti-IL-5 Antibody", *Am J. Respir. Cell. Mol. Biol.*, 13:360-365 (1995).

Lauri, et al. "Decreased Adhesion to Endothelial Cells and Matrix Proteins of $H-2K^b$ Gene Transfected Tumour Cells", *British J. Cancer*, 68: 862-867 (1993).

Lazer, et al. "Benzoxazolamines and Benzothiazolamines: Potent, Enantioselective Inhibitors of Leukotriene Biosynthesis with a Novel Mechanism of Action", *J. Med. Chem.*, 37(7): 913-923 (1994).

Li, et al. "An Atherogenic Diet Rapidly Induces VCAM-1, a Cytokine-Regulatable Mononuclear Leukocyte Adhesion Molecule, in Rabbit Aortic Endothelium", *Arterioscler. Thromb.*, 13(2): 197-204 (1993).

Luque, et al., "Activated Conformations of Very Late Activation Integrins Detected by a Group of Antibodies (HUTS) Specific for a Novel Regulatory Region (355-425) of the Common β1 Chain", *J. Biol. Chem.*, 271(19) 11067-11075 (1966).

Ma, et al. "Accelerating Effect Induced by the Structure of α-Amino Acid in the Copper Catalyzed Coupling Reaction of Aryl Halides with α-Amino Acids. Synthesis of Benzolactam-V8", *J. Am. Chem. Soc.*, 120(48): 12459-12467 (1998).

Marr-Leisy, et al. "The Comparative Spreading Behavior of Enantiomeric and Racemic Tyrosine Amphiphiles", *Colloid & Polymer Sci.*, 263:791-798 (1985).

Miller, "Colloquium C15: Natalizumab (anti0VLA4 antibody) in Multiple Sclerosis", *Journal of Neurochemistry*, C15-04, 85: (Suppl. 1) (2003).

Miller, "Colloquium C15: Comparison of the Ability of Anti-VLA-4 Antibody and a Small Molecule VLA-4 Antagonist to Regulate Ongoing Relapsing EAE", Journal of Neurochemistry, C15-02, 85: (Suppl. 1) (2003).

Mulligan, et al. "Role of $\beta_1$, $\beta_2$ Integrins and ICAM-1 in Lung Injury after Deposition of IgG and IgA Immune Complexes", *J. Immunol.*, 150(6): 2407-2417 (1993).

Ohta, et al., "Conversion of 2,5-Diphenyl- and 2,5-Dibenzyl-pyrazines to 2,5-Diketopiperazines", *Chem.. Pharm. Bull*, 27(12):2980-2987 (1979).

Ohta, et al., "Emeheterone: Synthesis and Structural Revision", *Heterocycles*, 31(9) 1655-1662 (1990).

Okahara, et al., "Involvement of Very Late Activation Antigen 4 (VLA-4) and Vascular Cell Adhesion Molecule 1(VCAM-1) in Tumor Necrosis Factor αEnhancement of Experimental Metastasis", *Can. Res.*, 54: 3233-3236 (1994).

Orosz, et al., "Promotion of Experimental Liver Metastasis by Tumor Necrosis Factor", *Int. J. Cancer*, 60:867-871 (1995).

Osborn, "Leukocyte Adhesion to Endothelium in Inflammation", *Cell*, 62: 3-6 (1990).

Paavonen, et al. "In Vivo Evidence of the Role of $\alpha_4\beta_1$-VCAM-1 Interaction in Sarcoma, but not in Carcinoma Extravasation", *Int. J. Can.*, 58: 298-302 (1994).

Palmer, et al., "Sequence and Tissue Distribution of the Integrin α9 Subunit, a Novel Partner of β1 That Is Widely Distributed in Epithelia and Muscle", *J. Cell Biol.*, 123(5) 1289-1297 (1993).

Papaioannou, et al., "Facile Preparation of the 1-Hydorxybenzotriazolyl Ester of N-Tritypyroglutamic Acid and its Application to the Synthesis of TRH, [D-His² ]TRH and Analogues Incorporation cis-and trans-4-Hydroxy-Lproline", *Acta Chemica Scand.*, 49:103-114 (1995).

Paul, et al., "Anti-integrin (LFA,-1, VLA-4, and Mac-1) Antibody Treatment and Acute Cardiac Graft Rejection in the Rat", *Transpl. Int.*, 9:420-425 (1996).

Paul, et al. "Monoclonal Antibodies Against LFA-1 and VLA-4 Inhibit Graft Vasculitis in Rat Cardiac Allografts", *Transpl. Proceed*, 25(1): 813-814 (1993).

Piraino, et al., "Prolonged Reversal of Chronic Experimental Allergic Encephalomyelitis Using a Small Molecule Inhibitor of α4 Integrin", *Journal of Neuroimmunology*, 131:147-159 (2002).

Postigo, et al. "Increased Binding of Synovial T Lumphocytes from Rheumatoid Arthritis to Endothelial-Leukocyte Adhesion Molecule-1 (ELAM-1) and Vascular Cell Adhesion Molecule-1 (VCAM-1)", *J. Clin. Invest.* 89: 1445-1452 (1992).

Pretolani, et al. "Antibody to Very Late Activation Antigen 4 Prevents Antigen-induced Bronchial Hyperreactivity and Cellular Infiltration in the Guinea Pig Airways", *J. Exp. Med.*, 180:795-805 (1994).

Prusiner, "Novel Proteinaceous Infectious Particles Cause Scrapie", *Science*, 216:136-144 (1982).

Scott, et al. Secreted phospholipase A2 enzymes as therapeutic targets. *Expert Opinion Ther. Targets*, 7/3, 427-40 (2003).

Hikita, et al. Integrin alpha4betal (VLA-4) expression and activity in retinal and peripheral neurons. *Mol. Cell Neurosci.*, 23/3, 427-39 (2003).

Granata, et al. Secretory phospholipases A2 as multivalent mediators of inflammatory and allergic disorders. *Int. Arch. Allergy Immunol.*, 31/3, 153-63 (2003).

Gascoigne, et al. The effect of anti-integrin monoclonal antibodies on antigen-induced pulmonary inflammation in allergic rabbits. *Pulm. Pharmacol., Ther.*, 16/5, 279-85 (2003).

Sandborn, et al, "Biologic Therapy of Inflammatory Bowel Disease," *Gastroenterology*, 122:1592-1608 (2002).

Sasseville, et al. "Monocyte Adhesion to Endothelium in Simian Immunodeficiency Virus-Induced AIDS Encephalitis is Mediated by Vascular Cell Adhesion Molecule-1/$\alpha_4 \beta_1$ Integrin Interactions", *Am. J. Path.*, 144(1): 27-40 (1994).

Schadendorf, et al. "Tumour Progression and Metastatic Behaviour In Vivo Correlates with Integrin Expression on Melanocytic Tumours", *J. Path.*, 170: 429-434 (1993).

Schlegel, et al., "Inhibition of T Cell Costimulation by VCAM-1 Prevents Murine Graft-Versus-Host Disease Across Minor Histocompatibility Barriers", *J. Immunol.*, 155:3856-3865 (1995).

Schneider, et al., "The Role of $\alpha 4$ (CD49d) and $\beta 2$ (CD18) Integrins in Eosinophil and Neutrophil Migration to Allergic Lung Inflammation in the Brown Norway Rat", *Am. J. Respir. Cell. Mol. Biol.*, 20:448-457 (1999).

Simchowitz, et al., "Polyvalent Cations Inhibit Human Neutrophil Chemotaxis by Interfering with the Ploymerization of Actin", *J. Biol. Chem.*, 265(23)13457-13463 (1990).

Springer, "Adhesion Receptors of the Immune System", *Nature*, 346: 425-434 (1990).

Springer, "Traffic Signals for Lymphocyte Recirculation and Leukocyte Emigration: The Multistep Paradigm", *Cell*, 76:301-314 (1994).

Steinbach, et al., "Expression of Cell Adhesion Molecules in an Established and Characterized New Human Renal Cancer Cell Line, CCF-RC7", *Urol. Res.*, 23:175-183 (1995).

Tarkowski et al., PubMed Abstract (*Int Arch Allergy Immunol.*) 121(1):25-33 (Abstract only) (2000).

Teranishi, et al. "Synthesis and Chemiluminescence of Coelenterazine (*Oplophorus* Luciferin) Analogues", *Bull. Chem. Soc. Jpn.*, 63(11): 3132-3140 (1990).

Tilley, et al., "VLA-4 Antagonists", *Drugs of the Future*, 26(10):985-998 (2001).

Toniolo, et al., Nitro-Heteroaromatic Derivatives of Amino-Acids and Peptides. 3. Application of Ultraviolet-Visible Absorption and Circular Dichroism to N-(3-nitro-2-pyridyl)amino-acids. Chemical J. Chem. Soc., Pekin Transactions, 1, Org. & Bio—org. Chem., Sep. 2010, 1179-81 (1972).

Trollmo, et al. "Expression of the Mucosal Lymphocyte Integrin $\alpha^E \beta_7$ and its Ligand E-Cadherin in the Synovium of Patients with Rheumatoid Arthritis", *Scand. J. Immunol.*, 44:293-298 (1996).

Van Dinther-Janssen, et al. "The VLA-4/VCAM-1 Pathway is Involved in Lymphocyte Adhesion to Endothelium in Rheumatoid Synovium", *J. Immunology*, 147(12): 4207-4210 (1991).

Van Dinther-Janssen, et al. "Role of the CS1 Adhesion Motif of Fibronectin in T Cell Adhesion to Synovial Membrane and Peripheral Lymph Node Endothelium", *Annals. Rheumatic Dis.*, 52: 672-676 (1993).

Vedder, et al. "Role of Neutrophils in Generalized Reperfusion Injury Associated with Resuscitation from Shock", *Surgery*, 106: 509-516 (1989).

Verhoef, et al., "Transport of Peptide and Protein Drugs Across Biological Membranes", *Eur. J. Drug Metab. Pharmacokinetics*, 15(2):83-93 (1990).

Wen et al., "1,2,5-Thiadiazolid-3,4-Dione-1-Oxide", *Org. Prep. Proceed.*, 1(4):255-258 (1969).

Wen, et al., "The Chemistry of 1,2,3-Thiadiazoles. II. 3,4-Disubstituted Derivatives of 1,2,5-Thiadiazole 1,1-Dioxide", *J. Org. Chem.*, 40(19):2743-2748 (1975).

Whittaker, "A New Synthesis and the Chemical Properties of 5-Aminopyrimidine", *Chem. Society*, 354:1565-1570 (1951).

Wolff, "Some Considerations for Prodrug Design." Burger's Medicinal Chemistry and Drug Discovery, 5th ed, vol. 1, John Wiley & Sons, (1995), pp. 975-977.

Wyzsza, et al., Chemical Abstract DN 70:96568, also cited as Roczniki Chemii, 42/10, 1647-60 (1968) (English translation not provided).

Yamamoto, et al. "Total Synthesis of (±)-Celacinnine, (±)-celallocinnine, (±)-celafurine, and (±)- celabenzine", *J. Am. Chem. Soc.*, 103:6133-6136 (1981).

Yang, et al. "Inhibition of Insutitis and Prevention of Diabetes in Nonobese Diabetic Mice by Blocking L-selecting and Very Late Antigen 4 Adhesion Receptors", *Proc. Natl. Acad. Sci., USA*, 90: 10494-10498 (1993).

Yang, et al., "Prolongation of Rat Islet Allograft Survival by Treatment with Monoclonal Antibodies Against VLA-4 and LFA-1", *Transplantation*, 60:71-76 (1995).

Yednock, et al., "$\alpha 4 \beta^1$ Inegrin-Dependent Cell Adhesion is Regulated by a Low Affinity Receptor Pool That is Conformationally Responsive to Ligand", *J. Biol. Chem.*, 270: 28740-28750 (1995).

Yednock, et al. "Prevention of Experimental Autoimmune Encephalomyelitis by Antibodies Against $\alpha_4 \beta_1$ Inegrin", *Nature*, 356: 63-66 (1992).

Yakosaki, et al., "The Integrin $\alpha 9 \beta 1$ Mediates Cell Attachment to a Non-RGD Site in the Third Fibronection Type III Repeat of Tenascin", *J. Biol. Chem.*, 269:26692-26696 (1994).

Zhu, et al., "The Direct Formation of Functionalized Alky(aryl)zinc Halides by Oxidative Addition of Highly Reactive Zinc with Organic Halides and Their Reactions with Acid Chlorides, $\alpha \beta$-Unsaturated Ketones, and Allylic, Aryl, and Vinyl Halides", *J. Org. Chem.*, 56:1445-1453 (1991).

| Compound | Compound Name | A IC$_{50}$ (μM) | B IC$_{50}$ (μM) |
|---|---|---|---|
| 1 | (R)-1-(2,3-dihydro-1H-inden-1-yl)-2-oxo-N-(pyridin-4-yl)-1,2-dihydropyridine-3-carboxamide | (++) | (++) |
| 2 | 1-(2,3-Dihydro-1H-inden-1-yl)-2-oxo-N-(pyridin-4-yl)-1,2-dihydropyridine-3-carboxamide | (++) | (++) |
| 3 | N-(4-Chlorophenyl)-1-(2,3-dihydro-1H-inden-1-yl)-2-oxo-1,2-dihydropyridine-3-carboxamide | (++) | |
| 4 | (S)-1-(2,3-Dihydro-1H-inden-1-yl)-2-oxo-N-(pyridin-4-yl)-1,2-dihydropyridine-3-carboxamide | (+) | |
| 5 | (S)-N-(4-Chlorophenyl)-1-(2,3-dihydro-1H-inden-1-yl)-2-oxo-1,2-dihydropyridine-3-carboxamide | (+) | |
| 6 | (R)-N-(4-Chlorophenyl)-1-(2,3-dihydro-1H-inden-1-yl)-2-oxo-1,2-dihydropyridine-3-carboxamide | (++) | |
| 7 | N-(4-Chlorophenyl)-1-((1S,2R)-2-hydroxy-2,3-dihydro-1H-inden-1-yl)-2-oxo-1,2-dihydropyridine-3-carboxamide | (+) | |
| 8 | 1-((1S,2R)-2-Hydroxy-2,3-dihydro-1H-inden-1-yl)-2-oxo-N-(pyridin-4-yl)-1,2-dihydropyridine-3-carboxamide | (+) | |
| 9 | N-(4-Chlorophenyl)-1-((1R,2S)-2-hydroxy-2,3-dihydro-1H-inden-1-yl)-2-oxo-1,2-dihydropyridine-3-carboxamide | (+) | |
| 10 | 1-((1R,2S)-2-Hydroxy-2,3-dihydro-1H-inden-1-yl)-2-oxo-N-(pyridin-4-yl)-1,2-dihydropyridine-3-carboxamide | (-) | |
| 11 | N-(4-chlorophenyl)-1-(4-methoxy-2,3-dihydro-1H-inden-1-yl)-2-oxo-1,2-dihydropyridine-3-carboxamide | (++) | (+++) |
| 12 | 1-(6-Methoxy-2,3-dihydro-1H-inden-1-yl)-2-oxo-N-(pyridin-4-yl)-1,2-dihydropyridine-3-carboxamide | (-) | |
| 13 | N-(4-chlorophenyl)-1-(6-methoxy-2,3-dihydro-1H-inden-1-yl)-2-oxo-1,2-dihydropyridine-3-carboxamide | (-) | |
| 14 | N-(4-chlorophenyl)-1-(5-methoxy-2,3-dihydro-1H-inden-1-yl)-2-oxo-1,2-dihydropyridine-3-carboxamide | (++) | |
| 15 | 1-(6-methoxy-2,3-dihydro-1H-inden-1-yl)-2-oxo-N-(pyridin-4-yl)-1,2-dihydropyridine-3-carboxamide | (++) | |

FIG. 1A

| Compound | Compound Name | A IC$_{50}$ (μM) | B IC$_{50}$ (μM) |
|---|---|---|---|
| 16 | 1-(6-bromo-2,3-dihydro-1H-inden-1-yl)-N-(4-chlorophenyl)-2-oxo-1,2-dihydropyridine-3-carboxamide | (-) | |
| 17 | 1-(6-bromo-2,3-dihydro-1H-inden-1-yl)-2-oxo-N-(pyridin-4-yl)-1,2-dihydropyridine-3-carboxamide | (+) | |
| 18 | 1-(4-methoxy-2,3-dihydro-1H-inden-1-yl)-2-oxo-N-(pyridin-4-yl)-1,2-dihydropyridine-3-carboxamide | (++) | (+++) |
| 19 | 1-(7-methoxy-2,3-dihydro-1H-inden-1-yl)-2-oxo-N-(pyridin-4-yl)-1,2-dihydropyridine-3-carboxamide | (++) | (++) |
| 20 | N-(7-chlorophenyl)-1-(4-methoxy-2,3-dihydro-1H-inden-1-yl)-2-oxo-1,2-dihydropyridine-3-carboxamide | (++) | |
| 21 | N-(4-chlorophenyl)-1-(3-methyl-2,3-dihydro-1H-inden-1-yl)-2-oxo-1,2-dihydropyridine-3-carboxamide | (++) | |
| 22 | 1-(3-methyl-2,3-dihydro-1H-inden-1-yl)-2-oxo-N-(pyridin-4-yl)-1,2-dihydropyridine-3-carboxamide | (++) | |
| 23 | 1-(4-bromo-2,3-dihydro-1H-inden-1-yl)-2-oxo-N-(pyridin-4-yl)-1,2-dihydropyridine-3-carboxamide | (++) | (++) |
| 24 | 1-(4-bromo-2,3-dihydro-1H-inden-1-yl)-N-(4-chlorophenyl)-2-oxo-1,2-dihydropyridine-3-carboxamide | (++) | |
| 25 | 1-(4-methoxy-2,3-dihydro-1H-inden-1-yl)-2-oxo-N-(pyridin-4-yl)-1,2-dihydropyridine-3-carboxamide | (++) | (++) |
| 26 | 1-(4-methoxy-2,3-dihydro-1H-inden-1-yl)-2-oxo-N-(pyridin-4-yl)-1,2-dihydropyridine-3-carboxamide | (++) | (+++) |
| 27 | N-(biphenyl-4-yl)-1-(4-methoxy-2,3-dihydro-1H-inden-1-yl)-2-oxo-1,2-dihydropyridine-3-carboxamide | (+++) | (+++) |
| 28 | 1-(4-methoxy-2,3-dihydro-1H-inden-1-yl)-2-oxo-N-(4-phenoxyphenyl)-1,2-dihydropyridine-3-carboxamide | (+++) | (+++) |
| 29 | N-(4-bromophenyl)-1-(4-methoxy-2,3-dihydro-1H-inden-1-yl)-2-oxo-1,2-dihydropyridine-3-carboxamide | (++) | (+++) |
| 30 | 1-(4-isopropoxy-2,3-dihydro-1H-inden-1-yl)-2-oxo-N-(pyridin-4-yl)-1,2-dihydropyridine-3-carboxamide | (++) | (+++) |
| 31 | N-(4-chlorophenyl)-1-(4-isopropoxy-2,3-dihydro-1H-inden-1-yl)-2-oxo-1,2-dihydropyridine-3-carboxamide | (++) | (+++) |

FIG. 1B

| Compound | Compound Name | A IC$_{50}$ (μM) | B IC$_{50}$ (μM) |
|---|---|---|---|
| 32 | 1-(4-methoxy-2,3-dihydro-1H-inden-1-yl)-2-oxo-N-(4-phenoxyphenyl)-1,2-dihydropyridine-3-carboxamide | (++) | (++) |
| 33 | 1-(4-methoxy-2,3-dihydro-1H-inden-1-yl)-2-oxo-N-(4-phenoxyphenyl)-1,2-dihydropyridine-3-carboxamide | (++) | (+++) |
| 34 | N-(biphenyl-4-yl)-1-(4-methoxy-2,3-dihydro-1H-inden-1-yl)-2-oxo-1,2-dihydropyridine-3-carboxamide | (++) | (+++) |
| 35 | N-(biphenyl-4-yl)-1-(4-methoxy-2,3-dihydro-1H-inden-1-yl)-2-oxo-1,2-dihydropyridine-3-carboxamide | (++) | (+++) |
| 36 | 1-(4-bromo-2,3-dihydro-1H-inden-1-yl)-2-oxo-N-(pyridin-4-yl)-1,2-dihydropyridine-3-carboxamide | (++) | (++) |
| 37 | 1-(4-bromo-2,3-dihydro-1H-inden-1-yl)-2-oxo-N-(pyridin-4-yl)-1,2-dihydropyridine-3-carboxamide | (++) | (++) |
| 38 | 1-(4-methoxy-2,3-dihydro-1H-inden-1-yl)-2-oxo-N-(4-(trifluoromethoxy)phenyl)-1,2-dihydropyridine-3-carboxamide | (++) | (++) |
| 39 | N-cyclohexyl-1-(4-methoxy-2,3-dihydro-1H-inden-1-yl)-2-oxo-1,2-dihydropyridine-3-carboxamide | (+) | (++) |
| 40 | N-(4-fluorophenyl)-1-(4-methoxy-2,3-dihydro-1H-inden-1-yl)-2-oxo-1,2-dihydropyridine-3-carboxamide | (++) | (+++) |
| 41 | N-(4-iodophenyl)-1-(4-methoxy-2,3-dihydro-1H-inden-1-yl)-2-oxo-1,2-dihydropyridine-3-carboxamide | (++) | (+++) |
| 42 | 1-(4-methoxy-2,3-dihydro-1H-inden-1-yl)-2-oxo-N-phenyl-1,2-dihydropyridine-3-carboxamide | | (++) |
| 43 | N-(4,4-difluorocyclohexyl)-1-(4-methoxy-2,3-dihydro-1H-inden-1-yl)-2-oxo-1,2-dihydropyridine-3-carboxamide | | (++) |
| 44 | N-(3,4-difluorophenyl)-1-(4-methoxy-2,3-dihydro-1H-inden-1-yl)-2-oxo-1,2-dihydropyridine-3-carboxamide | | (++) |
| 45 | 1-(4-methoxy-2,3-dihydro-1H-inden-1-yl)-N-(4-(4-methoxyphenoxy)phenyl)-2-oxo-1,2-dihydropyridine-3-carboxamide | | (+++) |
| 46 | 1-(4-cyclopropyl-2,3-dihydro-1H-inden-1-yl)-2-oxo-N-(pyridin-4-yl)-1,2-dihydropyridine-3-carboxamide | (++) | |
| 47 | N-(4-chlorophenyl)-1-(4-cyclopropyl-2,3-dihydro-1H-inden-1-yl)-2-oxo-1,2-dihydropyridine-3-carboxamide | (++) | |

FIG. 1C

| Compound | Compound Name | A IC$_{50}$ (μM) | B IC$_{50}$ (μM) |
|---|---|---|---|
| 48 | 1-(7,8-dihydro-6H-indeno[5,4-d][1,3]dioxol-6-yl)-2-oxo-N-(pyridin-4-yl)-1,2-dihydropyridine-3-carboxamide | (++) | |
| 49 | N-(4-chlorophenyl)-1-(7,8-dihydro-6H-indeno[5,4-d][1,3]dioxol-6-yl)-2-oxo-1,2-dihydropyridine-3-carboxamide | (++) | |
| 50 | N-(4-chlorophenyl)-2-oxo-1-(4-(trifluoromethoxy)-2,3-dihydro-1H-inden-1-yl)-1,2-dihydropyridine-3-carboxamide | (++) | (++) |
| 51 | 2-oxo-N-(pyridin-4-yl)-1-(4-(trifluoromethoxy)-2,3-dihydro-1H-inden-1-yl)-1,2-dihydropyridine-3-carboxamide | (++) | (+++) |
| 52 | 1-(4-(methylthio)-2,3-dihydro-1H-inden-1-yl)-2-oxo-N-(pyridin-4-yl)-1,2-dihydropyridine-3-carboxamide | (++) | |
| 53 | tert-butyl 4-(1-(2-oxo-3-(pyridin-4-ylcarbamoyl)pyridin-1(2H)-yl)-2,3-dihydro-1H-inden-4-yl)piperazine-1-carboxylate | (++) | (++) |
| 54 | tert-butyl 4-(1-(3-(4-chlorophenylcarbamoyl)-2-oxopyridin-1(2H)-yl)-2,3-dihydro-1H-inden-4-yl)piperazine-1-carboxylate | (++) | (+++) |
| 55 | 1-(4-morpholino-2,3-dihydro-1H-inden-1-yl)-2-oxo-N-(pyridin-4-yl)-1,2-dihydropyridine-3-carboxamide | (++) | (+++) |
| 56 | N-(4-chlorophenyl)-1-(4-morpholino-2,3-dihydro-1H-inden-1-yl)-2-oxo-1,2-dihydropyridine-3-carboxamide | (+++) | (+++) |
| 57 | 1-(4-morpholino-2,3-dihydro-1H-inden-1-yl)-2-oxo-N-(4-phenoxyphenyl)-1,2-dihydropyridine-3-carboxamide | (++) | (+++) |
| 58 | N-(4-fluorophenyl)-1-(4-morpholino-2,3-dihydro-1H-inden-1-yl)-2-oxo-1,2-dihydropyridine-3-carboxamide | (+++) | (+++) |
| 59 | N-(4-bromophenyl)-1-(4-morpholino-2,3-dihydro-1H-inden-1-yl)-2-oxo-1,2-dihydropyridine-3-carboxamide | (+++) | (+++) |
| 60 | N-cyclohexyl-1-(4-morpholino-2,3-dihydro-1H-inden-1-yl)-2-oxo-1,2-dihydropyridine-3-carboxamide | (-) | (++) |
| 61 | N-(4-iodophenyl)-1-(4-morpholino-2,3-dihydro-1H-inden-1-yl)-2-oxo-1,2-dihydropyridine-3-carboxamide | | (+++) |
| 62 | 1-(4-morpholino-2,3-dihydro-1H-inden-1-yl)-2-oxo-N-p-tolyl-1,2-dihydropyridine-3-carboxamide | | (+++) |
| 63 | 1-(4-morpholino-2,3-dihydro-1H-inden-1-yl)-2-oxo-N-phenyl-1,2-dihydropyridine-3-carboxamide | | (+++) |

FIG. 1D

| Compound | Compound Name | A IC$_{50}$ (μM) | B IC$_{50}$ (μM) |
|---|---|---|---|
| 64 | 1-(4-morpholino-2,3-dihydro-1H-inden-1-yl)-2-oxo-N-phenyl-1,2-dihydropyridine-3-carboxamide | | (+++) |
| 65 | N-(4,4-difluorocyclohexyl)-1-(4-morpholino-2,3-dihydro-1H-inden-1-yl)-2-oxo-1,2-dihydropyridine-3-carboxamide | | (++) |
| 66 | N-(4-methoxyphenyl)-1-(4-morpholino-2,3-dihydro-1H-inden-1-yl)-2-oxo-1,2-dihydropyridine-3-carboxamide | | (+++) |
| 67 | N-(4-(difluoromethoxy)phenyl)-1-(4-morpholino-2,3-dihydro-1H-inden-1-yl)-2-oxo-1,2-dihydropyridine-3-carboxamide | | (+++) |
| 68 | 1-(4-morpholino-2,3-dihydro-1H-inden-1-yl)-2-oxo-N-(4-(trifluoromethoxy)phenyl)-1,2-dihydropyridine-3-carboxamide | | (+++) |
| 69 | 1-(4-morpholino-2,3-dihydro-1H-inden-1-yl)-2-oxo-N-(4-(trifluoromethyl)phenyl)-1,2-dihydropyridine-3-carboxamide | | (+++) |
| 70 | N-(4-cyanophenyl)-1-(4-morpholino-2,3-dihydro-1H-inden-1-yl)-2-oxo-1,2-dihydropyridine-3-carboxeamid | | (+++) |
| 71 | 1-(4-(4-hydroxypiperidin-1-yl)-2,3-dihydro-1H-inden-1-yl)-2-oxo-N-(pyridin-4-yl)-1,2-dihydropyridine-3-carboxamide | | (+++) |
| 72 | N-(4-chlorophenyl)-1-(4-(4-hydroxypiperidin-1-yl)-2,3-dihydro-1H-inden-1-yl)-2-oxo-1,2-dihydropyridine-3-carboxamide | | (+++) |
| 73 | N-(4-(4-methoxyphenylamino)phenyl)-1-(4-morpholino-2,3-dihydro-1H-inden-1-yl)-2-oxo-1,2-dihydropyridine-3-carboxamide | | (+++) |
| 74 | N-(3,4-difluorophenyl)-1-(4-morpholino-2,3-dihydro-1H-inden-1-yl)-2-oxo-1,2-dihydropyridine-3-carboxamide | | (+++) |
| 75 | tert-butyl 4-(1-(3-(4-fluorophenylcarbamoyl)-2-oxopyridin-1(2H)-yl)-2,3-dihydro-1H-inden-4-yl)piperazine-1-carboxylate | | (++) |
| 76 | tert-butyl 4-(1-(3-(4-chlorophenylcarbamoyl)-2-oxopyridin-1(2H)-yl)-2,3-dihydro-1H-inden-4-yl)piperazine-1-carboxylate | | (+++) |
| 77 | N-(4-(dimethylamino)phenyl)-1-(4-morpholino-2,3-dihydro-1H-inden-1-yl)-2-oxo-1,2-dihydropyridine-3-carboxamide | | (++) |

FIG. 1E

| Compound | Compound Name | A IC$_{50}$ (μM) | B IC$_{50}$ (μM) |
|---|---|---|---|
| 78 | *1-(4-(cyclopropylamino)-2,3-dihydro-1H-inden-1-yl)-2-oxo-N-(pyridin-4-yl)-1,2-dihydropyridine-3-carboxamide* | (++) | (+++) |
| 79 | *N-(4-chlorophenyl)-1-(4-(methylsulfonyl)-2,3-dihydro-1H-inden-1-yl)-2-oxo-1,2-dihydropyridine-3-carboxamide* | (+) | |
| 80 | *1-(4-(methylsulfonyl)-2,3-dihydro-1H-inden-1-yl)-2-oxo-N-(pyridin-4-yl)-1,2-dihydropyridine-3-carboxamide* | (-) | |
| 81 | *N-(4-chlorophenyl)-2-oxo-1-(4-(piperazin-1-yl)-2,3-dihydro-1H-inden-1-yl)-1,2-dihydropyridine-3-carboxamide* | (++) | (++) |
| 82 | *2-oxo-1-(4-(piperazin-1-yl)-2,3-dihydro-1H-inden-1-yl)-N-(pyridin-4-yl)-1,2-dihydropyridine-3-carboxamide* | (+) | (++) |
| 83 | *N-(4-fluorophenyl)-2-oxo-1-(4-(piperazin-1-yl)-2,3-dihydro-1H-inden-1-yl)-1,2-dihydropyridine-3-carboxamide* | | (++) |
| 84 | *N-(4-bromophenyl)-2-oxo-1-(4-(piperazin-1-yl)-2,3-dihydro-1H-inden-1-yl)-1,2-dihydropyridine-3-carboxamide* | | (++) |
| 85 | *N-(4-chlorophenyl)-1-(4-(4-(2-hydroxyethyl)piperazin-1-yl)-2,3-dihydro-1H-inden-1-yl)-2-oxo-1,2-dihydropyridine-3-carboxamide* | (++) | (+++) |
| 86 | *N-(4-chlorophenyl)-1-(4-(4-(2-(2-(2-hydroxyethoxy)ethoxy)ethyl)piperazin-1-yl)-2,3-dihydro-1H-inden-1-yl)-2-oxo-1,2-dihydropyridine-3-carboxamide* | | (+++) |
| 87 | *N-(4-chlorophenyl)-1-(4-(4-methylpiperazin-1-yl)-2,3-dihydro-1H-inden-1-yl)-2-oxo-1,2-dihydropyridine-3-carboxamide* | (++) | (++) |
| 88 | *1-(4-(4-methylpiperazin-1-yl)-2,3-dihydro-1H-inden-1-yl)-2-oxo-N-(pyridin-4-yl)-1,2-dihydropyridine-3-carboxamide* | (+) | (++) |
| 89 | *1-(4-(4-acetylpiperazin-1-yl)-2,3-dihydro-1H-inden-1-yl)-N-(4-chlorophenyl)-2-oxo-1,2-dihydropyridine-3-carboxamide* | (+++) | (+++) |
| 90 | *1-(4-(4-acetylpiperazin-1-yl)-2,3-dihydro-1H-inden-1-yl)-2-oxo-N-(pyridin-4-yl)-1,2-dihydropyridine-3-carboxamide* | (++) | (++) |

FIG. 1F

| Compound | Compound Name | A IC$_{50}$ (μM) | B IC$_{50}$ (μM) |
|---|---|---|---|
| 91 | N-(4-chlorophenyl)-1-(4-(4-(methylsulfonyl)piperazin-1-yl)-2,3-dihydro-1H-inden-1-yl)-2-oxo-1,2-dihydropyridine-3-carboxamide | (++) | (+++) |
| 92 | tert-butyl 2-(2-(2-(2-(4-(1-(3-(4-chlorophenylcarbamoyl)-2-oxopyridin-1(2H)-yl)-2,3-dihydro-1H-inden-4-yl)piperazin-1-yl)-2-oxoethoxy)ethoxy)ethoxy)ethylcarbamate | | (+++) |
| 93 | 1-(4-(4-(2-(2-(2-(2-aminoethoxy)ethoxy)ethoxy)acetyl)piperazin-1-yl)-2,3-dihydro-1H-inden-1-yl)-N-(4-chlorophenyl)-2-oxo-1,2-dihydropyridine-3-carboxamide | | (++) |
| 94 | N-(4'-hydroxybiphenyl-4-yl)-1-(4-methoxy-2,3-dihydro-1H-inden-1-yl)-2-oxo-1,2-dihydropyridine-3-carboxamide | (++) | (++) |
| 95 | 1-(4-Methoxy-2,3-dihydro-1H-inden-1-yl)-N-(4'-methoxybiphenyl-4-yl)-2-oxo-1,2-dihydropyridine-3-carboxamide | (++) | (+++) |
| 96 | N-(3'-ethoxybiphenyl-4-yl)-1-(4-methoxy-2,3-dihydro-1H-inden-1-yl)-2-oxo-1,2-dihydropyridine-3-carboxamide | (++) | (+++) |
| 97 | 1-(4-methoxy-2,3-dihydro-1H-inden-1-yl)-N-(2'-methoxybiphenyl-4-yl)-2-oxo-1,2-dihydropyridine-3-carboxamide | (++) | (+++) |
| 98 | N-(4'-aminobiphenyl-4-yl)-1-(4-methoxy-2,3-dihydro-1H-inden-1-yl)-2-oxo-1,2-dihydropyridine-3-carboxamide | (++) | (++) |
| 99 | N-(4'-(2-(2-(2-aminoethoxy)ethoxy)ethoxy)biphenyl-4-yl)-1-(4-methoxy-2,3-dihydro-1H-inden-1-yl)-2-oxo-1,2-dihydropyridine-3-carboxamide | (+) | (+) |
| 100 | N-(3'-(2-(2-(2-aminoethoxy)ethoxy)ethoxy)biphenyl-4-yl)-1-(4-methoxy-2,3-dihydro-1H-inden-1-yl)-2-oxo-1,2-dihydropyridine-3-carboxamide | (++) | (+) |
| 101 | N-(3'-hydroxybiphenyl-4-yl)-1-(4-methoxy-2,3-dihydro-1H-inden-1-yl)-2-oxo-1,2-dihydropyridine-3-carboxamide | (++) | (+++) |
| 102 | tert-butyl 2-(2-(2-(4-(4-(1-(4-methoxy-2,3-dihydro-1H-inden-1-yl)-2-oxo-1,2-dihydropyridine-3-carboxamido)phenoxy)phenoxy)ethoxy)ethoxy)-ethylcarbamate | (++) | (+++) |
| 103 | N-(4-(4-(2-(2-(2-aminoethoxy)ethoxy)ethoxy)phenoxy) phenyl)-1-(4-methoxy-2,3-dihydro-1H-inden-1-yl)-2-oxo-1,2-dihydropyridine-3-carboxamide | (+) | (++) |

FIG. 1G

| Compound | Compound Name | A IC$_{50}$ (μM) | B IC$_{50}$ (μM) |
|---|---|---|---|
| 104 | 2-oxo-1-(4-(pyridin-3-yl)-2,3-dihydro-1H-inden-1-yl)-N-(pyridin-4-yl)-1,2-dihydropyridine-3-carboxamide | (++) | (+++) |
| 105 | 1-(4-nitro-2,3-dihydro-1H-inden-1-yl)-2-oxo-N-(pyridin-4-yl)-1,2-dihydropyridine-3-carboxamide | (++) | (++) |
| 106 | 1-(4-amino-2,3-dihydro-1H-inden-1-yl)-2-oxo-N-(pyridin-4-yl)-1,2-dihydropyridine-3-carboxamide | (++) | (++) |
| 107 | 1-(4-cyano-2,3-dihydro-1H-inden-1-yl)-2-oxo-N-(pyridin-4-yl)-1,2-dihydropyridine-3-carboxamide | (++) | (++) |
| 108 | 1-(4-chloro-2,3-dihydro-1H-inden-1-yl)-2-oxo-N-(pyridin-4-yl)-1,2-dihydropyridine-3-carboxamide | (++) | (++) |
| 109 | 1-(4-(methylamino)-2,3-dihydro-1H-inden-1-yl)-2-oxo-N-(pyridin-4-yl)-1,2-dihydropyridine-3-carboxamide |  | (++) |
| 110 | 1-(4-(dimethylamino)-2,3-dihydro-1H-inden-1-yl)-2-oxo-N-(pyridin-4-yl)-1,2-dihydropyridine-3-carboxamide | (++) | (+++) |
| 111 | 1-(4-acetamido-2,3-dihydro-1H-inden-1-yl)-2-oxo-N-(pyridin-4-yl)-1,2-dihydropyridine-3-carboxamide | (++) | (+++) |
| 112 | 1-(4-methyl-2,3-dihydro-1H-inden-1-yl)-2-oxo-N-(pyridin-4-yl)-1,2-dihydropyridine-3-carboxamide |  | (++) |
| 113 | 2-oxo-1-(4-phenyl-2,3-dihydro-1H-inden-1-yl)-N-(pyridin-4-yl)-1,2-dihydropyridine-3-carboxamide |  | (+++) |
| 114 | 1-(4-(methylcarbamoyl)-2,3-dihydro-1H-inden-1-yl)-2-oxo-N-(pyridin-4-yl)-1,2-dihydropyridine-3-carboxamide |  | (++) |
| 115 | N-(4-bromophenyl)-1-(4-hydroxy-2,3-dihydro-1H-inden-1-yl)-2-oxo-1,2-dihydropyridine-3-carboxamide | (++) | (++) |
| 116 | N-(biphenyl-4-yl)-1-(4-hydroxy-2,3-dihydro-1H-inden-1-yl)-2-oxo-1,2-dihydropyridine-3-carboxamide | (++) | (+++) |
| 117 | N-(4-bromophenyl)-1-(4-(2-hydroxyethoxy)-2,3-dihydro-1H-inden-1-yl)-2-oxo-1,2-dihydropyridine-3-carboxamide |  | (+++) |
| 118 | N-(4-bromophenyl)-1-(4-(2-(2-(2-hydroxyethoxy)ethoxy)ethoxy)-2,3-dihydro-1H-inden-1-yl)-2-oxo-1,2-dihydropyridine-3-carboxamide |  | (+++) |
| 119 | N-(biphenyl-4-yl)-1-(4-(2-(2-(2-hydroxyethoxy)ethoxy)ethoxy)-2,3-dihydro-1H-inden-1-yl)-2-oxo-1,2-dihydropyridine-3-carboxamide | (+++) | (+++) |

FIG. 1H

| Compound | Compound Name | A IC$_{50}$ (μM) | B IC$_{50}$ (μM) |
|---|---|---|---|
| 120 | *tert-butyl 2-(2-(2-(1-(3-(biphenyl-4-ylcarbamoyl)-2-oxopyridin-1(2H)-yl)-2,3-dihydro-1H-inden-4-yloxy)ethoxy)ethoxy)ethylcarbamate* | | (+++) |
| 121 | *1-(4-(2-(2-(2-aminoethoxy)ethoxy)ethoxy)-2,3-dihydro-1H-inden-1-yl)-N-(biphenyl-4-yl)-2-oxo-1,2-dihydropyridine-3-carboxamide trifluoroacetate* | | (++) |

(+++)    IC$_{50}$    < 0.1 μM
(++)     IC$_{50}$    0.1 μM – 10 μM
(+)      IC$_{50}$    > 10 μM
(-)      Compound tested, activity below level of detection in assay used (IC$_{50}$ > 100 μM)

A: MadCam cell adhesion assay
B: MadCam SRU cell adhesion assay

FIG. 1I

| Compound | Compound Structure | A IC$_{50}$ (μM) | B IC$_{50}$ (μM) |
|---|---|---|---|
| 122 | 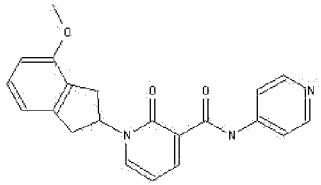 | (+) | (++) |
| 123 | 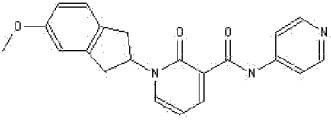 | | (++) |
| 124 | 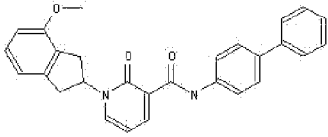 | | (++) |
| 125 | 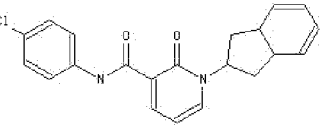 | (-) | |
| 126 | 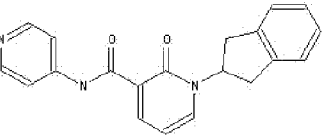 | (++) | |
FIG. 2A

| Compound | Compound Structure | A IC$_{50}$ (μM) | B IC$_{50}$ (μM) |
|---|---|---|---|
| 127 | 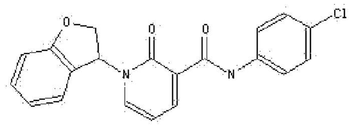 | (+) | |
| 128 | 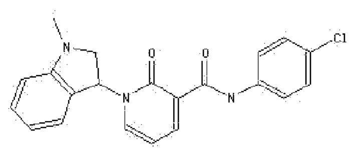 | (++) | |
| 129 | 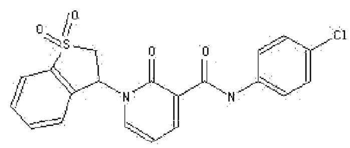 | (++) | |
| 130 | 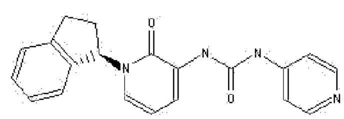 | (+) | (++) |
| 131 | 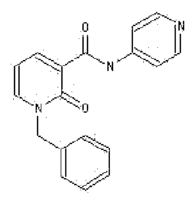 | (++) | (++) |
| 132 | 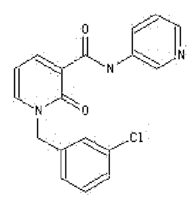 | (−) | |

FIG. 2B

| Compound | Compound Structure | A IC$_{50}$ (µM) | B IC$_{50}$ (µM) |
|---|---|---|---|
| 133 | 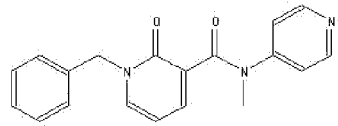 | (-) | |
| 134 | 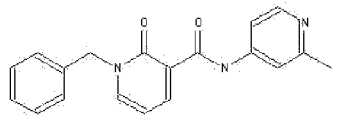 | (+) | (++) |
| 135 | 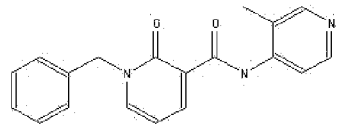 | (+) | |
| 136 | 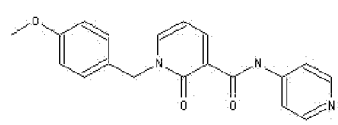 | (++) | |
| 137 | 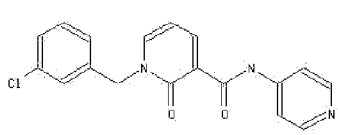 | (+) | |
| 138 | 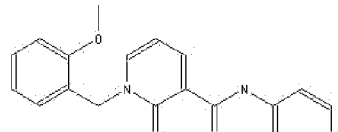 | (++) | |
FIG. 2C

| Compound | Compound Structure | A IC50 (μM) | B IC50 (μM) |
|---|---|---|---|
| 139 | 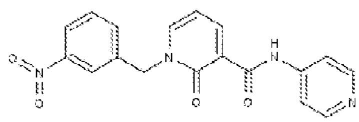 | (+) | |
| 140 | 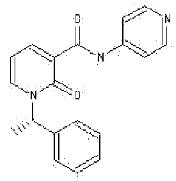 | (++) | |
| 141 | 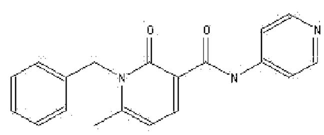 | (-) | |
| 142 | 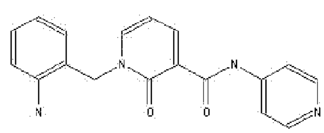 | (+) | (++) |
| 143 | 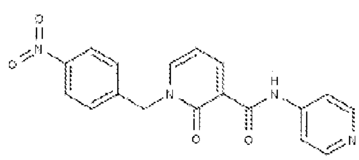 | (-) | |
| 144 | 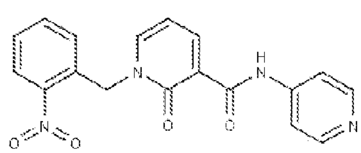 | (++) | |

FIG. 2D

| Compound | Compound Structure | A IC$_{50}$ (μM) | B IC$_{50}$ (μM) |
|---|---|---|---|
| 145 | 3-fluorobenzyl-pyridone-carboxamide-4-pyridyl | (+) | |
| 146 | 4-fluorobenzyl-pyridone-carboxamide-4-pyridyl | (+) | |
| 147 | 2-methylbenzyl-pyridone-carboxamide-4-pyridyl | (++) | |
| 148 | 4-chlorobenzyl-pyridone-carboxamide-4-pyridyl | (++) | |
| 149 | 2-chloro-6-fluorobenzyl-pyridone-carboxamide-4-pyridyl | (+) | |
| 150 | 3-methylbenzyl-pyridone-carboxamide-4-pyridyl | (+) | |

FIG. 2E

| Compound | Compound Structure | A IC$_{50}$ (µM) | B IC$_{50}$ (µM) |
|---|---|---|---|
| 151 | 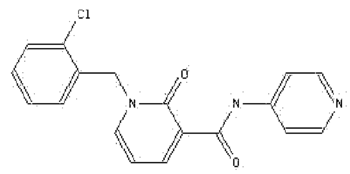 | (+) | |
| 152 | 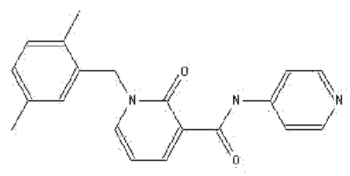 | (++) | |
| 153 | 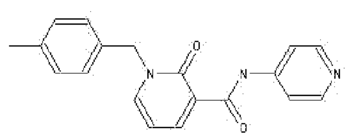 | (++) | |
| 154 | 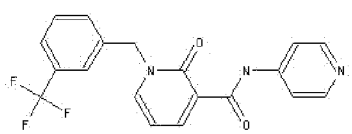 | (++) | |
| 155 | 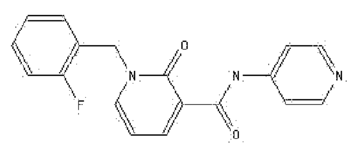 | (++) | |
| 156 | 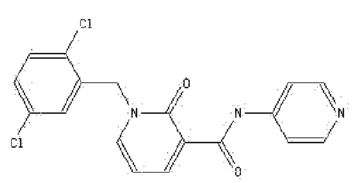 | (++) | |

FIG. 2F

| Compound | Compound Structure | A IC$_{50}$ (μM) | B IC$_{50}$ (μM) |
|---|---|---|---|
| 157 | 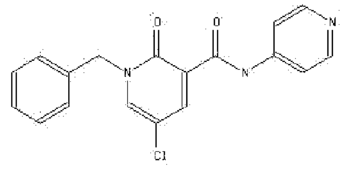 | (-) | |
| 158 | 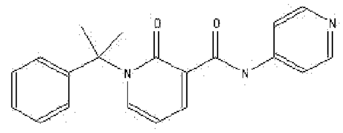 | (+) | |
| 159 | 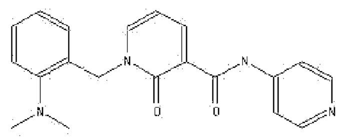 | (+) | |
| 160 | 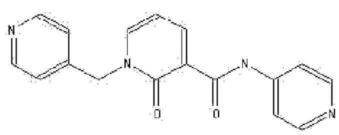 | (-) | |
| 161 | 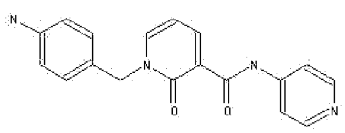 | (+) | |
| 162 | 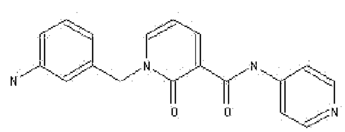 | (+) | |

FIG. 2G

| Compound | Compound Structure | A IC₅₀ (μM) | B IC₅₀ (μM) |
|---|---|---|---|
| 163 | 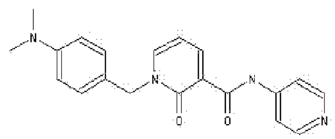 | (++) | |
| 164 | 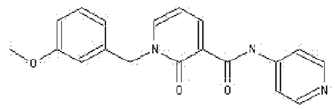 | (++) | |
| 165 | 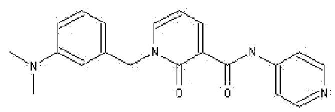 | (++) | |
| 166 | 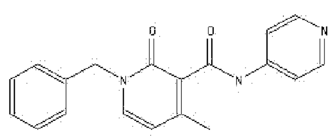 | (+) | |
| 167 | 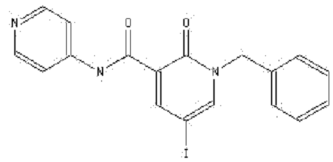 | (+) | |
| 168 | 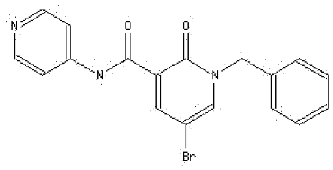 | (+) | |

FIG. 2H

| Compound | Compound Structure | A IC$_{50}$ (μM) | B IC$_{50}$ (μM) |
|---|---|---|---|
| 169 | 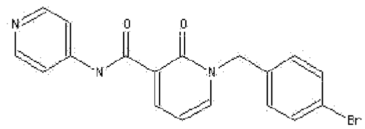 | (++) | |
| 170 | 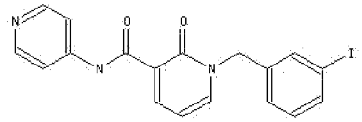 | (++) | |
| 171 | 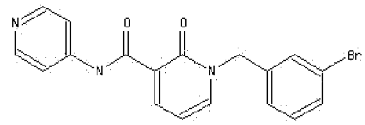 | (++) | |
| 172 | 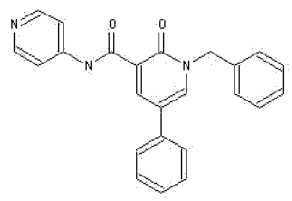 | (-) | |
| 173 | 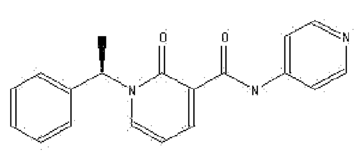 | (++) | (++) |
| 174 | 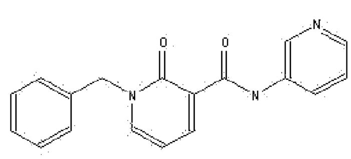 | (+) | |

FIG. 2I

| Compound | Compound Structure | A IC$_{50}$ (μM) | B IC$_{50}$ (μM) |
|---|---|---|---|
| 175 | 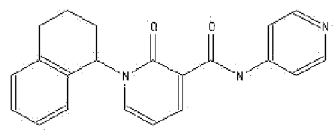 | (++) | |
| 176 | 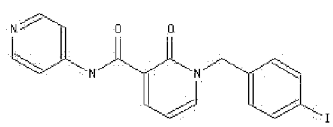 | (++) | |
| 177 | 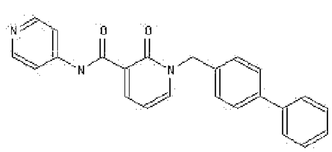 | (++) | |
| 178 | 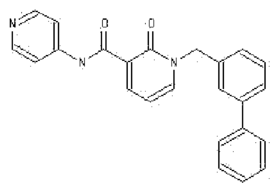 | (++) | |
| 179 | 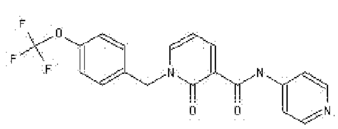 | (-) | |
| 180 | 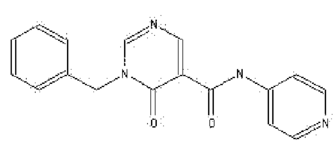 | (-) | |

FIG. 2J

| Compound | Compound Structure | A IC$_{50}$ (μM) | B IC$_{50}$ (μM) |
|---|---|---|---|
| 181 | 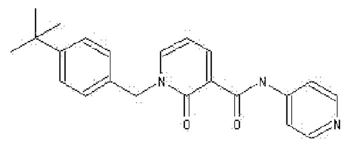 | (++) | |
| 182 | 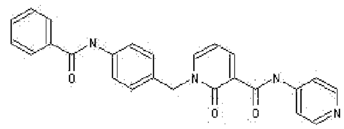 | (++) | |
| 183 | 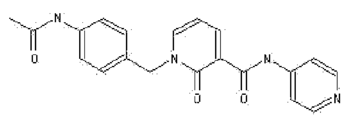 | (-) | |
| 184 | 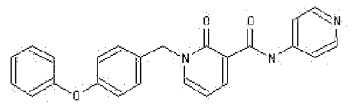 | (+) | |
| 185 | 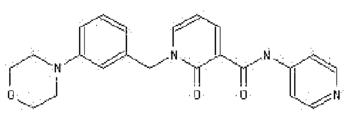 | (++) | (++) |
| 186 | 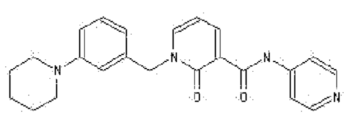 | (++) | (+++) |

FIG. 2K

| Compound | Compound Structure | A IC$_{50}$ (μM) | B IC$_{50}$ (μM) |
|---|---|---|---|
| 187 | 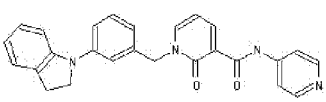 | (++) | |
| 188 | 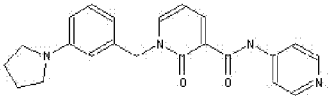 | (++) | |
| 189 | 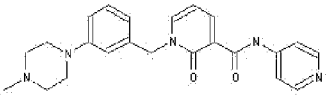 | (++) | |
| 190 | 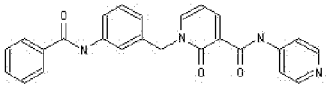 | (++) | |
| 191 | 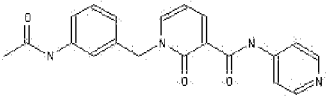 | (++) | |
| 192 | 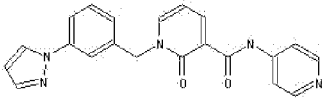 | (++) | |
FIG. 2L

| Compound | Compound Structure | A IC$_{50}$ (μM) | B IC$_{50}$ (μM) |
|---|---|---|---|
| 193 | 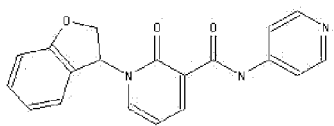 | (+) | (++) |
| 194 | 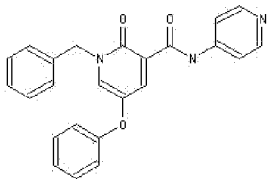 | (-) | |
| 195 | 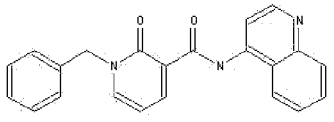 | (+) | |
| 196 | 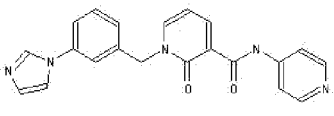 | (++) | |
| 197 | 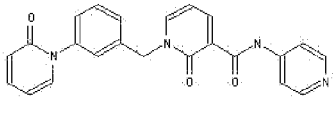 | (+) | |
| 198 | 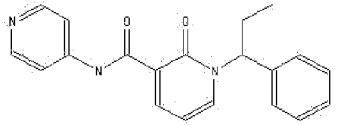 | (++) | |
FIG. 2M

| Compound | Compound Structure | A IC$_{50}$ (μM) | B IC$_{50}$ (μM) |
|---|---|---|---|
| 199 | 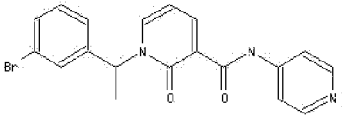 | (++) | |
| 200 | 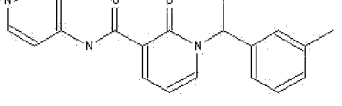 | (++) | |
| 201 | 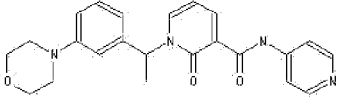 | (++) | |
| 202 | 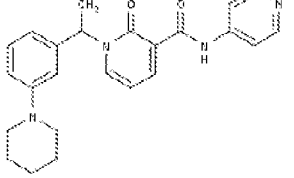 | (++) | (+++) |
| 203 | 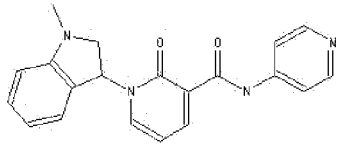 | (++) | |
| 204 | 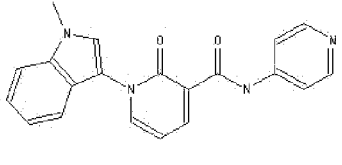 | (−) | |
FIG. 2N

| Compound | Compound Structure | A IC$_{50}$ (μM) | B IC$_{50}$ (μM) |
|---|---|---|---|
| 205 | 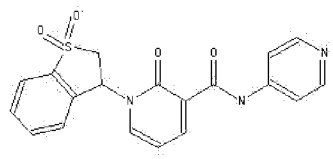 | (+) | |
| 206 | 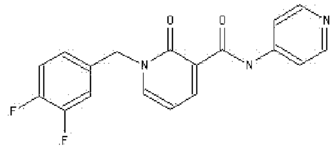 | (+) | |
| 207 | 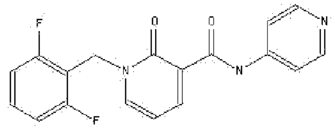 | (−) | |
| 208 | 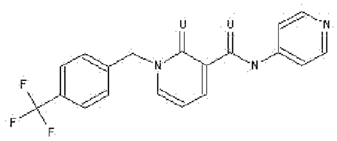 | (+) | |
| 209 | 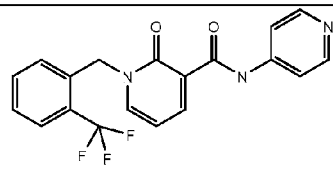 | (−) | |
| 210 | 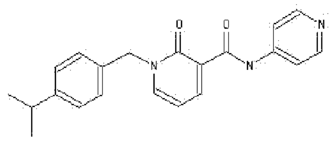 | (+) | |

FIG. 2O

| Compound | Compound Structure | A<br>IC$_{50}$ (µM) | B<br>IC$_{50}$ (µM) |
|---|---|---|---|
| 211 | 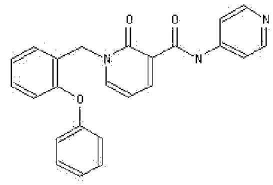 | (+) | |
| 212 | 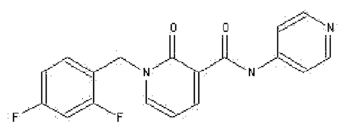 | (+) | |
| 213 | 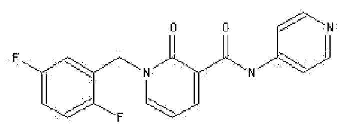 | (+) | |
| 214 | 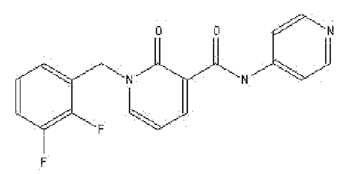 | (+) | |
| 215 | 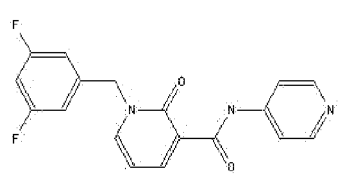 | (+) | |
| 216 | 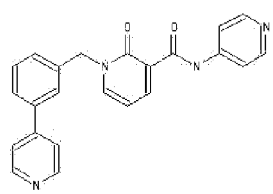 | (++) | (++) |

FIG. 2P

| Compound | Compound Structure | A IC$_{50}$ (μM) | B IC$_{50}$ (μM) |
|---|---|---|---|
| 217 | 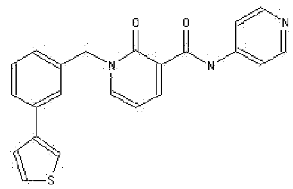 | (++) | (++) |
| 218 | 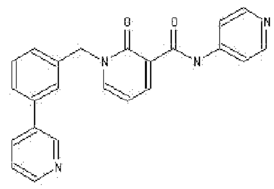 | (++) | (++) |
| 219 | 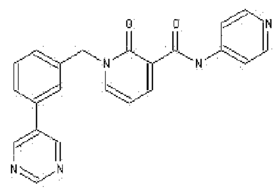 | (+) | |
| 220 | 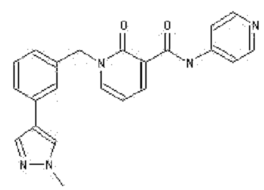 | (+) | |
| 221 | 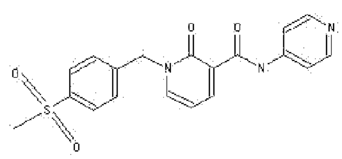 | (+) | |
| 222 | 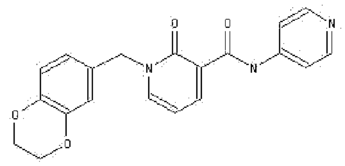 | (-) | |

FIG. 2Q

| Compound | Compound Structure | A<br>IC$_{50}$ (μM) | B<br>IC$_{50}$ (μM) |
|---|---|---|---|
| 223 | 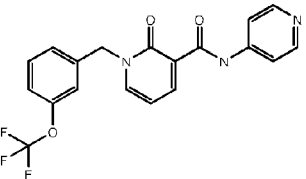 | (+) | |
| 224 | 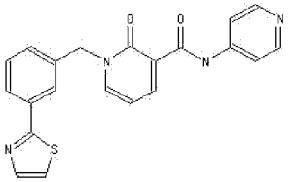 | (+) | |
| 225 | 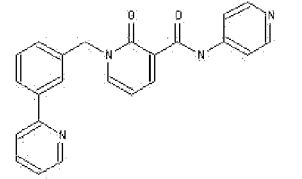 | (+) | |
| 226 | 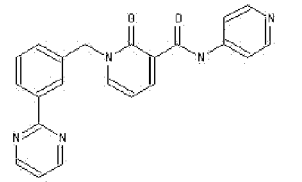 | (+) | |
| 227 | 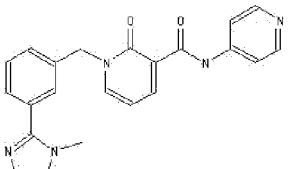 | (−) | |
| 228 | 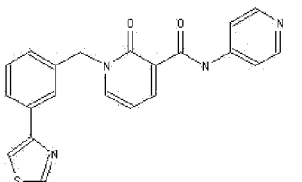 | (−) | |
FIG. 2R

| Compound | Compound Structure | A IC$_{50}$ (μM) | B IC$_{50}$ (μM) |
|---|---|---|---|
| 229 | 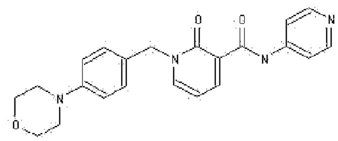 | (-) | |
| 230 | 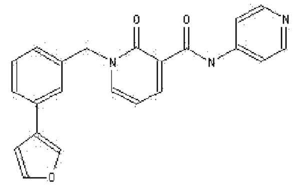 | (++) | (++) |
| 231 | 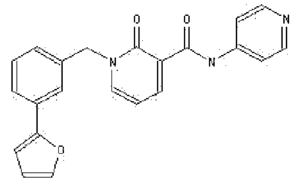 | (++) | (++) |
| 232 | 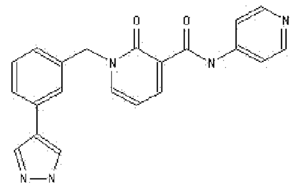 | (++) | (++) |
| 233 | 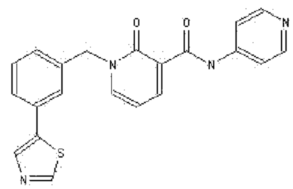 | (++) | (++) |
| 234 | 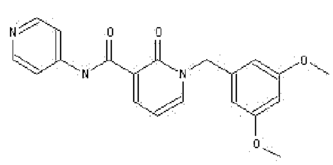 | (-) | (+) |

FIG. 2S

| Compound | Compound Structure | A IC$_{50}$ (μM) | B IC$_{50}$ (μM) |
|---|---|---|---|
| 235 | 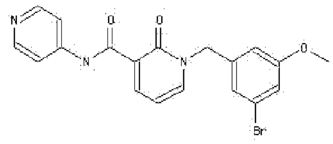 | (-) | (+) |
| 236 | 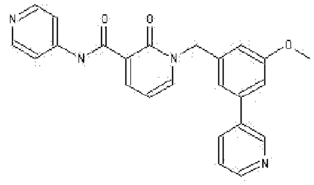 | (+) | (+) |
| 237 | 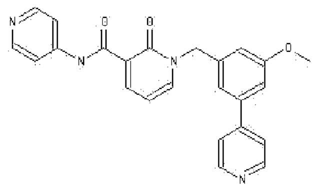 | (-) | (+) |
| 238 | 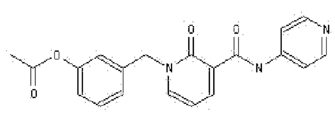 | (++) | (++) |
| 239 | 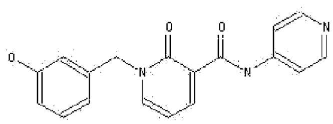 | (-) | (++) |
| 240 | 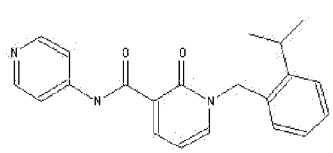 | (++) | (++) |

FIG. 2T

| Compound | Compound Structure | A IC$_{50}$ (μM) | B IC$_{50}$ (μM) |
|---|---|---|---|
| 241 | 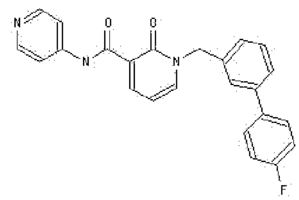 | | (+++) |
| 242 | 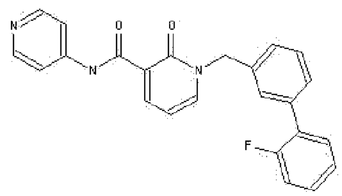 | | (++) |
| 243 | 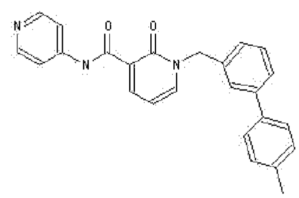 | | (+++) |
| 244 | 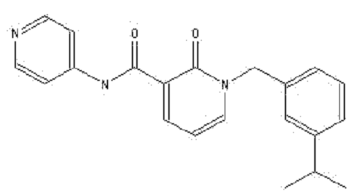 | | (++) |
| 245 | 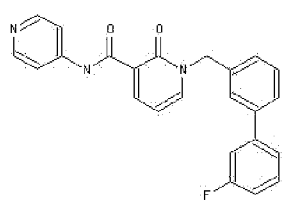 | | (++) |
| 246 | 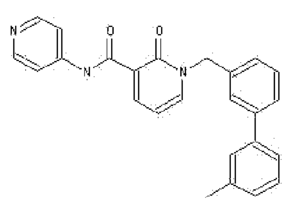 | | (++) |

FIG. 2U

| Compound | Compound Structure | A IC$_{50}$ (μM) | B IC$_{50}$ (μM) |
|---|---|---|---|
| 247 | 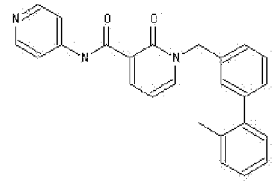 | | (++) |
| 248 | 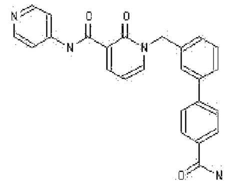 | | (+) |
| 249 | 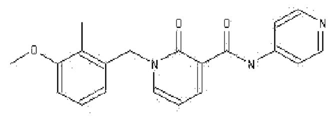 | | (++) |
| 250 | 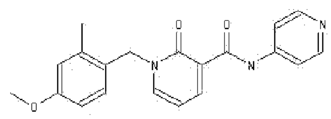 | | (++) |
| 251 | 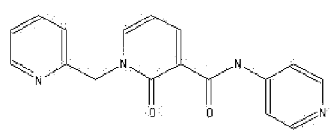 | (+) | |
| 252 | 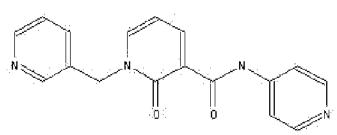 | (+) | |

FIG. 2V

| Compound | Compound Structure | A IC$_{50}$ (μM) | B IC$_{50}$ (μM) |
|---|---|---|---|
| 253 | 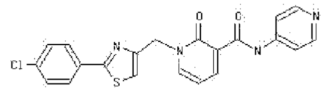 | (+) | |
| 254 | 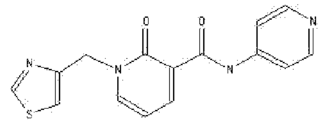 | (+) | |
| 255 | 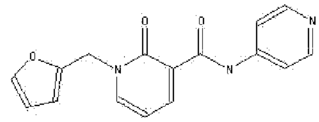 | (-) | |
| 256 | 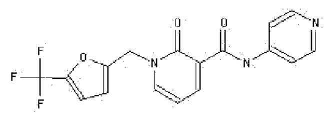 | (+) | (+) |
| 257 | 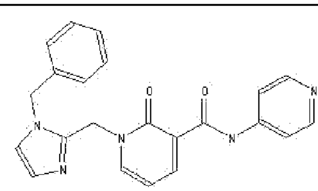 | > 10 | (-) |
| 258 | 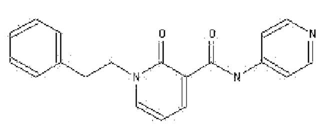 | (+) | |

FIG. 2W

| Compound | Compound Structure | A IC$_{50}$ (μM) | B IC$_{50}$ (μM) |
|---|---|---|---|
| 259 | 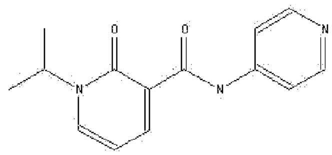 | (+) | |
| 260 | 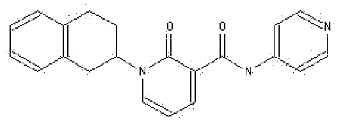 | (++) | |
| 261 | 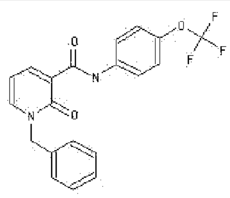 | (++) | (++) |
| 262 | 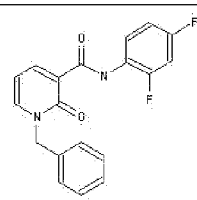 | (-) | |
| 263 | 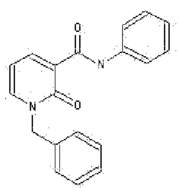 | (+) | (+) |
| 264 | 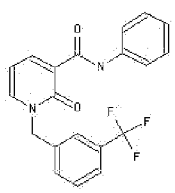 | (+) | |

FIG. 2X

| Compound | Compound Structure | A IC$_{50}$ (μM) | B IC$_{50}$ (μM) |
|---|---|---|---|
| 265 | 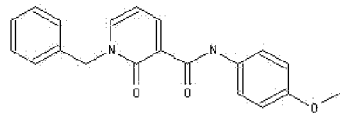 | (-) | |
| 266 | 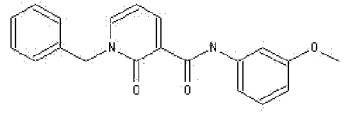 | (-) | |
| 267 | 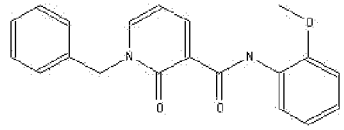 | (-) | |
| 268 | 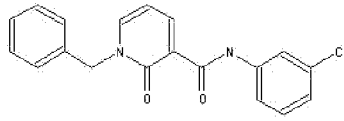 | (-) | |
| 269 | 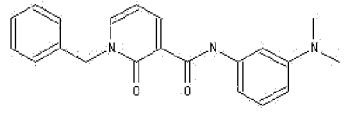 | (-) | |
| 270 | 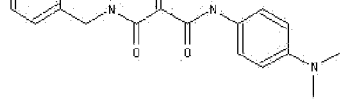 | (+) | |
FIG. 2Y

| Compound | Compound Structure | A IC$_{50}$ ($\mu$M) | B IC$_{50}$ ($\mu$M) |
|---|---|---|---|
| 271 | 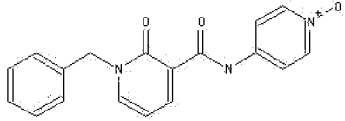 | (-) | |
| 272 | 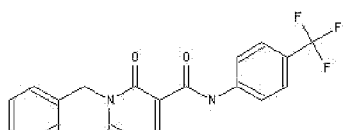 | (++) | |
| 273 | 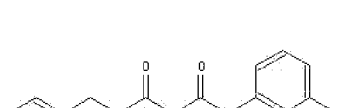 | (-) | |
| 274 | 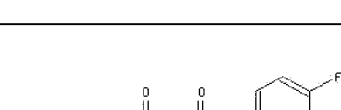 | (++) | |
| 275 | 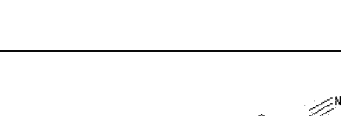 | (+) | |
| 276 | 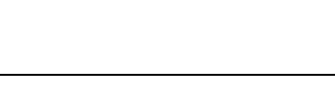 | (+) | |
FIG. 2Z

| Compound | Compound Structure | A IC$_{50}$ (μM) | B IC$_{50}$ (μM) |
|---|---|---|---|
| 277 | 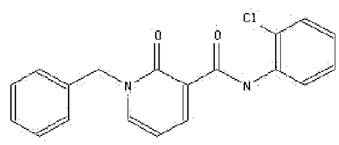 | (-) | |
| 278 | 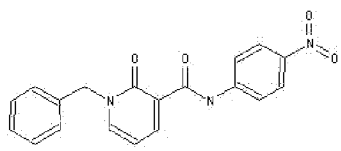 | (-) | |
| 279 | 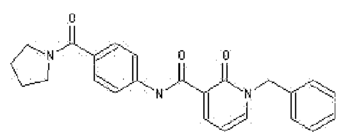 | (-) | |
| 280 | 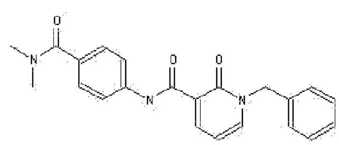 | (-) | |
| 281 | 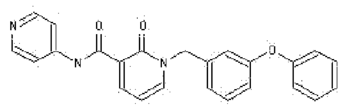 | (++) | (++) |
| 282 | 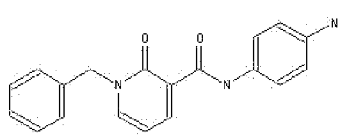 | (-) | |

FIG. 2AA

| Compound | Compound Structure | A IC$_{50}$ (μM) | B IC$_{50}$ (μM) |
|---|---|---|---|
| 283 | 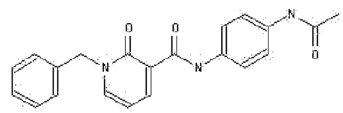 | (-) | |
| 284 | 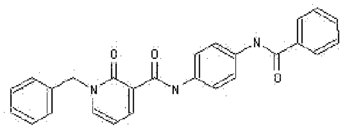 | (-) | |
| 285 | 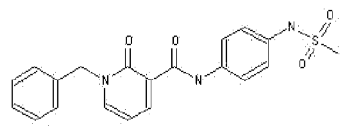 | (-) | |
| 286 | 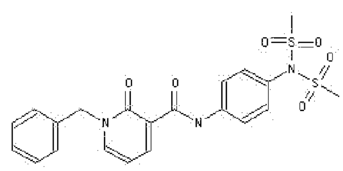 | (-) | |
| 287 | 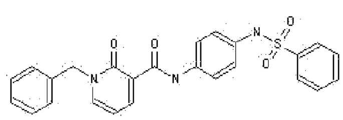 | (-) | |
| 288 | 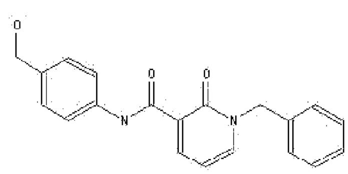 | (-) | |

FIG. 2BB

| Compound | Compound Structure | A IC$_{50}$ (μM) | B IC$_{50}$ (μM) |
|---|---|---|---|
| 289 | 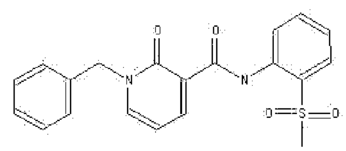 | (-) | |
| 290 | 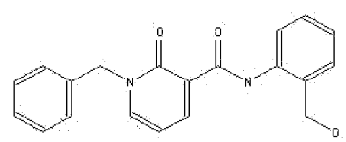 | (+) | |
| 291 | 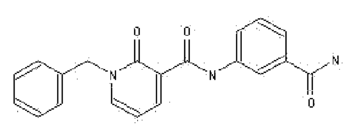 | (-) | |
| 292 | 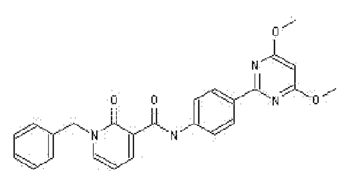 | (++) | (++) |
| 293 | 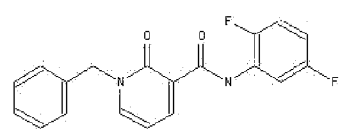 | (-) | |
| 294 | 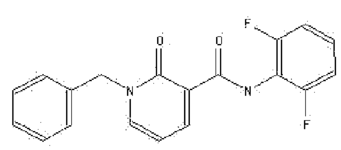 | (-) | |

FIG. 2CC

| Compound | Compound Structure | A IC$_{50}$ (μM) | B IC$_{50}$ (μM) |
|---|---|---|---|
| 295 | 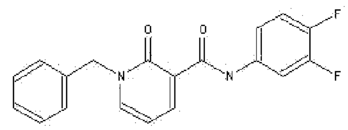 | (+) | |
| 296 | 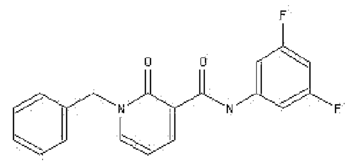 | (-) | |
| 297 | 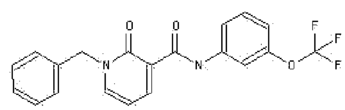 | (+) | |
| 298 | 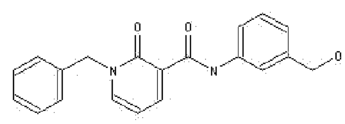 | (-) | |
| 299 | 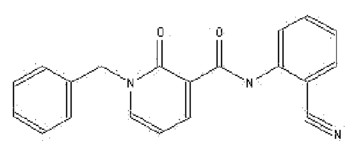 | (-) | |
| 300 | 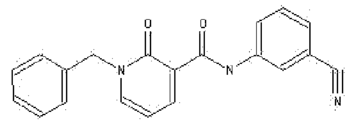 | (-) | |

FIG. 2DD

| Compound | Compound Structure | A IC$_{50}$ (μM) | B IC$_{50}$ (μM) |
|---|---|---|---|
| 301 | 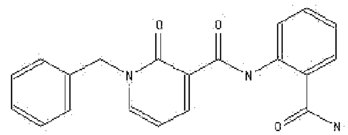 | (-) | |
| 302 | 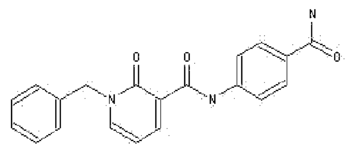 | (-) | |
| 303 | 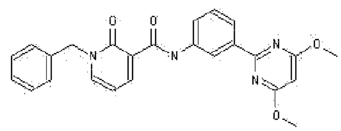 | (-) | |
| 304 | 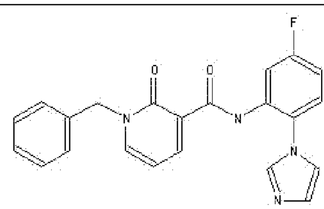 | (-) | |
| 305 | 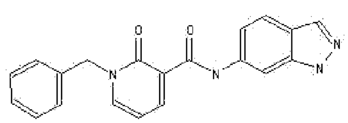 | (+) | |
| 306 | 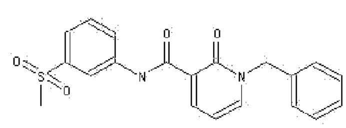 | (-) | |

FIG. 2EE

| Compound | Compound Structure | A IC$_{50}$ (μM) | B IC$_{50}$ (μM) |
|---|---|---|---|
| 307 | 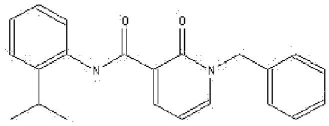 | (-) | |
| 308 | 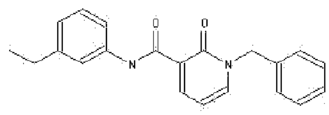 | (-) | |
| 309 | 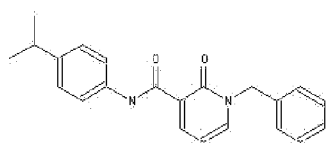 | (+) | |
| 310 | 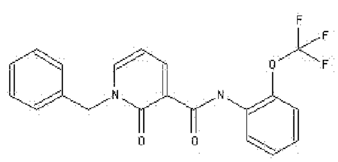 | (-) | |
| 311 | 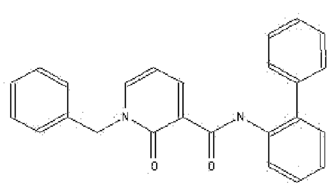 | (-) | |
| 312 | 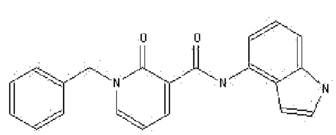 | (-) | |

FIG. 2FF

| Compound | Compound Structure | A IC$_{50}$ (μM) | B IC$_{50}$ (μM) |
|---|---|---|---|
| 313 | 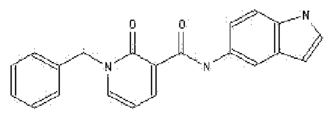 | (-) | |
| 314 | 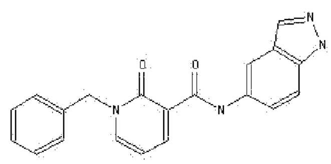 | (-) | |
| 315 | 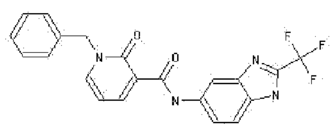 | (-) | |
| 316 | 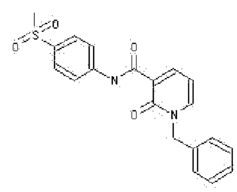 | (-) | |
| 317 | 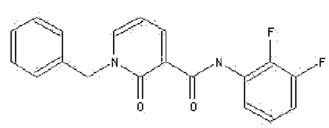 | (-) | |
| 318 | 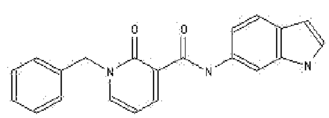 | (-) | (-) |

FIG. 2GG

| Compound | Compound Structure | A IC$_{50}$ (μM) | B IC$_{50}$ (μM) |
|---|---|---|---|
| 319 | 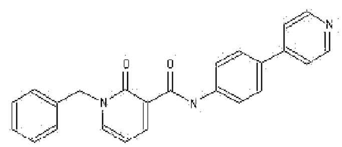 | (-) | (+) |
| 320 | 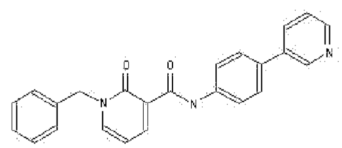 | (+) | (++) |
| 321 | 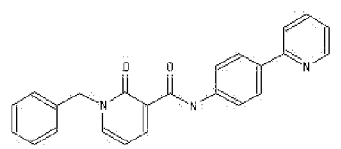 | (+) | (++) |
| 322 | 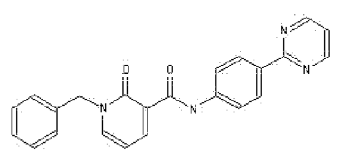 | (-) | (+) |
| 323 | 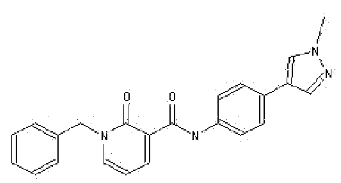 | (+) | (+) |
| 324 | 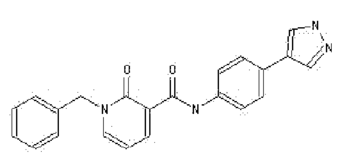 | (+) | (+) |

FIG. 2HH

| Compound | Compound Structure | A IC$_{50}$ (μM) | B IC$_{50}$ (μM) |
|---|---|---|---|
| 325 | 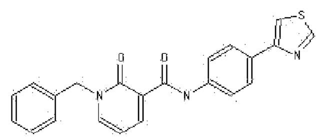 | (+) | (++) |
| 326 | 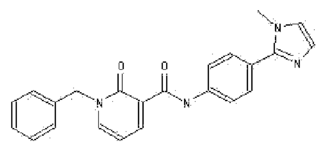 | (+) | (+) |
| 327 | 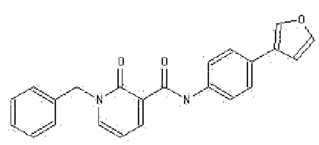 | (+) | (++) |
| 328 | 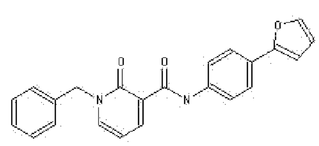 | (++) | (++) |
| 329 | 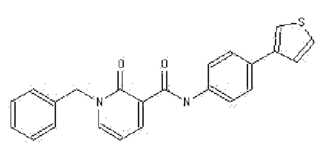 | (++) | (++) |
| 330 | 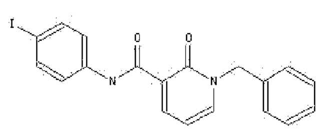 | (+) | (++) |

FIG. 2II

| Compound | Compound Structure | A IC$_{50}$ (μM) | B IC$_{50}$ (μM) |
|---|---|---|---|
| 331 | 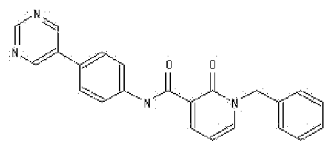 | (-) | (++) |
| 332 | 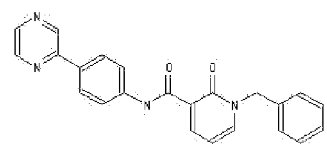 | (-) | (+) |
| 333 | 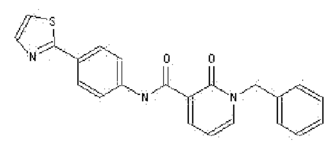 | (-) | (++) |
| 334 | 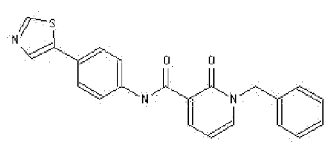 | (++) | (++) |
| 335 | 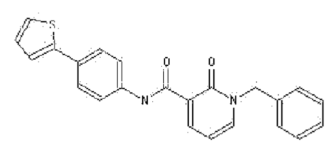 | (++) | (++) |
| 336 | 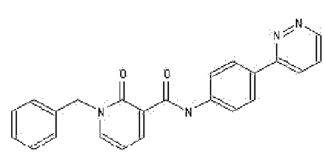 | (-) | (-) |

FIG. 2JJ

| Compound | Compound Structure | A IC$_{50}$ (μM) | B IC$_{50}$ (μM) |
|---|---|---|---|
| 337 | 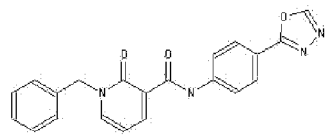 | (-) | (++) |
| 338 | 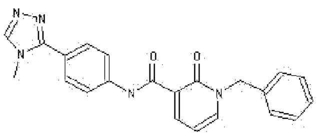 | | (+) |
| 339 | 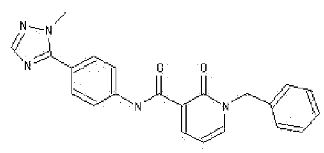 | | (+) |
| 340 | 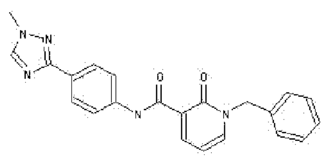 | | (+) |
| 341 | 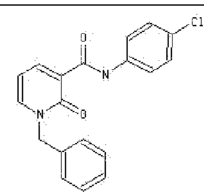 | (++) | (++) |
| 342 | 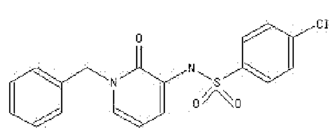 | (-) | |

FIG. 2KK

| Compound | Compound Structure | A IC$_{50}$ (μM) | B IC$_{50}$ (μM) |
|---|---|---|---|
| 343 | 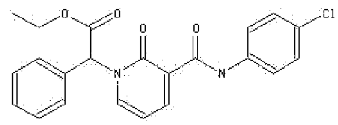 | (+) | |
| 344 | 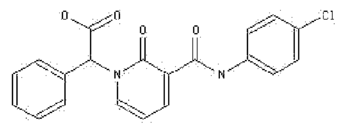 | (-) | |
| 345 | 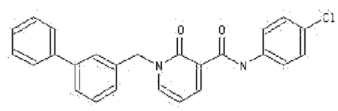 | (++) | |
| 346 | 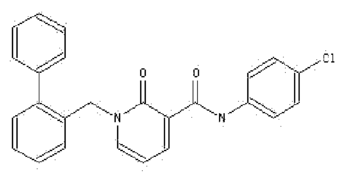 | (-) | |
| 347 | 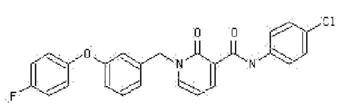 | (+) | |
| 348 | 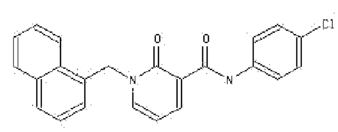 | (++) | |

FIG. 2LL

| Compound | Compound Structure | A IC$_{50}$ (μM) | B IC$_{50}$ (μM) |
|---|---|---|---|
| 349 | 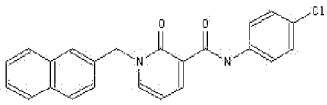 | (++) | |
| 350 | 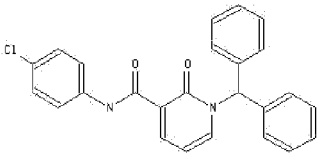 | (-) | |
| 351 | 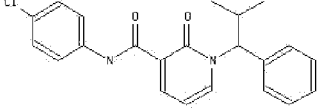 | (-) | |
| 352 | 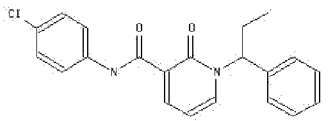 | (-) | |
| 353 | 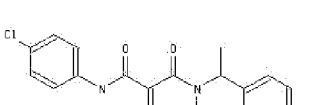 | (++) | |
| 354 | 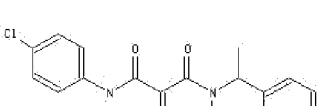 | (++) | |
FIG. 2MM

| Compound | Compound Structure | A IC$_{50}$ (μM) | B IC$_{50}$ (μM) |
|---|---|---|---|
| 355 | 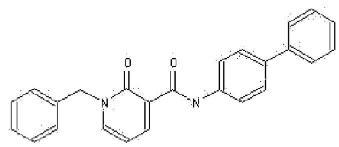 | (++) | (++) |
| 356 | 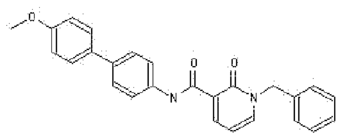 | (++) | (++) |
| 357 | 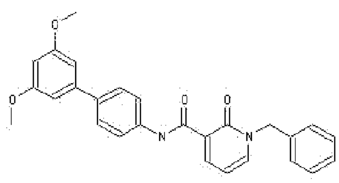 | (++) | (++) |
| 358 | 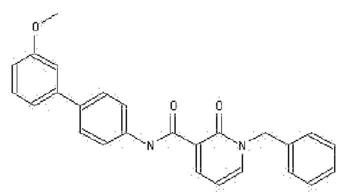 | (++) | (+++) |
| 359 | 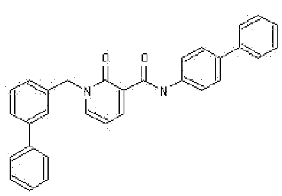 | (++) | (+++) |
| 360 | 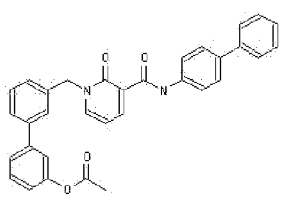 | (++) | (+++) |

FIG. 2NN

| Compound | Compound Structure | A IC$_{50}$ (μM) | B IC$_{50}$ (μM) |
|---|---|---|---|
| 361 | 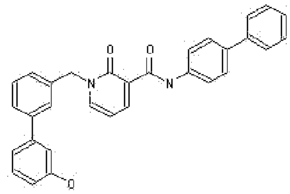 | (++) | (+++) |
| 362 | 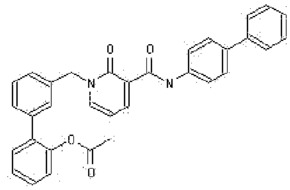 | | (+++) |
| 363 | 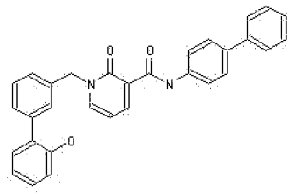 | | (+++) |
| 364 | 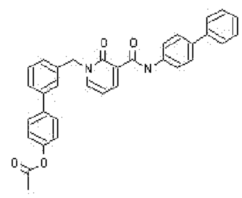 | | (+++) |
| 365 | 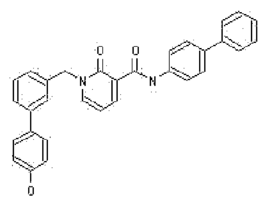 | | (+++) |
| 366 | 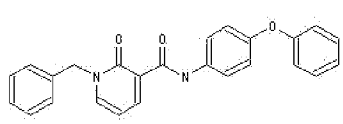 | (++) | (++) |

FIG. 2OO

| Compound | Compound Structure | A IC$_{50}$ ($\mu$M) | B IC$_{50}$ ($\mu$M) |
|---|---|---|---|
| 367 | 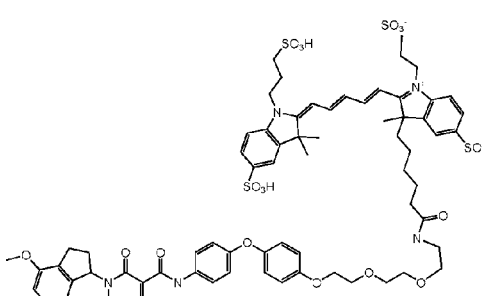 | > 10 | (+) |
| 368 | 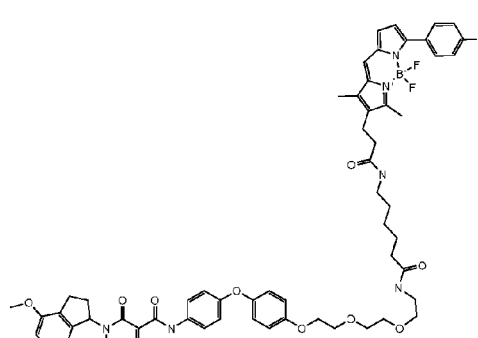 | | > 10 |
| 369 | 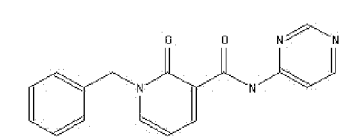 | (-) | |
| 370 | 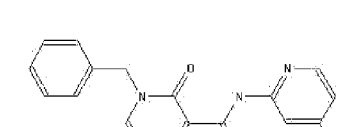 | (-) | |
| 371 | 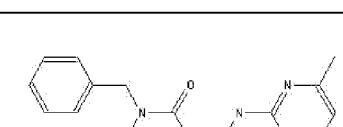 | (-) | |
FIG. 2PP

| Compound | Compound Structure | A IC$_{50}$ (μM) | B IC$_{50}$ (μM) |
|---|---|---|---|
| 372 | 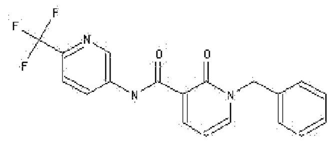 | (-) | |
| 373 | 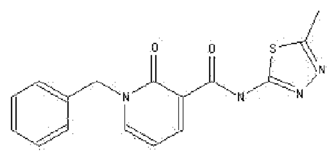 | (+) | |
| 374 | 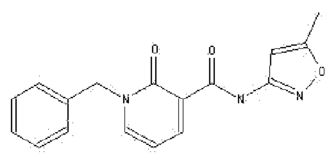 | (+) | |
| 375 | 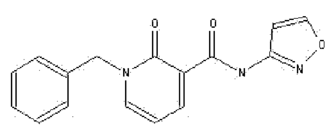 | (-) | |
| 376 | 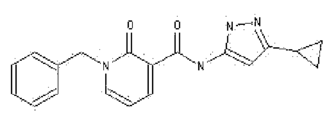 | (-) | |
| 377 | 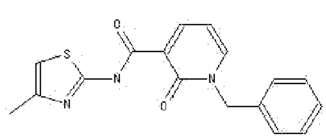 | (-) | |

FIG. 2QQ

| Compound | Compound Structure | A IC$_{50}$ (μM) | B IC$_{50}$ (μM) |
|---|---|---|---|
| 378 | 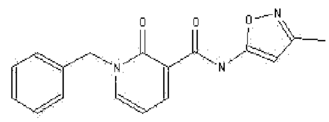 | (−) | |
| 379 | 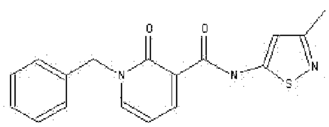 | (+) | |
| 380 | 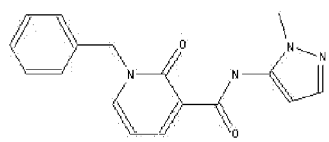 | (+) | |
| 381 | 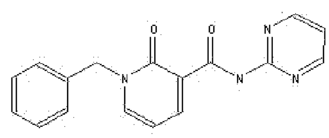 | (−) | |
| 382 | 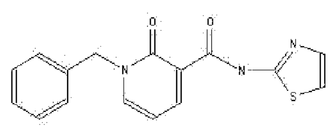 | (−) | |
| 383 | 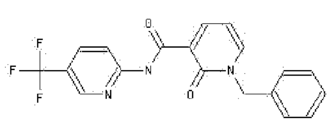 | (−) | |

FIG. 2RR

| Compound | Compound Structure | A IC$_{50}$ (μM) | B IC$_{50}$ (μM) |
|---|---|---|---|
| 384 | 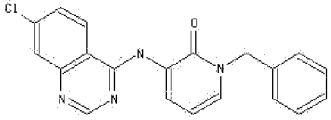 | (-) | |
| 385 | 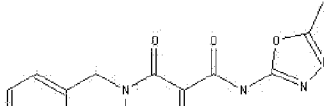 | (-) | |
| 386 | 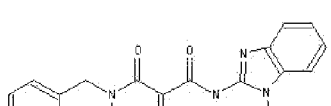 | (-) | |
| 387 | 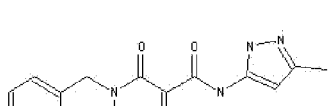 | (-) | |
| 388 | 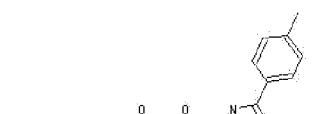 | (-) | |
| 389 | 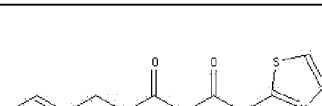 | (+) | |
FIG. 2SS

| Compound | Compound Structure | A IC$_{50}$ (µM) | B IC$_{50}$ (µM) |
|---|---|---|---|
| 390 | 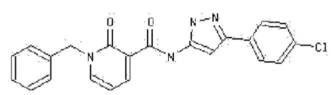 | (+) | |
| 391 | 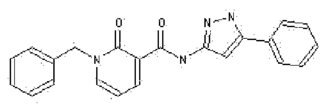 | (+) | |
| 392 | 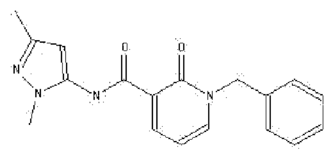 | (−) | |
| 393 | 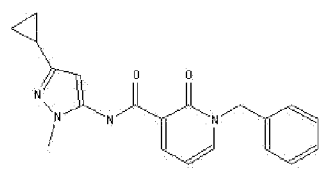 | (−) | |
| 394 | 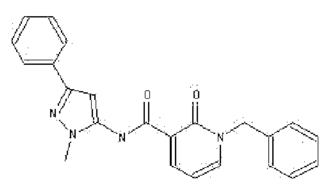 | (++) | |
| 395 | 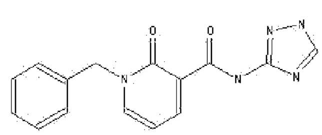 | (+) | |

FIG. 2TT

| Compound | Compound Structure | A IC$_{50}$ (μM) | B IC$_{50}$ (μM) |
|---|---|---|---|
| 396 | 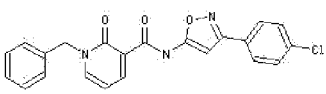 | (+) | |
| 397 | 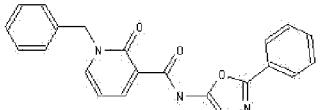 | (+) | (-) |
| 398 | 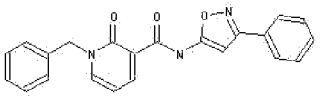 | (-) | |
| 399 | 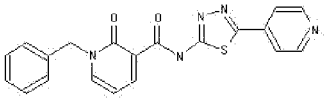 | (-) | |
| 400 | 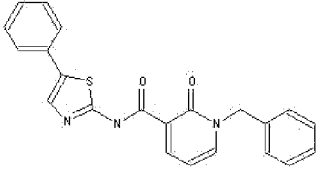 | (-) | |
| 401 | 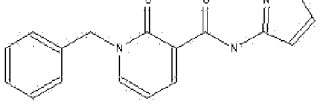 | (-) | (-) |
FIG. 2UU

| Compound | Compound Structure | A IC$_{50}$ (μM) | B IC$_{50}$ (μM) |
|---|---|---|---|
| 402 | 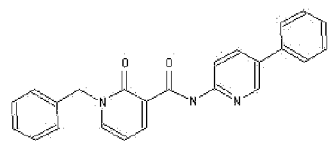 | (+) | (++) |
| 403 | 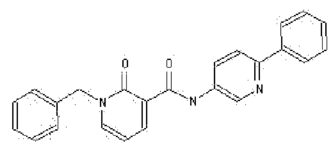 | (+) | (++) |
| 404 | 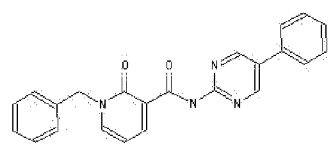 | (−) | (+) |
| 405 | 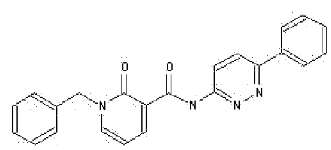 | (−) | (−) |
| 406 | 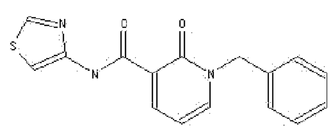 | (−) | (+) |
| 407 | 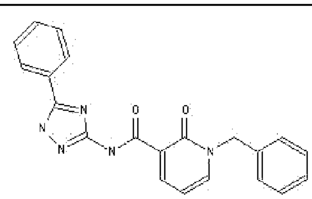 | (−) | (−) |

FIG. 2VV

| Compound | Compound Structure | A IC$_{50}$ (μM) | B IC$_{50}$ (μM) |
|---|---|---|---|
| 408 | 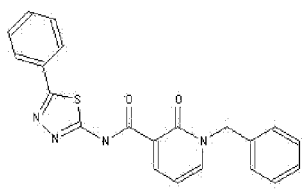 | (-) | (-) |
| 409 | 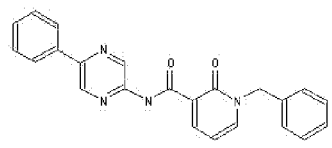 | (-) | (-) |
| 410 | 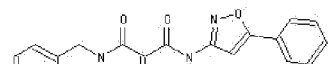 | (-) | (-) |
| 411 | 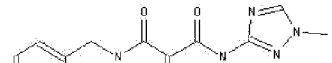 | (-) | (-) |
| 412 | 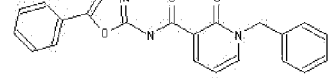 | (-) | (-) |
| 413 | 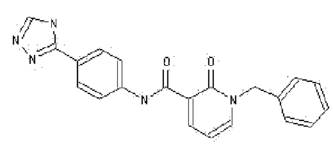 | (-) | (-) |
FIG. 2WW

| Compound | Compound Structure | A IC$_{50}$ (μM) | B IC$_{50}$ (μM) |
|---|---|---|---|
| 414 | 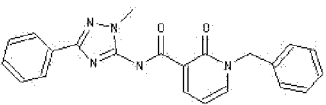 | (-) | (-) |
| 415 | 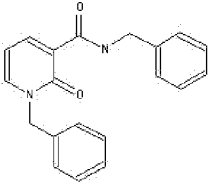 | (-) | (-) |
| 416 | 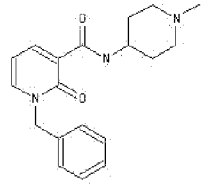 | (-) | |
| 417 | 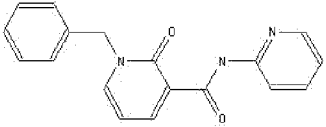 | (-) | |
| 418 | 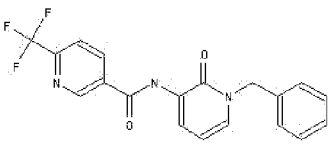 | (-) | |
| 419 | 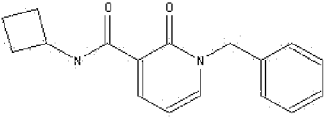 | (-) | |
FIG. 2XX

| Compound | Compound Structure | A IC$_{50}$ (μM) | B IC$_{50}$ (μM) |
|---|---|---|---|
| 420 | 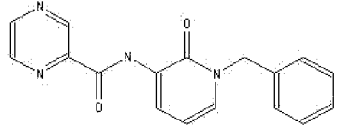 | (-) | |
| 421 | 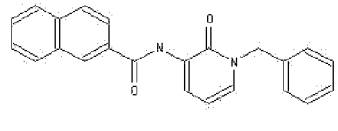 | (+) | |
| 422 | 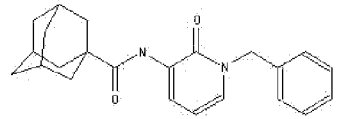 | (-) | |
| 423 | 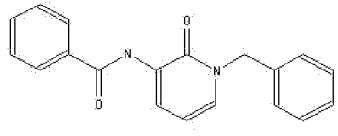 | (-) | |
| 424 | 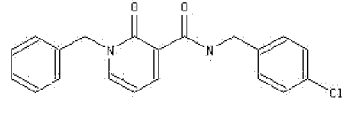 | (+) | |
| 425 | 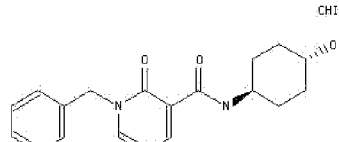 | (-) | |
FIG. 2YY

| Compound | Compound Structure | A IC$_{50}$ (μM) | B IC$_{50}$ (μM) |
|---|---|---|---|
| 426 | 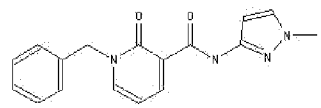 | (-) | |
| 427 | 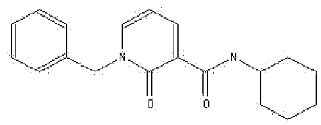 | (++) | (-) |
| 428 | 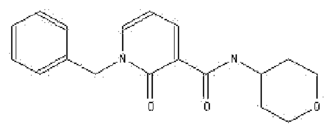 | (+) | |
| 429 | 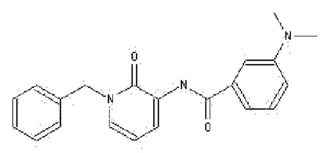 | (-) | |
| 430 | 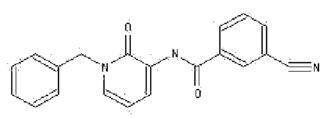 | (-) | |
| 431 | 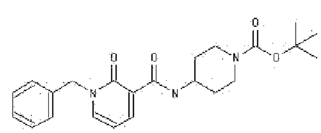 | (+) | |

FIG. 2ZZ

| Compound | Compound Structure | A IC$_{50}$ (μM) | B IC$_{50}$ (μM) |
|---|---|---|---|
| 432 | 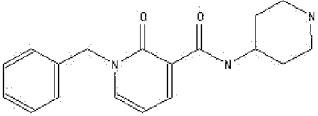 | (-) | |
| 433 | 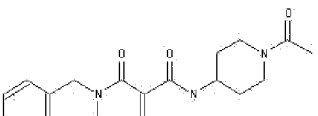 | (+) | |
| 434 | 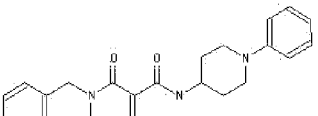 | (+) | |
| 435 | 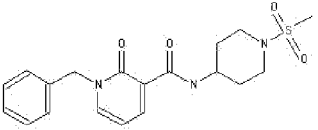 | (-) | |
| 436 | 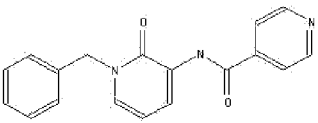 | (+) | |
| 437 | 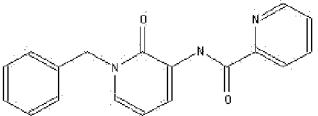 | (+) | |
FIG. 2AAA

| Compound | Compound Structure | A IC$_{50}$ (μM) | B IC$_{50}$ (μM) |
|---|---|---|---|
| 438 | 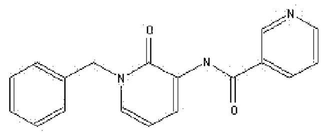 | (+) | |
| 439 | 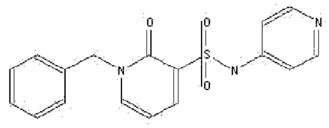 | (+) | |
| 440 | 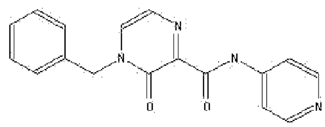 | (+) | |
| 441 | 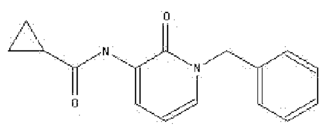 | (+) | |
| 442 | 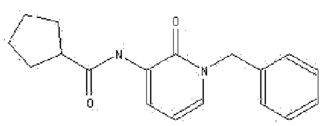 | (−) | |

(+++) IC$_{50}$ < 0.1 μM
(++) IC$_{50}$ 0.1 μM – 10 μM
(+) IC$_{50}$ > 10 μM
(−) Compound tested, activity below level of detection in assay used (IC$_{50}$ > 100 μM)

A: MadCam cell adhesion assay
B: MadCam SRU cell adhesion assay

FIG. 2BBB

PYRIDINONE ANTAGONISTS OF ALPHA-4 INTEGRINS

CROSS REFERENCE TO RELATED APPLICATIONS

This application claims the benefit under 35 U.S.C. §119 (e) of U.S. Provisional Application Ser. No. 61/172,876, filed Apr. 27, 2009, which is hereby incorporated by reference in its entirety.

BACKGROUND OF THE INVENTION

1. Field of the Invention

This invention relates to compounds which inhibit leukocyte adhesion and, in particular, leukocyte adhesion mediated by $\alpha_4\beta_7$. Accordingly, compounds of this invention are useful in the treatment and prevention of diseases mediated by $\alpha_4\beta_7$ binding and cell adhesion and activation such as multiple sclerosis, asthma, allergic rhinitis, rheumatoid arthritis, septic arthritis, restenosis, inflammatory bowel disease including ulcerative colitis and Crohn's disease, dermatitis, psoriasis, and the like.

2. State of the Art

The following publications, patents and patent applications are cited in this application as superscript numbers:

[1] Tidswell, et al., *J. of Immunology*, 1497-1505 (1997)
[2] Springer, *Nature*, 346:425-434 (1990)
[3] Osborn, *Cell*, 62:3-6 (1990)
[4] Vedder, et al., *Surgery*, 106:509 (1989)
[5] Pretolani, et al., *J. Exp. Med.*, 0.180:795 (1994)
[6] Abraham. et al., *J. Clin. Invest.*, 93:776 (1994)
[7] Mulligan, et al., *J. Immunology*, 150:2407 (1993)
[8] Cybulsky, et al., *Science*, 251:788 (1991)
[9] Li, et al., *Arterioscler. Thromb.*, 13:197 (1993)
[10] Sasseville, et al., *Am. J. Path.*, 144:27 (1994)
[11] Yang, et al., *Proc. Nat. Acad. Science (USA)*, 90:10494 (1993)
[12] Burkly, et al., *Diabetes*, 43:529 (1994)
[13] Baron, et al., *J. Clin. Invest.*, 93:1700 (1994)
[14] Hamann, et al., *J. Immunology*, 152:3238 (1994)
[15] Yednock, et al., *Nature*, 356:63 (1992)
[16] Baron, et al., *J. Exp. Med.*, 177:57 (1993)
[17] van Dinther-Janssen, et al., *J. Immunology*, 147:4207 (1991)
[18] van Dinther-Janssen, et al., *Annals. Rheumatic Dis.*, 52:672 (1993)
[19] Elices, et al, *J. Clin. Invest.*, 93:405 (1994)
[20] Postigo, et al., *J. Clin. Invest.*, 89:1445 (1991)
[21] Paul, et al., *Transpl. Proceed*, 25:813 (1993)
[22] Okarhara, et al., *Can. Res.*, 54:3233 (1994)
[23] Paavonen, et al., *Int. J. Can.*, 58:298 (1994)
[24] Schadendorf et al., *J. Path.*, 170:429 (1993)
[25] Bao, et al., *Diff*, 52:239 (1993)
[26] Lauri, et al., *British J. Cancer*, 68:862 (1993)
[27] Kawaguchi, et al., *Japanese J. Cancer Res.*, 83:1304 (1992)
[28] Kogan, et al., U.S. Pat. No. 5,510,332, issued Apr. 23, 1996
[29] International Patent Appl. Publication No. WO 96/01644

All of the above publications, patents and patent applications are herein incorporated by reference in their entirety to the same extent as if each individual publication, patent or patent application was specifically and individually indicated to be incorporated by reference in its entirety.

Integrins are heterodimeric adhesion receptors that mediate cell-cell and cell-extracellular matrix interactions. The $\beta_7$ integrin subfamily has two known members: $\alpha_4\beta_7$ and $\alpha_E\beta_7$. These $\beta_7$ integrins are expressed primarily by leukocytes. $\beta_7$ integrins are unique among known integrins in their ability to recognize certain ligands expressed on the surface of endothelial and epithelial cells in mucosal organs.[1]

$\alpha_4\beta_7$ is a lymphocyte homing receptor and plays a crucial role in the migration of these cells to the intestine and associated lymphoid tissue, such as Peyer's patches in the intestine. $\alpha_4\beta_7$ mediates adhesion to a ligand on Peyer's patch high endothelial venules ("HEV[4]"). The ligand on Peyer's patch HEV is MAdCAM-1, a glycoprotein in the Ig superfamily. MAdCAM-1 is expressed on Peyer's patch HEV, mesenteric lymph node HEV, and lamina propria venules within the gut. Antibodies against $\alpha_4$ or $\beta_7$ subunits inhibit attachment of circulating lymphocytes to Peyer's patch HEV in vivo.[1]

Memory T cells that circulate preferentially to intestinal tissues express high levels of $\alpha_4\beta_7$, whereas those that circulate to other organs are mostly $\alpha_4\beta_1$. These $\alpha_4\beta_7$ memory T cells express a related integrin, $\alpha_4\beta_1$, which is not able to mediate cell adhesion to MAdCAM-1. However, both $\alpha_4\beta_7$ and $\alpha_4\beta_1$, can mediate adhesion to VCAM-1 and to fibronectin.[1]

Intercellular adhesion mediated by $\alpha_4\beta_7$ and other cell surface receptors is associated with a number of inflammatory responses. At the site of an injury or other inflammatory stimulus, activated vascular endothelial cells express molecules that are adhesive for leukocytes. The mechanics of leukocyte adhesion to endothelial cells involves, in part, the recognition and binding of cell surface receptors on leukocytes to the corresponding cell surface molecules on endothelial cells. Once bound, the leukocytes migrate across the blood vessel wall to enter the injured site and release chemical mediators to combat infection. For reviews of adhesion receptors of the immune system, see, for example, Springer[2] and Osborn.[3]

Inflammatory brain disorders, such as experimental autoimmune encephalomyelitis (EAE), multiple sclerosis (MS) and meningitis, are examples of central nervous system disorders in which the endothelium/leukocyte adhesion mechanism results in destruction to otherwise healthy brain tissue. Large numbers of leukocytes migrate across the blood brain barrier (BBB) in subjects with these inflammatory diseases. The leukocytes release toxic mediators that cause extensive tissue damage resulting in impaired nerve conduction and paralysis.

In other organ systems, tissue damage also occurs via an adhesion mechanism resulting in migration or activation of leukocytes. For example, it has been shown that the initial insult following myocardial ischemia to heart tissue can be further complicated by leukocyte entry to the injured tissue causing still further insult.[4] Other inflammatory conditions mediated by an adhesion mechanism include, by way of example, asthma,[5-7] Alzheimer's disease, atherosclerosis,[8-9] AIDS dementia,[10] diabetes (including acute juvenile onset diabetes),[11-13] inflammatory bowel disease (including ulcerative colitis and Crohn's disease),[4] multiple sclerosis,[15-16] rheumatoid arthritis,[17-20] tissue transplantation,[21] tumor metastasis,[22-27] meningitis, encephalitis, stroke, and other cerebral traumas, nephritis, retinitis, atopic dermatitis, psoriasis, myocardial ischemia and acute leukocyte-mediated lung injury such as that which occurs in adult respiratory distress syndrome.

Despite advances in the understanding of leukocyte adhesion, the art has only recently addressed the use of inhibitors of adhesion in the treatment of inflammatory conditions.[28,29] Novel alpha4 antagonists are needed for the development of additional treatment options for inflammatory diseases, such as MS, asthma, Crohn's disease and rheumatoid arthritis.

Furthermore, assays useful for the diagnosis of $\alpha_4\beta_7$ mediated conditions are needed. The current invention addresses these and other needs.

SUMMARY OF THE INVENTION

In various aspects, the invention provides compounds of Formula (Ia):

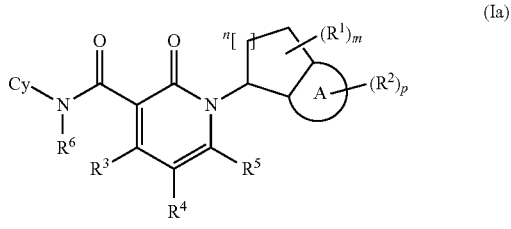

or a salt or solvate or single stereoisomer or mixture of stereoisomers thereof,
wherein
m is an integer selected from 0 to 4;
n is an integer selected from 0 to 3;
p is an integer selected from 0 to 4;
ring A is a member selected from substituted or unsubstituted aryl and substituted or unsubstituted heteroaryl;
Cy is a member selected from substituted or unsubstituted $(C_3-C_{10})$cycloalkyl, substituted or unsubstituted 3- to 10-membered heterocycloalkyl, substituted or unsubstituted aryl and substituted or unsubstituted heteroaryl;
each $R^1$ and each $R^2$ is a member independently selected from H, substituted or unsubstituted $(C_1-C_{10})$alkyl, substituted or unsubstituted 2- to 10-membered heteroalkyl, substituted or unsubstituted $(C_3-C_{10})$cycloalkyl, substituted or unsubstituted 3- to 10-membered heterocycloalkyl, substituted or unsubstituted aryl, substituted or unsubstituted heteroaryl, nitro, CN, halogen, $OR^{12}$, $SR^{12}$, $NR^{12}R^{13}$, $C(O)R^{14}$, $C(O)NR^{12}R^{13}$, $OC(O)NR^{12}R^{13}$, $C(O)OR^{12}$, $NR^{15}C(O)R^{14}$, $NR^{15}C(O)OR^{12}$, $NR^{15}C(O)NR^{12}R^{13}$, $NR^{15}C(S)NR^{12}R^{13}$, $NR^{15}S(O)_2NR^{14}$, $S(O)_2NR^{12}R^{13}$ and $S(O)_zR^{14}$,
wherein
z is 1 or 2;
$R^{12}$, $R^{13}$ and $R^{15}$ are members independently selected from H, acyl, substituted or unsubstituted $(C_1-C_{10})$alkyl, substituted or unsubstituted 2- to 10-membered heteroalkyl, substituted or unsubstituted aryl, substituted or unsubstituted heteroaryl, substituted or unsubstituted $(C_3-C_{10})$cycloalkyl, substituted or unsubstituted 3- to 10-membered heterocycloalkyl; and
$R^{14}$ is a member independently selected from substituted or unsubstituted $(C_1-C_{10})$alkyl, substituted or unsubstituted 2- to 10-membered heteroalkyl, substituted or unsubstituted aryl, substituted or unsubstituted heteroaryl, substituted or unsubstituted $(C_3-C_{10})$cycloalkyl, substituted or unsubstituted 3- to 10-membered heterocycloalkyl,
wherein $R^{12}$ and $R^{13}$, together with the nitrogen atoms to which they are attached, are optionally joined to form a 4- to 7-membered ring, and
wherein two adjacent $R^1$, together with the atoms to which they are attached, are optionally joined to form a 5- to 7-membered ring, and wherein two adjacent $R^2$, together with the atoms to which they are attached, are optionally joined to form a 5- to 7-membered ring;
$R^3$, $R^4$ and $R^5$ are members independently selected from H, substituted or unsubstituted $(C_1-C_4)$alkyl, halogen and CN; and
$R^6$ is a member selected from H and substituted or unsubstituted $(C_1-C_4)$alkyl.

The invention is also directed to a compound of Formula (Ia'), Formula (Ib), or

Formula (Ic)

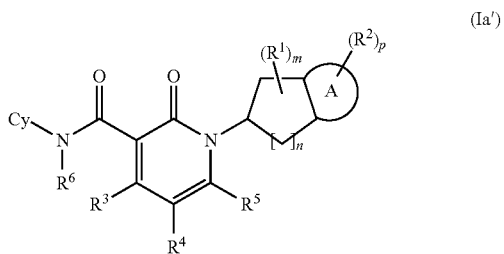

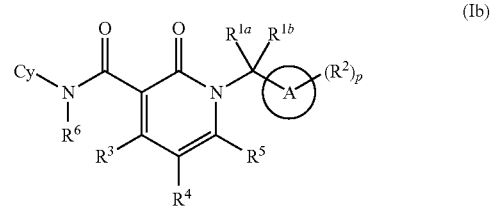

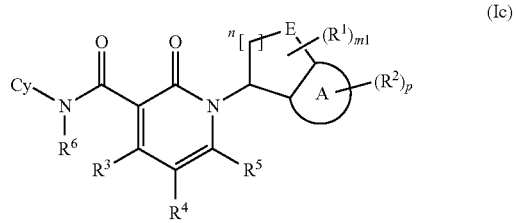

wherein Cy, $R^1$, $R^2$, $R^3$, $R^4$, $R^5$, $R^6$, n, p, m, and A are as defined as for Formula (Ia);
m1 is an integer selected from 0 to 3;
$R^{1a}$ and $R^{1b}$ are independently selected from the same group as for $R^1$ and $R^2$ as defined above.

Also included in the invention is a salt or solvate or single stereoisomer or mixture of stereoisomers thereof, wherein m is an integer selected from 0 to 4, n is an integer selected from 0 to 4, p is an integer selected from 0 to 6 and m1 is an integer selected from 0 to 3. In one example, n is selected from 1 to 4. In another example, n is selected from 1 and 2. In yet another example, n is 1. In a further example, m is 0 or 1. In another example, p is 0 or 1.

In Formula (Ia), Formula (Ia'), Formula (Ib) or Formula (Ic), ring A is a member selected from substituted or unsubstituted aryl (e.g., phenyl, naphthyl) and substituted or unsubstituted heteroaryl (e.g., pyridyl, thiophene, thiazole, imidazolyl).

In Formula (Ia), Formula (Ia'), Formula (Ib) or Formula (Ic), Cy is a member selected from substituted or unsubstituted cycloalkyl (e.g., $C_3-C_{10}$ cycloalkyl), substituted or unsubstituted heterocycloalkyl (e.g., 3- to 10-membered heterocycloalkyl), substituted or unsubstituted aryl (e.g., phenyl or naphthyl) and substituted or unsubstituted heteroaryl (e.g., pyridyl). In one example in the above structures, Cy is substituted or unsubstituted aryl (e.g., phenyl or naphthyl) or substituted or unsubstituted heteroaryl (e.g., pyridyl). In a particular example, Cy in the above structures is a member selected from substituted or unsubstituted phenyl (e.g., substituted or unsubstituted 4-chloro-phenyl or substituted or unsubstituted 4-phenoxyphenyl), substituted or unsubstituted naphthyl, substituted or unsubstituted biphenyl (e.g., substituted or unsubstituted biphenyl-4-yl) and substituted or unsubstituted pyridyl (e.g., substituted or unsubstituted 4-pyridyl).

In Formula (Ia), Formula (Ia'), Formula (Ib) or Formula (Ic), each $R^1$, each $R^2$, $R^{1a}$ and $R^{1b}$ are members independently selected from H, substituted or unsubstituted alkyl (e.g., $C_1$-$C_{10}$ alkyl), substituted or unsubstituted heteroalkyl (e.g., 2- to 10-membered heteroalkyl), substituted or unsubstituted cycloalkyl (e.g., $C_3$-$C_{10}$ cycloalkyl), substituted or unsubstituted heterocycloalkyl (e.g., 3- to 10-membered heterocycloalkyl), substituted or unsubstituted aryl (e.g., substituted or unsubstituted phenyl or naphthyl), substituted or unsubstituted heteroaryl (e.g., substituted or unsubstituted pyridyl), nitro, CN, halogen (e.g., I, F, Cl or Br), $OR^{12}$, $SR^{12}$, $NR^{12}R^{13}$, $C(O)R^{14}$, $C(O)NR^{12}R^{13}$, $OC(O)NR^{12}R^{13}$, $C(O)OR^{12}$, $NR^{15}C(O)R^{14}$, $NR^{15}C(O)OR^{12}$, $NR^{15}C(O)NR^{12}R^{13}$, $NR^{15}C(S)NR^{12}R^{13}$, $NR^{15}S(O)_2R^{14}$, $S(O)_2NR^{12}R^{13}$ and $S(O)_zR^{14}$, wherein z is 1 or 2. $R^{12}$, $R^{13}$ and $R^{15}$ are members independently selected from H, acyl, substituted or unsubstituted alkyl (e.g., $C_1$-$C_{10}$ alkyl), substituted or unsubstituted heteroalkyl (e.g., 2- to 10-membered heteroalkyl), substituted or unsubstituted aryl, substituted or unsubstituted heteroaryl, substituted or unsubstituted cycloalkyl (e.g., $C_3$-$C_{10}$ cycloalkyl) and substituted or unsubstituted heterocycloalkyl (e.g., 3- to 10-membered heterocycloalkyl). $R^{14}$ is a member independently selected from substituted or unsubstituted alkyl (e.g., $C_1$-$C_{10}$ alkyl), substituted or unsubstituted heteroalkyl (e.g., 2- to 10-membered heteroalkyl), substituted or unsubstituted aryl, substituted or unsubstituted heteroaryl, substituted or unsubstituted cycloalkyl (e.g., $C_3$-$C_{10}$ cycloalkyl) and substituted or unsubstituted heterocycloalkyl (e.g., 3- to 10-membered heterocycloalkyl). $R^{12}$ and $R^{13}$, together with the nitrogen atoms to which they are attached, are optionally joined to form a 4- to 7-membered ring. Two adjacent $R^1$, together with the atoms to which they are attached, are optionally joined to form a 5- to 7-membered ring. Two adjacent $R^2$, together with the atoms to which they are attached, are optionally joined to form a 5- to 7-membered ring.

In Formula (Ia), Formula (Ia'), Formula (Ib) or Formula (Ic), $R^3$, $R^4$ and $R^5$ are members independently selected from H, substituted or unsubstituted alkyl (e.g., $C_1$-$C_4$ alkyl), halogen (e.g., I, F, Cl, Br), substituted or unsubstituted aryl, —O-aryl, and CN. In a particular example in the above structures, $R^3$, $R^4$ and $R^5$ are each H.

In Formula (Ia), Formula (Ia'), Formula (Ib) or Formula (Ic), $R^6$ is a member selected from H, substituted or unsubstituted alkyl (e.g., $C_1$-$C_6$ alkyl), substituted or unsubstituted heteroalkyl (e.g., 2- to 6-membered heteroalkyl), substituted or unsubstituted cycloalkyl (e.g., $C_3$-$C_8$ cycloalkyl), substituted or unsubstituted heterocycloalkyl (e.g., 3- to 8-membered heterocycloalkyl), substituted or unsubstituted aryl (e.g., substituted or unsubstituted phenyl), substituted or unsubstituted heteroaryl (e.g., substituted or unsubstituted pyridyl), $NR^{12}R^{13}$, $C(O)R^{14}$, $C(O)NR^{12}R^{13}$, $C(O)OR^{12}$ and $S(O)_zR^{14}$, wherein z is 1 or 2 and $R^{12}$, $R^{13}$ and $R^{14}$ are defined as herein above. In one example, $R^6$ is a member selected from H and substituted or unsubstituted alkyl (e.g., $C_1$-$C_4$ alkyl). In a particular example in the above structures, $R^6$ is H.

In Formula (Ic), E is selected from O, S, C(O), $S(O)_2$ and $NR^{40}$, wherein $R^{40}$ is a member selected from substituted or unsubstituted alkyl (e.g., $C_1$-$C_{10}$ alkyl). In one example, $R^{40}$ is unsubstituted $C_1$-$C_4$ alkyl (e.g., methyl or ethyl).

In one embodiment, the invention is directed to compounds of FIG. 1 and/or FIG. 2 or salts or solvates thereof.

In another embodiment is provided a pharmaceutical composition comprising a compound according to any one of the preceding claims and a pharmaceutically acceptable carrier.

In another embodiment, the invention is directed to a method of treating an inflammatory disease comprising administering to a mammalian subject in need thereof a pharmaceutically effective amount of a compound of the invention. In one embodiment, the inflammatory disease is a member selected from asthma, inflammatory bowel disease, ulcerative colitis, Crohn's disease, multiple sclerosis, rheumatoid arthritis, tumor metastasis, graft versus host disease, and organ or tissue rejection. In one embodiment the disease is ulcerative colitis or Crohn's disease.

In yet another embodiment, the invention is directed to use of a compound of the invention in an in vitro assay measuring binding of an α4β1 or α4β7 integrin to an integrin ligand. In one embodiment, the integrin ligand is a member selected from fibronectin (FN), VCAM-1, osteopontin and MadCAM.

In one embodiment, the assay comprises:
 (i) binding the ligand to a surface;
 (ii) contacting the ligand with a cell expressing the integrin, in the presence of the compound; and
 (iii) measuring the amount of cells bound to the surface.

In another embodiment, the invention is directed to use of a compound of the invention in an in vitro assay measuring binding of the compound to an α4β1 or α4β7 integrin in the presence of a candidate molecule. In another embodiment, the invention is directed to use of a compound of the invention in an in vitro assay for identifying a candidate molecule capable of binding to α4β1 or α4β7 integrin. In one embodiment, the assay is a competitive binding assay.

BRIEF DESCRIPTION OF THE DRAWINGS

FIG. 1 is a table summarizing exemplary compounds of the invention (compounds 1-121) and their in vitro biological activities. The MadCAM Adhesion Assay (A) and the MadCAM SRU Adhesion Assay (B), which were used to generate the presented data, are described herein in Examples 32 and 33, respectively.

FIG. 2 is a table summarizing exemplary compounds of the invention and their in vitro biological activities. The MadCAM Adhesion Assay (A) and the MadCAM SRU Adhesion Assay (B), which were used to generate the presented data, are described herein in Examples 32 and 33, respectively.

DETAILED DESCRIPTION OF THE INVENTION

Definitions

The definitions and explanations below are for the terms as used throughout this entire document including both the specification and the claims. Throughout the specification and the appended claims, a given formula or name shall encompass all isomers thereof, such as stereoisomers, geometrical isomers, optical isomers, tautomers, and mixtures thereof where such isomers exist, as well as pharmaceutically acceptable salts and solvates thereof, such as hydrates.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

Where multiple substituents are indicated as being attached to a structure, those substituents are independently selected. For example "ring A is optionally substituted with 1, 2 or 3 $R_q$ groups" indicates that ring A is substituted with 1, 2 or 3 $R_q$ groups, wherein the $R_q$ groups are independently selected (i.e., can be the same or different).

Compounds were named using Autonom 2000 4.01.305, which is available from Beilstein Information Systems, Inc, Englewood, Colo.; ChemDraw v.10.0, (available from Cambridgesoft at 100 Cambridge Park Drive, Cambridge, Mass. 02140), or ACD Name pro, which is available from Advanced Chemistry Development, Inc., at 110 Yonge Street, 14$^{th}$ floor, Toronto, Ontario, Canada M5c 1T4. Alternatively, the names were generated based on the IUPAC rules or were derived from names originally generated using the aforementioned nomenclature programs.

Where substituent groups are specified by their conventional chemical formulae, written from left to right, they equally encompass the chemically identical substituents, which would result from writing the structure from right to left. For example, "—$CH_2O$—" is intended to also recite "—$OCH_2$—".

The term "alkyl," by itself or as part of another substituent, means, unless otherwise stated, a straight or branched chain hydrocarbon radical, which can be fully saturated, mono- or polyunsaturated and can include di- and multivalent radicals, having the number of carbon atoms designated (i.e. $C_1$-$C_{10}$ means one to ten carbon atoms). Examples of saturated hydrocarbon radicals include, but are not limited to, groups such as methyl, ethyl, n-propyl, iso-propyl, n-butyl, tert-butyl, iso-butyl, sec-butyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Typically, an alkyl group will have from 1 to 24 carbon atoms, with those groups having from 1 to 10 carbon atoms, from 1 to 8 carbon atoms or from 1 to 4 carbon atoms being preferred. A "lower alkyl" group is an alkyl group having from 1 to 4 carbon atoms. The term "alkyl" includes "alkylene" wherever appropriate, e.g., when the formula indicates that the alkyl group is divalent or when substituents are joined to form a ring.

The term "alkylene" by itself or as part of another substituent means a divalent radical derived from an alkane, as exemplified, but not limited, by —$CH_2CH_2CH_2CH_2$—. Typically, an alkyl (or alkylene) group will have from 1 to 24 carbon atoms, with those groups having 10 or fewer carbon atoms (e.g., 1 to 8 carbon atoms) being preferred in the present invention. A "lower alkylene" is an alkylene group, generally having from 1 to 4 carbon atoms.

The term "alkenyl" by itself or as part of another substituent is used in its conventional sense, and refers to a radical derived from an alkene, as exemplified, but not limited, by substituted or unsubstituted vinyl and substituted or unsubstituted propenyl. Typically, an alkenyl group will have from 1 to 24 carbon atoms, with those groups having from 1 to 10 carbon atoms being preferred.

The term "alkynyl" by itself or as part of another substituent is used in its conventional sense, and refers to a radical derived from an alkyne, as exemplified, but not limited, by substituted or unsubstituted prop-1-ynyl, prop-2-ynyl (i.e., propargyl), and substituted or unsubstituted ethynyl. Typically, an alkynyl group will have from 1 to 24 carbon atoms, with those groups having from 1 to 10 carbon atoms being preferred.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si, S, B and P and wherein the nitrogen and sulfur atoms can optionally be oxidized and the nitrogen atom can optionally be quaternized. The heteroatom(s) can be placed at any interior position of the heteroalkyl group or at the position at which the alkyl group is attached to the remainder of the molecule. Examples of heteroalkyl groups include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms can be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —$CO_2R'$ represents both —C(O)OR' and —OC(O)R'. Typically, a heteroalkyl group will have from 2 to 24 atoms (2- to 24-membered), with those groups having from 2 to 10 atoms or from 2 to 8 atoms being preferred. The term "heteroalkyl" includes "heteroalkylene" wherever appropriate, e.g., when the formula indicates that the heteroalkyl group is divalent or when substituents are joined to form a ring.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. A "cycloalkyl" or "heterocycloalkyl" substituent can be attached to the remainder of the molecule directly or through a linker. An exemplary linker is alkylene. Examples of cycloalkyl include, but are not limited to, cyclopentyl, cyclohexyl, 1-cyclohexenyl, 3-cyclohexenyl, cycloheptyl, and the like. The term "cycloalkyl" also includes bridged, polycyclic (e.g., bicyclic) structures, such as norbornane and adamantane. Typically, a cycloalkyl group will have from 3 to 24 carbon atoms, with those groups having from 3 to 10 carbon atoms (e.g., $C_3$-$C_8$ cycloalkyl) being preferred.

In one example, a "heterocycloalkyl" group (also referred to as "heterocyclic group", "heterocycle", or "heterocyclyl") is a carbocyclic ring (e.g., 3- to 8-membered ring) containing at least one and up to 5 heteroatoms (e.g., from 1 to 4 heteroatoms selected from nitrogen, oxygen and sulfur), or a fused ring system of 4- to 8-membered rings, containing at least one and up to 10 heteroatoms (e.g., from 1 to 5 heteroatoms selected from nitrogen, oxygen and sulfur) in stable combinations known to those of skill in the art. Attachment to the remainder of the molecule can be through either a carbon atom or a heteroatom. Exemplary heterocycloalkyl or heterocyclic groups of the present invention include morpholinyl, thiomorpholinyl, thiomorpholinyl S-oxide, thiomorpholinyl S,S-dioxide, piperazinyl, homopiperazinyl, pyrrolidinyl, pyrrolinyl, imidazolidinyl, tetrahydropyranyl, piperidinyl, tetrahydrofuranyl, tetrahydrothienyl, piperidinyl, homopiperidinyl, homomorpholinyl, homothiomorpholinyl, homothiomorpholinyl S,S-dioxide, oxazolidinonyl, dihydropyrazolyl, dihydropyrrolyl, dihydropyrazolyl, dihydropyridyl, dihydropyrimidinyl, dihydrofuryl, dihydropyranyl, tetrahydrothienyl S-oxide, tetrahydrothienyl S,S-dioxide and homothiomorpholinyl S-oxide. Other examples of "heterocycloalkyl" include but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic moiety that can be a single ring or a combination of multiple rings (e.g., from 1 to 3 rings), which are fused together or linked covalently and wherein at least one ring is aromatic. Non-limiting examples of aryl groups include phenyl, 1-naphthyl, 2-naphthyl, 4-biphenyl.

The term "heteroaryl" refers to aromatic moieties (e.g., a single ring or combination of multiple rings, fused or linked covalently) that contain from one to ten (preferably 1 to 5) heteroatoms selected from N, O, S, Si and B (preferably N, O and S), wherein the nitrogen and sulfur atoms are optionally oxidized, and the nitrogen atom(s) are optionally quaternized. A heteroaryl group can be attached to the remainder of the molecule through a carbon- or heteroatom. Non-limiting examples of heteroaryl groups include pyridyl, pyrimidinyl, quinolinyl, benzothienyl, indolyl, indolinyl, pyridazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzothiazolyl, benzimidazolyl, benzofuranyl, furanyl, thienyl, pyrrolyl, oxadiazolyl, thiadiazolyl, triazolyl, tetrazolyl, isothiazolyl, naphthyridinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridyl, benzotetrahydrofuranyl, benzotetrahydrothienyl, purinyl, benzodioxolyl, triazinyl, pteridinyl, benzothiazolyl, imidazopyridyl, imidazothiazolyl, dihydrobenzisoxazinyl, benzisoxazinyl, benzoxazinyl, dihydrobenzisothiazinyl, benzopyranyl, benzothiopyranyl, chromonyl, chromanonyl, pyridyl-N-oxide, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, benzothiopyranyl S,S-dioxide. Preferred heteroaryl groups include imidazolyl, pyrazolyl, thiadiazolyl, triazolyl, isoxazolyl, isothiazolyl, imidazolyl, thiazolyl, oxadiazolyl, and pyridyl. Other exemplary heteroaryl groups include 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable aryl group substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group or heteroaryl group is attached to an alkyl group (e.g., benzyl, phenethyl, pyridylmethyl and the like).

Each of the above terms (e.g., "alkyl", "cycloalkyl", "heteroalkyl", heterocycloalkyl", "aryl" and "heteroaryl") are meant to include both substituted and unsubstituted forms of the indicated radical. Preferred substituents for each type of radical are provided below.

Substituents for the alkyl, cycloalkyl, heteroalkyl and heterocycloalkyl radicals (including those groups often referred to as alkylene, alkenyl, heteroalkylene, heteroalkenyl, alkynyl, cycloalkenyl, and heterocycloalkenyl) are generically referred to as "alkyl group substituents," and they can be one or more of a variety of groups selected from, but not limited to, substituted or unsubstituted heteroalkyl, substituted or unsubstituted aryl, substituted or unsubstituted heteroaryl, substituted or unsubstituted cycloalkyl, substituted or unsubstituted heterocycloalkyl, —OR', —SR', =O, =NR', =N—OR', —NR'R", -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NRSO$_2$R', —N(SO$_2$R')(SO$_2$R'), —CN and —NO$_2$ in a number ranging from zero to (2 m'+1), where m' is the total number of carbon atoms in such radical. R', R", R''' and R'''' each independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R''' and R'''' groups when more than one of these groups is present. When R' and R" are attached to the same nitrogen atom, they can be combined with the nitrogen atom to form a 5-, 6-, or 7-membered ring. For example, —NR'R" is meant to include 1-pyrrolidinyl and 4-morpholinyl.

Substituents for the aryl and heteroaryl groups are generically referred to as "aryl group substituents." The substituents are selected from, for example, substituted or unsubstituted alkyl, substituted or unsubstituted cycloalkyl, substituted or unsubstituted heteroalkyl, substituted or unsubstituted heterocycloalkyl, substituted or unsubstituted aryl, substituted or unsubstituted heteroaryl, —OR', =O, =NR', =N—OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system, wherein R', R'', R''' and R'''' are independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R'', R''' and R'''' when more than one of these groups is present.

Two hydrogen atoms on adjacent atoms of the aryl or heteroaryl ring can optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the hydrogen atoms on adjacent atoms of the aryl or heteroaryl ring can optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the ring so formed can optionally be replaced with a double bond. Alternatively, two of the hydrogen atoms on adjacent atoms of the aryl or heteroaryl ring can optionally be replaced with a substituent of the formula —(CRR')$_s$—X—(CR''R''')$_d$—, where s and d are independently integers of from 0 to 3, and X is —O—, —NR'—, —S—, —S(O)—, —S(O)$_2$—, or —S(O)$_2$NR'—, wherein the substituents R, R', R'' and R''' are independently selected from hydrogen and substituted or unsubstituted (C$_1$-C$_6$)alkyl.

As used herein, the term "acyl" describes the group —C(O)R. Exemplary species for R include substituted or unsubstituted alkyl, substituted or unsubstituted cycloalkyl, substituted or unsubstituted aryl, substituted or unsubstituted heteroaryl, and substituted or unsubstituted heterocycloalkyl.

As used herein, the term "fused ring system" means at least two rings, wherein each ring has at least 2 atoms in common with another ring. "Fused ring systems can include aromatic as well as non aromatic rings. Examples of "fused ring systems" are naphthalenes, indoles, quinolines, chromenes and the like.

As used herein, the term "heteroatom" includes oxygen (O), nitrogen (N), sulfur (S), silicon (Si), boron (B) and phosphorus (P). Preferred heteroatoms are O, S and N.

The symbol "R" is a general abbreviation that represents a substituent group. Exemplary substituent groups include substituted or unsubstituted alkyl, substituted or unsubstituted cycloalkyl, substituted or unsubstituted heteroalkyl, substituted or unsubstituted aryl, substituted or unsubstituted heteroaryl, and substituted or unsubstituted heterocycloalkyl groups.

As used herein, the term "aromatic ring" or "non-aromatic ring" is consistent with the definition commonly used in the art. For example, aromatic rings include phenyl and pyridyl. Non-aromatic rings include cyclohexanes.

The phrase "therapeutically effective amount" as used herein means that amount of a compound, material, or composition of the present invention, which is effective for producing a desired therapeutic effect, at a reasonable benefit/risk ratio applicable to any medical treatment. For example, a "therapeutically effective amount" can be an amount effective to reduce or lessen at least one symptom of the disease or condition being treated or to reduce or delay onset of one or more clinical markers or symptoms associated with the disease or condition, or to modify or reverse the disease process.

The terms "treatment" or "treating" when referring to a disease or condition, includes producing a therapeutic effect. Exemplary therapeutic effects include delaying onset or reducing at least one symptom associated with the disease, positively affecting (e.g., reducing or delaying onset) of a clinical marker associated with the disease and slowing or reversing disease progression.

The term "pharmaceutically acceptable salts" includes salts of the compounds of the invention, which are prepared with nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, magnesium salts and the like. When compounds of the present invention contain relatively basic functionalities (e.g., amines), acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, diphosphoric, monohydrogenphosphoric, dihydrogenphosphoric, sulfuric, monohydrogensulfuric, hydriodic and the like, as well as the salts derived from relatively nontoxic organic acids like formic, acetic, propionic, isobutyric, malic, maleic, malonic, benzoic, succinic, suberic, fumaric, lactic, mandelic, phthalic, benzenesulfonic, p-tolylsulfonic, citric, tartaric, methanesulfonic, 2-hydroxyethylsulfonic, salicylic, stearic and the like. Also included are salts of amino acids such as arginate and the like, and salts of organic acids like glucuronic or galactunoric acids and the like (see, for example, Berge et al., *Journal of Pharmaceutical Science*, 1977, 66: 1-19). Similarly, pharmaceutically acceptable cations include, but are not limited to sodium, potassium, calcium, aluminum, lithium and ammonium. Certain specific compounds of the present invention contain both basic and acidic functionalities that allow the compounds to be converted into either base or acid addition salts.

When a residue is defined as "O$^-$", e.g., in "—COO$^-$", then the formula is meant to optionally include an organic or inorganic cationic counterion. In one example, the resulting salt form of the compound is pharmaceutically acceptable. Further, when a compound of the invention includes an acidic group, such as a carboxylic acid group, e.g., written as the substituent "—COOH", "—CO$_2$H" or "—C(O)$_2$H", then the formula is meant to optionally include the corresponding "de-protonated" form of that acidic group, e.g., "—COO$^-$", "—CO$_2$$^-$" or "—C(O)$_2$$^-$", respectively.

The neutral forms of the compounds can be regenerated, for example, by contacting the salt with a base or acid and isolating the parent compound in the conventional manner. The parent form of the compound can differ from the various salt forms in certain physical properties, such as solubility in polar solvents, but otherwise the salts are equivalent to the parent form of the compound for the purposes of the present invention.

In addition to salt forms, the present invention provides compounds, which are in a prodrug form. Prodrugs of the compounds described herein are those compounds that readily undergo chemical changes under physiological conditions to provide the compounds of the present invention. Non-limiting examples of "pharmaceutically acceptable derivative" or "prodrug" include pharmaceutically acceptable esters, phosphate esters, sulfonate esters or salts thereof as well as other derivatives of a compound of this invention which, upon administration to a recipient, is capable of providing, either directly or indirectly, a compound of this invention. Particularly favored derivatives or prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or lymphatic system) relative to the parent species.

Prodrugs include a variety of esters (i.e., carboxylic acid ester). Ester groups, which are suitable as prodrug groups are generally known in the art and include benzyloxy, di($C_1$-$C_6$) alkylaminoethyloxy, acetoxymethyl, pivaloyloxymethyl, phthalidoyl, ethoxycarbonyloxyethyl, 5-methyl-2-oxo-1,3-dioxol-4-yl methyl, and ($C_1$-$C_6$)alkoxy esters, optionally substituted by N-morpholino and amide-forming groups such as di($C_1$-$C_6$)alkylamino. Preferred ester prodrug groups include $C_1$-$C_6$ alkoxy esters. Those skilled in the art will recognize various synthetic methodologies that may be employed to form pharmaceutically acceptable prodrugs of the compounds of the invention (e.g., via esterification of a carboxylic acid group).

In an exemplary embodiment, the prodrug is suitable for treatment/prevention of those diseases and conditions that require the drug molecule to cross the blood brain barrier. In a preferred embodiment, the prodrug enters the brain, where it is converted into the active form of the drug molecule. In another example, a prodrug is used to enable an active drug molecule to reach the inside of the eye after topical application of the prodrug to the eye. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention can exist in multiple crystalline or amorphous forms ("polymorphs"). In general, all physical forms are of use in the methods contemplated by the present invention and are intended to be within the scope of the present invention. "Compound or a pharmaceutically acceptable salt, hydrate, polymorph or solvate of a compound" intends the inclusive meaning of "or", in that materials meeting more than one of the stated criteria are included, e.g., a material that is both a salt and a solvate is encompassed.

The compounds of the present invention can contain unnatural proportions of atomic isotopes at one or more of the atoms that constitute such compounds. For example, the compounds can be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are intended to be encompassed within the scope of the present invention.

The term "solvate" is intended to refer to a complex formed by combination of solute molecules or ions with solvent molecules. The solvent can be an organic compound, an inorganic compound, or a mixture of both. Exemplary solvents for the formation of solvates include, but are not limited to, methanol, N,N-dimethylformamide, tetrahydrofuran, dimethylsulfoxide, toluene, and water. In one embodiment, solvents having a higher boiling point, such as for example, DMF, DMA, and the like.

Compositions Including Stereoisomers

Compounds of the invention can exist in particular geometric or stereoisomeric forms. The invention contemplates all such compounds, including cis- and trans-isomers, (−)- and (+)-enantiomers, diastereomers, (D)-isomers, (L)-isomers, the racemic mixtures thereof, and other mixtures thereof, such as enantiomerically or diastereomerically enriched mixtures, as falling within the scope of the invention. Additional asymmetric carbon atoms can be present in a substituent such as an alkyl group. All such isomers, as well as mixtures thereof, are intended to be included in this invention. When the compounds described herein contain olefinic double bonds or other centers of geometric asymmetry, and unless specified otherwise, it is intended that the compounds include both E and Z geometric isomers. Likewise, all tautomeric forms and mixtures of tautomers are included.

Optically active (R)- and (S)-isomers and d and l isomers can be prepared using chiral synthons or chiral reagents, or resolved using conventional techniques. Resolution of the racemates can be accomplished, for example, by conventional methods such as crystallization in the presence of a resolving agent; chromatography, using, for example a chiral HPLC column; or derivatizing the racemic mixture with a resolving reagent to generate diastereomers, separating the diastereomers via chromatography, and removing the resolving agent to generate the original compound in enantiomerically enriched form. Any of the above procedures can be repeated to increase the enantiomeric purity of a compound. If, for instance, a particular enantiomer of a compound of the present invention is desired, it can be prepared by asymmetric synthesis, or by derivatization with a chiral auxiliary, where the resulting diastereomeric mixture is separated and the auxiliary group cleaved to provide the pure desired enantiomers. Alternatively, where the molecule contains a basic functional group, such as an amino group, or an acidic functional group, such as a carboxyl group, diastereomeric salts can be formed with an appropriate optically active acid or base, followed by resolution of the diastereomers thus formed by fractional crystallization or chromatographic means known in the art, and subsequent recovery of the pure enantiomers. In addition, separation of enantiomers and diastereomers is frequently accomplished using chromatography employing chiral, stationary phases, optionally in combination with chemical derivatization (e.g., formation of carbamates from amines).

As used herein, the term "chiral", "enantiomerically enriched" or "diastereomerically enriched" refers to a compound having an enantiomeric excess (ee) or a diastereomeric excess (de) of greater than about 50%, preferably greater than about 70% and more preferably greater than about 90%. In general, higher than about 90% enantiomeric or diastereomeric excess is particularly preferred, e.g., those compositions with greater than about 95%, greater than about 97% and greater than about 99% ee or de.

The terms "enantiomeric excess" and "diastereomeric excess" are used interchangeably herein. Compounds with a single stereocenter are referred to as being present in "enantiomeric excess", those with at least two stereocenters are referred to as being present in "diastereomeric excess".

The term "enantiomeric excess" is related to the older term "optical purity" in that both are measures of the same phenomenon. The value of ee will be a number from 0 to 100, zero being racemic and 100 being enantiomerically pure. A compound which in the past might have been called 98% optically pure is now more precisely characterized by 96% ee. A 90% ee reflects the presence of 95% of one enantiomer and 5% of the other(s) in the material in question.

Hence, in one embodiment, the invention provides a composition including a first stereoisomer and at least one additional stereoisomer of a compound of the invention. The first stereoisomer can be present in a diastereomeric or enantiomeric excess of at least about 80%, preferably at least about 90% and more preferably at least about 95%. In a particularly preferred embodiment, the first stereoisomer is present in a diastereomeric or enantiomeric excess of at least about 96%, at least about 97%, at least about 98%, at least about 99% or at least about 99.5%. In another embodiment, the compound of the invention is enantiomerically or diastereomerically pure (diastereomeric or enantiomeric excess is about 100%). Enantiomeric or diastereomeric excess can be determined relative to exactly one other stereoisomer, or can be determined relative to the sum of at least two other stereoisomers. In an exemplary embodiment, enantiomeric or diastereomeric excess is determined relative to all other detectable stereoisomers, which are present in the mixture. Stereoisomers are detectable if a concentration of such stereoisomer in the analyzed mixture can be determined using common analytical methods, such as chiral HPLC.

Integrins are a large family of homologous transmembrane linker proteins that are the principal receptors on animal cells for binding most extracellular matrix proteins, such as collagen, fibronectin, and laminin The integrins are heterodimers comprised of an α chain and a β chain. To date, twenty different integrin heterodimers, made from 9 different α subunits and 14 different β subunits, have been identified. The term "α4 integrins" refers to the class of heterodimer, enzyme-linked cell-surface receptors that contain the α4 subunit paired with any of the β subunits. VLA-4 is an example of an α4 integrin, and is a heterodimer of the α4 and β1 subunits, and is also referred to as α4β1 integrin.

Compositions

In various aspects, the invention provides a compound having a structure according to Formula (Ia), Formula (Ia'), Formula (Ib) or Formula (Ic):

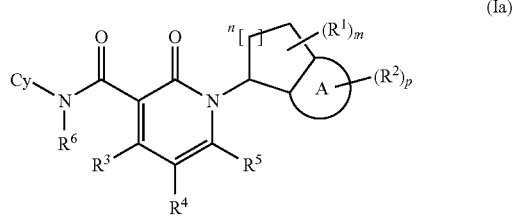
(Ia)

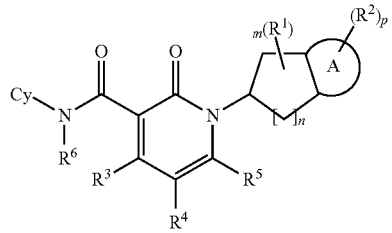
(Ia')

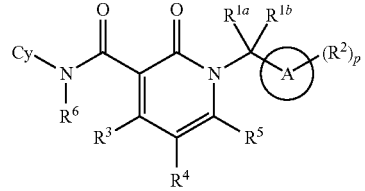
(Ib)

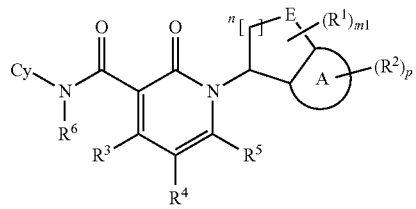
(Ic)

or a salt or solvate thereof, wherein m is an integer selected from 0 to 4, n is an integer selected from 0 to 4, p is an integer selected from 0 to 6 and m1 is an integer selected from 0 to 3. In one example, n is selected from 1 to 4. In another example, n is selected from 1 and 2. In yet another example, n is 1. In a further example, m is 0 or 1. In another example, p is 0 or 1.

In Formula (Ia), Formula (Ia'), Formula (Ib) or Formula (Ic), ring A is a member selected from substituted or unsubstituted aryl (e.g., phenyl, naphthyl) and substituted or unsubstituted heteroaryl (e.g., pyridyl, thiophene, thiazole, imidazolyl).

In Formula (Ia), Formula (Ia'), Formula (Ib) or Formula (Ic), Cy is a member selected from substituted or unsubstituted cycloalkyl (e.g., $C_3$-$C_{10}$ cycloalkyl), substituted or unsubstituted heterocycloalkyl (e.g., 3- to 10-membered heterocycloalkyl), substituted or unsubstituted aryl (e.g., phenyl or naphthyl) and substituted or unsubstituted heteroaryl (e.g., pyridyl). In one example in the above structures, Cy is substituted or unsubstituted aryl (e.g., phenyl or naphthyl) or substituted or unsubstituted heteroaryl (e.g., pyridyl). In a particular example, Cy in the above structures is a member selected from substituted or unsubstituted phenyl (e.g., substituted or unsubstituted 4-chloro-phenyl or substituted or unsubstituted 4-phenoxyphenyl), substituted or unsubstituted naphthyl, substituted or unsubstituted biphenyl (e.g., substituted or unsubstituted biphenyl-4-yl) and substituted or unsubstituted pyridyl (e.g., substituted or unsubstituted 4-pyridyl).

In Formula (Ia), Formula (Ia'), Formula (Ib) or Formula (Ic), each $R^1$, each $R^2$, $R^{1a}$ and $R^{1b}$ are members independently selected from H, substituted or unsubstituted alkyl (e.g., $C_1$-$C_{10}$ alkyl), substituted or unsubstituted heteroalkyl (e.g., 2- to 10-membered heteroalkyl), substituted or unsubstituted cycloalkyl (e.g., $C_3$-$C_{10}$ cycloalkyl), substituted or unsubstituted heterocycloalkyl (e.g., 3- to 10-membered heterocycloalkyl), substituted or unsubstituted aryl (e.g., substituted or unsubstituted phenyl or naphthyl), substituted or unsubstituted heteroaryl (e.g., substituted or unsubstituted pyridyl), nitro, CN, halogen (e.g., I, F, Cl or Br), $OR^{12}$, $SR^{12}$, $NR^{12}R^{13}$, $C(O)R^{14}$, $C(O)NR^{12}R^{13}$, $OC(O)NR^{12}R^{13}$, $C(O)OR^{12}$, $NR^{15}C(O)R^{14}$, $NR^{15}$, $C(O)OR^{12}$, $NR^{15}C(O)NR^{12}R^{13}$, $NR^{15}C(S)NR^{12}R^{13}$, $NR^{15}S(O)_2R^{14}$, $S(O)_2NR^{12}R^{13}$ and $S(O)_zR^{14}$, wherein z is 1 or 2. $R^{12}$, $R^{13}$ and $R^{15}$ are members independently selected from H, acyl, substituted or unsubstituted alkyl (e.g., $C_1$-$C_{10}$ alkyl), substituted or unsubstituted heteroalkyl (e.g., 2- to 10-membered heteroalkyl), substituted or unsubstituted aryl, substituted or unsubstituted heteroaryl, substituted or unsubstituted cycloalkyl (e.g., $C_3$-$C_{10}$ cycloalkyl) and substituted or unsubstituted heterocycloalkyl (e.g., 3- to 10-membered heterocycloalkyl). $R^{14}$ is a member independently selected from substituted or unsubstituted alkyl (e.g., $C_1$-$C_{10}$ alkyl), substituted or unsubstituted heteroalkyl (e.g., 2- to 10-membered heteroalkyl), substituted or unsubstituted aryl, substituted or unsubstituted heteroaryl, substituted or unsubstituted cycloalkyl (e.g., $C_3$-$C_{10}$ cycloalkyl) and substituted or unsubstituted heterocycloalkyl (e.g., 3- to 10-membered heterocycloalkyl). $R^{12}$ and $R^{13}$, together with the nitrogen atoms to which they are attached, are optionally joined to form a 4- to 7-membered ring. Two adjacent $R^1$, together with the atoms to which they are attached, are optionally joined to form a 5- to 7-membered ring. Two adjacent $R^2$, together with the atoms to which they are attached, are optionally joined to form a 5- to 7-membered ring.

In Formula (Ia), Formula (Ia'), Formula (Ib) or Formula (Ic), $R^3$, $R^4$ and $R^5$ are members independently selected from H, substituted or unsubstituted alkyl (e.g., $C_1$-$C_4$ alkyl), halogen (e.g., I, F, Cl, Br), substituted or unsubstituted aryl, —O-aryl, and CN. In a particular example in the above structures, $R^3$, $R^4$ and $R^5$ are each H.

In Formula (Ia), Formula (Ia'), Formula (Ib) or Formula (Ic), $R^6$ is a member selected from H, substituted or unsubstituted alkyl (e.g., $C_1$-$C_6$ alkyl), substituted or unsubstituted heteroalkyl (e.g., 2- to 6-membered heteroalkyl), substituted or unsubstituted cycloalkyl (e.g., $C_3$-$C_8$ cycloalkyl), substituted or unsubstituted heterocycloalkyl (e.g., 3- to 8-membered heterocycloalkyl), substituted or unsubstituted aryl (e.g., substituted or unsubstituted phenyl), substituted or unsubstituted heteroaryl (e.g., substituted or unsubstituted pyridyl), $NR^{12}R^{13}$, $C(O)R^{14}$, $C(O)NR^{12}R^{13}$, $C(O)OR^{12}$ and $S(O)_zR^{14}$, wherein z is 1 or 2 and $R^{12}$, $R^{13}$ and $R^{14}$ are defined as herein above. In one example, $R^6$ is a member selected from H and substituted or unsubstituted alkyl (e.g., $C_1$-$C_4$ alkyl). In a particular example in the above structures, $R^6$ is H.

In Formula (Ic), E is selected from O, S, C(O), $S(O)_2$ and $NR^{40}$, wherein $R^{40}$ is a member selected from substituted or unsubstituted alkyl (e.g., $C_1$-$C_{10}$ alkyl). In one example, $R^{40}$ is unsubstituted $C_1$-$C_4$ alkyl (e.g., methyl or ethyl).

In one example, in Formula (Ia) or (Ia'), n is 1 and $R^3$, $R^4$, $R^5$ and $R^6$ are each H. In another example, in Formula (Ib), $R^3$, $R^4$, $R^5$ and $R^6$ are each H. Hence, an exemplary compound of the invention has a structure according to Formula (IIa), Formula (IIa'), or Formula (IIb):

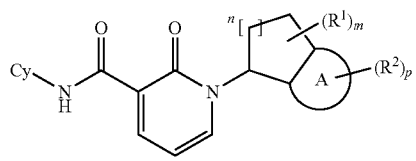

(IIa)

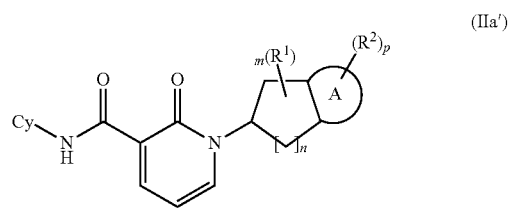

(IIa')

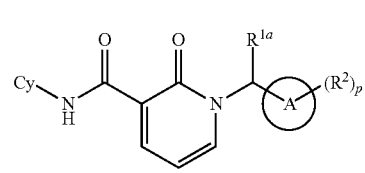

(IIb)

wherein m, p, Cy, ring A, $R^1$, $R^{1a}$, $R^2$ and $R^6$ are defined as for Formula (Ia), Formula (Ia'), and Formula (Ib), above. In one example, in Formula (IIa), Formula (IIa') or Formula (IIb), ring A is substituted or unsubstituted phenyl or substituted or unsubstituted thiophene. In another example, in Formula (IIa), Formula (IIa') or Formula (IIb), Cy is a member selected from substituted or unsubstituted aryl (e.g., phenyl or naphthyl) and substituted or unsubstituted heteroaryl (e.g., pyridyl).

Ring A

In one example, in Formula (Ia), Formula (Ia'), Formula (Ib), Formula (IIa), Formula (IIa'), or Formula (IIb), ring A is a 5- or 6-membered aromatic or heteroaromatic ring. Exemplary rings for A include phenyl, pyridine, thiophene, thiazole and oxazole. In another example, A is phenyl or thiophene and the compound of the invention has a structure according to Formula (IIIa), Formula (IIIa'), or Formula (IIIb):

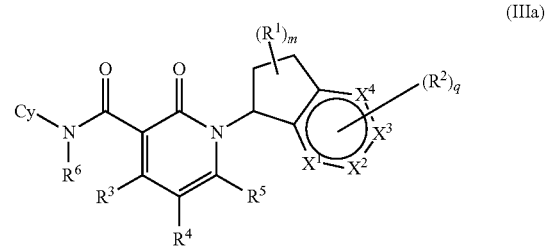

(IIIa)

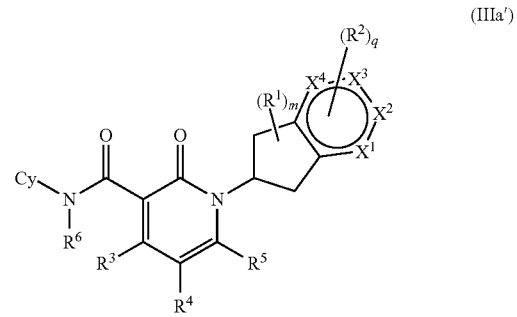

(IIIa')

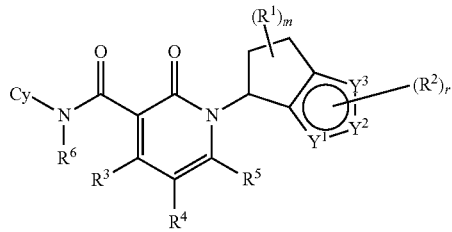

(IIIb)

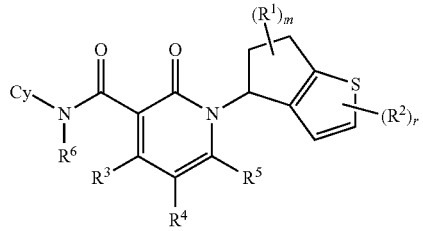

(VI)

or a salt or solvate thereof, wherein m, Cy, $R^1$, $R^2$, $R^3$, $R^4$, $R^5$ and $R^6$ are defined as above. The integer q is selected from 0 to 4. The integer r is selected from 0 to 2. In one example, in the above formulae, each of $R^3$, $R^4$, $R^5$ and $R^6$ is H.

In Formula (IIIa) or (IIIa'), $X^1$, $X^2$, $X^3$ and $X^4$ are members independently selected from N and $CR^2$, wherein each $R^2$ is independently defined as above.

In Formula (IIIb), $Y^1$, $Y^2$ and $Y^3$ are members independently selected from S, O, N, $NR^{2a}$ and $CR^2$, with the proviso that at least one of $Y^1$, $Y^2$ and $Y^3$ is other than $CR^2$. Each $R^2$ is defined as hereinabove. $R^{2a}$ is a member selected from H, substituted or unsubstituted alkyl (e.g., substituted or unsubstituted $C_1$-$C_8$ alkyl), substituted or unsubstituted heteroalkyl (e.g., substituted or unsubstituted 2- to 8-membered heteroalkyl), substituted or unsubstituted cycloalkyl (e.g., substituted or unsubstituted $C_3$-$C_8$ cycloalkyl), substituted or unsubstituted heterocycloalkyl (e.g., substituted or unsubstituted 3- to 8-membered heterocycloalkyl), substituted or unsubstituted aryl, and substituted or unsubstituted heteroaryl. In one example, $R^{ea}$ is selected from H and substituted or unsubstituted $C_1$-$C_6$ alkyl (e.g., methyl or ethyl).

In a further example, the compounds of the invention have a structure according to Formula (IV), Formula (V) or Formula (VI):

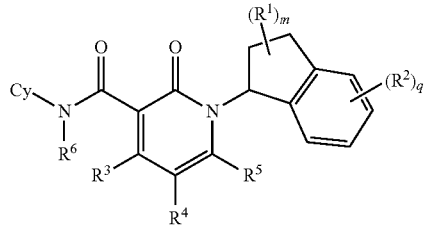

(IV)

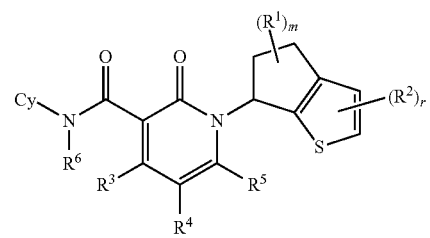

(V)

or a tautomer, salt or solvate thereof, wherein m, Cy, $R^1$, $R^2$, $R^3$, $R^4$, $R^5$ and $R^6$ are defined as above. The integer q is selected from 0 to 4. The integer r is selected from 0 to 2.

In one example according to any of the above embodiments, $R^6$ is H.

Unexpectedly, the inventors have discovered that in vitro biological activity is generally higher, when the pyridinone (pyridone) ring is unsubstituted or substituted with a small substituent, such as F. Hence, in another example according to any of the above embodiments, each of $R^3$, $R^4$ and $R^5$ is independently selected from H, halogen (e.g., F, Cl), CN and $C_1$-$C_3$ alkyl. Preferably, each of $R^3$, $R^4$ and $R^5$ is independently selected from H and F. In a further example, each of $R^3$, $R^4$ and $R^5$ is H. In yet another example, each of $R^3$, $R^4$, $R^5$ and $R^6$ is H and the compound of the invention has a structure according to Formula (IVa), Formula (Va), or Formula (VIa):

(IVa)

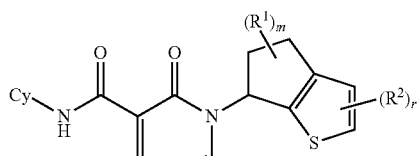

(Va)

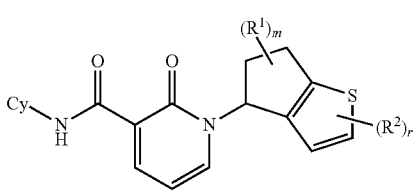

(VIa)

or a tautomer, salt or solvate thereof, wherein m, Cy, $R^1$, $R^2$ are defined as above. The integer q is selected from 0 to 4. The integer r is selected from 0 to 2.

In one example, the compound of the invention has a structure according to Formula (IVb) or Formula (IVc):

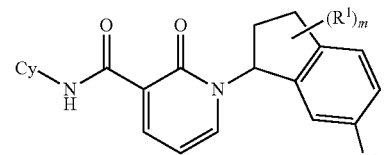

(IVb)

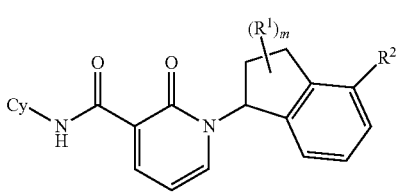

(IVc)

or a salt or solvate thereof, wherein Cy, $R^1$, $R^2$ and m are defined as herein above.

Ring Cy

Cy in any of the above formulae can be a ring or fused ring system. In one embodiment, Cy in any of the above formulae is a member selected from substituted or unsubstituted cycloalkyl (e.g., $C_3$-$C_8$ cycloalkyl), substituted or unsubstituted heterocycloalkyl (e.g., 3- to 8-membered heterocycloalkyl), substituted or unsubstituted aryl and substituted or unsubstituted heteroaryl. In a particular example, Cy is a member selected from substituted or unsubstituted aryl (e.g., phenyl, biphenyl, naphthyl) and substituted or unsubstituted heteroaryl (e.g., pyridyl, quinolinyl, quinazolinyl). In another example, Cy is selected from 6-membered aryl and 6-membered heteroaryl moieties of the formula:

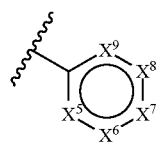

wherein $X^5$, $X^6$, $X^7$, $X^8$ and $X^9$ are members independently selected from N and $CR^{16}$, wherein each $R^{16}$ is independently selected from aryl group substituents. In one example, each $R^{16}$ is a member independently selected from H, substituted or unsubstituted alkyl (e.g., substituted or unsubstituted $C_1$-$C_8$ alkyl), substituted or unsubstituted heteroalkyl (e.g., substituted or unsubstituted 2- to 8-membered heteroalkyl), substituted or unsubstituted cycloalkyl (e.g., substituted or unsubstituted $C_3$-$C_8$ cycloalkyl), substituted or unsubstituted heterocycloalkyl (e.g., substituted or unsubstituted 3- to 8-membered heterocycloalkyl), substituted or unsubstituted aryl, substituted or unsubstituted heteroaryl, halogen, CN, $OR^{17}$, $SR^{17}$, $NR^{17}R^{18}$, $C(O)R^{19}$, $C(O)NR^{17}R^{18}$, $OC(O)NR^{17}R^{18}$, $C(O)OR^{17}$, $NR^{20}C(O)R^{19}$, $NR^{20}C(O)OR^{17}$, $NR^{20}C(O)NR^{17}R^{18}$, $NR^{20}C(S)NR^{17}R^{18}$, $NR^{20}S(O)_2R^{19}$, $S(O)_2NR^{17}R^{18}$ and $S(O)_pR^{19}$, wherein p is 1 or 2.

Each $R^{17}$, each $R^{18}$ and each $R^{20}$ is a member independently selected from H, acyl, substituted or unsubstituted alkyl (e.g., substituted or unsubstituted $C_1$-$C_8$ alkyl), substituted or unsubstituted heteroalkyl (e.g., substituted or unsubstituted 2- to 8-membered heteroalkyl), substituted or unsubstituted cycloalkyl (e.g., substituted or unsubstituted $C_3$-$C_8$ cycloalkyl), substituted or unsubstituted heterocycloalkyl (e.g., substituted or unsubstituted 3- to 8-membered heterocycloalkyl), substituted or unsubstituted aryl, and substituted or unsubstituted heteroaryl. $R^{17}$ and $R^{18}$, together with the nitrogen atom to which they are attached, are optionally joined to form a 5- to 7-membered ring. Each $R^{19}$ is a member independently selected from substituted or unsubstituted alkyl (e.g., substituted or unsubstituted $C_1$-$C_8$ alkyl), substituted or unsubstituted heteroalkyl (e.g., substituted or unsubstituted 2- to 8-membered heteroalkyl), substituted or unsubstituted cycloalkyl (e.g., substituted or unsubstituted $C_3$-$C_8$ cycloalkyl), substituted or unsubstituted heterocycloalkyl (e.g., substituted or unsubstituted 3- to 8-membered heterocycloalkyl), substituted or unsubstituted aryl, and substituted or unsubstituted heteroaryl. Adjacent $R^{16}$, together with the carbon atoms to which they are attached, are optionally joined to form a 5- to 7-membered ring.

In one example, the compound of the invention has a structure according to

Formula (VII):

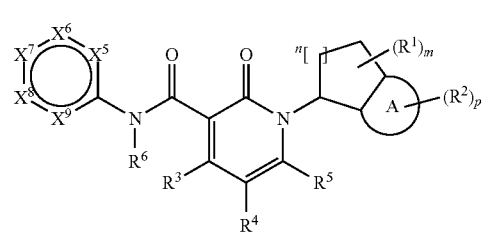

(VII)

wherein m, n, p, A, $R^1$, $R^2$, $R^3$, $R^4$, $R^5$ and $R^6$ are defined as above. $X^5$, $X^6$, $X^7$, $X^8$ and $X^9$ are also defined as herein above.

In one example, the compound of the invention has a structure according to Formula (VIIIa) or Formula (VIIIb):

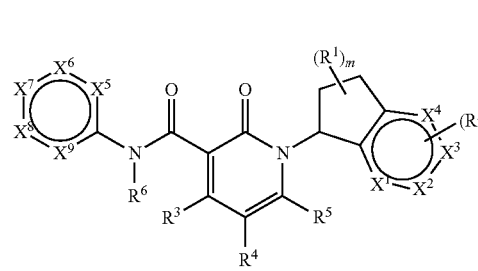

(VIIIa)

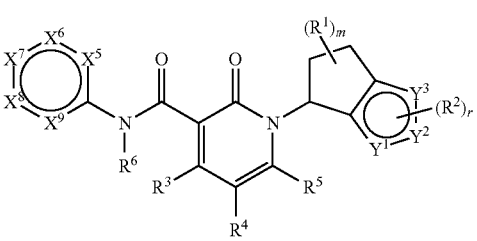

(VIIIb)

wherein m, p, $R^1$, $R^2$, $R^3$, $R^4$, $R^5$ and $R^6$ are defined as above. $Y^1$, $Y^2$, $Y^3$, the integer r, $X^1$, $X^2$, $X^3$, $X^4$, $X^5$, $X^6$, $X^7$, $X^8$ and $X^9$ are defined as herein above.

In a further example, the compounds of the invention have a structure according to Formula (IX), Formula (X) or Formula ($X^1$):

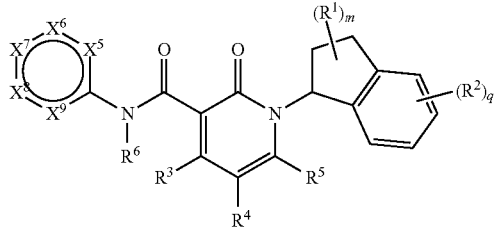
(IX)

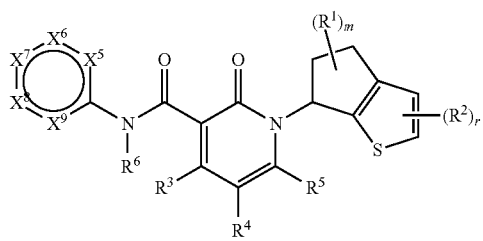
(X)

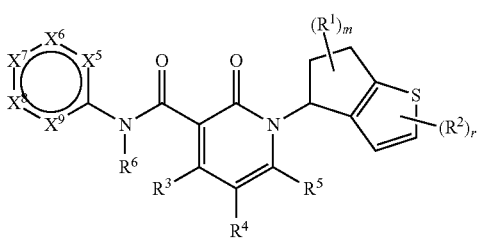
(XI)

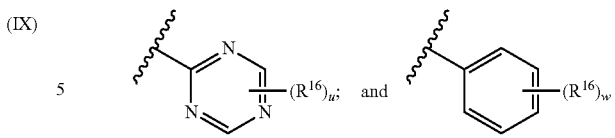

wherein w is an integer selected from 0 to 5, s is an integer selected from 0 to 4, t is an integer selected from 0 to 3 and u is an integer selected from 0 to 2.

In another example, Cy is a fused ring system, which includes at least one of the above rings. In one example, Cy is a member selected from benzo- or pyrido-imidazole, benzo- or pyrido-oxazole, benzo- or pyrido-thiazole, benzo- or pyrido-isoxazole and benzo- or pyrido-isothiazole.

In a further example, Cy in any of the above embodiments is 4-substituted or 3-substituted phenyl or pyridyl. For example, Cy has a structure selected from:

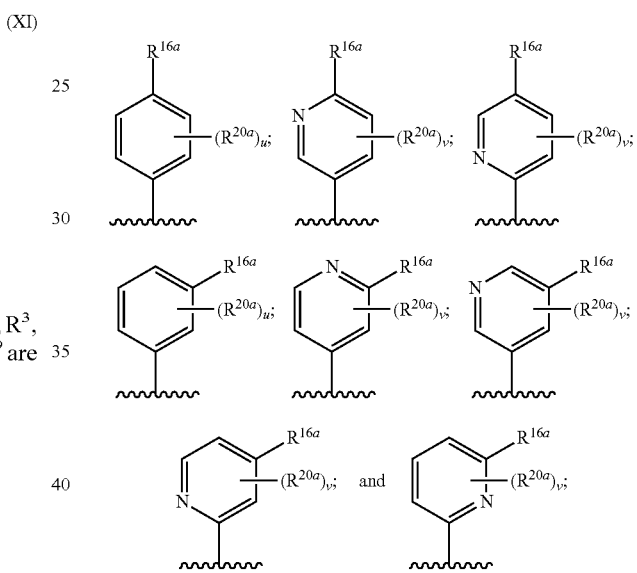

wherein u is an integer selected from 0 to 4 and v is an integer selected from 0 to 3. $R^{16a}$ is defined as $R^{16}$ herein above with the difference that $R^{16a}$ is other than H. In one example, $R^{16a}$ in the above structures is $OR^{17}$, wherein $R^{17}$ is defined as herein above. In one example, $R^{17}$ is a member selected from substituted or unsubstituted alkyl. In a particular example, $R^{16a}$ is a member selected from methoxy and ethoxy. Each $R^{20a}$ in the above structures is independently selected and is defined as $R^{16}$ herein above. In one example, each $R^{20a}$ in the above structures is H.

Other exemplary rings for Cy include:

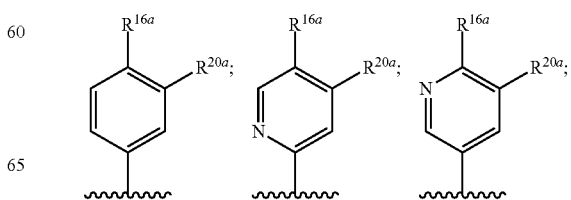

or a tautomer, salt or solvate thereof, wherein m, q, $R^1$, $R^2$, $R^3$, $R^4$, $R^5$ and $R^6$ are defined as above. $X^5$, $X^6$, $X^7$, $X^8$ and $X^9$ are defined as herein above.

In a further embodiment, Cy or the moiety:

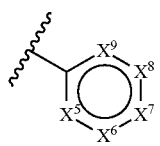

in any of the above formulae is a member selected from:

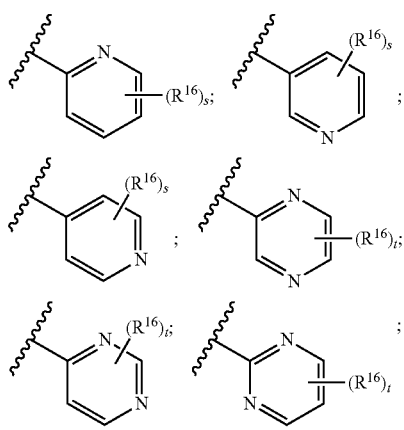

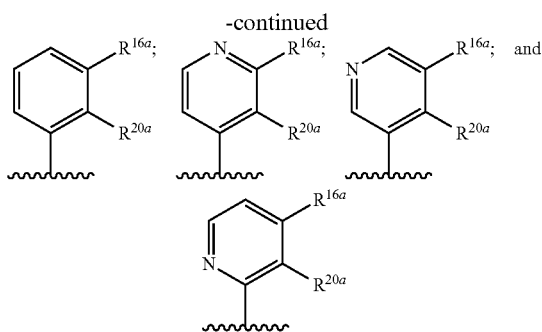

wherein $R^{16a}$ and $R^{20a}$ are defined as herein above, except that both, $R^{16a}$ and $R^{20a}$, are other than H. $R^{16a}$ and $R^{20a}$, together with the atoms to which they are attached, are optionally joined to form a 5- to 7-membered ring.

In a particular example, the compound of the invention has a structure according to Formula (XII):

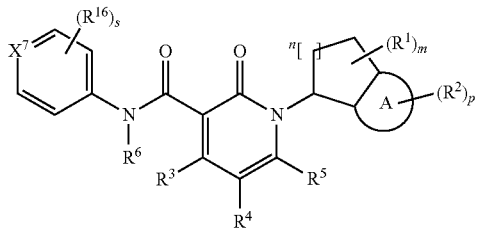

(XII)

or a salt or solvate thereof, wherein ring A, $R^1$, $R^2$, $R^3$, $R^4$, $R^5$, $R^6$, m, n, p, s, $X^7$ and $R^{16}$ are defined as herein above.

In another example, the compound of the invention has a structure according to Formula (XIIa) or Formula (XIIb):

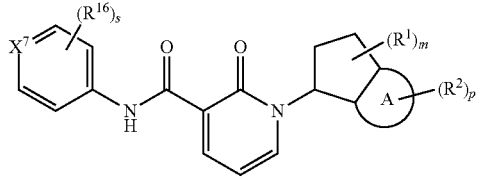

(XIIa)

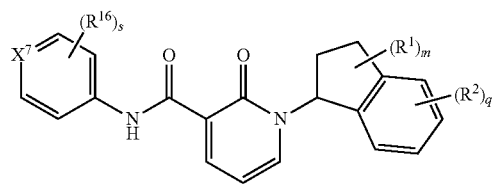

(XIIb)

wherein ring A, $R^1$, $R^2$, m, p, q, s, $X^7$ and $R^{16}$ are defined as herein above. In one example, $X^7$ in the above structures is a member selected from N and $CR^{16a}$, wherein $R^{16a}$ is defined as $R^{16}$ herein above, except that $R^{16a}$ is other than H.

In yet another example according to any of the above embodiments, Cy is substituted or unsubstituted 4-pyridyl or 4-substituted phenyl. Exemplary compounds of the invention have a structure according to Formula (XIIc) or Formula (XIId):

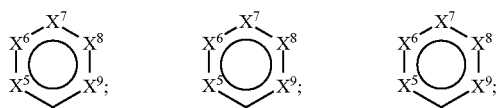

(XIIc)

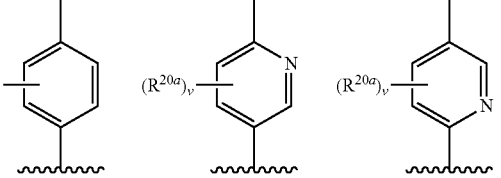

(XIId)

wherein $R^1$, $R^2$, $R^{16a}$, m and q are defined as herein above.

In one example according to any of the above embodiments, $R^{16a}$ is selected from halogen (e.g., F, Cl, Br), halogen substituted lower $C_1$-$C_4$ alkyl (e.g., $CF_3$), lower alkyl (e.g., methyl, ethyl), substituted or unsubstituted aryl (e.g., substituted or unsubstituted phenyl or substituted or unsubstituted pyridyl), substituted or unsubstituted heteroaryl (e.g., furan, thiophene, thiazole), $OR^{17}$, wherein $R^{17}$ is defined as herein above. In a particular example, $R^{17}$ in $OR^{17}$ is selected from $CF_3$, substituted or unsubstituted aryl (e.g., phenyl) and substituted or unsubstituted heteroaryl. In another example, $R^{16a}$ is $NR^{17}R^{18}$, wherein $R^{17}$ and $R^{18}$ are defined as herein above. In one example, in $NR^{17}R^{18}$, $R^{17}$ is H and $R^{18}$ is selected from substituted or unsubstituted phenyl. In another example according to any of the above embodiments, $R^{16a}$ is a member selected from halogen (e.g., F, Cl, Br), substituted or unsubstituted phenyl and substituted or unsubstituted phenyloxy.

In yet another example, Cy is a member selected from:

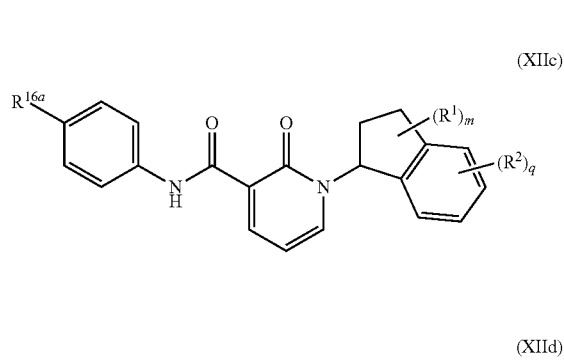

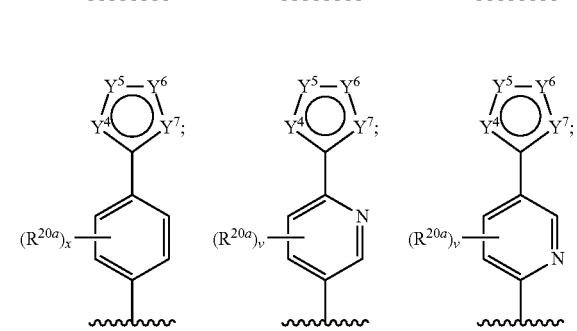

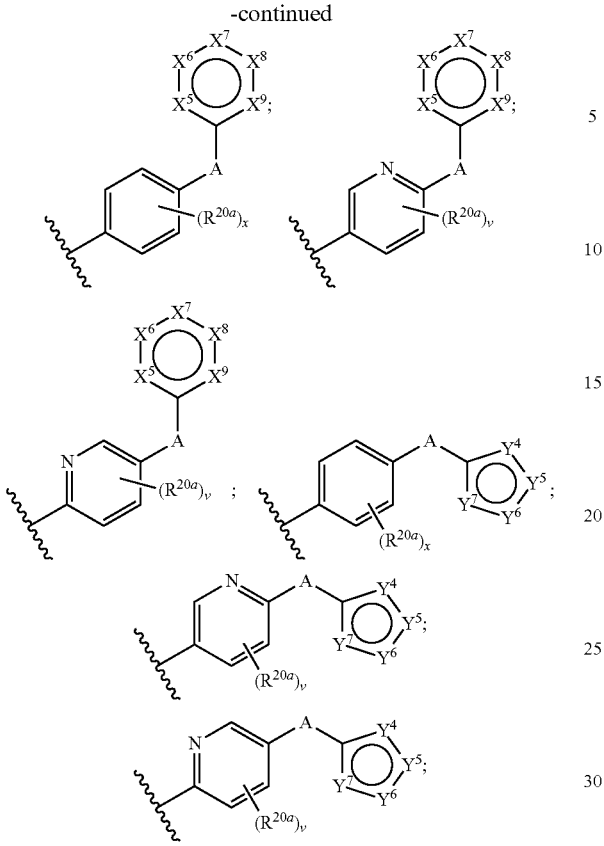

wherein v is an integer selected from 0 to 3 and x is an integer selected from 0 to 4. A is O, S or $NR^{30}$, wherein $R^{30}$ is a member selected from H and $C_1$-$C_4$ alkyl (e.g., methyl). Each $R^{20a}$ in the above structures is independently selected and is defined as herein above. In one example, each $R^{20a}$ in the above structures is H. $X^5$, $X^6$, $X^7$, $X^8$ and $X^9$ are defined as herein above. In one example, $X^6$, $X^7$, $X^8$ and $X^9$ are independently selected from N and CH.

In yet another example, Cy is a member selected from:

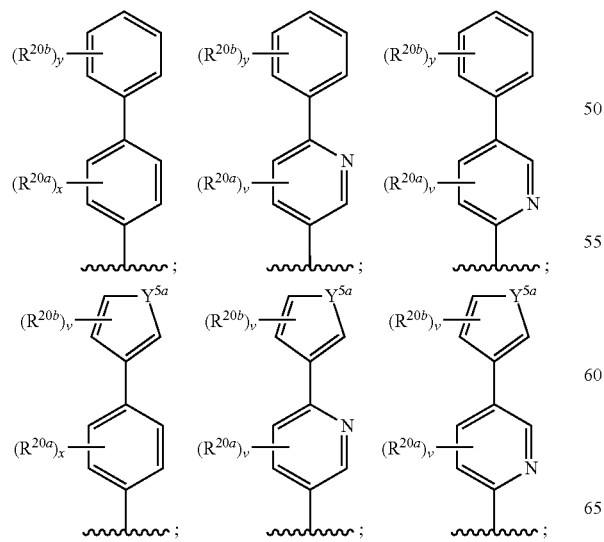

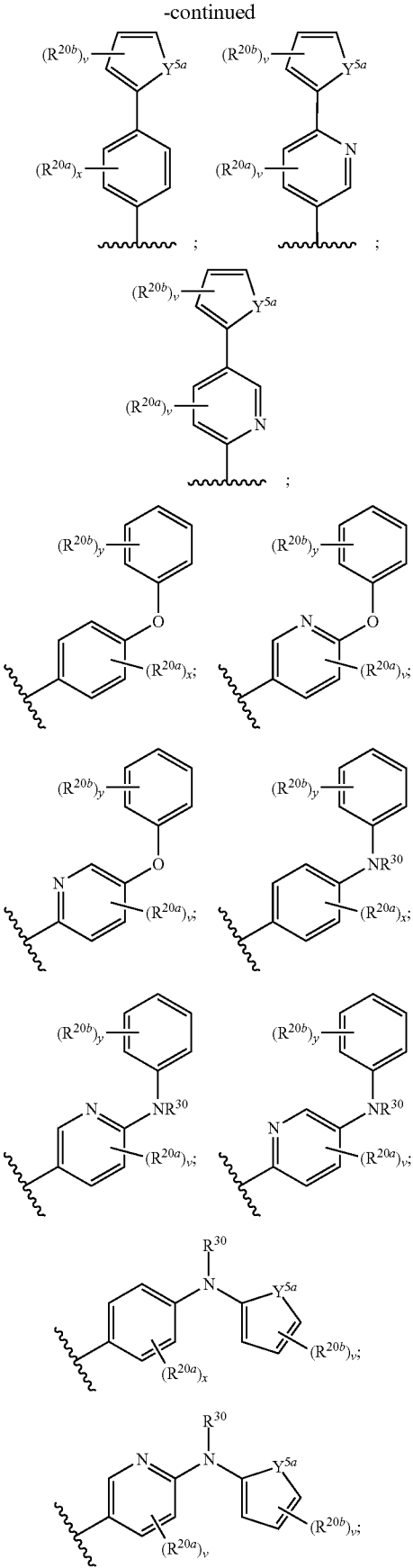

-continued

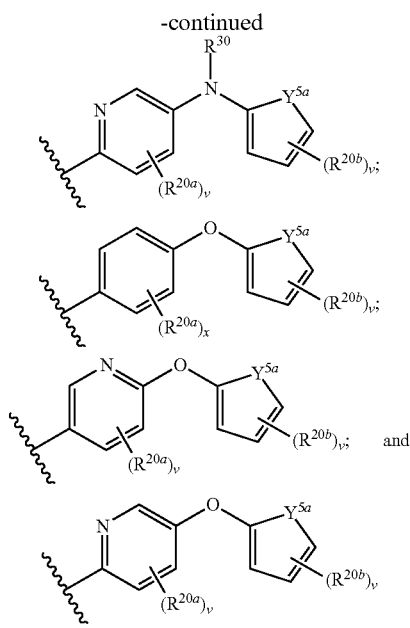

wherein each v is an integer independently selected from 0 to 3, x is an integer selected from 0 to 4 and y is an integer selected from 0 to 5. $Y^{5a}$ is selected from O and S. $R^{20a}$ and $R^{30}$ are defined as herein above. $R^{20b}$ is defined as $R^{20a}$, wherein $R^{20a}$ and $R^{20b}$ are independently selected. In one example in the above structures each $R^{20a}$ is H. In another example, each $R^{20b}$ in the above structures is H. In yet another example, each $R^{20a}$ and each $R^{20b}$ in the above structures is H. In yet another example, v in $(R^{20b})_v$ is 1 and $R^{20b}$ is methoxy.

In another example, Cy is a 5-membered heteroaryl moiety of the formula:

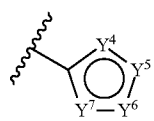

wherein $Y^4$, $Y^5$, $Y^6$ and $Y^7$ are members independently selected from S, O, N, $NR^{22}$ and $CR^{23}$, with the proviso that at least one of $Y^1$, $Y^2$ and $Y^3$ is other than $CR^{23}$. Each $R^{22}$ and each $R^{23}$ is a member independently selected from aryl group substituents. In one example, each $R^{22}$ and each $R^{23}$ is a member independently selected from H, substituted or unsubstituted alkyl (e.g., substituted or unsubstituted $C_1$-$C_8$ alkyl), substituted or unsubstituted heteroalkyl (e.g., substituted or unsubstituted 2- to 8-membered heteroalkyl), substituted or unsubstituted cycloalkyl (e.g., substituted or unsubstituted $C_3$-$C_8$ cycloalkyl), substituted or unsubstituted heterocycloalkyl (e.g., substituted or unsubstituted 3- to 8-membered heterocycloalkyl), substituted or unsubstituted aryl, and substituted or unsubstituted heteroaryl. In one example, $R^{22}$ and $R^{23}$ are members independently selected from H and substituted or unsubstituted $C_1$-$C_6$ alkyl (e.g., methyl or ethyl). Each $R^{23}$ can further be selected from $OR^{17}$, $SR^{17}$, $NR^{17}R^{18}$, $C(O)R^{19}$, $C(O)NR^{17}R^{18}$, $OC(O)NR^{17}R^{18}$, $C(O)OR^{17}$, $NR^{20}C(O)R^{19}$, $NR^{20}C(O)OR^{17}$, $NR^{20}C(O)NR^{17}R^{18}$, $NR^{20}C(S)NR^{17}R^{18}$, $NR^{20}S(O)_2R^{19}$, $S(O)_2NR^{17}R^{18}$ and $S(O)_pR^{19}$, wherein p is 1 or 2, wherein $R^{17}$, $R^{18}$, $R^{19}$ and $R^{20}$ are defined as herein above.

In one example, the compound of the invention has a structure according to Formula (XIII):

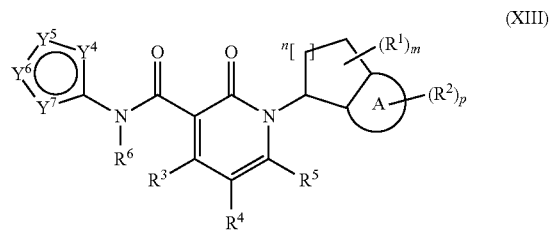

wherein m, n, p, A, $R^1$, $R^2$, $R^3$, $R^4$, $R^5$ and $R^6$ are defined above. $Y^4$, $Y^5$, $Y^6$ and $Y^7$ are also defined as herein above.

In one example, the compound of the invention has a structure according to Formula (XIIIa) or Formula (XIIIb):

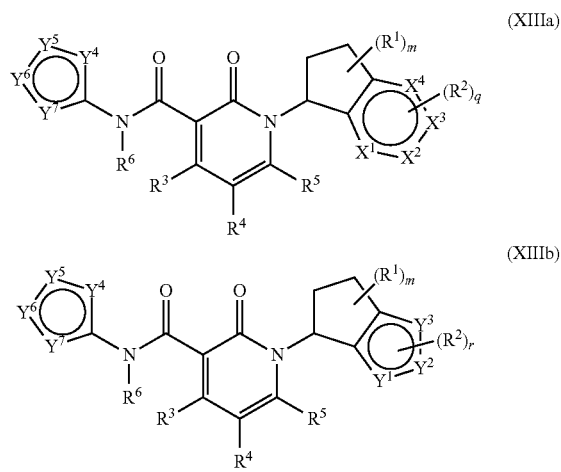

wherein m, q, r, $R^1$, $R^2$, $R^3$, $R^4$, $R^5$ and $R^6$ are defined as above. $X^1$, $X^2$, $X^3$, $X^4$, $Y^1$, $Y^2$, $Y^3$, $Y^4$, $Y^5$, $Y^6$ and $Y^7$ are defined as herein above.

In a further example, the compounds of the invention have a structure according to Formula (XIV), Formula (XV) or Formula (XVI):

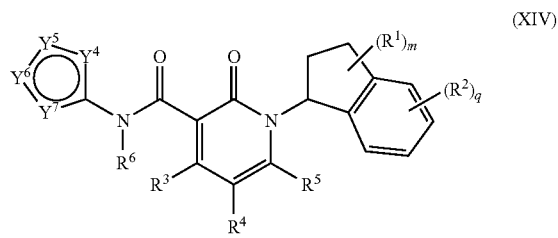

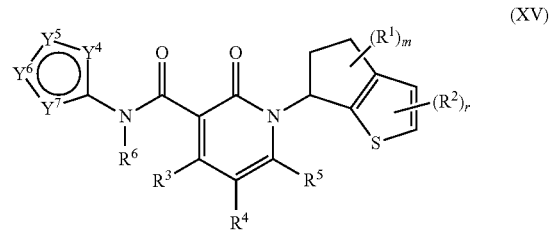

-continued

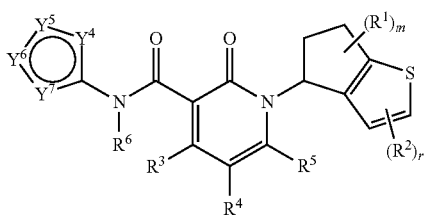

(XVI)

or a tautomer, salt or solvate thereof, wherein m, q, r, R$^1$, R$^2$, R$^3$, R$^4$, R$^5$ and R$^6$ are defined as above. Y$^1$, Y$^2$, Y$^3$, Y$^4$, Y$^5$, Y$^6$ and Y$^7$ are defined as herein above.

In one example, Cy or the moiety

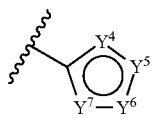

in any of the above formulae and embodiments, is a member selected from:

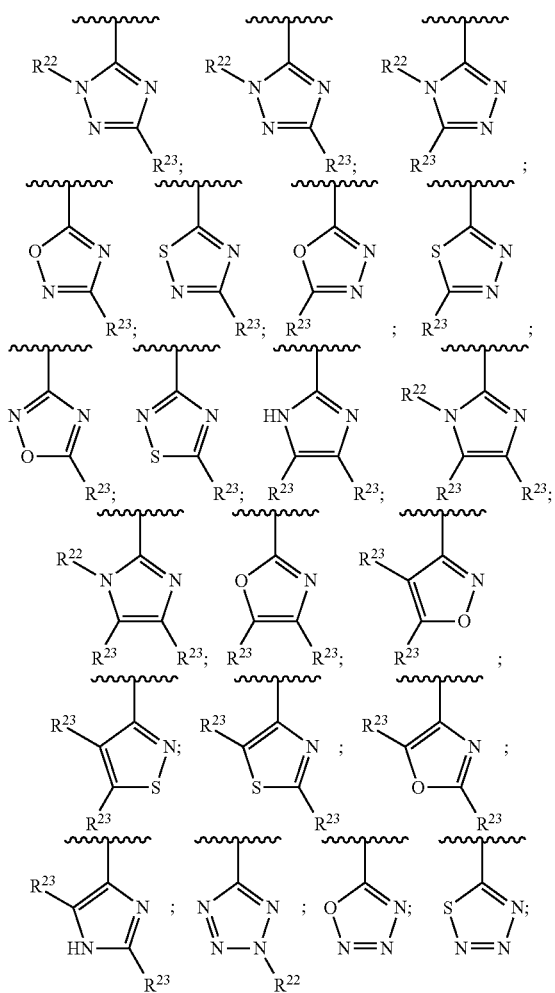

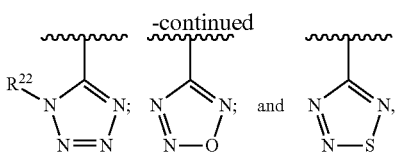

or a tautomer or mixture of tautomers thereof, wherein R$^{22}$ and R$^{23}$ are defined as hereinabove.

In one embodiment, in the above structures, each R$^{23}$ is a member independently selected from H, C$_1$-C$_4$ alkyl and alkoxy.

Exemplary compounds of the invention and their in vitro biological activities are listed in the table of FIG. 1.

In Vitro Activities

Certain compounds of the invention exhibit various in vitro biological activities. Specifically, certain compounds of the invention inhibit binding of alpha4 integrins to their respective ligands. Those compounds are termed alpha4 antagonists. For example, compounds of the invention inhibit binding of alpha4 integrins (e.g., alpha4beta7 or VLA-4) to their natural ligands, such as fibronectin, VCAM-1 or MadCAM. In vitro assays for the determination of such activities are known in the art (see e.g., WO2000/51974, incorporated herein by reference). Exemplary assay formats are described herein (see e.g., Examples 32-38).

In one example, the compounds of the invention inhibit binding of alpha4beta7 to MadCAM in a MadCAM adhesion assay (e.g., at least one of the assays described in Examples 32 and 33) with an IC$_{50}$ of less than about 50 µM, less than about 40 µM, less than about 30 µM, less than about 20 µM or less than about 10 µM. In another example, the compounds of the invention inhibit binding of alpha4beta7 to MadCAM in a MadCAM adhesion assay with an IC$_{50}$ of less than about 9 µM, less than about 8 µM, less than about 7 µM, less than about 6 µM, less than about 5 µM, less than about 4 µM, less than about 3 µM, less than about 2 µM, or less than about 1 µM. In yet another example, the compounds of the invention inhibit binding of alpha4beta7 to MadCAM in a MadCAM adhesion assay with an IC$_{50}$ of less than about 0.9 µM, less than about 0.8 µM, less than about 0.7 µM, less than about 0.6 µM, less than about 0.5 µM, less than about 0.4 µM, less than about 0.3 µM, less than about 0.2 µM. In a particular example, the compounds of the invention inhibit binding of alpha4beta7 to MadCAM in a MadCAM adhesion assay with an IC$_{50}$ of less than about 0.1 µM (100 nM). In another particular example, the compounds of the invention inhibit binding of alpha4beta7 to MadCAM in a MadCAM adhesion assay with an IC$_{50}$ of less than about 90 nM, less than about 80 nM, less than about 70 nM, less than about 60 nM, less than about 50 nM, less than about 40 nM, less than about 30 nM or less than about 20 nM. In another particular example, the compounds of the invention inhibit binding of alpha4beta7 to MadCAM in a MadCAM adhesion assay with an IC$_{50}$ of less than about 10 nM.

In Vivo Activities

Certain compounds of the invention exhibit in vivo biological activities, such as those described herein in Examples 39-41.

Synthesis of the Compounds of the Invention

The compounds of the invention can be prepared using methods known in the art of organic synthesis and those described herein (see, e.g., Examples 1 to 13). The starting materials and various intermediates may be obtained from commercial sources, prepared from commercially available compounds, and/or prepared using known synthetic methods.

For example, the compounds of the invention, as well as all intermediates, can be synthesized by known processes using either solution or solid phase techniques. Exemplary procedures for preparing compounds of the invention are outlined in the following schemes.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and P. G. M. Wuts, *Protecting Groups in Organic Synthesis*, Third Edition, Wiley, New York, 1999, and references cited therein.

In one example, the compounds of the invention are prepared using a procedure outlined in Scheme 1, below:

In Scheme 1, the amine (a) is coupled to the dimethyl 2-(3-methoxyallylidene)malonate (b). The resulting malonate derivative (c) is cyclized in the presence of a base, such as NaH, to give the 2-oxo-1,2-dihydropyridine analog (d). The carboxylic acid group of (d) is utilized to form an amide bond with an amine derivative incorporating the ring Cy, thereby forming a compound of the invention.

Compounds of formula (a) in Scheme 1 can be synthesized from the corresponding ketone (f) by reaction with a hydroxylamine and subsequent reduction of the resulting oxime (g), e.g., as outlined in Scheme 2, below.

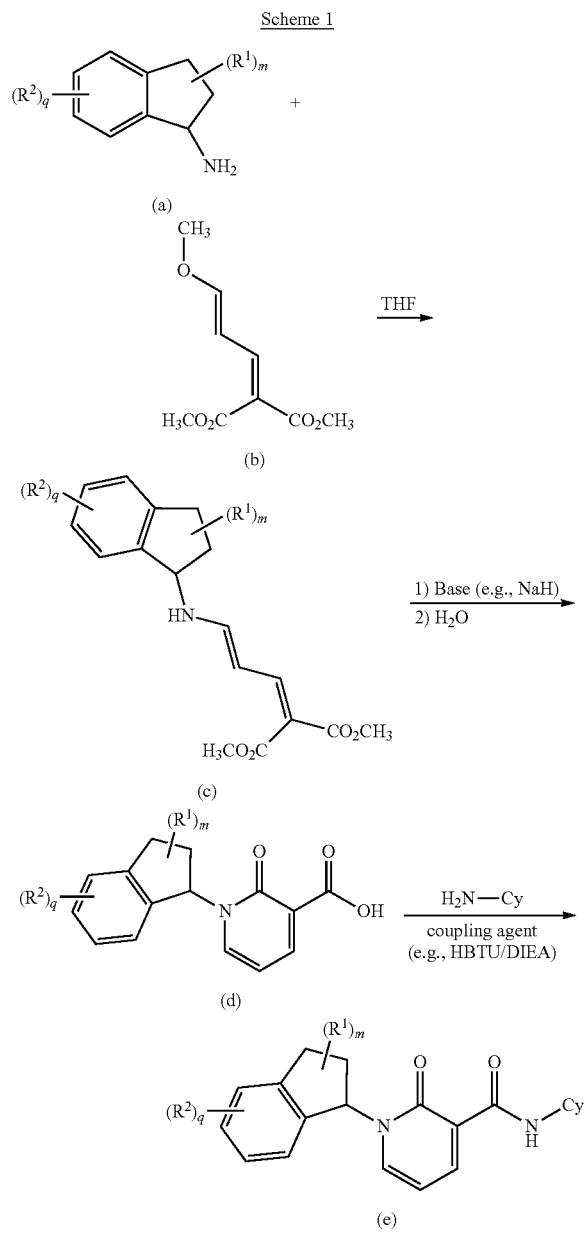

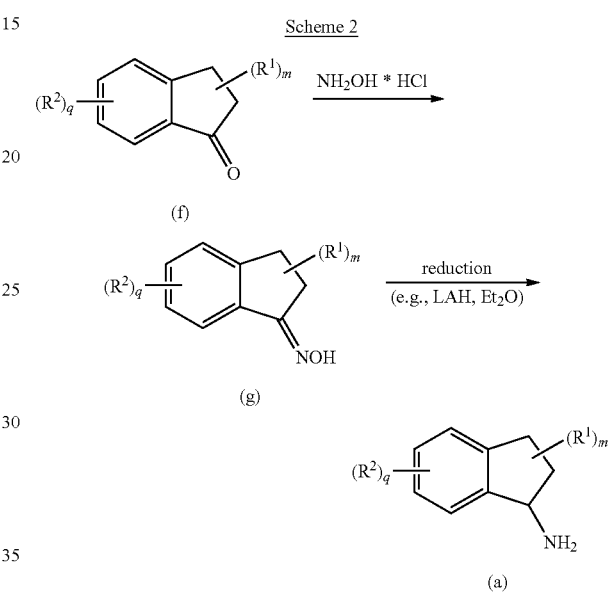

Alternatively compounds of formula (a) can be synthesized from the corresponding ketone as outlined in Scheme 3a, below.

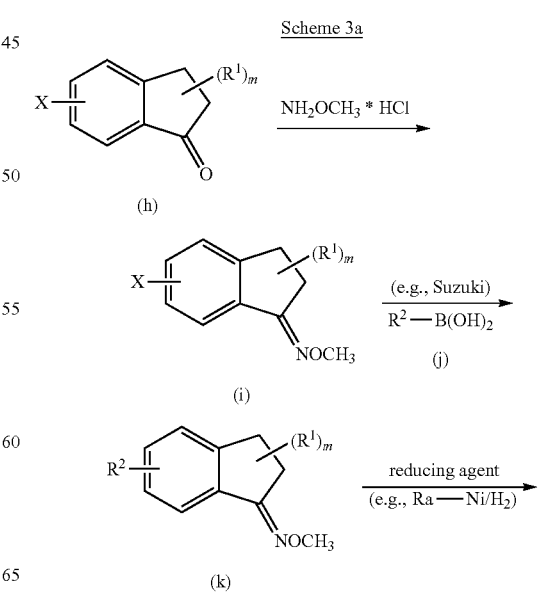

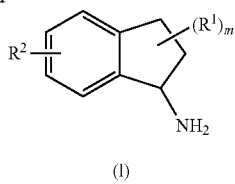

In Scheme 3a, X is Br or I. $R^1$ and $R^2$ are as defined herein above. In Scheme 3, the halogen-substituted ketone (h) is first converted to the alkyl-oxime (i). The halogen can then be replaced with another group (e.g., an alkyl group, an amine, or an alkoxy group) using a variety of known chemistries. In one example, the halogen X (e.g., Br) is replaced with an alkyl or cycloalkyl group using a Suzuki or Suzuki-type reaction, e.g., employing a boronic acid reagent (j) to afford analog (k). The oxime can subsequently be reduced to the corresponding amine (l).

In another example, the halogen of compound (h) is replaced with an amino group, e.g., using a Buchwald or Buchwald-type reaction as outlined in Scheme 3b, below.

are optionally joined to form a 4 to 7-membered heterocyclic ring. Exemplary heterocyclic rings include piperazinyl (e.g., N-methyl-piperazinyl) and morpholinyl groups. In Scheme 3b, the halogen X (e.g., Br) of the oxime (i) is replaced with an amine (m) using a metal catalyst, such as a transition metal catalyst to afford the amine (n). The oxime moiety of (n) can then be reduced to the amine forming analog (O). Catalysts useful for the above transformation are known to those of skill in the art. It is well within the capabilities of a skilled person to select a suitable catalyst. Typically, the Buchwald or Buchwald-type reaction will be palladium-catalyzed. However, other transition metal catalysts can also be used. For example, the starting material can be heated together with a palladium catalyst, a palladium ligand and a base. In one example, the catalyst is palladium acetate (e.g., $Pd(OAc)_2$) or a palladium phosphine, such as triphenyl phosphine, $Pd(PPh_3)_4$. The reaction (i.e., replacing a halogen with an amino group) can also be performed later in the synthesis, e.g., after the pyridone ring has already been formed.

Alternatively, in Scheme 3a or 3b, X is F, which can be replaced with a thiol or an alkylthio (thioether) group as outlined in Scheme 4, below.

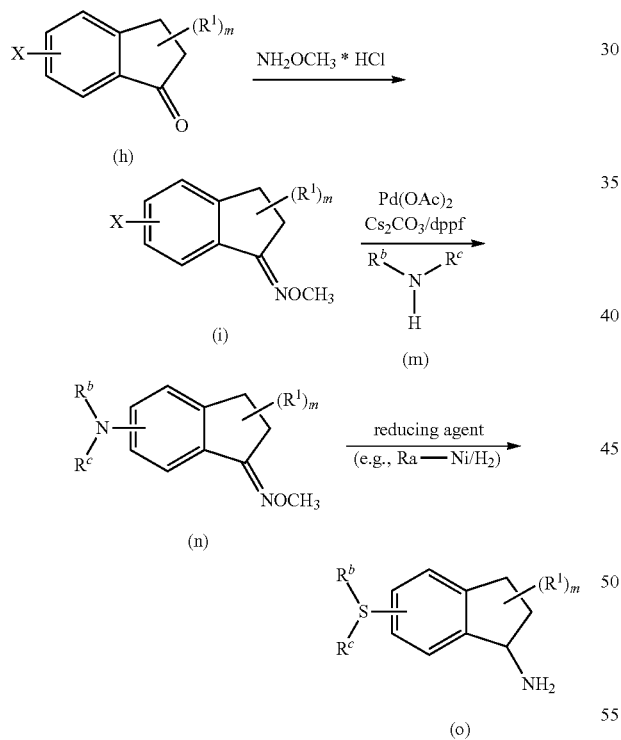

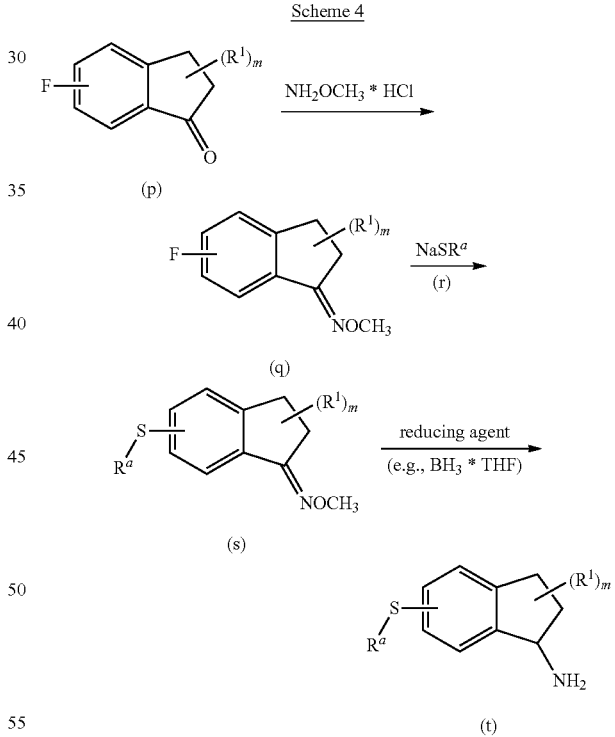

In Scheme 3b, X is Br or I and $R^a$ and $R^b$ are members independently selected from H, substituted or unsubstituted alkyl (e.g., $C_1$-$C_{10}$ alkyl), substituted or unsubstituted heteroalkyl (e.g., 2- to 10-membered heteroalkyl), substituted or unsubstituted aryl, substituted or unsubstituted heteroaryl, substituted or unsubstituted cycloalkyl (e.g., $C_3$-$C_{10}$ cycloalkyl) and substituted or unsubstituted heterocycloalkyl (e.g., 3- to 10-membered heterocycloalkyl). $R^a$ and $R^b$, together with the nitrogen atom, to which they are attached, In Scheme 4, the fluoro-substituted ketone (p) is first converted to the alkyl-oxime (q). The halogen can then be replaced with a thioether group by reacting compound (q) with an alkyl thiolate (r), wherein $R^a$ is alkyl (e.g., $C_1$-$C_4$ alkyl, such as methyl or ethyl), to afford the thioether (s), which can be further reduced to the amine (t). The thioether group can optionally be oxidized to a sulfonyl group, e.g., later in the synthesis, using an oxidizing agent, such as mCPBA, as outlined in Scheme 5, below.

Scheme 5

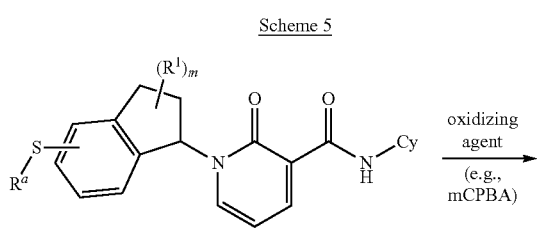

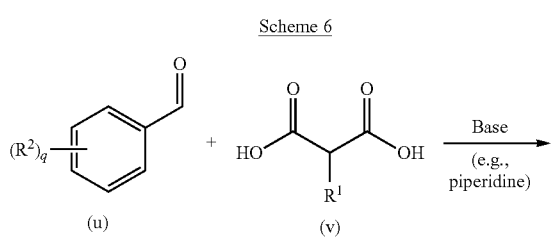

Useful ketone analogs, such as (f), (h) and (p) in Schemes 2, 3 and 4, respectively, can be prepared using a procedure outlined in Scheme 6, below.

Scheme 6

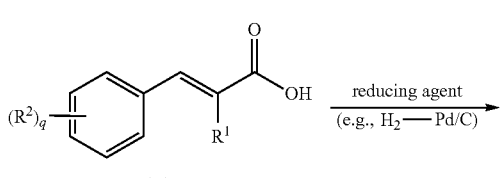

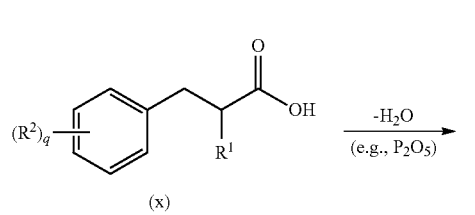

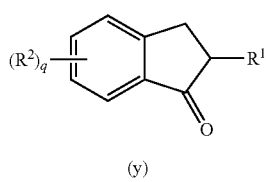

In Scheme 6, condensation of the aldehyde (u) with malonic acid or a malonic acid derivative (v) affords the unsaturated analog (w). The double bond can be reduced to afford the saturated derivative (x). Cyclization of (x) to the dihydroindenone (y) can be accomplished, e.g., using a dehydrating agent, such as $P_2O_5$.

In another example, amino-substituted compounds of the invention are prepared using a procedure outlined in Scheme 7, below.

Scheme 7

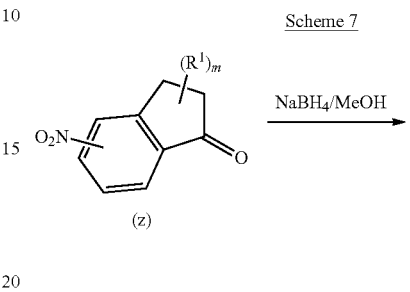

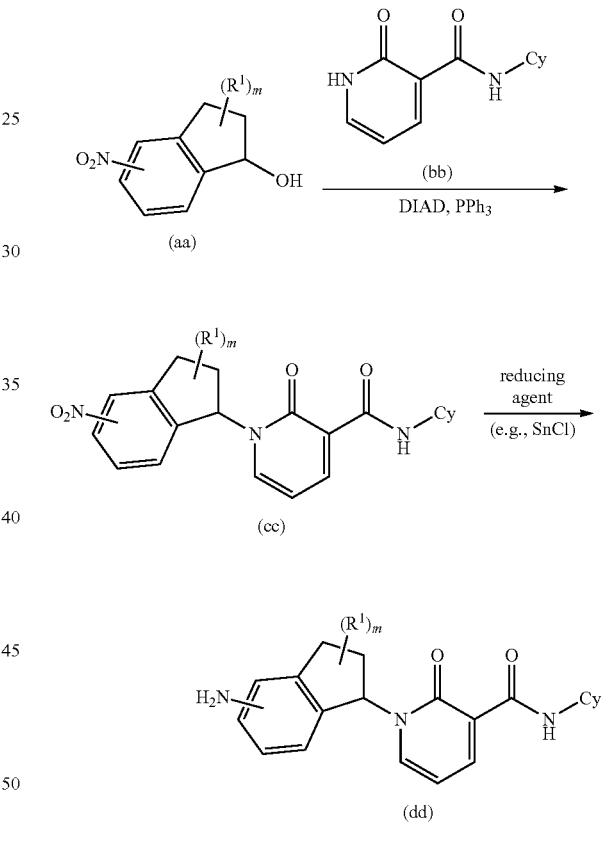

In Scheme 7, Cy and $R^1$ are defined as herein above. In Scheme 7, the nitro-substituted ketone (z) is first reduced to the corresponding alcohol (aa), which is coupled to the pyridone (bb) thereby forming analog (cc). The nitro group of (cc) is then reduced to the corresponding amine (dd).

The amino analog (dd) of Scheme 7 can be further converted to the secondary amine (ee) or the tertiary amine (ff). Alternatively the amino group of (dd) can be replaced with a halogen to afford the halogen-substituted analog (gg) or a nitrile (CN) group, e.g., via Sandmeyer or Sandmeyer-type reactions. These conversions are summarized in Scheme 8, below.

Scheme 8

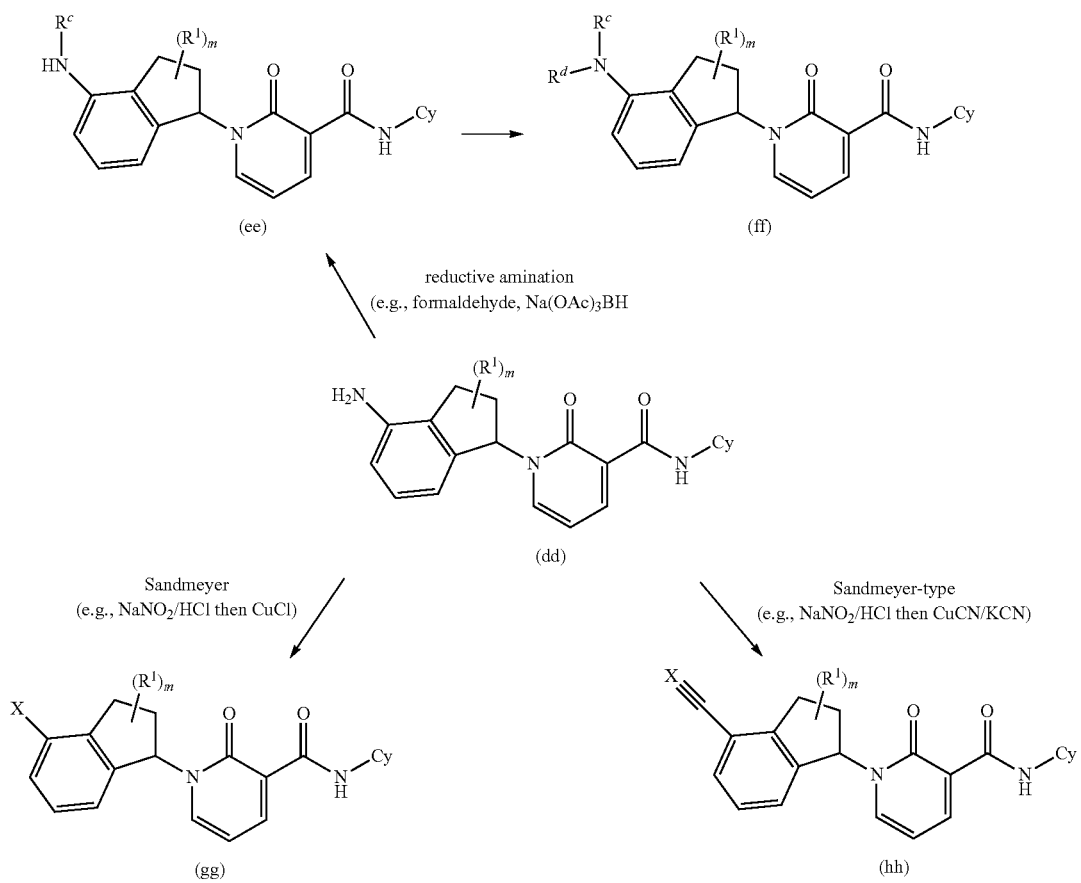

In Scheme 8, X is halogen (e.g., Cl, Br or I) and $R^c$ and $R^d$ are members independently selected from H, substituted or unsubstituted alkyl (e.g., $C_1$-$C_{10}$ alkyl), substituted or unsubstituted heteroalkyl (e.g., 2- to 10-membered heteroalkyl), substituted or unsubstituted aryl, substituted or unsubstituted heteroaryl, substituted or unsubstituted cycloalkyl (e.g., $C_3$-$C_{10}$ cycloalkyl) and substituted or unsubstituted heterocycloalkyl (e.g., 3- to 10-membered heterocycloalkyl). $R^c$ and $R^d$, together with the nitrogen atom, to which they are attached, are optionally joined to form a 4 to 7-membered heterocyclic ring.

In another example, the compounds of the invention are prepared using a procedure outlined in Scheme 9, below. Phenolic hydroxyl groups at various positions on the molecule can be used to attach a linker moiety, such as a protected (e.g., Boc-protected) amino-ethylene or -propylene glycol moiety, e.g., via a Mitsunobu or Mitsunobu-type reaction. After coupling, the amino protecting group can be removed to afford a primary amino group, which can be used to covalently attach the compound to another molecule, such as a second compound of the invention (to create a dimeric inhibitor) or a branched linker molecule (e.g., glycerol) to create a conjugate. The linker can be used to covalently attach one or more additional compounds of the invention to create a multimeric conjugate. Dimeric and multimeric integrin antagonists and their syntheses have been described e.g., in WO2006/010054 and WO2005/070921, the disclosures of which are incorporated herein by reference in their entirety.

Scheme 9

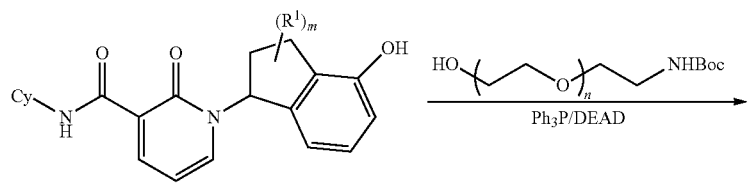

-continued

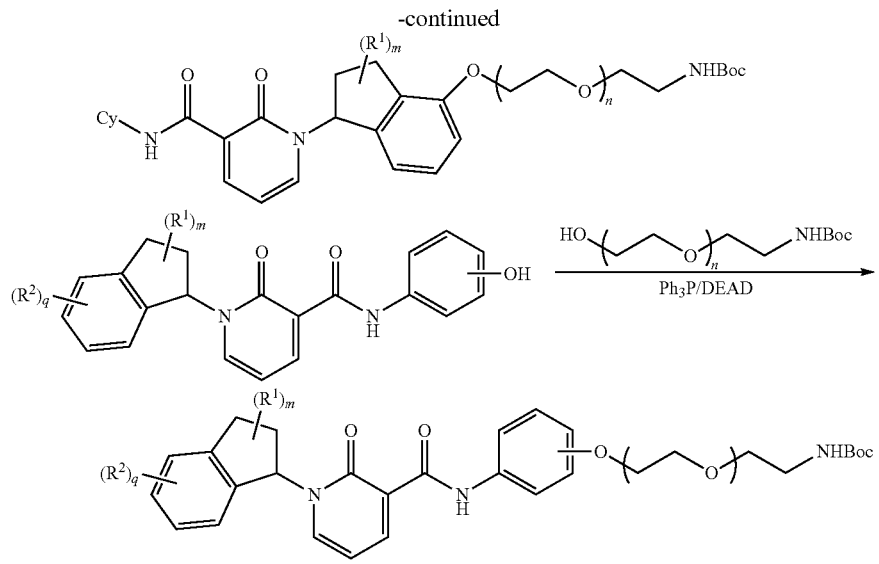

Further, compounds of Formula (Ia), Formula (Ia'), Formula (Ib) and Formula (Ic) can be synthesized following the procedures outlined in the above schemes using the starting compounds shown in Scheme 10. Such compounds shown in Scheme 10 can be purchased from commercial sources or synthesized using the methods disclosed herein or methods known to one of skill in the art.

Scheme 10

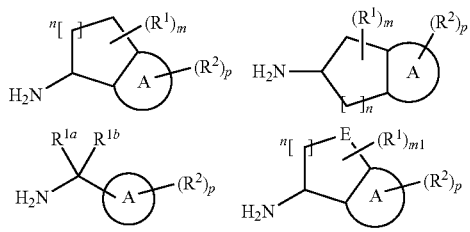

Pharmaceutical Compositions

The invention further provides pharmaceutical compositions including a compound of the invention, e.g., those of Formulae (I) to (XV), and a pharmaceutically acceptable carrier. Pharmaceutically acceptable carriers are described herein. A pharmaceutical composition of the invention may include one or more compounds of the invention in association with one or more pharmaceutically acceptable carriers and optionally other active ingredients.

The compounds of the invention may be administered orally, topically, parenterally, by inhalation or spray or rectally in dosage unit formulations containing at least one pharmaceutically acceptable carrier. The term "carrier" includes adjuvants, diluents, excipients and vehicles. The term "parenteral" as used herein includes percutaneous, subcutaneous, intravascular (e.g., intravenous), intramuscular, or intrathecal injection or infusion techniques and the like. The pharmaceutical compositions containing compounds of the invention may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preservative agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques. In some cases such coatings may be prepared by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules, wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil. Formulations for oral use may also be presented as lozenges.

Aqueous suspensions contain the active materials in admixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil or a mineral oil or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol, glucose or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be a sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the invention may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

Compounds of the invention may be administered parenterally in a sterile medium. The compound, depending on the vehicle and concentration used, can either be suspended or dissolved in the vehicle. Advantageously, adjuvants such as local anesthetics, preservatives and buffering agents can be dissolved in the vehicle.

For disorders of the eye or other external tissues, e.g., mouth and skin, the formulations are preferably applied as a topical gel, spray, ointment or cream, or as a scleral suppository, containing the active ingredients in a total amount of, for example, 0.075 to 30% w/w, preferably 0.2 to 20% w/w and most preferably 0.4 to 15% w/w. When formulated in an ointment, the active ingredients may be employed with either paraffinic or a water-miscible ointment base.

Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound, which enhances absorption or penetration of the active ingredient through the skin or other affected areas. Examples of such dermal penetration enhancers include dimethylsulfoxide and related analogs. The compounds of this invention can also be administered by a transdermal device. Preferably topical administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane. The transdermal patch may include the compound in a suitable solvent system with an adhesive system, such as an acrylic emulsion, and a polyester patch. The oily phase of the emulsions of this invention may be constituted from known ingredients in a known manner. While the phase may comprise merely an emulsifier, it may comprise a mixture of at least one emulsifier with a fat or oil or with both a fat and an oil. Preferably, a hydrophilic emulsifier is included together with a lipophilic emulsifier, which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base, which forms the oily, dispersed phase of the cream formulations. Emulsifiers and emulsion stabilizers suitable for use in the formulation of the invention include Tween 60, Span 80, cetostearyl alcohol, myristyl alcohol, glyceryl monostearate, and sodium lauryl sulfate, among others. The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The anti-inflammatory active ingredients are preferably present in such formulations in a concentration of 0.5 to 20%, advantageously 0.5 to 10% and particularly about 1.5% w/w. For therapeutic purposes, the active compounds of this combination invention are ordinarily combined with one or more adjuvants appropriate to the indicated route of administration. The compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Dosage levels of the order of from about 0.005 mg to about 80 mg per kilogram of body weight per day are useful in the treatment of the diseases and conditions described herein (e.g., about 0.35 mg to about 5.6 g per human patient per day, based on an average adult person weight of 70 kg). The amount of active ingredient that may be combined with the carrier materials to produce a single dosage form will vary depending upon the host treated and the particular mode of administration. Dosage unit forms will generally contain between from about 1 mg to about 500 mg of an active ingredient. The daily dose can be administered in one to four doses per day. In the case of skin conditions, it may be preferable to apply a topical preparation of compounds of this invention to the affected area one to four times a day.

Formulations suitable for inhalation or insufflation include solutions and suspensions in pharmaceutically acceptable aqueous or organic solvents, or mixtures thereof, and powders. The liquid or solid compositions may contain suitable pharmaceutically acceptable excipients as describe above. The compositions may be administered by oral or nasal respiratory route for local or systemic effect. Compositions may be nebulized by use of inert gases or vaporized, and breathed directly from the nebulizing/vaporizing device or the nebulizing device may be attached to a facemask tent or intermittent positive pressure-breathing machine.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

For administration to non-human animals, the composition may also be added to the animal feed or drinking water. It may be convenient to formulate the animal feed and drinking water compositions so that the animal takes in a therapeutically appropriate quantity of the composition along with its diet. It may also be convenient to present the composition as a premix for addition to the feed or drinking water.

Methods

The conjugates of this invention are anticipated to exhibit inhibition, in vivo, of adhesion of leukocytes to endothelial cells mediated by integrins, alpha4beta7 and VLA-4 by competitive binding to the integrin. Preferably, the compounds of this invention can be used in intravenous formulations for the treatment of diseases mediated by such integrins or diseases involving leukocyte adhesion. Such diseases include inflammatory diseases in mammalian patients such as asthma, Alzheimer's disease, atherosclerosis, AIDS dementia, diabetes (including acute juvenile onset diabetes), inflammatory bowel disease (including ulcerative colitis and Crohn's disease), multiple sclerosis (MS), idiopathic pulmonary fibrosis (IPF; also referred to as cryptogenic fibrosing alveolitis), rheumatoid arthritis (RA), tissue transplantation, tumor metastasis, liquid tumors, meningitis, encephalitis, stroke, and other cerebral traumas, nephritis, retinitis, atopic dermatitis, psoriasis, myocardial ischemia and acute leukocyte-mediated lung injury such as that which occurs in adult respiratory distress syndrome. The compounds and pharmaceutical formulations of the present invention are especially useful in the treatment of inflammatory diseases of the stomach/gut/intestines, such as inflammatory bowel diseases (IBD), including Crohn's disease and ulcerative colitis.

Inflammatory bowel disease refers to the group of disorders that cause the intestines to become inflamed, generally manifested with symptoms including abdominal cramps and pain, diarrhea, weight loss and intestinal bleeding. IBD is a collective term for two similar diseases termed ulcerative colitis (UC) and Crohn's disease (CD).

Crohn's disease is a chronic autoimmune disorder that results in inflammation of the gastrointestinal (GI) tract. Although any area of the GI tract may be involved, CD most commonly affects the small intestine and/or colon. In Crohn's disease, all layers of the intestine may be involved, and there can be normal healthy bowel in between patches of diseased bowel. CD is associated with fibrosis, stenosis and fissuring, fistulae between disease tracts and adjacent structures (i.e., bladder, other bowel segments, skin) and abscess. CD patients are typically present with diarrhea, abdominal pain and weight loss. The abdominal pain usually is insidious and may be associated with a tender, inflammatory mass. Fever, weight loss, stomatitis, perianal fistulae and/or fissure, arthritis, and erythema nodosum are all commonly seen. There is considerable morbidity associated with CD, particularly in patients with disease not controlled by currently available drugs. Up to 75% of patients with moderate to severe disease require surgery and up to 75% to these patients will experience post surgical disease recurrence within 10 years and up to 50% will undergo a repeat surgery within 20 years. This high rate of recurrence indicates a need for both, new effective treatments for the active disease and maintenance of disease remission.

Ulcerative colitis is a chronic, episodic, inflammatory disease of the large intestine and rectum characterized by bloody diarrhea. Ulcerative colitis is an inflammatory response limited largely to the colonic mucosa and submucosa. Ulcerative colitis can be categorized according to location: "proctitis" involves only the rectum, "proctosigmoiditis" affects the rectum and sigmoid colon, "left-sided colitis" encompasses the entire left side of the large intestine, "pancolitis" inflames the entire colon. Lymphocytes and macrophages are numerous in lesions of inflammatory bowel disease and may contribute to inflammatory injury. An exemplary animal model of inflammatory bowel disease (IBD) is carried out with HLA-B27 transgenic rats. These rats overexpress the human HLA-B27 molecule (heavy chain and beta globulin gene) that is associated with spondyloarthropathies, a group of inflammatory conditions affecting the skeleton. Prior to onset of skeletal inflammatory changes these animals develop non-granulomatous inflammation in the small intestine and diffuse crypt abscesses on the colon, a pathology that is similar to that of Crohn's Disease in humans. Efficacy studies can be performed in the HLA-B27 transgenic rat IBD model with compounds of this invention, e.g., as described herein.

Asthma is a disease characterized by increased responsiveness of the tracheobronchial tree to various stimuli potentiating paroxysmal constriction of the bronchial airways. The stimuli cause release of various mediators of inflammation from IgE-coated mast cells including histamine, eosinophilic and neutrophilic chemotactic factors, leukotrines, prostaglandin and platelet activating factor. Release of these factors recruits basophils, eosinophils and neutrophils, which cause inflammatory injury. Animal models for the in vivo study of asthma include the rat asthma model, the mouse asthma model and the sheep model, e.g., those described herein.

Atherosclerosis is a disease of arteries (e.g., coronary, carotid, aorta and iliac). The basic lesion, the atheroma, consists of a raised focal plaque within the intima, having a core of lipid and a covering fibrous cap. Atheromas compromise arterial blood flow and weaken affected arteries. Myocardial and cerebral infarcts are a major consequence of this disease. Macrophages and leukocytes are recruited to atheromas and contribute to inflammatory injury.

Rheumatoid arthritis is a chronic, relapsing inflammatory disease that primarily causes impairment and destruction of joints. Rheumatoid arthritis usually first affects the small joints of the hands and feet but then may involve the wrists, elbows, ankles and knees. The arthritis results from interaction of synovial cells with leukocytes that infiltrate from the circulation into the synovial lining of the joints. See e.g., Paul, *Immunology* (3d ed., Raven Press, 1993). Over time, bone erosion, destruction of cartilage, and complete loss of joint integrity can occur. Eventually, multiple organ systems may be affected.

Joint damage in rheumatoid arthritis begins with the proliferation of synovial macrophages and fibroblasts after a triggering incident, possibly autoimmune or infectious. Lymphocytes infiltrate perivascular regions, and endothelial cells proliferate. Neovascularization then occurs. Blood vessels in the affected joint become occluded with small clots of inflammatory cells. Over time, inflamed synovial tissue begins to grow irregularly, forming invasive pannus tissue. Pannus invades and destroys cartilage and bone. Multiple cytokines, interleukins, proteinases, and growth factors are released, causing further joint destruction and the development of systemic complications. See, Firestein G. S. Etiology and pathogenesis of rheumatoid arthritis, Ruddy S, Harris E D, Sledge C B, Kelley W N, eds. Kelley's Textbook of Rheumatology, 7th ed. Philadelphia: W.B. Saunders, 2005:996-1042 Animal models for the study of rheumatoid arthritis include Adjuvant Induced Arthritis ("AIA") and Collagen Induced Arthritis ("CIA").

Another indication for the compounds of this invention is in the treatment of organ or graft rejection mediated by VLA-4. Over recent years there has been a considerable improvement in the efficiency of surgical techniques for transplanting tissues and organs such as skin, kidney, liver, heart, lung, pancreas and bone marrow. Perhaps the principal outstanding problem is the lack of satisfactory agents for inducing immunotolerance in the recipient to the transplanted allograft or organ. When allogeneic cells or organs are transplanted into a host (i.e., the donor and donee are different individuals from the same species), the host immune system is likely to mount an immune response to foreign antigens in the transplant (host-versus-graft disease) leading to destruction of the transplanted tissue. CD8+ cells, CD4 cells and monocytes are all involved in the rejection of transplant tissues. Compounds of this invention which bind to alpha-4 integrin are useful, inter alia, to block alloantigen-induced immune responses in the donee thereby preventing such cells from participating in the destruction of the transplanted tissue or organ. See, e.g., Paul et al., *Transplant International* 9, 420-425 (1996); Georczynski et al., *Immunology* 87, 573-580 (1996); Georcyznski et al., *Transplant. Immunol.* 3, 55-61 (1995); Yang et al., *Transplantation* 60, 71-76 (1995); Anderson et al., *APMIS* 102, 23-27 (1994).

A related use for compounds of this invention, which bind to VLA-4 is in modulating the immune response involved in "graft versus host" disease ("GVHD"). See e.g., Schlegel et al., *J. Immunol.* 155, 3856-3865 (1995). GVHD is a potentially fatal disease that occurs when immunologically competent cells are transferred to an allogeneic recipient. In this situation, the donor's immunocompetent cells may attack tissues in the recipient. Tissues of the skin, gut epithelia and liver are frequent targets and may be destroyed during the course of GVHD. The disease presents an especially severe problem when immune tissue is being transplanted, such as in bone marrow transplantation; but less severe GVHD has also been reported in other cases as well, including heart and liver transplants. The therapeutic agents of the present invention are used, inter alia, to block activation of the donor T-cells thereby interfering with their ability to lyse target cells in the host.

Appropriate in vivo models for demonstrating efficacy in treating inflammatory conditions include EAE (experimental autoimmune encephalomyelitis) in mice, rats, guinea pigs or primates, as well as other inflammatory models dependent upon $\alpha_4$ integrins.

A further use of the compounds of this invention is inhibiting tumor metastasis. Several tumor cells have been reported to express VLA-4 and compounds, which bind VLA-4 block adhesion of such cells to endothelial cells. Steinback et al., *Urol. Res.* 23, 175-83 (1995); Orosz et al., *Int. J. Cancer* 60, 867-71 (1995); Freedman et al., *Leuk. Lymphoma* 13, 47-52 (1994); Okahara et al., *Cancer Res.* 54, 3233-6 (1994).

A further use of the compounds of this invention is in treating multiple sclerosis. Multiple sclerosis is a progressive neurological autoimmune disease that is thought to be the result of an autoimmune reaction in which certain leukocytes attack and initiate the destruction of myelin, the insulating sheath covering nerve fibers. In an animal model for multiple sclerosis, murine monoclonal antibodies directed against VLA-4 have been shown to block the adhesion of leukocytes to the endothelium, and thus prevent inflammation of the central nervous system and subsequent paralysis in the animals.[16]

The most common demyelinating disease is multiple sclerosis, but many other metabolic and inflammatory disorders result in deficient or abnormal myelination. MS is a chronic neurologic disease, which appears in early adulthood and progresses to a significant disability in most cases. There are approximately 350,000 cases of MS in the United States alone. Outside of trauma, MS is the most frequent cause of neurologic disability in early to middle adulthood.

MS is characterized by chronic inflammation, demyelination and gliosis (scarring). Demyelination may result in either negative or positive effects on axonal conduction. Positive conduction abnormalities include slowed axonal conduction, variable conduction block that occurs in the presence of high- but not low-frequency trains of impulses or complete conduction block. Positive conduction abnormalities include ectopic impulse generation, spontaneously or following mechanical stress and abnormal "cross-talk" between demyelinated exons.

T-cells reactive against myelin proteins, either myelin basic protein (MBP) or myelin proteolipid protein (PLP) have been observed to mediate CNS inflammation in experimental allergic encephalomyelitis. Patients have also been observed as having elevated levels of CNS immunoglobulin (Ig). It is further possible that some of the tissue damage observed in MS is mediated by cytokine products of activated T cells, macrophages or astrocytes.

Today, 80% patients diagnosed with MS live 20 years after onset of illness. Therapies for managing MS include: (1) treatment aimed at modification of the disease course, including treatment of acute exacerbation and directed to long-term suppression of the disease; (2) treatment of the symptoms of MS; (3) prevention and treatment of medical complications; and (4) management of secondary personal and social problems.

The onset of MS may be dramatic or so mild as to not cause a patient to seek medical attention. The most common symptoms include weakness in one or more limbs, visual blurring due to optic neuritis, sensory disturbances, diplopia and ataxia. The course of disease may be stratified into three general categories: (1) relapsing MS, (2) chronic progressive MS, and (3) inactive MS. Relapsing MS is characterized by recurrent attacks of neurologic dysfunction. MS attacks generally evolve over days to weeks and may be followed by complete, partial or no recovery. Recovery from attacks generally occurs within weeks to several months from the peak of symptoms, although rarely some recovery may continue for 2 or more years.

Chronic progressive MS results in gradually progressive worsening without periods of stabilization or remission. This form develops in patients with a prior history of relapsing MS, although in 20% of patients, no relapses can be recalled. Acute relapses also may occur during the progressive course.

A third form is inactive MS. Inactive MS is characterized by fixed neurologic deficits of variable magnitude. Most patients with inactive MS have an earlier history of relapsing MS.

Disease course is also dependent on the age of the patient. For example, favourable prognostic factors include early onset (excluding childhood), a relapsing course and little residual disability 5 years after onset. By contrast, poor prognosis is associated with a late age of onset (i.e., age 40 or older) and a progressive course. These variables are interdependent, since chronic progressive MS tends to begin at a later age that relapsing MS. Disability from chronic progressive MS is usually due to progressive paraplegia or quadriplegia (paralysis) in patients. In one aspect of the invention, patients will preferably be treated when the patient is in remission rather than in a relapsing stage of the disease.

Short-term use of either adrenocorticotropic hormone or oral corticosteroids (e.g., oral prednisone or intravenous methylprednisolone) is the only specific therapeutic measure for treating patients with acute exacerbation of MS.

Newer therapies for MS include treating the patient with interferon beta-1b, interferon beta-1a, and Copaxone® (formerly known as copolymer 1). These three drugs have been shown to significantly reduce the relapse rate of the disease. These drugs are self-administered intramuscularly or subcutaneously.

However, none of the current treatment modalities inhibit demyelination, let alone promotes or allows spontaneous remyelination or reduces paralysis. One aspect of the invention contemplates treating MS with agents disclosed herein either alone or in combination with other standard treatment modalities.

Radiation also can induce demyelination. Central nervous system (CNS) toxicity due to radiation is believed to be cause by (1) damage to vessel structures, (2) deletion of oligodendrocyte-2 astrocyte progenitors and mature oligodendrocytes, (3) deletion of neural stem cell populations in the hippocampus, cerebellum and cortex, and generalized alterations of cytokine expression. Most radiation damage results from radiotherapies administered during the treatment of certain cancers. See for review Belka et al., 2001 Br. J. Cancer 85: 1233-9. However, radiation exposure may also be an issue for astronauts (Hopewell, 1994 Adv. Space Res. 14: 433-42) as well as in the event of exposure to radioactive substances.

Pharmaceutical compositions of the invention are suitable for use in a variety of drug delivery systems. Suitable formulations for use in the present invention are found in *Remington's Pharmaceutical Sciences*, Mace Publishing Company, Philadelphia, Pa., 17th ed. (1985), the disclosure of which is incorporated herein in its entirety.

The amount administered to the patient will vary depending upon what is being administered, the purpose of the administration, such as prophylaxis or therapy, the state of the patient, the manner of administration, and the like. In therapeutic applications, compositions are administered to a patient already suffering from a disease in an amount sufficient to cure or at least partially arrest the symptoms of the disease and its complications. An amount adequate to accomplish this is defined as "therapeutically effective dose." Amounts effective for this use will depend on the disease condition being treated as well as by the judgment of the attending clinician depending upon factors such as the severity of the inflammation, the age, weight and general condition of the patient, and the like, with reference to the appropriate animal model data, such as that provided herein. Methods for estimating appropriate human dosages, based on such data, are known in the art. (see, for example, Wagner, J. G. Pharmacokinetics for the Pharmaceutical Scientist. Technomic, Inc., Lancaster, Pa. 1993).

The compositions administered to a patient are in the form of pharmaceutical compositions described above. These compositions may be sterilized by conventional sterilization techniques, or may be sterile filtered. The resulting aqueous solutions may be packaged for use as is, or lyophilized, the lyophilized preparation being combined with a sterile aqueous carrier prior to administration.

Compounds having the desired biological activity may be modified as necessary to provide desired properties such as improved pharmacological properties (e.g., in vivo stability, bio-availability), or the ability to be detected in diagnostic applications. Stability can be assayed in a variety of ways such as by measuring the half-life of the proteins during incubation with peptidases or human plasma or serum. A number of such protein stability assays have been described (see, e.g., Verhoef et al., Eur. J. Drug Metab. Pharmacokinet., 1990, 15(2):83-93).

Inflammatory diseases that are included for treatment by the compositions, compounds and methods disclosed herein include generally conditions relating to demyelination. Histologically, myelin abnormalities are either demyelinating or dysmyelinating. Demyelination implies the destruction of myelin. Dysmyelination refers to defective formation or maintenance of myelin resulting from dysfunction of the oligodendrocytes. Preferably, the compositions and methods disclosed herein are contemplated to treat diseases and conditions relating to demyelination and aid with remyelination.

Additional diseases or conditions contemplated for treatment include meningitis, encephalitis, and spinal cord injuries and conditions generally which induce demyelination as a result of an inflammatory response.

The compositions, compounds and cocktails disclosed herein are contemplated for use in treating conditions and diseases associated with demyelination. Diseases and conditions involving demyelination include, but are not limited to, multiple sclerosis, congenital metabolic disorders (e.g., phenylketonuria (PKU), Tay-Sachs disease, Niemann-Pick disease, Gaucher's disease, Hurler's syndrome, Krabbe's disease and other leukodystrophies that impact the developing sheath), neuropathies with abnormal myelination (e.g., Guillain Barré, chronic immune demyelinating polyneuropathy (CIDP), multifocal CIDP, Multifocal Motor Neuropathy (MMN), anti-MAG (Myelin-Associated Glycoprotein) syndrome, GALOP (Gait disorder, Autoantibody, Late-age, Onset, Polyneuropathy) syndrome, anti-sulfatide antibody syndrome, anti-GM2 antibody syndrome, POEMS (Polyneuropathy, Organomegaly, Endocrinopathy, M-Protein and Skin changes) syndrome also known as Crow-Fukase Syndrome and Takatsuki disease, perineuritis, IgM anti-GD1b antibody syndrome), drug related demyelination (e.g., caused by the administration of chloroquine, FK506, perhexyline, procainamide, and zimeldine), other hereditary demyelinating conditions (e.g., carbohydrate-deficient glycoprotein, Cockayne's syndrome, congenital hypomyelinating, congenital muscular dystrophy, Farber's disease, Marinesco-Sjögren syndrome, metachromatic leukodystrophy, Pelizaeus-Merzbacher disease, Refsum disease, prion related conditions, and Salla disease) and other demyelinating conditions (e.g., meningitis, encephalitis (also known as acute disseminated encephalomyelitis, ADEM), or spinal cord injury) or diseases.

There are various disease models that can be used to study these diseases in vivo. For example, animal models include but are not limited to:

TABLE 4

| Disease Model | Species |
| --- | --- |
| EAE | Mouse, rat, guinea pig |
| Myelin-oligodendrocyte glycoprotein (MOG) induced EAE | Rat |
| TNF-α transgenic model of demyelination | Mouse |

These conditions and diseases are also contemplated for palliative or ameliorating treatments.

Compounds of this invention are also capable of binding or antagonizing the actions of $\alpha_4\beta_1$, and $\alpha_4\beta_7$ integrins. Accordingly, compounds of this invention are also useful for preventing or reversing the symptoms, disorders or diseases induced by the binding of these integrins to their respective ligands.

In another aspect of the invention, the compounds and compositions described herein can be used to inhibit immune cell migration from the bloodstream to the central nervous system in the instance of, for example, multiple sclerosis, or to areas which result in inflammatory-induced destruction of the myelin. Preferably, these reagents inhibit immune cell migration in a manner that inhibits demyelination and that further may promote remyelination. The reagents may also prevent demyelination and promote remyelination of the central nervous system for congenital metabolic disorders in which infiltrating immune cells affect the development myelin sheath, mainly in the CNS. The reagents preferably also reduce paralysis when administered to a subject with paralysis induced by a demyelinating disease or condition.

Use of Compounds of the Invention in an In Vitro Assay

The invention further provides a method of using a compound of the invention in an in vitro assay measuring binding of an α4β1 or α4β7 integrin to an integrin ligand, such as fibronectin (FN), VCAM-1, osteopontin and MadCAM. For example, the compound of the invention can be used as a reference compound in such assay in order to compare and evaluate the binding capacity of other test compounds (i.e., candidate molecules) to bind the integrin, or its capacity to disrupt binding of the ligand to the integrin (i.e., competitive binding assay). The term "in vitro assay" includes cell-based (e.g., ex vivo) assays. An exemplary cell-based in vitro assay measuring the capacity of test compounds to inhibit binding of MadCAM to cell-surface alpha4beta7 integrins is described herein. An exemplary assay comprises the steps of (i) binding the ligand (e.g., recombinant MadCAM-antibody conjugate) to a surface (e.g., a well-plate); (ii) contacting the ligand with a cell that expresses the integrin (e.g. alpha4beta7) on its cell-surface in the presence of a compound of the invention; and (iii) measuring the amount of cells bound to the surface. For example, the integrins on the surface of the cells bind to the immobilized ligand. Such binding is inhibited by a compound of the invention as the compound binds to the integrin and thus reduces binding of the integrin to the ligand.

The invention further provides a method of using a compound of the invention in an in vitro assay measuring binding of the compound to an α4β1 or α4β7 integrin in the presence of a test molecule. For example, solubilized integrin or membrane preparations containing the integrin can be incubated with a test molecule in the presence of a compound of the invention labeled with a radioactive, colorimetric, fluorescent or other label, which can be used for detection. The test molecule competes with the labeled compound for binding to the integrin. By measuring the amount of labeled compound bound to the integrin, the capability of the test molecule to the integrin can be determined. Hence, the invention further provides a method of using the compounds of the invention in an in vitro assay for identifying a candidate molecule capable of binding to α4β1 or α4β7 integrin. A candidate molecule exhibits a detectable binding activity in the respective assay (e.g., an $IC_{50}$ of not more than 10 μM and preferably not more than 5 μM or not more than 1 μM).

In one example according to any of the above embodiments, the in vitro assay is a competitive binding assay.

The disclosures in this document of all articles and references, including patents, are incorporated herein by reference in their entirety.

The invention is illustrated further by the following examples, which are not to be construed as limiting the invention in scope or spirit to the specific procedures described in them. Analogous structures and alternative synthetic routes within the scope of the invention will be apparent to those skilled in the art.

EXAMPLES

General

Reagents and solvents obtained from commercial suppliers were used without further purification unless otherwise stated. Thin layer chromatography was performed on pre-coated 0.25 mm silica gel plates (E. Merck, silica gel 60, $F_{254}$). Visualization was achieved using UV illumination or staining with phosphomolybdic acid, ninhydrin or other common staining reagents. Flash chromatography was performed using either a Biotage Flash 40 system and prepacked silica gel columns or hand packed columns (E. Merck silica gel 60, 230-400 mesh). Preparatory HPLC was performed on a Varian Prepstar high performance liquid chromatograph. $^1$H and $^{13}$C NMR spectra were recorded at 300 MHz and 75 MHz, respectively, on a Varian Gemini or Bruker Avance spectrometer. Chemical shifts are reported in parts per million (ppm) downfield relative to tetramethylsilane (TMS) or to proton resonances resulting from incomplete deuteration of the NMR solvent (δscale). Mass spectra were recorded on an Agilent series 1100 mass spectrometer connected to an Agilent series 1100 HPLC.

Further, abbreviations used throughout have the following meanings:

μ=Micro
Ac=Acetate
bd=Broad doublet
BINAP=2,2'-Bis(diphenylphosphino)-1,1'-binaphthyl
BOC=tert-Butyloxycarbonyl
BSA=Bovine serum albumin
d=Doublet
DCM=Dichloromethane
dd=Double doublet
DEAD=Diethyl azodicarboxylate
DIAD=Diisopropyl azodicarboxylate
DIEA=Diisopropylethylamine
DME=Dimethylether
DMF=Dimethylformamide
DMSO=Dimethylsulfoxide
dppf=1,1'-Bis(diphenylphosphino)ferrocene
dppp=1,1-Bis(diphenylphosphino)methane
EDC=1-Ethyl-3-[3-dimethylaminopropyl]carbodiimide hydrochloride
eq=Equivalents
Et=Ethyl
FBS=fetal bovine serum
g=Grams
HBTU=2-(1H-Benzotriazol-1-yl)-1,1,3,3-tetramethyluronium hexafluorophosphate
HEPES=4-2-Hydroxyethyl-1-piperazineethanesulfonic acid
HOBt=1-Hydroxybenzotriazole
HPLC=High performance liquid chromatography
hr=Hours
LAH=Lithium aluminum hydride
m=Multiplet
M=Molar
m-CPBA=meta-Chloroperoxybenzoic acid
MeOH=Methanol
mg=Milligrams
MHz=Megahertz
min=Minute
ml=Milliliters
mM=Millimolar
mmol=Millimole
MS (ESI)=Electrospray ionization mass spectrometry
N=Normal
NMR=Nuclear magnetic resonance
Pd/C=Palladium on carbon
Pd$_2$(dba)$_3$=Tris(dibenzylideneacetone)dipalladium(0)
Ph=Phenyl
psi=Pounds per square inch
q=Quartet
Ra-Ni=Raney-Nickel
rpm=Rotation per minute
RT=Room temperature
s=Singlet
t=Triplet
TFA=Trifluoroacetic acid
THF=Tetrahydrofuran
uL or μl=Microliters
w/v=Weight/volume
δ=Chemical shift Compound purity was typically determined by HPLC/MS analysis using a variety of analytical methods. Exemplary methods are described below.

Method [1]=20% [B]: 80% [A] to 70% [B]: 30% [A] gradient in 1.75 min, then hold, at 2 mL/min, where [A]=0.1% trifluoroacetic acid in water; [B]=0.1% trifluoroacetic acid in acetonitrile on a Phenomenex Luna C18 (2) 4.6 mm×30 cm column, 3 micron packing, 210 nm detection, at 35° C.

Method [2]=50% [B]: 50% [A] to 95% [B]: 5% [A] gradient in 2.5 min, then hold, at 2 mL/min, where [A]=0.1% trifluoroacetic acid in water; [B]=0.1% trifluoroacetic acid in acetonitrile on a Phenomenex Luna C18 (2) 4.6 mm×30 cm column, 3 micron packing, 210 nm detection, at 35° C.

Method [3]=5% [B]: 95% [A] to 20% [B]: 80% [A] gradient in 2.5 min, then hold, at 2 mL/min, where [A]=0.1% trifluoroacetic acid in water; [B]=0.1% trifluoroacetic acid in acetonitrile on a Phenomenex Luna C18 (2) 4.6 mm×30 cm column, 3 micron packing, 210 nm detection, at 35° C.

Method [4]=20% [B]: 80% [A] to 70% [B]: 30% [A] gradient in 2.33 min, then hold, at 1.5 mL/min, where [A]=0.1% trifluoroacetic acid in water; [B]=0.1% trifluoroacetic acid in acetonitrile on a Phenomenex Luna C18 (2) 4.6 mm×30 cm column, 3 micron packing, 210 nm detection, at 35° C.

Method [5]=50% [B]: 50% [A] to 95% [B]: 5% [A] gradient in 3.33 min, then hold, at 1.5 mL/min, where [A]=0.1% trifluoroacetic acid in water; [B]=0.1% trifluoroacetic acid in acetonitrile on a Phenomenex Luna C18 (2) 4.6 mm×30 cm column, 3 micron packing, 210 nm detection, at 35° C.

Method [6]=5% [B]: 95% [A] to 20% [B]: 80% [A] gradient in 3.33 min, then hold, at 1.5 mL/min, where [A]=0.1% trifluoroacetic acid in water; [B]=0.1% trifluoroacetic acid in acetonitrile on a Phenomenex Luna C18 (2) 4.6 mm×30 cm column, 3 micron packing, 210 nm detection, at 35° C.

Method [7]=20% [B]: 80% [A] to 70% [B]: 30% [A] gradient in 10.0 min, then hold, at 1.5 mL/min, where [A]=0.1% trifluoroacetic acid in water; [B]=0.1% trifluoroacetic acid in acetonitrile on a Phenomenex Luna C18 (2) 4.6 mm×3 cm column, 3 micron packing, 210 nm detection, at 35° C.

Method [8]=10% [B]: 90% [A] to 40% [B]: 60% [A] gradient in 10.0 min, then hold, at 1.5 mL/min, where [A]=0.1% trifluoroacetic acid in water; [B]=0.1% trifluoroacetic acid in acetonitrile on a Phenomenex Luna C18 (2) 4.6 mm×3 cm column, 3 micron packing, 210 nm detection, at 35° C.

Method [9]=23% [B]: 77% [A] to 30% [B]: 70% [A] gradient in 15.0 min, then hold, at 1.0 mL/min, where [A]=0.1% trifluoroacetic acid in water; [B]=0.1% trifluoroacetic acid in acetonitrile on a Zorbex SB-phenyl C18 2.1 mm×5 cm column, 5 micron packing, 210 nm detection, at 30° C.

Example 1

1.1. Synthesis of (R)-1-(2,3-dihydro-1H-inden-1-yl)-2-oxo-N-(pyridin-4-yl)-1,2-dihydropyridine-3-carboxamide (1)

Protocol A

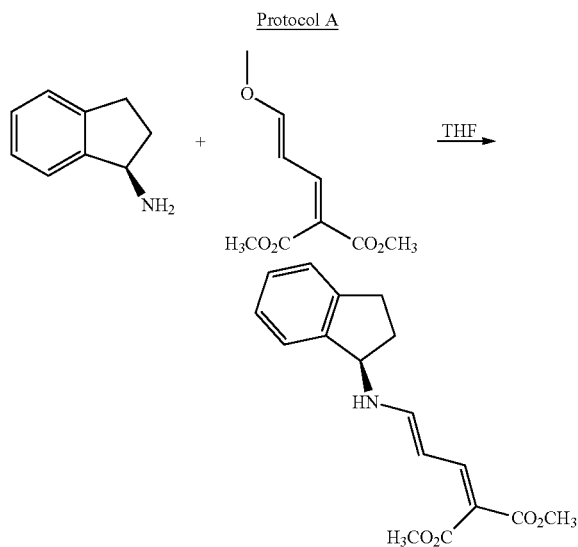

A 500 ml round-bottom flask was charged with 5.0 g (1.0 eq.) (R)-2,3-dihydro-1H-inden-1-amine and 7.5 g (1.0 eq.) dimethyl 2-(3-methoxyallylidene)malonate in 120 ml dry THF. The mixture was heated at 65° C. under $N_2$ for 3 hrs. Then the solvent was removed in vacuo, and the crude mixture was purified by silica gel flash column chromatography to afford (R)-dimethyl 2-(3-(2,3-dihydro-1H-inden-1-ylamino)allylidene)malonate as a yellow solid (11.0 g) in 97% yield.

Protocol B

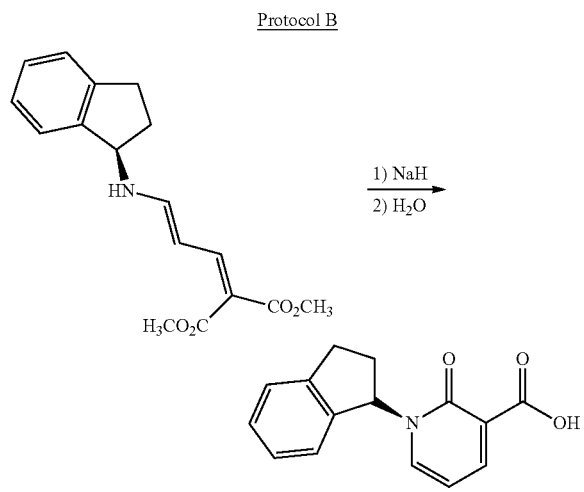

To a solution of 11.0 g (1.0 eq) (R)-dimethyl 2-(3-(2,3-dihydro-1H-inden-1-ylamino)allylidene)malonate in 80 ml dry MeOH was slowly added 3.65 g (2.5 eq) NaH (60% dispersion in mineral oil) under $N_2$ protection. The reaction was stirred at room temperature for 10 minutes and was then heated at 60° C. After 20 minutes, to the reaction mixture were added 30 ml water. The resulting mixture was heated at 60° C. for an additional 20 minutes. The solvent was removed in vacuo. The residue was diluted with 50 ml water, and extracted with hexane (2×50 ml) to remove mineral oil. Then the aqueous mixture was acidified with 2N HCl to pH 1-2 and extracted with ethyl acetate (2×100 ml). The combined organic phase was washed with 100 ml brine, dried over sodium sulfate and concentrated in vacuo to afford (R)-1-(2,3-dihydro-1H-inden-1-yl)-2-oxo-1,2-dihydropyridine-3-carboxylic acid as a white solid (8.7 g, yield 93%) which was used without further purification.

Protocol C

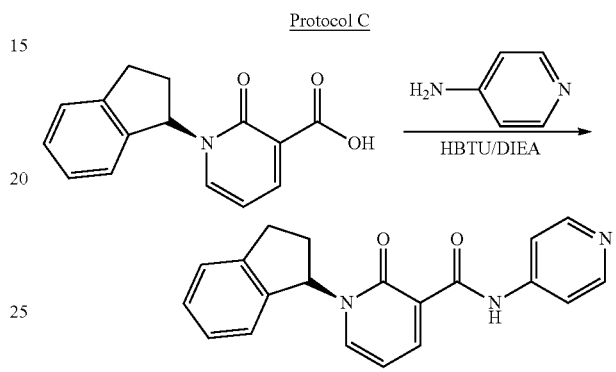

To a solution of 7.8 g (1.0 eq.) (R)-1-(2,3-dihydro-1H-inden-1-yl)-2-oxo-1,2-dihydropyridine-3-carboxylic acid in 100 ml DMF was added DIEA (10 ml, 2.5 eq.), HBTU (13.8 g, 1.2 eq.) and 4-amine-pyridin (3.45 g, 1.2 eq.). The resulting mixture was stirred at rt. overnight. The reaction was diluted with 300 ml water. The precipitate was collected by filtration, and washed with 2×50 ml water. The solid was purified on short flash column in silica gel to provide white solid 8.1 g (80%) (R)-1-(2,3-dihydro-1H-inden-1-yl)-2-oxo-N-(pyridin-4-yl)-1,2-dihydropyridine-3-carboxamide. Retention time (min)=2.592, method [7], MS (ESI) 332.1 (M+H); $^1$H NMR (300 MHz, DMSO-d6) δ 12.99 (s, 1H), 8.72 (d, 2H), 8.49 (d, 1H), 8.19 (d, 2H), 7.68 (d, 1H), 7.36 (m, 2H), 7.33 (m, 1H), 7.24 (m, 1H), 7.15 (d, 1H), 6.61 (t, 1H), 6.49-6.52 (m, 1H), 3.03-3.16 (m, 1H), 2.71-2.98 (m, 1H), 2.66-2.69 (m, 1H), 2.06-2.14 (m, 1H).

1.2. Synthesis of Additional Compounds using Protocols A, B and C

The following compounds were synthesized from appropriate starting materials using Protocols A, B and C, above or slightly modified versions thereof.

1-(2,3-Dihydro-1H-inden-1-yl)-2-oxo-N-(pyridin-4-yl)-1,2-dihydropyridine-3-carboxamide (2)

Retention time (min)=2.757, method [7], MS (ESI) 332.1 (M+H); $^1$H NMR (300 MHz, DMSO-d6) δ 12.98 (s, 1H), 8.71 (d, 2H), 8.48 (d, 1H), 8.18 (d, 2H), 7.68 (d, 1H), 7.36 (m, 2H), 7.33 (m, 1H), 7.24 (t, 1H), 7.15 (d, 1H), 6.61 (t, 1H), 6.49-6.52 (m, 1H), 3.01-3.19 (m, 1H), 2.71-2.98 (m, 1H), 2.65-2.69 (m, 1H), 2.11-2.14 (m, 1H).

N-(4-Chlorophenyl)-1-(2,3-dihydro-1H-inden-1-yl)-2-oxo-1,2-dihydropyridine-3-carboxamide (3)

Retention time (min)=8.869, method [7], MS (ESI) 365.0 (M+H); $^1$H NMR (300 MHz, CDCl$_3$) δ 12.17 (s, 1H), 8.59

(dd, 1H), 7.74 (d, 2H), 7.28-7.39 (m, 5H), 7.21 (dd, 1H), 7.19 (d, 1H), 6.61 (q, 1H), 6.39 (t, 1H), 2.99-3.16 (m, 1H), 2.79-2.91 (m, 1H), 1.97-2.09 (m, 1H).

(S)-1-(2,3-Dihydro-1H-inden-1-yl)-2-oxo-N-(pyridin-4-yl)-1,2-dihydropyridine-3-carboxamide (4)

Retention time (min)=2.691, method [7], MS (ESI) 332.1 (M+H); $^1$H NMR (300 MHz, DMSO-d6) δ 12.38 (s, 1H), 843-8.47 (m, 3H), 7.69 (d, 2H), 7.59 (d, 1H), 7.40 (m, 2H), 7.35 (m, 1H), 7.24 (t, 1H), 7.15 (d, 1H), 6.50-6.59 (m, 2H), 3.02-3.18 (m, 12H), 2.70-2.99 (m, 1H), 2.62-2.68 (m, 1H), 2.02-2.14 (m, 1H).

(S)—N-(4-Chlorophenyl)-1-(2,3-dihydro-1H-inden-1-yl)-2-oxo-1,2-dihydropyridine-3-carboxamide (5)

Retention time (min)=8.464, method [7], MS (ESI) 365.1 (M+H); $^1$H NMR (300 MHz, CDCl$_3$) δ 12.18 (s, 1H), 8.58 (d, 1H), 7.74 (d, 2H), 7.28-7.39 (m, 5H), 7.21 (d, 1H), 7.19 (d, 1H), 6.61 (q, 1H), 6.39 (t, 1H), 2.91-3.18 (m, 1H), 2.79-2.89 (m, 1H), 2.05-2.09 (m, 1H).

(R)—N-(4-Chlorophenyl)-1-(2,3-dihydro-1H-inden-1-yl)-2-oxo-1,2-dihydropyridine-3-carboxamide (6)

Retention time (min)=9.461, method [7], MS (ESI) 365.1 (M+H); $^1$H NMR (300 MHz, CDCl$_3$) δ 12.16 (s, 1H), 8.60 (d, 1H), 7.74 (d, 2H), 7.28-7.39 (m, 5H), 7.21 (d, 1H), 7.19 (d, 1H), 6.61 (q, 1H), 6.39 (t, 1H), 2.91-3.16 (m, 1H), 2.79-2.89 (m, 1H), 2.05-2.09 (m, 1H).

N-(4-Chlorophenyl)-1-((1S,2R)-2-hydroxy-2,3-dihydro-1H-inden-1-yl)-2-oxo-1,2-dihydropyridine-3-carboxamide (7)

Retention time (min)=7.443, method [7], MS (ESI) 381.1 (M+H); $^1$H NMR (300 MHz, CDCl$_3$) δ 12.06 (s, 1H), 8.51 (dd, 1H), 7.68 (d, 2H), 7.28-7.40 (m, 5H), 7.22 (m, 1H), 7.13 (d, 1H), 6.44 (d, 1H), 6.37 (t, 1H), 4.97 (m, 1H), 3.36 (dd, 1H), 3.05 (dd, 1H), 2.81 (d, 1H).

1-((1S,2R)-2-Hydroxy-2,3-dihydro-1H-inden-1-yl)-2-oxo-N-(pyridin-4-yl)-1,2-dihydropyridine-3-carboxamide (8)

Retention time (min)=1.869, method [7], MS (ESI) 348.1 (M+H); $^1$H NMR (300 MHz, DMSO-d6) δ 12.42 (s, 1H), 8.45-8.50 (m, 3H), 7.69 (d, 2H), 7.49 (d, 1H), 7.23-7.39 (m, 3H), 7.08 (d, 1H), 6.57 (t, 1H), 6.48 (d, 1H), 5.31 (d, 1H), 4.66 (m, 1H), 3.24 (m, 1H), 2.90-2.96 (d, 1H).

N-(4-Chlorophenyl)-1-((1R,2S)-2-hydroxy-2,3-dihydro-1H-inden-1-yl)-2-oxo-1,2-dihydropyridine-3-carboxamide (9)

Retention time (min)=7.441, method [7], MS (ESI) 381.1 (M+H); $^1$H NMR (300 MHz, CDCl$_3$) δ 12.09 (s, 1H), 8.51 (d, 1H), 7.66 (d, 2H), 7.23-7.39 (m, 5H), 7.22 (m, 1H), 7.13 (d, 1H), 6.44 (d, 1H), 6.37 (t, 1H), 4.99 (m, 1H), 3.37 (dd, 1H), 3.05 (dd, 1H), 2.81 (d, 1H).

1-((1R,2S)-2-Hydroxy-2,3-dihydro-1H-inden-1-yl)-2-oxo-N-(pyridin-4-yl)-1,2-dihydropyridine-3-carboxamide (10)

Retention time (min)=1.882, method [7], MS (ESI) 348.1 (M+H); $^1$H NMR (300 MHz, DMSO-d6) δ 12.44 (s, 1H), 8.45-8.50 (m, 3H), 7.68 (d, 2H), 7.49 (d, 1H), 7.23-7.39 (m, 3H), 7.08 (d, 1H), 6.57 (t, 1H), 6.48 (d, 1H), 5.31 (d, 1H), 4.64 (m, 1H), 3.24 (m, 1H), 2.96 (d, 1H).

Example 2

2.1. Synthesis of N-(4-chlorophenyl)-1-(4-methoxy-2,3-dihydro-1H-inden-1-yl)-2-oxo-1,2-dihydropyridine-3-carboxamide (11)

Protocol D

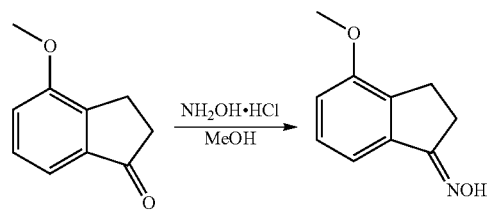

To a solution of 4-methoxy-2,3-dihydro-1H-inden-1-one (1.0 g, 1.0 eq.) in 25 ml MeOH was added NH$_2$OH.HCl (0.493 g, 1.15 eq.) and sodium acetate (0.597 g, 1.18 eq.). The resulting mixture was stirred at room temperature overnight. The reaction mixture was diluted with 100 ml ice-water. The white precipitate was collected by filtration, washed with 3×20 ml water and dried in vacuo to afford 1.08 g (yield 99%) 4-methoxy-2,3-dihydro-1H-inden-1-one oxime which was used to next step without further purification.

Protocol E

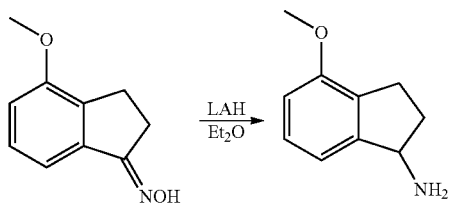

A solution of 4-methoxy-2,3-dihydro-1H-inden-1-one oxime (1.0 g, 1.0 eq.) in 40 ml dry ether was cooled to −78° C. under N$_2$ atmosphere. Then LiAlH$_4$ in ether solution (30 ml, 1M, 5.5 eq.) was added to reaction dropwise. The resulting mixture was stirred at −78° C. for 10 minutes, and gradually warmed to room temperature. Then the mixture was heated at refluxing overnight. The reaction mixture was diluted with 50 ml ether and quenched by sequentially adding 1.2 ml water, 1.2 ml 15% NaOH aqueous solution and 3.4 ml water. The mixture was filtered through celite pad. The inorganic solid was rinsed with 3×20 ml ether. The organic phase was dried over Na$_2$SO$_4$, and evaporated in vacuo to afford a clear oil 0.5 g (yield 54.3%) 4-methoxy-2,3-dihydro-1H-inden-1-amine which was used to next step without further purification.

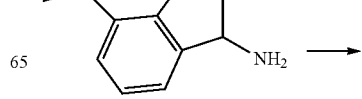

-continued

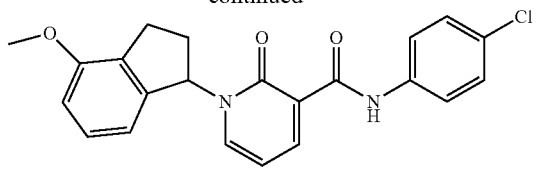

Following Protocols A, B and C, 4-methoxy-2,3-dihydro-1H-inden-1-amine was converted to N-(4-chlorophenyl)-1-(4-methoxy-2,3-dihydro-1H-inden-1-yl)-2-oxo-1,2-dihydropyridine-3-carboxamide. Retention time (min)=9.577, method [7], MS (ESI) 395.1 (M+H); $^1$H NMR (300 MHz, CDCl$_3$) δ 12.18 (s, 1H), 8.58 (d, 1H), 7.73 (d, 2H), 7.19-7.32 (m, 4H), 6.84 (d, 1H), 6.71 (d, 1H), 6.60 (t, 1H), 6.38 (t, 1H), 3.88 (s, 3H), 2.90-3.09 (m, 2H), 2.81-2.88 (m, 1H), 1.97-2.06 (m, 1H).

2.2. Synthesis of Additional Compounds

The following compounds were synthesized from appropriate starting materials using Protocols D, E, A, B and C above or slightly modified versions thereof.

1-(6-Methoxy-2,3-dihydro-1H-inden-1-yl)-2-oxo-N-(pyridin-4-yl)-1,2-dihydropyridine-3-carboxamide (12)

Retention time (min)=3.113, method [7], MS (ESI) 362.1 (M+H); $^1$H NMR (300 MHz, DMSO-d6) δ 12.41 (s, 1H), 8.42-8.47 (m, 3H), 7.69 (d, 2H), 7.53 (d, 1H), 7.28 (d, 1H), 6.89 (d, 1H), 6.71 (s, 1H), 6.56 (t, 1H), 6.47 (m, 1H), 3.65 (s, 3H), 3.01-3.08 (m, 1H), 2.71-2.98 (m, 1H), 2.62-2.69 (m, 1H), 2.06-2.11 (m, 1H).

N-(4-chlorophenyl)-1-(6-methoxy-2,3-dihydro-1H-inden-1-yl)-2-oxo-1,2-dihydropyridine-3-carboxamide (13)

Retention time (min)=9.412, method [7], MS (ESI) 395.1 (M+H); $^1$H NMR (300 MHz, CDCl$_3$) δ 12.18 (s, 1H), 8.59 (dd, 1H), 7.75 (d, 2H), 7.19-7.32 (m, 4H), 6.90 (d, 1H), 6.55-6.61 (m, 2H), 6.40 (t, 1H), 3.75 (s, 3H), 2.90-3.08 (m, 2H), 2.78-2.88 (m, 1H), 1.97-2.09 (m, 1H).

N-(4-chlorophenyl)-1-(5-methoxy-2,3-dihydro-1H-inden-1-yl)-2-oxo-1,2-dihydropyridine-3-carboxamide (14)

Retention time (min)=9.404, method [7], MS (ESI) 417.1 (M+Na); $^1$H NMR (300 MHz, CDCl$_3$) δ 12.19 (s, 1H), 8.58 (dd, 1H), 7.74 (d, 2H), 7.32 (d, 2H), 7.18 (d, 1H), 7.06 (d, 1H), 6.89 (s, 1H), 6.83 (d, 1H), 6.49 (m, 1H), 6.37 (t, 1H), 3.83 (s, 3H), 2.90-3.13 (m, 2H), 2.78-2.87 (m, 1H), 1.99-2.09 (m, 1H).

1-(6-methoxy-2,3-dihydro-1H-inden-1-yl)-2-oxo-N-(pyridin-4-yl)-1,2-dihydropyridine-3-carboxamide (15)

Retention time (min)=3.067, method [7], MS (ESI) 362.1 (M+H); $^1$H NMR (300 MHz, CDCl$_3$) δ 12.39 (s, 1H), 8.50-8.59 (m, 3H), 7.68 (d, 2H), 7.23 (d, 1H), 7.04 (d, 1H), 6.84 (s, 1H), 6.50 (d, 1H), 6.47 (m, 1H), 6.38 (t, 1H), 3.82 (s, 3H), 2.91-3.11 (m, 2H), 2.79-2.88 (m, 1H), 1.99-2.10 (m, 1H).

1-(6-bromo-2,3-dihydro-1H-inden-1-yl)-N-(4-chlorophenyl)-2-oxo-1,2-dihydropyridine-3-carboxamide (16)

Retention time (min)=10.360, method [7], MS (ESI) 445.0 (M+H); $^1$H NMR (300 MHz, CDCl$_3$) δ 12.11 (s, 1H), 8.59 (dd, 1H), 7.73 (d, 2H), 7.46 (d, 1H), 7.20-7.33 (m, 5H), 6.61 (t, 1H), 6.45 (t, 1H), 2.91-3.08 (m, 2H), 2.79-2.89 (m, 1H), 2.07-2.11 (m, 1H).

1-(6-bromo-2,3-dihydro-1H-inden-1-yl)-2-oxo-N-(pyridin-4-yl)-1,2-dihydropyridine-3-carboxamide (17)

Retention time (min)=3.842, method [7], MS (ESI) 411.1 (M+H); $^1$H NMR (300 MHz, CDCl$_3$) δ 12.27 (s, 1H), 8.61 (d, 1H), 8.58 (d, 2H), 7.58 (d, 2H), 7.46 (d, 1H), 7.18-7.38 (m, 2H), 6.61 (t, 1H), 6.44 (t, 1H), 2.90-3.14 (m, 2H), 2.80-2.89 (m, 1H), 1.84-2.09 (m, 1H).

1-(4-methoxy-2,3-dihydro-1H-inden-1-yl)-2-oxo-N-(pyridin-4-yl)-1,2-dihydropyridine-3-carboxamide (18)

Retention time (min)=3.095, method [7], MS (ESI) 362.2 (M+H); $^1$H NMR (300 MHz, DMSO-d6) δ 12.37 (s, 1H), 8.41-8.47 (m, 3H), 7.69 (d, 2H), 7.58 (d, 1H), 7.25 (t, 1H), 6.93 (d, 1H), 6.70 (d, 1H), 6.49-6.58 (m, 2H), 3.81 (s, 3H), 3.00-3.08 (m, 1H), 2.71-2.98 (m, 1H), 2.65-2.69 (m, 1H), 2.03-2.12 (m, 1H).

1-(7-methoxy-2,3-dihydro-1H-inden-1-yl)-2-oxo-N-(pyridin-4-yl)-1,2-dihydropyridine-3-carboxamide (19)

Retention time (min)=2.848, method [7], MS (ESI) 362.0 (M+H); $^1$H NMR (300 MHz, DMSO-d6) δ 12.43 (s, 1H), 8.42-8.47 (m, 3H), 7.69 (d, 2H), 7.00-7.39 (m, 2H), 6.97 (d, 1H), 6.88 (d, 1H), 6.51 (t, 1H), 6.38 (m, 1H), 3.61 (s, 3H), 2.90-3.08 (m, 1H), 2.71-2.88 (m, 1H), 2.61-2.69 (m, 1H), 1.97-2.04 (m, 1H).

N-(7-chlorophenyl)-1-(4-methoxy-2,3-dihydro-1H-inden-1-yl)-2-oxo-1,2-dihydropyridine-3-carboxamide (20)

Retention time (min)=8.530, method [7], MS (ESI) 395.1 (M+H); $^1$H NMR (300 MHz, CDCl$_3$) δ 12.22 (s, 1H), 8.57 (d, 1H), 7.75 (d, 2H), 7.27-7.39 (m, 3H), 7.10 (d, 1H), 6.97 (d, 1H), 6.74 (d, 1H), 6.49 (m, 1H), 6.38 (t, 1H), 3.68 (s, 3H), 2.94-3.15 (m, 2H), 2.75-2.88 (m, 1H), 2.04-2.11 (m, 1H).

N-(4-chlorophenyl)-1-(3-methyl-2,3-dihydro-1H-inden-1-yl)-2-oxo-1,2-dihydropyridine-3-carboxamide (21)

Retention time (min)=9.284, method [7], MS (ESI) 379.0 (M+H); $^1$H NMR (300 MHz, CDCl$_3$) δ 12.16 (s, 1H), 8.62 (dd, 1H), 7.74 (d, 2H), 7.24-7.45 (m, 6H), 6.98 (d, 1H), 6.63 (m, 1H), 6.46 (t, 1H), 3.19-3.39 (m, 1H), 2.97-3.12 (m, 1H), 1.52 (m, 1H), 1.46 (d, 3H)

1-(3-methyl-2,3-dihydro-1H-inden-1-yl)-2-oxo-N-(pyridin-4-yl)-1,2-dihydropyridine-3-carboxamide (22)

Retention time (min)=3.413, method [7], MS (ESI) 346.1 (M+H); $^1$H NMR (300 MHz, DMSO-d6) δ 12.99 (s, 1H), 8.76

(d, 2H), 8.63 (d, 1H), 8.21 (d, 2H), 7.85 (d, 1H), 7.31-7.49 (m, 3H), 7.26 (t, 1H), 6.97 (d, 1H), 6.68 (t, 1H), 6.49-6.57 (m, 1H), 3.22-3.33 (m, 1H), 2.84-2.95 (m, 1H), 2.65-2.69 (m, 1H), 1.65-1.78 (m, 1H), 1.36 (d, 3H).

1-(4-bromo-2,3-dihydro-1H-inden-1-yl)-2-oxo-N-(pyridin-4-yl)-1,2-dihydropyridine-3-carboxamide (23)

Retention time (min)=3.715, method [7], MS (ESI) 411.0 (M+H); $^1$H NMR (300 MHz, DMSO-d6) δ 12.34 (s, 1H), 8.52-8.61 (m, 3H), 7.67 (d, 2H), 7.52 (d, 1H), 7.27 (m, 1H), 7.15 (t, 1H), 7.05 (d, 1H), 6.71 (t, 1H), 6.45 (t, 1H), 2.91-3.22 (m, 2H), 2.84-2.90 (m, 1H), 2.00-2.11 (m, 1H).

1-(4-bromo-2,3-dihydro-1H-inden-1-yl)-N-(4-chlorophenyl)-2-oxo-1,2-dihydropyridine-3-carboxamide (24)

Retention time (min)=9.577, method [7], MS (ESI) 395.1 (M+H); $^1$H NMR (300 MHz, CDCl$_3$) δ 12.08 (s, 1H), 8.57 (dd, 1H), 7.69 (d, 2H), 7.49 (d, 1H), 7.28 (d, 2H), 7.19 (m, 1H), 7.13 (t, 1H), 7.02 (d, 1H), 6.68 (t, 1H), 6.40 (t, 1H), 2.85-3.19 (m, 2H), 2.79-2.84 (m, 1H), 1.97-2.08 (m, 1H).

1-(4-methoxy-2,3-dihydro-1H-inden-1-yl)-2-oxo-N-(pyridin-4-yl)-1,2-dihydropyridine-3-carboxamide (25)

The title compound (enantiomer A) was obtained through chiral separation of the racemic mixture. Retention time (min)=6.118, method [7], MS (ESI) 362.1 (M+H); $^1$H NMR (300 MHz, CDCl$_3$) δ 12.37 (s, 1H), 8.58 (dd, 1H), 8.52 (d, 2H), 7.69 (d, 2H), 7.23-7.29 (m, 2H), 6.85 (d, 1H), 6.71 (d, 1H), 6.60 (m, 1H), 6.40 (t, 1H), 3.88 (s, 3H), 2.91-3.09 (m, 2H), 2.79-2.89 (m, 1H), 1.96-2.07 (m, 1H).

1-(4-methoxy-2,3-dihydro-1H-inden-1-yl)-2-oxo-N-(pyridin-4-yl)-1,2-dihydropyridine-3-carboxamide (26)

The title compound (enantiomer B) was obtained through chiral separation of the racemic mixture. Retention time (min)=6.123, method [7], MS (ESI) 362.1 (M+H); $^1$H NMR (300 MHz, CDCl$_3$) δ 12.34 (s, 1H), 8.55 (dd, 1H), 8.49 (d, 2H), 7.65 (d, 2H), 7.20-7.26 (m, 2H), 6.82 (d, 1H), 6.69 (d, 1H), 6.58 (m, 1H), 6.37 (t, 1H), 3.85 (s, 3H), 2.91-3.08 (m, 2H), 2.76-2.88 (m, 1H), 1.93-2.04 (m, 1H).

N-(biphenyl-4-yl)-1-(4-methoxy-2,3-dihydro-1H-inden-1-yl)-2-oxo-1,2-dihydropyridine-3-carboxamide (27)

Retention time (min)=10.542, method [7], MS (ESI) 437.2 (M+H); $^1$H NMR (300 MHz, CDCl$_3$) δ 12.19 (s, 1H), 8.59 (dd, 1H), 7.82 (d, 2H), 7.56-7.59 (m, 4H), 7.30-7.42 (m, 2H), 7.17-7.28 (m, 3H), 6.82 (d, 1H), 6.70 (d, 1H), 6.61 (m, 1H), 6.36 (t, 1H), 3.86 (s, 3H), 2.91-3.09 (m, 2H), 2.77-2.89 (m, 1H), 1.94-2.05 (m, 1H).

1-(4-methoxy-2,3-dihydro-1H-inden-1-yl)-2-oxo-N-(4-phenoxyphenyl)-1,2-dihydropyridine-3-carboxamide (28)

Retention time (min)=10.455, method [7], MS (ESI) 453.2 (M+H); $^1$H NMR (300 MHz, CDCl$_3$) δ 12.09 (s, 1H), 8.59 (dd, 1H), 7.76 (d, 2H), 7.18-7.32 (m, 4H), 6.95-7.12 (m, 5H), 6.84 (d, 1H), 6.74 (d, 1H), 6.63 (m, 1H), 6.37 (t, 1H), 3.91 (s, 3H), 2.95-3.12 (m, 2H), 2.78-2.93 (m, 1H), 1.96-2.08 (m, 1H).

N-(4-bromophenyl)-1-(4-methoxy-2,3-dihydro-1H-inden-1-yl)-2-oxo-1,2-dihydropyridine-3-carboxamide (29)

Retention time (min)=9.797, method [7], MS (ESI) 441.1 (M+H); $^1$H NMR (300 MHz, CDCl$_3$) δ 12.19 (s, 1H), 8.58 (dd, 1H), 7.68 (d, 2H), 7.45 (d, 2H), 7.19-7.28 (m, 2H), 6.84 (d, 1H), 6.71 (d, 1H), 6.60 (m, 1H), 6.38 (t, 1H), 3.88 (s, 3H), 2.86-3.09 (m, 2H), 2.78-2.84 (m, 1H), 1.95-2.06 (m, 1H).

1-(4-isopropoxy-2,3-dihydro-1H-inden-1-yl)-2-oxo-N-(pyridin-4-yl)-1,2-dihydropyridine-3-carboxamide (30)

Retention time (min)=4.451, method [7], MS (ESI) 390.1 (M+H); $^1$H NMR (300 MHz, DMSO-d6) δ 12.39 (s, 1H), 8.58 (dd, 1H), 8.52 (d, 2H), 7.68 (d, 2H), 7.19-7.28 (m, 2H), 6.83 (d, 1H), 6.68 (d, 1H), 6.57 (m, 1H), 6.40 (t, 1H), 4.56-4.64 (m, 2H), 2.90-3.10 (m, 2H), 2.77-2.86 (m, 1H), 1.94-2.05 (m, 1H), 1.35-1.40 (m, 3H).

N-(4-chlorophenyl)-1-(4-isopropoxy-2,3-dihydro-1H-inden-1-yl)-2-oxo-1,2-dihydropyridine-3-carboxamide (31)

Retention time (min)=10.240, method [7], MS (ESI) 423.1 (M+H); $^1$H NMR (300 MHz, CDCl$_3$) δ 12.16 (s, 1H), 8.55 (dd, 1H), 7.70 (d, 2H), 7.16-7.30 (m, 4H), 6.81 (d, 1H), 6.64 (d, 1H), 6.54 (m, 1H), 6.36 (t, 1H), 4.53-4.61 (m, 2H), 2.83-3.05 (m, 2H), 2.74-2.81 (m, 1H), 1.90-2.02 (m, 1H), 1.32-1.37 (m, 3H).

1-(4-methoxy-2,3-dihydro-1H-inden-1-yl)-2-oxo-N-(4-phenoxyphenyl)-1,2-dihydropyridine-3-carboxamide (32)

The title compound (enantiomer A) was obtained through chiral separation of the racemic mixture. Retention time (min)=10.451, method [7], MS (ESI) 453.2 (M+H); $^1$H NMR (300 MHz, CDCl$_3$) δ 12.09 (s, 1H), 8.59 (dd, 1H), 7.74 (d, 2H), 7.18-7.34 (m, 4H), 6.98-7.09 (m, 5H), 6.84 (d, 1H), 6.73 (d, 1H), 6.63 (m, 1H), 6.38 (t, 1H), 3.88 (s, 3H), 2.93-3.11 (m, 2H), 2.79-2.91 (m, 1H), 1.96-2.07 (m, 1H).

1-(4-methoxy-2,3-dihydro-1H-inden-1-yl)-2-oxo-N-(4-phenoxyphenyl)-1,2-dihydropyridine-3-carboxamide (33)

The title compound (enantiomer B) was obtained through chiral separation of the racemic mixture. Retention time (min)=10.452, method [7], MS (ESI) 453.2 (M+H); $^1$H NMR (300 MHz, CDCl$_3$) δ 12.07 (s, 1H), 8.56 (dd, 1H), 7.74 (d, 2H), 7.16-7.31 (m, 4H), 6.95-7.07 (m, 5H), 6.81 (d, 1H), 6.70 (d, 1H), 6.59 (m, 1H), 6.35 (t, 1H), 3.85 (s, 3H), 2.94-3.09 (m, 2H), 2.76-2.90 (m, 1H), 1.93-2.074 (m, 1H).

N-(biphenyl-4-yl)-1-(4-methoxy-2,3-dihydro-1H-inden-1-yl)-2-oxo-1,2-dihydropyridine-3-carboxamide (34)

The title compound (enantiomer A) was obtained through chiral separation of the racemic mixture. Retention time (min)=10.564, method [7], MS (ESI) 437.2 (M+H); $^1$H NMR (300 MHz, CDCl$_3$) δ 12.21 (s, 1H), 8.61 (dd, 1H), 7.86 (d, 2H), 7.59-7.62 (m, 4H), 7.30-7.44 (m, 2H), 7.19-7.29 (m, 3H), 6.84 (d, 1H), 6.73 (d, 1H), 6.62 (m, 1H), 6.39 (t, 1H), 3.89 (s, 3H), 2.90-3.12 (m, 2H), 2.80-2.89 (m, 1H), 1.97-2.08 (m, 1H).

N-(biphenyl-4-yl)-1-(4-methoxy-2,3-dihydro-1H-inden-1-yl)-2-oxo-1,2-dihydropyridine-3-carboxamide (35)

The title compound (enantiomer B) was obtained through chiral separation of the racemic mixture. Retention time (min)=10.564, method [7], MS (ESI) 437.2 (M+H); $^1$H NMR (300 MHz, CDCl$_3$) δ 12.21 (s, 1H), 8.58 (dd, 1H), 7.83 (d, 2H), 7.55-7.59 (m, 4H), 7.39-7.42 (m, 2H), 7.17-7.31 (m, 3H), 6.82 (d, 1H), 6.71 (d, 1H), 6.61 (m, 1H), 6.36 (t, 1H), 3.86 (s, 3H), 2.91-3.08 (m, 2H), 2.79-2.89 (m, 1H), 1.947-2.05 (m, 1H).

1-(4-bromo-2,3-dihydro-1H-inden-1-yl)-2-oxo-N-(pyridin-4-yl)-1,2-dihydropyridine-3-carboxamide (36)

The title compound (enantiomer A) was obtained through chiral separation of the racemic mixture. Retention time (min)=3.960, method [7], MS (ESI) 411.0 (M+H); $^1$H NMR (300 MHz, DMSO-d6) δ 12.32 (s, 1H), 8.60 (dd, 1H), 8.52 (d, 2H), 7.67 (d, 2H), 7.52 (d, 1H), 7.27 (m, 1H), 7.15 (t, 1H), 7.05 (d, 1H), 6.71 (m, 1H), 6.45 (t, 1H), 3.01-3.22 (m, 2H), 2.83-2.94 (m, 1H), 2.00-2.11 (m, 1H).

1-(4-bromo-2,3-dihydro-1H-inden-1-yl)-2-oxo-N-(pyridin-4-yl)-1,2-dihydropyridine-3-carboxamide (37)

The title compound (enantiomer B) was obtained through chiral separation of the racemic mixture. Retention time (min)=3.933, method [7], MS (ESI) 411.0 (M+H); $^1$H NMR (300 MHz, DMSO-d6) δ 12.32 (s, 1H), 8.60 (dd, 1H), 8.52 (d, 2H), 7.67 (d, 2H), 7.52 (d, 1H), 7.27 (m, 1H), 7.15 (t, 1H), 7.05 (d, 1H), 6.71 (m, 1H), 6.45 (t, 1H), 2.98-3.18 (m, 2H), 2.80-2.92 (m, 1H), 2.97-2.09 (m, 1H).

1-(4-methoxy-2,3-dihydro-1H-inden-1-yl)-2-oxo-N-(4-(trifluoromethoxy)phenyl)-1,2-dihydropyridine-3-carboxamide (38)

Retention time (min)=10.216, method [7], MS (ESI) 445.1 (M+H); $^1$H NMR (300 MHz, CDCl$_3$) δ 12.22 (s, 1H), 8.58 (d, 1H), 7.79 (d, 2H), 7.18-7.29 (m, 4H), 6.84 (d, 1H), 6.72 (d, 1H), 6.60 (m, 1H), 6.39 (t, 1H), 3.88 (s, 3H), 2.93-3.11 (m, 2H), 2.79-2.91 (m, 1H), 1.96-2.07 (m, 1H).

N-cyclohexyl-1-(4-methoxy-2,3-dihydro-1H-inden-1-yl)-2-oxo-1,2-dihydropyridine-3-carboxamide (39)

Retention time (min)=7.962, method [7], MS (ESI) 367.2 (M+H); $^1$H NMR (300 MHz, DMSO-d6) δ 9.83 (m, 1H), 8.49 (d, 1H), 7.20-7.25 (m, 1H), 7.10-7.13 (m, 1H), 6.82 (d, 1H), 6.68 (d, 1H), 6.58 (m, 1H), 6.29 (t, 1H), 3.99-4.01 (m, 1H), 3.86 (s, 3H), 2.92-3.08 (m, 2H), 2.76-2.89 (m, 1H), 1.92-2.00 (m, 3H), 1.72-1.90 (m, 3H), 1.26-1.48 (m, 5H).

N-(4-fluorophenyl)-1-(4-methoxy-2,3-dihydro-1H-inden-1-yl)-2-oxo-1,2-dihydropyridine-3-carboxamide (40)

Retention time (min)=7.946, method [7], MS (ESI) 379.1 (M+H); $^1$H NMR (300 MHz, CDCl$_3$) δ 12.09 (s, 1H), 8.57 (dd, J=2.1 Hz, 7.2 Hz, 1H), 7.68-7.78 (m, 2H), 7.18-7.30 (overlap with CDCl$_3$, 2H), 7.02 (m, 2H), 6.82 (d, J=8.1 Hz, 1H), 6.70 (d, J=7.5 Hz, 1H), 6.58 (dd, J=5.7 Hz, 8.1 Hz, 1H), 6.40 (t, J=7.2 Hz, 1H), 3.87 (s, 3H), 2.75-3.10 (m, 3H), 1.95-2.05 (m, 1H).

N-(4-iodophenyl)-1-(4-methoxy-2,3-dihydro-1H-inden-1-yl)-2-oxo-1,2-dihydropyridine-3-carboxamide (41)

Retention time (min)=9.596, method [7], MS (ESI) 487.0 (M+H); $^1$H NMR (300 MHz, CDCl$_3$) δ 12.10 (s, 1H), 8.60 (dd, J=2.1 Hz, 7.2 Hz, 1H), 7.67 (d, J=8.7 Hz, 2H), 7.59 (d, J=8.7 Hz, 2H), 7.20-7.35 (overlap with CDCl$_3$, 2H), 6.87 (d, J=7.8 Hz, 1H), 6.74 (d, J=7.8 Hz, 1H), 6.60 (dd, J=5.7 Hz, 7.8 Hz, 1H), 6.41 (t, J=7.2 Hz, 1H), 3.92 (s, 3H), 2.80-3.14 (m, 3H), 1.95-2.05 (m, 1H).

1-(4-methoxy-2,3-dihydro-1H-inden-1-yl)-2-oxo-N-phenyl-1,2-dihydropyridine-3-carboxamide (42)

Retention time (min)=8.181, method [7], MS (ESI) 361.2 (M+H); $^1$H NMR (300 MHz, CDCl$_3$) δ 12.05 (s, 1H), 8.60 (dq, J=7.0 Hz, 1.2 Hz, 1H), 7.67 (d, J=8.4 Hz, 2H), 7.36 (t, J=8.4 Hz, 2H), 7.27 (overlap with CDCl$_3$, 1H), 7.20 ((dq, J=7.0 Hz, 1.2 Hz, 1H), 7.13 (t, J=7.5 Hz, 1H), 6.85 (d, J=8.1 Hz, 1H), 6.73 (d, J=7.5 Hz, 1H), 6.63 (dd, J=6.0 Hz, 7.8 Hz, 1H), 6.40 (t, J=7.0 Hz, 1H), 3.90 (s, 3H), 2.78-3.16 (m, 3H), 1.95-2.05 (m, 1H).

N-(4,4-difluorocyclohexyl)-1-(4-methoxy-2,3-dihydro-1H-inden-1-yl)-2-oxo-1,2-dihydropyridine-3-carboxamide (43)

Retention time (min)=7.374, method [7], MS (ESI) 403.2 (M+H); $^1$H NMR (300 MHz, CDCl$_3$) δ 10.00 (d, J=7.2 Hz, 1H), 8.49 (dd, J=7.0 Hz, 2.4 Hz, 1H), 7.26 (overlap with CDCl$_3$, 1H), 7.16 ((dd, J=7.0, 2.4 Hz, 1H), 6.83 (d, J=8.1 Hz, 1H), 6.69 (d, J=7.5 Hz, 1H), 6.56 (dd, J=5.7 Hz, 8.1 Hz, 1H), 6.33 (t, J=7.0 Hz, 1H), 4.05-4.20 (m, 1H), 3.88 (s, 3H), 2.78-3.16 (m, 3H), 1.85-2.12 (m, 9H).

N-(3,4-difluorophenyl)-1-(4-methoxy-2,3-dihydro-1H-inden-1-yl)-2-oxo-1,2-dihydropyridine-3-carboxamide (44)

Retention time (min)=9.140, method [7], MS (ESI) 419.1 (M+Na); $^1$H NMR (300 MHz, CDCl$_3$) δ 12.22 (s, 1H), 8.58 (dd, J=2.1 Hz, 7.0 Hz, 1H), 7.87-7.95 (m, 1H), 7.20-7.35 (overlap with CDCl$_3$, 2H), 7.13 (q, J=8.7 Hz, 1H), 7.02 (m, 2H), 6.86 (d, J=8.1 Hz, 1H), 6.73 (d, J=7.8 Hz, 1H), 6.60 (dd, J=5.4 Hz, 8.4 Hz, 1H), 6.41 (t, J=7.0 Hz, 1H), 3.89 (s, 3H), 2.78-3.13 (m, 3H), 1.95-2.05 (m, 1H).

1-(4-methoxy-2,3-dihydro-1H-inden-1-yl)-N-(4-(4-methoxyphenoxy)phenyl)-2-oxo-1,2-dihydropyridine-3-carboxamide (45)

Retention time (min)=10.129, method [7], MS (ESI) 483.2 (M+H); $^1$H NMR (300 MHz, CDCl$_3$) δ 12.06 (s, 1H), 8.59 (m, 1H), 7.71 (d, J=8.7 Hz, 2H), 7.20-7.35 (overlap with CDCl$_3$, 3H), 6.87 (t, J=9.3 Hz, 4H), 6.80-6.92 (m, 3H), 6.73 (m, 1H), 6.41 (t, J=7.0 Hz, 1H), 3.89 (s, 3H), 3.80 (s, 3H), 2.78-3.13 (m, 3H), 1.95-2.05 (m, 1H).

Example 3

3.1. Synthesis of 1-(4-cyclopropyl-2,3-dihydro-1H-inden-1-yl)-2-oxo-N-(pyridin-4-yl)-1,2-dihydropyridine-3-carboxamide (46)

Protocol F

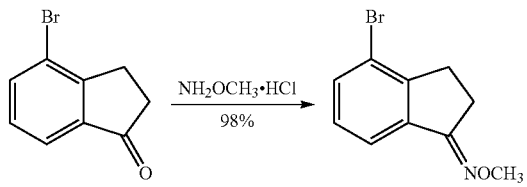

To a solution of 4-bromo-2,3-dihydro-1H-inden-1-one (2.2 g, 1.0 eq.) in 60 ml MeOH was added NH$_2$OCH$_3$.HCl (0.914 g, 1.15 eq.) and sodium acetate (0.924 g, 1.18 eq). The resulting mixture was stirred at room temperature overnight. The reaction solvent was removed in vacuo. The residue was diluted with 20 ml water and extracted by 2×50 ml ethyl acetate. The combined organic phase was washed with water, brine and dried over sodium sulfate. The solvent was removed in vacuo to afford clear oil 2.45 g (yield 98%) 4-bromo-2,3-dihydro-1H-inden-1-one O-methyl oxime which was used to next step without further purification.

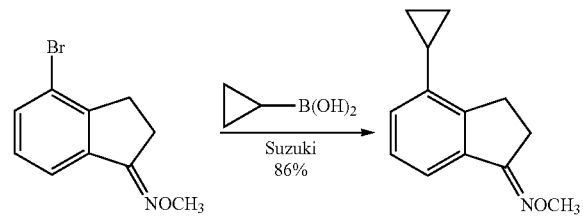

4-bromo-2,3-dihydro-1H-inden-1-one O-methyl oxime (1.0 g, 1.0 eq.), cyclopropylboronic acid (0.537, 1.5 eq.), Palladium acetate (0.094 g, 0.1 eq.), K$_3$PO$_4$ (3.09 g, 3.5 eq.) and tricyclohexylphosphine (0.234 g, 0.2 eq.) were combined in 50 ml Toluene and 1.6 ml water. The reaction mixture was heated at 100° C. for 3 hrs. The reaction mixture was filtered through a celite pad to remove inorganic salt. The filtrate was concentrated in vacuo, and the residue was directly purified on flash column to provide yellow oil 0.828 g (yield 99%) 4-cyclopropyl-2,3-dihydro-1H-inden-1-one O-methyl oxime.

Protocol H

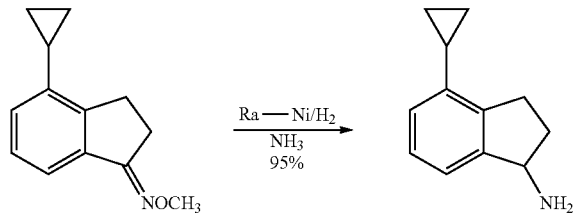

A solution of 4-cyclopropyl-2,3-dihydro-1H-inden-1-one O-methyl oxime (0.828 g) in 50 ml MeOH was saturated with NH$_3$ gas at 0° C., then added 3 ml Raney-Nickel in water. The mixture was hydrogenated (60 psi H2) at ambient temperature for 3 hrs. The catalyst was removed by filtration. The solvent was concentrated in vacuo to give green oil 0.6 g (yield 84%) 4-cyclopropyl-2,3-dihydro-1H-inden-1-amine which was used to next step without further purification.

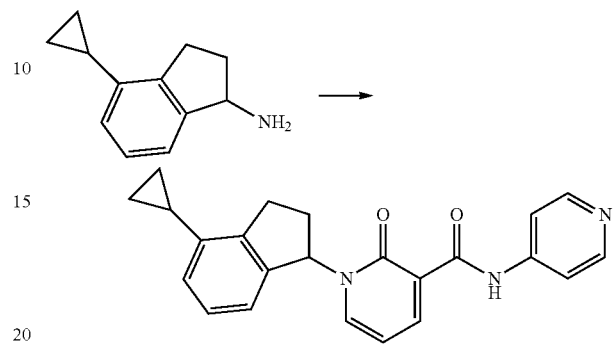

Following Protocol A, B and C$_{1-4}$-cyclopropyl-2,3-dihydro-1H-inden-Famine was converted to 1-(4-cyclopropyl-2,3-dihydro-1H-inden-1-yl)-2-oxo-N-(pyridin-4-yl)-1,2-dihydropyridine-3-carboxamide. Retention time (min)=4.435, method [7], MS (ESI) 372.2 (M+H); $^1$H NMR (300 MHz, DMSO-d6) δ 12.41 (s, 1H), 8.42-8.47 (m, 3H), 7.69 (d, 2H), 7.59 (d, 1H), 4.14 (t, 1H), 6.88 (d, 1H), 6.84 (d, 1H), 6.51-6.59 (m, 2H), 3.19 (m, 1H), 3.05 (m, 1H), 2.68 (m, 1H), 2.10 (m, 1H), 1.90 (m, 1H), 0.90-0.97 (m, 2H), 0.63-0.75 (m, 2H).

3.2. Synthesis of N-(4-chlorophenyl)-1-(4-cyclopropyl-2,3-dihydro-1H-inden-1-yl)-2-oxo-1,2-dihydropyridine-3-carboxamide (47)

The title compound was synthesized from appropriate starting materials using Protocols F, H, A, B and C above or slightly modified versions thereof.

Retention time (min)=10.978, method [7], MS (ESI) 405.1 (M+H); $^1$H NMR (300 MHz, CDCl$_3$) δ 12.13 (s, 1H), 8.59 (dd, 1H), 7.74 (d, 2H), 7.30 (d, 1H), 7.17-7.23 (m, 2H), 6.86-6.93 (m, 2H), 6.61 (m, 1H), 6.39 (t, 1H), 3.05-3.23 (m, 2H), 2.82-2.94 (m, 1H), 1.98-2.10 (m, 1H), 1.86-1.95 (m, 1H), 0.97-1.24 (m, 1H), 0.68-0.79 (m, 2H).

Example 4

4.1. Synthesis of 1-(7,8-dihydro-6H-indeno[5,4-d][1,3]dioxol-6-yl)-2-oxo-N-(pyridin-4-yl)-1,2-dihydropyridine-3-carboxamide (48)

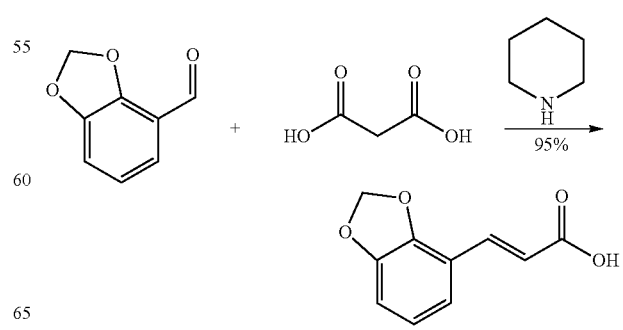

Benzo[d][1,3]dioxole-4-carbaldehyde (5.0 g, 1.0 eq.) was dissolved in 15 ml pyridine, then added malonic acid (6.58 g, 1.9 eq.) and piperidine (0.284 g, 0.1 eq.). The resulting mixture was heated at 105° C. for 3 hrs. After cooling to room temperature, the reaction mixture was poured into a solution of 25 ml concentrated HCl in 300 g ice. The white precipitate was collected by filtration; the solid was washed with 3×30 ml water and dried in air to afford white solid 6.2 g (yield 97%) (E)-3-(benzo[d][1,3]dioxol-4-yl)acrylic acid which was used without further purification.

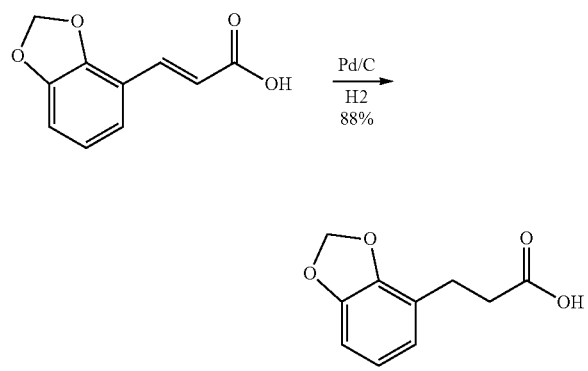 [SMILES: O=C(O)/C=C/c1cccc2c1OCO2 ; O=C(O)CCc1cccc2c1OCO2]

(E)-3-(benzo[d][1,3]dioxol-4-yl)acrylic acid was dissolved (5.5 g) in 150 ml 95% EtOH, added catalyst (0.55 g, 10% Palladium on carbon). The mixture was hydrogenated (60 psi H2) at ambient temperature for 3 hrs. The catalyst was removed by filtration. The solvent was evaporated in vacuo to give white solid 5 g (yield 90%) 3-(benzo[d][1,3]dioxol-4-yl)propanoic acid which was used without further purification.

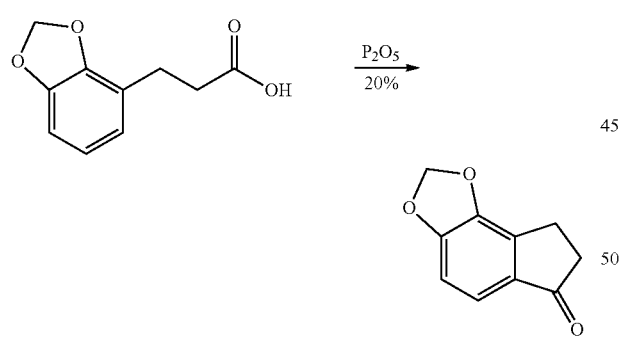

To a vigorously stirred mixture of $P_2O_5$ (15.6 g) in 100 ml dry benzene at reflux was added a solution of 3-(benzo[d][1,3]dioxol-4-yl)propanoic acid (5 g) in 50 ml benzene dropwise. The reaction kept refluxing for 45 mins, additional $P_2O_5$ (10 g) was added. After one hour, the reaction mixture was poured into 200 ml ice-water. The organic phase was separated and washed with 50 ml 1N NaOH aqueous solution and brine. The solvent was evaporated in vacuo to afford dark oil. The oil was purified on flash column in silica gel to provide yellow solid 0.889 g (yield 20%) 7,8-dihydro-6H-indeno[5,4-d][1,3]dioxol-6-one.

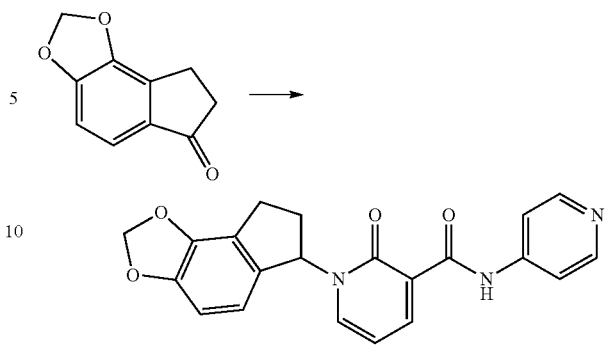

Following Protocol F, H, A, B and C, 7,8-dihydro-6H-indeno[5,4-d][1,3]dioxol-6-one was converted to 1-(7,8-dihydro-6H-indeno[5,4-d][1,3]dioxol-6-yl)-2-oxo-N-(pyridin-4-yl)-1,2-dihydropyridine-3-carboxamide. Retention time (min)=2.895, method [7], MS (ESI) 376.1 (M+H); $^1$H NMR (300 MHz, DMSO-d6) δ 12.39 (s, 1H), 8.41-8.47 (m, 3H), 7.68 (d, 2H), 7.60 (d, 1H), 6.82 (d, 1H), 6.65 (d, 1H), 6.53 (t, 1H), 6.38-6.42 (m, 1H), 6.05 (s, 3H), 2.91-3.08 (m, 1H), 2.83-2.89 (m, 1H), 2.63-2.675 (m, 1H), 2.02-2.17 (m, 1H).

4.2. Additional Compounds

The following compounds were synthesized from appropriate starting materials using the procedures outlined above in Example 4.1., or slightly modified versions thereof.

N-(4-chlorophenyl)-1-(7,8-dihydro-6H-indeno[5,4-d][1,3]dioxol-6-yl)-2-oxo-1,2-dihydropyridine-3-carboxamide (49)

Retention time (min)=9.105, method [7], MS (ESI) 431.1 (M+Na); $^1$H NMR (300 MHz, CDCl$_3$) δ 12.15 (s, 1H), 8.58 (dd, 1H), 7.73 (d, 2H), 7.31 (d, 2H), 7.20-7.28 (m, 1H), 6.77 (d, 1H), 6.47 (m, 1H), 6.39 (t, 1H), 6.02 (s, 2H), 2.97-3.03 (m, 2H), 2.78-2.90 (m, 1H), 2.01-2.14 (m, 1H).

N-(4-chlorophenyl)-2-oxo-1-(4-(trifluoromethoxy)-2,3-dihydro-1H-inden-1-yl)-1,2-dihydropyridine-3-carboxamide (50)

Retention time (min)=10.805, method [7], MS (ESI) 449.1 (M+H); $^1$H NMR (300 MHz, CDCl$_3$) δ 12.15 (s, 1H), 8.60 (d, 1H), 7.72 (d, 2H), 7.21-7.35 (m, 5H), 7.05 (d, 1H), 6.68 (t, 1H), 6.44 (t, 1H), 3.03-3.26 (m, 2H), 2.84-2.96 (m, 1H), 2.02-2.14 (m, 1H).

2-oxo-N-(pyridin-4-yl)-1-(4-(trifluoromethoxy)-2,3-dihydro-1H-inden-1-yl)-1,2-dihydropyridine-3-carboxamide (51)

Retention time (min)=4.679, method [7], MS (ESI) 416.1 (M+H); $^1$H NMR (300 MHz, DMSO-d6) δ 12.89 (s, 1H), 8.70 (d, 2H), 8.49 (dd, 1H), 8.17 (d, 2H), 7.82 (d, 1H), 7.31-7.41 (m, 2H), 7.17 (d, 1H), 6.55-6.66 (m, 2H), 3.16-3.26 (m, 1H), 2.96-3.07 (m, 1H), 2.68-2.80 (m, 1H), 2.14-2.26 (m, 1H).

Example 5

Synthesis of 1-(4-(methylthio)-2,3-dihydro-1H-inden-1-yl)-2-oxo-N-(pyridin-4-yl)-1,2-dihydropyridine-3-carboxamide (52)

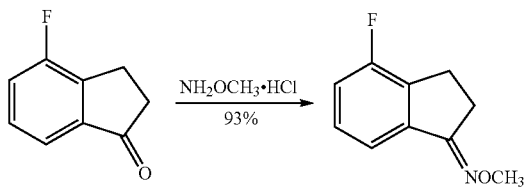

Following Protocol F, 4-fluoro-2,3-dihydro-1H-inden-1-one was converted to 4-fluoro-2,3-dihydro-1H-inden-1-one O-methyl oxime.

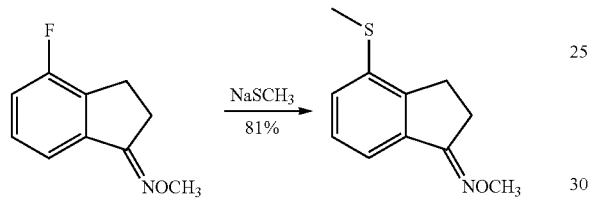

4-fluoro-2,3-dihydro-1H-inden-1-one O-methyl oxime (0.5 g, 1.0 eq) and sodium methanethiolate (0.215 g, 1.1 eq.) were combined in 20 ml dry DMF. The mixture was heated at 130° C. for 7 hrs under $N_2$ atmosphere. After reaction cooled to room temperature, the mixture was diluted with 60 ml ethyl acetate and 60 ml hexane, and washed with 3×50 ml water and brine. The crude mixture was purified on flash column in silica gel to provide white solid 0.47 g (yield 81%) 4-(methylthio)-2,3-dihydro-1H-inden-1-one O-methyl oxime.

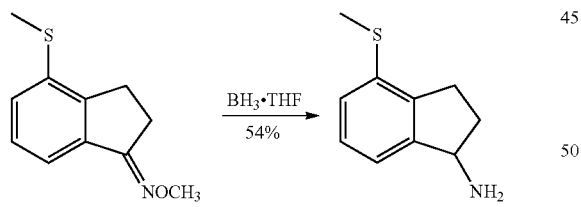

A solution of 4-(methylthio)-2,3-dihydro-1H-inden-1-one O-methyl oxime (0.47 g, 1.0 eq.) in 10 ml dry THF was cooled to 0° C. under $N_2$ atmosphere. Then Borane/THF complex (15 ml, 1M, 6.6 eq.) was added to reaction dropwise. The resulting mixture was stirred at room temperature for 10 minutes, and heated at refluxing overnight. The reaction was quenched by adding 100 ml ice-water. Then the mixture was extracted with 2×50 ml ethyl acetate. The combined organic phase was washed with 2N $Na_2CO_3$, and brine. Removal of solvent in vacuo afforded an oil 0.22 g (yield 54%) 4-(methylthio)-2,3-dihydro-1H-inden-1-amine which was used without further purification.

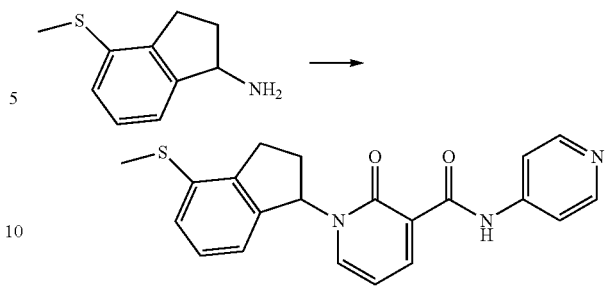

Following Protocol A, B and C, 4-(methylthio)-2,3-dihydro-1H-inden-1-amine was converted to 1-(4-(methylthio)-2,3-dihydro-1H-inden-1-yl)-2-oxo-N-(pyridin-4-yl)-1,2-dihydropyridine-3-carboxamide. Retention time (min)=3.590, method [7], MS (ESI) 378.1 (M+H); $^1H$ NMR (300 MHz, $CDCl_3$) δ 12.35 (s, 1H), 8.59 (dd, 1H), 8.52 (d, 2H), 7.69 (d, 2H), 7.23-7.31 (m, 2H), 7.16 (d, 1H), 6.89 (d, 1H), 6.62 (m, 1H), 6.42 (t, 1H), 3.00-3.08 (m, 1H), 2.92-3.08 (m, 1H), 2.84-2.91 (m, 1H), 2.53 (s, 3H), 1.99-2.11 (m, 1H).

Example 6

6.1. Synthesis of tert-butyl 4-(1-(2-oxo-3-(pyridin-4-ylcarbamoyl)pyridin-1(2H)-yl)-2,3-dihydro-1H-inden-4-yl)piperazine-1-carboxylate (53)

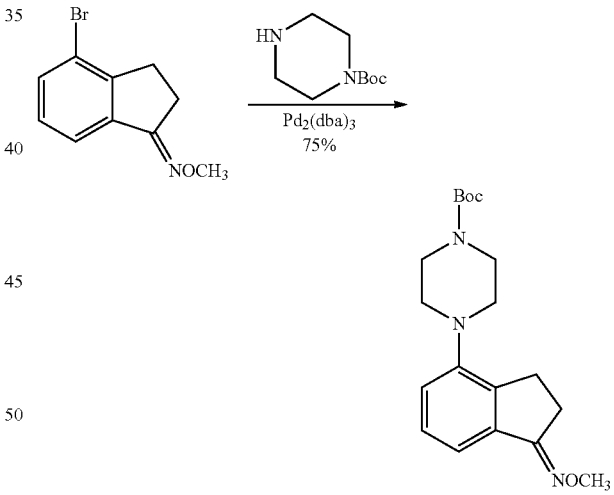

4-bromo-2,3-dihydro-1H-inden-1-one O-methyl oxime (2.5 g, 1.0 eq.), tert-butyl piperazine-1-carboxylate (2.91 g, 1.5 eq.), $Pd_2(dba)_3$ (0.76 g, 0.08 eq.), BINAP (0.63 g, 0.1 eq.) and Sodium t-butoxide (1.6 g, 1.6 eq.) were combined in 30 ml 1,4-dioxane. The reaction mixture was heated at 100° C. for 2.5 hrs under $N_2$. The reaction mixture was filtered through a celite pad to remove inorganic salt. The filtrate was concentrated in vacuo, and the residue mixture was directly purified on flash column to provide yellow solid 2.7 g (yield 75%) tert-butyl 4-(1-(methoxyimino)-2,3-dihydro-1H-inden-4-yl)piperazine-1-carboxylate.

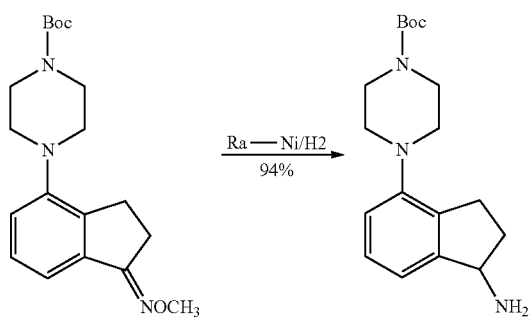

Following Protocol H, tert-butyl 4-(1-(methoxyimino)-2,3-dihydro-1H-inden-4-yl)piperazine-1-carboxylate was converted to tert-butyl 4-(1-amino-2,3-dihydro-1H-inden-4-yl)piperazine-1-carboxylate.

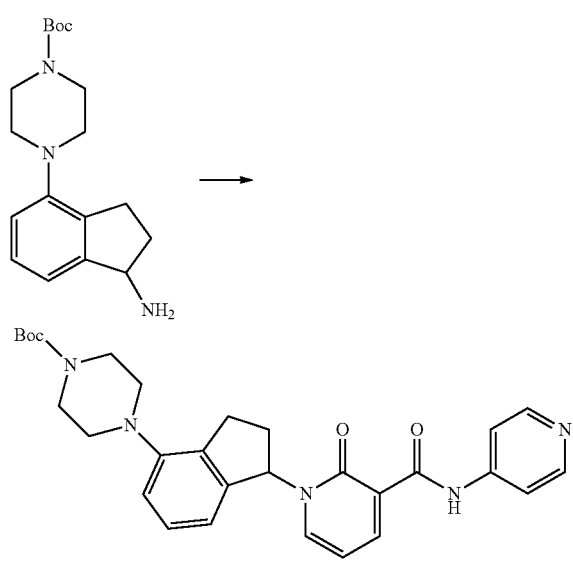

Following Protocol A, B and C, to tert-butyl 4-(1-amino-2,3-dihydro-1H-inden-4-yl)piperazine-1-carboxylate was converted to tert-butyl 4-(1-(2-oxo-3-(pyridin-4-ylcarbamoyl)pyridin-1(2H)-yl)-2,3-dihydro-1H-inden-4-yl)piperazine-1-carboxylate ( ) Retention time (min)=5.050, method [7], MS (ESI) 516.2 (M+H); $^1$H NMR (300 MHz, CDCl$_3$) δ 12.34 (s, 1H), 8.57 (dd, 1H), 8.50 (d, 2H), 7.66 (d, 2H), 7.20-7.27 (m, 2H), 6.87 (d, 1H), 6.74 (d, 1H), 6.56 (m, 1H), 6.39 (t, 1H), 3.54-3.57 (m, 4H), 2.91-3.08 (m, 6H), 2.76-2.88 (m, 1H), 1.95-2.06 (m, 1H), 1.46 (s, 9H).

6.2. Additional Compounds

The following compounds were synthesized from appropriate starting materials using the procedures outlined above in Example 6.1., or slightly modified versions thereof.

tert-butyl 4-(1-(3-(4-chlorophenylcarbamoyl)-2-oxopyridin-1(2H)-yl)-2,3-dihydro-1H-inden-4-yl)piperazine-1-carboxylate (54)

Retention time (min)=10.340, method [7], MS (ESI) 549.2 (M+H); $^1$H NMR (300 MHz, CDCl$_3$) δ 12.15 (s, 1H), 8.59 (dd, 1H), 7.73 (d, 2H), 7.32 (d, 2H), 7.20-7.28 (m, 2H), 6.89 (d, 1H), 6.76 (d, 1H), 6.60 (m, 1H), 6.40 (t, 1H), 3.57-3.60 (m, 4H), 2.90-3.09 (m, 6H), 2.78-2.89 (m, 1H), 1.97-2.09 (m, 1H), 1.48 (s, 9H).

1-(4-morpholino-2,3-dihydro-1H-inden-1-yl)-2-oxo-N-(pyridin-4-yl)-1,2-dihydropyridine-3-carboxamide (55)

Retention time (min)=2.219, method [7], MS (ESI) 417.2 (M+H); $^1$H NMR (300 MHz, CDCl$_3$) δ 12.37 (s, 1H), 8.59 (dd, 1H), 8.52 (d, 2H), 7.68 (d, 2H), 7.23-7.29 (m, 2H), 6.92 (d, 1H), 6.76 (d, 1H), 6.58 (t, 1H), 6.42 (t, 1H), 3.83-3.88 (m, 4H), 2.87-3.13 (m, 6H), 2.78-2.86 (m, 1H), 2.00-2.09 (m, 1H).

N-(4-chlorophenyl)-1-(4-morpholino-2,3-dihydro-1H-inden-1-yl)-2-oxo-1,2-dihydropyridine-3-carboxamide (56)

Retention time (min)=8.265, method [7], MS (ESI) 450.2 (M+H); $^1$H NMR (300 MHz, CDCl$_3$) δ 12.13 (s, 1H), 8.56 (dd, 1H), 7.70 (d, 2H), 7.20-7.30 (m, 4H), 6.88 (d, 1H), 6.73 (d, 1H), 6.56 (t, 1H), 6.37 (t, 1H), 3.80-3.85 (m, 4H), 2.83-3.10 (m, 6H), 2.74-2.81 (m, 1H), 1.93-2.06 (m, 1H).

1-(4-morpholino-2,3-dihydro-1H-inden-1-yl)-2-oxo-N-(4-phenoxyphenyl)-1,2-dihydropyridine-3-carboxamide (57)

Retention time (min)=9.261, method [7], MS (ESI) 508.3 (M+H); $^1$H NMR (300 MHz, CDCl$_3$) δ 12.08 (s, 1H), 8.57 (dd, 1H), 7.72 (d, 2H), 7.19-7.31 (m, 4H), 6.95-7.06 (m, 5H), 6.88 (d, 1H), 6.74 (d, 1H), 6.56 (t, 1H), 6.37 (t, 1H), 3.80-3.85 (m, 4H), 2.92-3.10 (m, 6H), 2.75-2.89 (m, 1H), 1.95-2.13 (m, 1H).

N-(4-fluorophenyl)-1-(4-morpholino-2,3-dihydro-1H-inden-1-yl)-2-oxo-1,2-dihydropyridine-3-carboxamide (58)

Retention time (min)=7.109, method [7], MS (ESI) 434.2 (M+H); $^1$H NMR (300 MHz, DMSO-d6) δ 12.11 (s, 1H), 8.43 (dd, 1H), 7.71-7.75 (m, 2H), 7.57 (m, 1H), 7.15-7.21 (m, 3H), 6.88 (d, 1H), 6.71 (d, 1H), 6.49-6.57 (m, 2H), 3.68-3.77 (m, 4H), 2.85-3.07 (m, 6H), 2.60-2.71 (m, 1H), 2.02-2.13 (m, 1H).

N-(4-bromophenyl)-1-(4-morpholino-2,3-dihydro-1H-inden-1-yl)-2-oxo-1,2-dihydropyridine-3-carboxamide (59)

Retention time (min)=8.050, method [7], MS (ESI) 495.1 (M+H); $^1$H NMR (300 MHz, CDCl$_3$) δ 12.16 (s, 1H), 8.56 (dd, 1H), 7.66 (d, 2H), 7.43 (d, 2H), 7.20-7.25 (m, 2H), 6.88 (d, 1H), 6.73 (d, 1H), 6.56 (t, 1H), 6.37 (t, 1H), 3.82-3.85 (m, 4H), 2.90-3.10 (m, 6H), 2.77-2.87 (m, 1H), 2.00-2.06 (m, 1H).

N-cyclohexyl-1-(4-morpholino-2,3-dihydro-1H-inden-1-yl)-2-oxo-1,2-dihydropyridine-3-carboxamide (60)

Retention time (min)=6.326, method [7], MS (ESI) 422.2 (M+H); $^1$H NMR (300 MHz, CDCl$_3$) δ 9.79 (d, 1H), 8.48 (dd, 1H), 7.10-7.20 (m, 2H), 6.86 (d, 1H), 6.70 (d, 1H), 6.54 (t, 1H), 6.28 (t, 1H), 3.95-4.04 (m, 1H), 3.81-3.85 (m, 4H), 2.73-3.09 (m, 6H), 1.90-2.02 (m, 3H), 1.71-1.78 (m, 2H), 1.60-1.69 (m, 1H), 1.21-1.46 (m, 5H).

N-(4-iodophenyl)-1-(4-morpholino-2,3-dihydro-1H-inden-1-yl)-2-oxo-1,2-dihydropyridine-3-carboxamide (61)

Retention time (min)=8.637, method [7], MS (ESI) 542.1 (M+H); $^1$H NMR (300 MHz, CDCl$_3$) δ 12.17 (s, 1H), 8.59 (dd, 1H), 7.64 (d, 2H), 7.56 (d, 2H), 7.23-7.28 (m, 2H), 6.91 (d, 1H), 6.75 (d, 1H), 6.59 (t, 1H), 6.39 (t, 1H), 3.85-3.88 (m, 4H), 2.88-3.13 (m, 6H), 2.77-2.86 (m, 1H), 1.97-2.09 (m, 1H).

1-(4-morpholino-2,3-dihydro-1H-inden-1-yl)-2-oxo-N-p-tolyl-1,2-dihydropyridine-3-carboxamide (62)

Retention time (min)=7.330, method [7], MS (ESI) 430.2 (M+H); $^1$H NMR (300 MHz, CDCl$_3$) δ 12.00 (s, 1H), 8.57 (dd, 1H), 7.63 (d, 2H), 7.18-7.25 (m, 2H), 7.13 (d, 2H), 6.88 (d, 1H), 6.73 (d, 1H), 6.58 (t, 1H), 6.35 (t, 1H), 3.82-3.85 (m, 4H), 2.92-3.10 (m, 6H), 2.76-2.89 (m, 1H), 2.30 (s, 3H), 1.95-2.06 (m, 1H).

1-(4-morpholino-2,3-dihydro-1H-inden-1-yl)-2-oxo-N-phenyl-1,2-dihydropyridine-3-carboxamide (63)

Retention time (min)=6.803, method [7], MS (ESI) 416.3 (M+H); $^1$H NMR (300 MHz, CDCl$_3$) δ 12.09 (s, 1H), 8.64 (dd, 1H), 7.79-7.82 (m, 2H), 7.31-7.40 (m, 2H), 7.24-7.28 (m, 2H), 7.16 (m, 1H), 6.93 (d, 1H), 6.80 (d, 1H), 6.64 (t, 1H), 6.42 (t, 1H), 3.86-3.91 (m, 4H), 2.98-3.16 (m, 6H), 2.81-2.95 (m, 1H), 2.01-2.12 (m, 1H).

1-(4-morpholino-2,3-dihydro-1H-inden-1-yl)-2-oxo-N-phenyl-1,2-dihydropyridine-3-carboxamide (64)

Retention time (min)=9.430, method [7], MS (ESI) 492.2 (M+H); $^1$H NMR (300 MHz, CDCl$_3$) δ 12.16 (s, 1H), 8.62 (dd, 1H), 7.85 (d, 2H), 7.58-7.61 (m, 4H), 7.40-7.45 (m, 2H), 7.23-7.33 (m, 3H), 6.91 (d, 1H), 6.77 (d, 1H), 6.62 (t, 1H), 6.40 (t, 1H), 3.83-3.89 (m, 4H), 2.90-3.13 (m, 6H), 2.79-2.89 (m, 1H), 1.99-2.11 (m, 1H).

N-(4,4-difluorocyclohexyl)-1-(4-morpholino-2,3-dihydro-1H-inden-1-yl)-2-oxo-1,2-dihydropyridine-3-carboxamide (65)

Retention time (min)=6.038, method [7], MS (ESI) 458.2 (M+H); $^1$H NMR (300 MHz, CDCl$_3$) δ 9.98 (d, 1H), 8.47 (dd, 1H), 7.14-7.21 (m, 2H), 6.86 (d, 1H), 6.70 (d, 1H), 6.52 (t, 1H), 6.30 (t, 1H), 4.07-4.11 (m, 1H), 3.82-3.85 (m, 4H), 2.90-3.09 (m, 6H), 2.74-2.87 (m, 1H), 1.66-2.11 (m, 9H).

N-(4-methoxyphenyl)-1-(4-morpholino-2,3-dihydro-1H-inden-1-yl)-2-oxo-1,2-dihydropyridine-3-carboxamide (66)

Retention time (min)=6.165, method [7], MS (ESI) 446.1 (M+H); $^1$H NMR (300 MHz, CDCl$_3$) δ 11.99 (s, 1H), 8.63 (dd, 1H), 7.73 (d, 2H), 7.23-7.31 (m, 2H), 6.90-6.95 (m, 3H), 6.79 (d, 1H), 6.63 (t, 1H), 6.341 (t, 1H), 3.88-3.93 (m, 4H), 3.83 (s, 3H), 2.93-3.16 (m, 6H), 2.80-2.91 (m, 1H), 2.01-2.12 (m, 1H).

N-(4-(difluoromethoxy)phenyl)-1-(4-morpholino-2,3-dihydro-1H-inden-1-yl)-2-oxo-1,2-dihydropyridine-3-carboxamide (67)

Retention time (min)=7.400, method [7], MS (ESI) 482.2 (M+H); $^1$H NMR (300 MHz, CDCl$_3$) δ 12.13 (s, 1H), 8.63 (dd, 1H), 7.79 (d, 2H), 7.23-7.31 (m, 2H), 7.13 (d, 2H), 6.94 (d, 1H), 6.79 (d, 1H), 6.62 (t, 1H), 6.50 (t, 1H), 6.43 (t, 1H), 3.88-3.91 (m, 4H), 2.93-3.16 (m, 6H), 2.80-2.91 (m, 1H), 2.01-2.12 (m, 1H).

1-(4-morpholino-2,3-dihydro-1H-inden-1-yl)-2-oxo-N-(4-(trifluoromethoxy)phenyl)-1,2-dihydropyridine-3-carboxamide (68)

Retention time (min)=8.696, method [7], MS (ESI) 500.2 (M+H); $^1$H NMR (300 MHz, CDCl$_3$) δ 12.21 (s, 1H), 8.60 (dd, 1H), 7.80 (d, 2H), 7.18-7.28 (m, 4H), 6.92 (d, 1H), 6.76 (d, 1H), 6.59 (t, 1H), 6.40 (t, 1H), 3.83-3.88 (m, 4H), 2.90-3.13 (m, 6H), 2.78-2.89 (m, 1H), 1.98-2.10 (m, 1H).

1-(4-morpholino-2,3-dihydro-1H-inden-1-yl)-2-oxo-N-(4-(trifluoromethyl)phenyl)-1,2-dihydropyridine-3-carboxamide (69)

Retention time (min)=8.662, method [7], MS (ESI) 484.2 (M+H); $^1$H NMR (300 MHz, CDCl$_3$) δ 12.35 (s, 1H), 8.58 (dd, 1H), 7.86 (d, 2H), 7.58 (d, 2H), 7.21-7.26 (m, 2H), 6.89 (d, 1H), 6.73 (d, 1H), 6.57 (t, 1H), 6.38 (t, 1H), 3.80-3.86 (m, 4H), 2.90-3.10 (m, 6H), 2.75-2.88 (m, 1H), 1.96-2.07 (m, 1H).

N-(4-cyanophenyl)-1-(4-morpholino-2,3-dihydro-1H-inden-1-yl)-2-oxo-1,2-dihydropyridine-3-carboxamide (70)

Retention time (min)=6.687, method [7], MS (ESI) 441.2 (M+H); $^1$H NMR (300 MHz, DMSO-d6) δ 12.49 (s, 1H), 8.44 (dd, 1H), 7.89 (d, 2H), 7.80 (d, 2H), 7.61-7.63 (m, 1H), 7.19 (t, 1H), 6.88 (d, 1H), 6.72 (d, 1H), 6.49-6.59 (m, 2H), 3.68-3.77 (m, 4H), 2.85-3.07 (m, 6H), 2.58-2.70 (m, 1H), 2.04-2.14 (m, 1H).

1-(4-(4-hydroxypiperidin-1-yl)-2,3-dihydro-1H-inden-1-yl)-2-oxo-N-(pyridin-4-yl)-1,2-dihydropyridine-3-carboxamide (71)

MS (ESI) 431.2 (M+H); $^1$H NMR (300 MHz, DMSO-d6) δ 12.38 (s, 1H), 8.42-8.47 (m, 3H), 7.61-7.69 (m, 3H), 7.14 (t, 1H), 6.86 (d, 1H), 6.66 (d, 1H), 6.48-6.59 (m, 2H), 4.68 (d, 1H), 3.57-3.64 (m, 1H), 3.12-3.23 (m, 2H), 2.88-3.06 (m, 2H), 2.46-2.83 (m, 3H), 2.03-2.12 (m, 1H), 1.76-1.84 (m, 2H), 1.46-1.57 (m, 2H).

N-(4-chlorophenyl)-1-(4-(4-hydroxypiperidin-1-yl)-2,3-dihydro-1H-inden-1-yl)-2-oxo-1,2-dihydropyridine-3-carboxamide (72)

Retention time (min)=4.433, method [7], MS (ESI) 464.2 (M+H); $^1$H NMR (300 MHz, DMSO-d6) δ 12.23 (s, 1H), 8.42 (dd, 1H), 7.75 (d, 2H), 7.58-7.61 (m, 1H), 7.38 (d, 2H), 7.14 (t, 1H), 6.86 (d, 1H), 6.65 (d, 1H), 6.48-6.57 (m, 2H), 4.68 (d, 1H), 3.57-3.64 (m, 1H), 3.15-3.23 (m, 2H), 2.93-3.06 (m, 2H), 2.46-2.91 (m, 3H), 2.03-2.12 (m, 1H), 1.81-1.86 (m, 2H), 1.46-1.56 (m, 2H).

N-(4-(4-methoxyphenylamino)phenyl)-1-(4-morpholino-2,3-dihydro-1H-inden-1-yl)-2-oxo-1,2-dihydropyridine-3-carboxamide (73)

Retention time (min)=7.749, method [7], MS (ESI) 537.2 (M+H); $^1$H NMR (300 MHz, DMSO-d6) δ 11.96 (s, 1H), 8.40 (dd, 1H), 7.81 (s, 1H), 7.50-7.56 (m, 3H), 7.18 (t, 1H), 7.00 (d, 2H), 6.82-6.92 (m, 5H), 6.70 (d, 1H), 6.49-6.55 (m, 2H), 3.71-3.74 (m, 4H), 3.68 (s, 3H), 2.85-3.08 (m, 6H), 2.58-2.69 (m, 1H), 2.01-2.13 (m, 1H).

N-(3,4-difluorophenyl)-1-(4-morpholino-2,3-dihydro-1H-inden-1-yl)-2-oxo-1,2-dihydropyridine-3-carboxamide (74)

Retention time (min)=7.787, method [7], MS (ESI) 452.2 (M+H); $^1$H NMR (300 MHz, CDCl$_3$) δ 12.20 (s, 1H), 8.59 (dd, 1H), 7.85-7.93 (m, 1H), 7.24-7.33 (m, 3H), 7.06-7.16 (m, 1H), 6.92 (d, 1H), 6.75 (d, 1H), 6.58 (t, 1H), 6.41 (t, 1H), 3.85-3.88 (m, 4H), 2.86-3.13 (m, 6H), 2.77-2.84 (m, 1H), 1.98-2.09 (m, 1H).

tert-butyl 4-(1-(3-(4-fluorophenylcarbamoyl)-2-oxopyridin-1(2H)-yl)-2,3-dihydro-1H-inden-4-yl)piperazine-1-carboxylate (75)

Retention time (min)=9.762, method [7], MS (ESI) 533.2 (M+H); $^1$H NMR (300 MHz, CDCl$_3$) δ 12.06 (s, 1H), 8.57 (dd, 1H), 7.68-7.72 (m, 2H), 7.19-7.24 (m, 2H), 6.98-7.04 (m, 2H), 6.86 (d, 1H), 6.73 (d, 1H), 6.57 (t, 1H), 6.37 (t, 1H), 3.53-3.59 (m, 4H), 2.91-3.08 (m, 6H), 2.78-2.89 (m, 1H), 1.99-2.06 (m, 1H), 1.45 (s, 9H).

tert-butyl 4-(1-(3-(4-chlorophenylcarbamoyl)-2-oxopyridin-1(2H)-yl)-2,3-dihydro-1H-inden-4-yl)piperazine-1-carboxylate (76)

Retention time (min)=11.439, method [7], MS (ESI) 594.2 (M+H); $^1$H NMR (300 MHz, CDCl$_3$) δ 12.14 (s, 1H), 8.56 (dd, 1H), 7.65 (d, 2H), 7.42 (d, 2H), 7.19-7.24 (m, 2H), 6.86 (d, 1H), 6.73 (d, 1H), 6.54 (t, 1H), 6.37 (t, 1H), 3.54-3.57 (m, 4H), 2.87-3.08 (m, 6H), 2.75-2.86 (m, 1H), 1.94-2.06 (m, 1H), 1.45 (s, 9H).

N-(4-(dimethylamino)phenyl)-1-(4-morpholino-2,3-dihydro-1H-inden-1-yl)-2-oxo-1,2-dihydropyridine-3-carboxamide (77)

Retention time (min)=3.575, method [7], MS (ESI) 459.2 (M+H); $^1$H NMR (300 MHz, CDCl$_3$) δ 11.87 (s, 1H), 8.59 (dd, 1H), 7.65 (d, 2H), 7.18-7.27 (m, 2H), 7.13 (d, 2H), 6.90 (d, 1H), 6.72-6.78 (m, 3H), 6.60 (t, 1H), 6.37 (t, 1H), 3.82-3.85 (m, 4H), 2.95-3.13 (m, 6H), 2.94 (s, 6H), 2.79-2.84 (m, 1H), 1.98-2.07 (m, 1H).

Example 7

Synthesis of 1-(4-(cyclopropylamino)-2,3-dihydro-1H-inden-1-yl)-2-oxo-N-(pyridin-4-yl)-1,2-dihydropyridine-3-carboxamide (78)

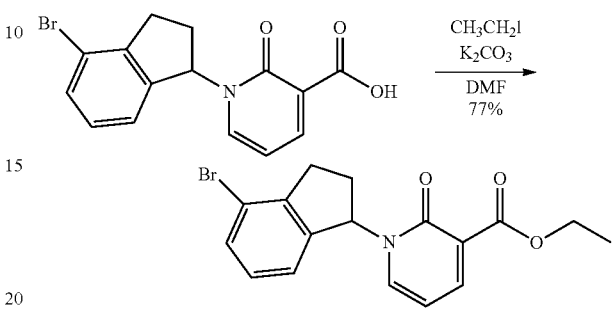

To a solution of 1-(4-bromo-2,3-dihydro-1H-inden-1-yl)-2-oxo-1,2-dihydropyridine-3-carboxylic acid (0.6 g, 1.0 eq.) in 20 ml DMF was added K$_2$CO$_3$ (0.744, 3.0 eq) and iodoethane (0.56 g, 2.0 eq.) The resulting mixture was stirred at room temperature overnight. The reaction was diluted with 60 ml ethyl acetate and 20 ml hexane; then washed with 3×50 ml water and 50 ml brine. The solvent was evaporated in vacuo to give oil 0.5 g (yield 77%) ethyl 1-(4-bromo-2,3-dihydro-1H-inden-1-yl)-2-oxo-1,2-dihydropyridine-3-carboxylate which was used without further purification.

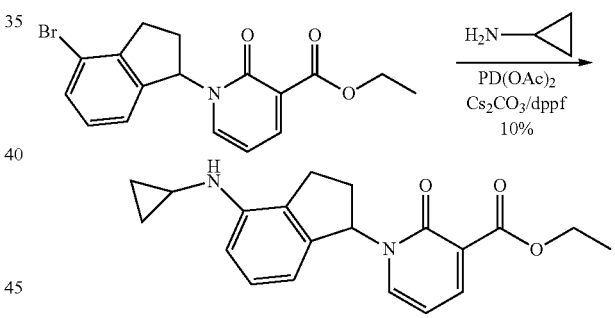

Ethyl 1-(4-bromo-2,3-dihydro-1H-inden-1-yl)-2-oxo-1,2-dihydropyridine-3-carboxylate (0.5 g, 1.0 eq.), cyclopropanamine (0.236 g, 3.0 eq.), Palladium acetate (0.062 g, 0.2 eq.), cesium carbonate (1.124 g, 2.5 eq.) and dppf (0.25 g, 0.3 eq.) were combined 20 ml Toluene in a sealed-tube. The mixture was flashed with N$_2$ for a minute. Then the resulting mixture was heated at 90° C. for 5 hrs. Removal in-organic salt through filtration afforded brown oil. The crude mixture was purified on flash column for give an oil 50 mg (yield 10%) ethyl 1-(4-(cyclopropylamino)-2,3-dihydro-1H-inden-1-yl)-2-oxo-1,2-dihydropyridine-3-carboxylate.

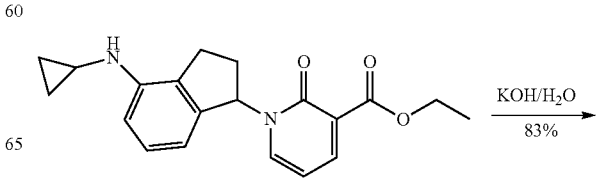

-continued

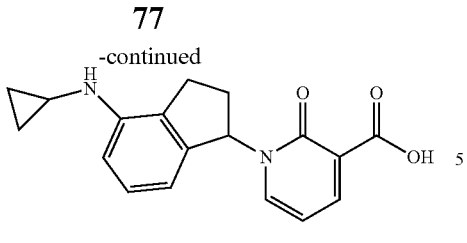

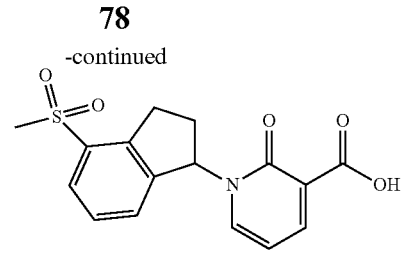

To a solution of Ethyl 1-(4-(cyclopropylamino)-2,3-dihydro-1H-inden-1-yl)-2-oxo-1,2-dihydropyridine-3-carboxylate (25 mg, 1.0 eq) in 2 ml MeOH and 1 ml water was added KOH (12.43 mg, 3.0 eq.). The mixture was heated at 60° C. for 15 mins. The solvent was removed in vacuo, the residue aqueous solution was acidified to pH 2-3 by adding 2N HCl. The white precipitate was collected by filtration, and dried in vacuo to provide solid 19 mg (yield 83%) 1-(4-(cyclopropyl amino)-2,3-dihydro-1H-inden-1-yl)-2-oxo-1,2-dihydropyridine-3-carboxylic acid which was used without further purification.

1-(4-(methylthio)-2,3-dihydro-1H-inden-1-yl)-2-oxo-1,2-dihydropyridine-3-carboxylic acid (80 mg, 1.0 eq.) was dissolved in 2 ml $CH_2Cl_2$. To the solution was added m-CPBA (115 mg, 2.5 eq.). The resulting mixture was stirred at room temperature overnight. The crude mixture was directly purified on flash column to afford white solid 17.8 mg (yield 20%) 1-(4-(methylsulfonyl)-2,3-dihydro-1H-inden-1-yl)-2-oxo-1,2-dihydropyridine-3-carboxylic acid.

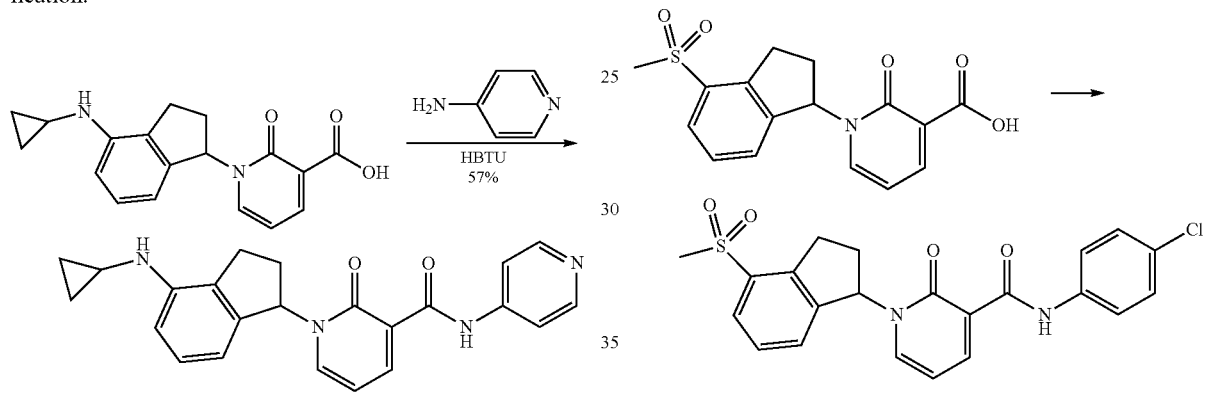

Following Protocol C, 1-(4-(cyclopropylamino)-2,3-dihydro-1H-inden-1-yl)-2-oxo-1,2-dihydropyridine-3-carboxylic acid was converted to 1-(4-(cyclopropylamino)-2,3-dihydro-1H-inden-1-yl)-2-oxo-N-(pyridin-4-yl)-1,2-dihydropyridine-3-carboxamide ( ) Retention time (min) =3.656, method [7], MS (ESI) 387.2 (M+H); $^1$H NMR (300 MHz, CDCl$_3$) δ 12.36 (s, 1H), 8.48-8.56 (m, 3H), 7.21 (d, 2H), 7.00-7.25 (m, 1H), 6.98 (d, 1H), 6.48-6.52 (m, 2H), 6.36 (t, 1H), 4.07 (d, 1H), 2.67-2.90 (m, 2H), 2.43-2.50 (m, 1H), 1.93-2.04 (m, 1H), 0.77-0.78 (m, 2H), 0.42-0.44 (m, 2H).

Following Protocol C, 1-(4-(methylsulfonyl)-2,3-dihydro-1H-inden-1-yl)-2-oxo-1,2-dihydropyridine-3-carboxylic acid was converted to N-(4-chlorophenyl)-1-(4-(methylsulfonyl)-2,3-dihydro-1H-inden-1-yl)-2-oxo-1,2-dihydropyridine-3-carboxamide ( ) Retention time (min)=7.196, method [7], MS (ESI) 443.1 (M+H); $^1$H NMR (300 MHz, CDCl$_3$) δ 12.03 (s, 1H), 8.59 (dd, 1H), 7.96 (d, 1H), 7.68 (d, 2H), 7.47 (t, 1H), 7.36 (d, 1H), 7.25 (d, 2H), 7.17 (d, 1H), 6.69 (t, 1H), 6.43 (t, 1H), 3.58-3.68 (m, 1H), 2.25-3.36 (m, 1H), 3.08 (s, 3H), 2.86-2.97 (m, 1H), 2.08-2.20 (m, 1H).

Example 8

8.1. Synthesis of N-(4-chlorophenyl)-1-(4-(methylsulfonyl)-2,3-dihydro-1H-inden-1-yl)-2-oxo-1,2-dihydropyridine-3-carboxamide (79)

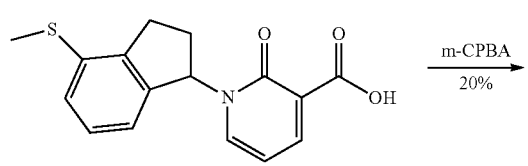

8.2. Synthesis of 1-(4-(methylsulfonyl)-2,3-dihydro-1H-inden-1-yl)-2-oxo-N-(pyridin-4-yl)-1,2-dihydropyridine-3-carboxamide (80)

The title compound was synthesized from appropriate starting materials using the procedures outlined above in Example 8.1., or slightly modified versions thereof.

Retention time (min)=1.332, method [7], MS (ESI) 410.0 (M+H); $^1$H NMR (300 MHz, DMSO-d6) δ 12.97 (s, 1H), 8.74 (d, 2H), 8.49 (d, 1H), 8.23 (d, 2H), 7.83-7.85 (m, 2H), 7.48-7.55 (m, 2H), 6.64 (t, 1H), 6.56 (t, 1H), 3.48-3.58 (m, 1H), 3.26-3.37 (m, 1H), 3.23 (s, 3H), 2.70-2.82 (m, 1H), 2.17-2.29 (m, 1H).

Example 9

9.1. Synthesis of N-(4-chlorophenyl)-2-oxo-1-(4-(piperazin-1-yl)-2,3-dihydro-1H-inden-1-yl)-1,2-dihydropyridine-3-carboxamide (81)

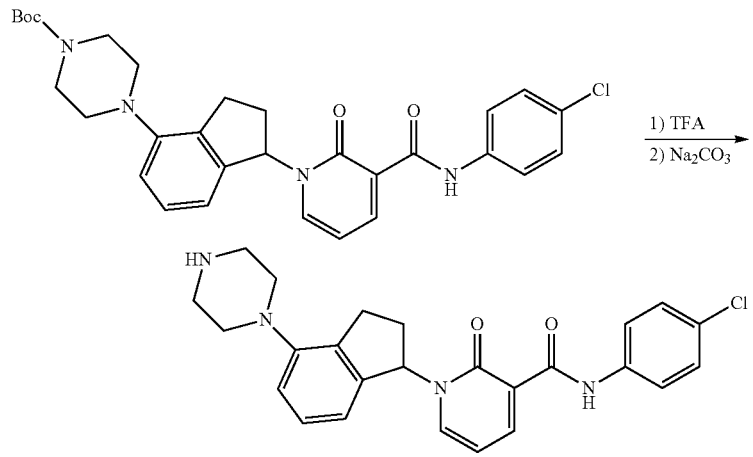

To a solution of tert-butyl 4-(1-(3-(4-chlorophenylcarbamoyl)-2-oxopyridin-1(2H)-yl)-2,3-dihydro-1H-inden-4-yl)piperazine-1-carboxylate (460 mg) in 5 ml $CH_2Cl_2$ was added 2 ml TFA. The mixture was stirred at room temperature for 2 hrs. The solvent and TFA were removed in vacuo. The residue was dissolved in 50 ml ethyl acetate, washed with 2×50 ml 2 M $Na_2CO_3$ and brine. The organic phase was dried over sodium sulfate; then evaporated in vacuo to provide white solid 338 mg (yield 90%) N-(4-chlorophenyl)-2-oxo-1-(4-(piperazin-1-yl)-2,3-dihydro-1H-inden-1-yl)-1,2-dihydropyridine-3-carboxamide. Retention time (min)=5.060, method [7], MS (ESI) 449.1 (M+H); $^1$H NMR (300 MHz, DMSO-d6) δ 12.23 (s, 1H), 8.42 (dd, 1H), 7.73 (d, 2H), 7.60 (m, 1H), 7.40 (d, 2H), 7.16 (t, 1H), 6.84 (d, 1H), 6.66 (d, 1H), 6.48-6.57 (m, 2H), 2.82-3.04 (m, 9H), 2.60-2.68 (m, 1H), 2.15-2.32 (m, 1H), 2.03-2.12 (m, 1H).

9.2. Additional Compounds

The following compounds were synthesized from appropriate starting materials using the procedures outlined above in Example 9.1., or slightly modified versions thereof.

2-oxo-1-(4-(piperazin-1-yl)-2,3-dihydro-1H-inden-1-yl)-N-(pyridin-4-yl)-1,2-dihydropyridine-3-carboxamide (82)

Retention time (min)=8.285, method [6], MS (ESI) 416.2 (M+H); $^1$H NMR (300 MHz, DMSO-d6) δ 12.37 (s, 1H), 8.42-8.47 (m, 3H), 7.66 (d, 2H), 7.62 (m, 1H), 7.16 (t, 1H), 6.85 (d, 1H), 6.68 (d, 1H), 6.48-6.57 (m, 2H), 2.83-3.06 (m, 10H), 2.60-2.69 (m, 1H), 2.03-2.12 (m, 1H).

N-(4-fluorophenyl)-2-oxo-1-(4-(piperazin-1-yl)-2,3-dihydro-1H-inden-1-yl)-1,2-dihydropyridine-3-carboxamide (83)

Retention time (min)=4.282, method [7], MS (ESI) 433.2 (M+H); $^1$H NMR (300 MHz, CDCl$_3$) δ 12.11 (s, 1H), 8.59 (dd, 1H), 7.73 (d, 2H), 7.71-7.75 (m, 2H), 7.21-7.27 (m, 2H), 7.00-7.26 (m, 2H), 6.91 (d, 1H), 6.73 (d, 1H), 6.58 (t, 1H), 6.39 (t, 1H), 2.90-3.07 (m, 10H), 2.76-2.87 (m, 1H), 1.97-2.08 (m, 1H).

N-(4-bromophenyl)-2-oxo-1-(4-(piperazin-1-yl)-2,3-dihydro-1H-inden-1-yl)-1,2-dihydropyridine-3-carboxamide (84)

Retention time (min)=5.915, method [7], MS (ESI) 493.1 (M+H); $^1$H NMR (300 MHz, CDCl$_3$) δ 12.16 (s, 1H), 8.56 (dd, 1H), 7.65 (d, 2H), 7.42 (d, 2H), 7.19-7.23 (m, 2H), 6.88 (d, 1H), 6.70 (d, 1H), 6.55 (t, 1H), 6.36 (t, 1H), 2.87-3.01 (m, 10H), 2.73-2.84 (m, 1H), 1.94-2.05 (m, 1H).

Example 10

10.1. Synthesis of N-(4-chlorophenyl)-1-(4-(4-(2-hydroxyethyl)piperazin-1-yl)-2,3-dihydro-1H-inden-1-yl)-2-oxo-1,2-dihydropyridine-3-carboxamide (85)

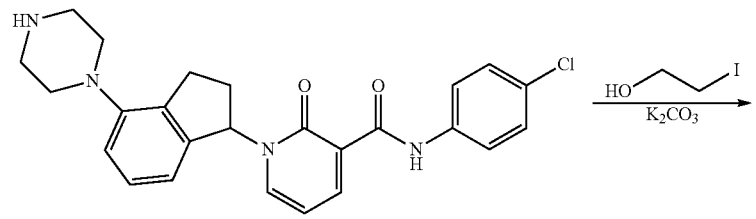

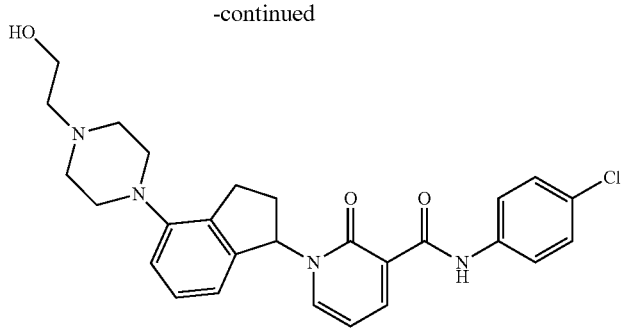

N-(4-chlorophenyl)-2-oxo-1-(4-(piperazin-1-yl)-2,3-dihydro-1H-inden-1-yl)-1,2-dihydropyridine-3-carboxamide (40 mg, 1.0 eq.), potassium carbonate (100 mg, 8.0 eq) were combined in 10 ml dry $CH_3CN$. The mixture was heated at refluxing for 5 mins To the solution was added 2-iodoethanol dropwise. The resulting mixture was kept refluxing overnight. The in-organic solid was removed by filtration. The filtrate was concentrated in vacuo. The crude mixture was purified on flash column (0-5% $NH_3$ in $CH_3CN$) in silica gel to get white solid 40 mg (yield 91%) N-(4-chlorophenyl)-1-(4-(4-(2-hydroxyethyl)piperazin-1-yl)-2,3-dihydro-1H-inden-1-yl)-2-oxo-1,2-dihydropyridine-3-carboxamide. Retention time (min)=4.967, method [7], MS (ESI) 493.2 (M+H); $^1$H NMR (300 MHz, $CDCl_3$) δ 12.18 (s, 1H), 8.59 (dd, 1H), 7.73 (d, 2H), 7.22-7.32 (m, 4H), 6.92 (d, 1H), 6.74 (d, 1H), 6.58 (t, 1H), 6.39 (t, 1H), 4.51 (m, 1H), 3.66-3.69 (m, 2H), 2.63-3.12 (m, 13H), 1.97-2.08 (m, 1H).

10.2. Synthesis of N-(4-chlorophenyl)-1-(4-(4-(2-(2-(2-hydroxyethoxy)ethoxy)ethyl)piperazin-1-yl)-2,3-dihydro-1H-inden-1-yl)-2-oxo-1,2-dihydropyridine-3-carboxamide (86)

The title compound was synthesized from appropriate starting materials using the procedures outlined above in Example 10.1., or slightly modified versions thereof. Retention time (min)=5.652, method [7], MS (ESI) 581.2 (M+H); $^1$H NMR (300 MHz, DMSO-d6) δ 12.22 (s, 1H), 9.71 (m, 1H), 8.44 (dd, 1H), 7.75 (d, 2H), 7.57-7.60 (m, 1H), 7.41 (d, 2H), 7.21 (t, 1H), 6.93 (d, 1H), 6.78 (d, 1H), 6.49-58 (m, 2H), 3.76-3.82 (m, 2H), 3.54-3.67 (m, 6H), 3.38-3.51 (m, 8H), 2.85-3.32 (m, 6H), 2.62-2.69 (m, 1H), 2.06-2.13 (m, 1H).

Example 11

11.1. Synthesis of N-(4-chlorophenyl)-1-(4-(4-methylpiperazin-1-yl)-2,3-dihydro-1H-inden-1-yl)-2-oxo-1,2-dihydropyridine-3-carboxamide (87)

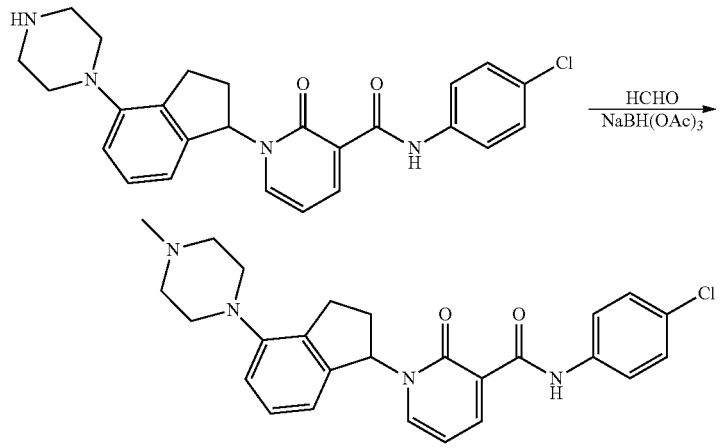

To a solution of N-(4-chlorophenyl)-2-oxo-1-(4-(piperazin-1-yl)-2,3-dihydro-1H-inden-1-yl)-1,2-dihydropyridine-3-carboxamide (40 mg, 1.0 eq.) in 2 ml 1,2-dichloroethane was added formaldehyde (30 mg, 10 eq.). The mixture was stirred at rt. for 5 mins To the reaction mixture was added $NaBH(OAc)_3$ (34 mg, 1.8 eq.). The resulting mixture was stirred at rt. for 30 mins; then diluted with 50 ml $CH_2Cl_2$, washed with 10 ml 2M $Na_2CO_3$, water and brine. The organic phase was dried over sodium sulfate, and evaporated in vacuo to afford white solid 39 mg (yield 92%) N-(4-chlorophenyl)-1-(4-(4-methylpiperazin-1-yl)-2,3-dihydro-1H-inden-1-yl)-2-oxo-1,2-dihydropyridine-3-carboxamide. Retention time (min)=5.063, method [7], MS (ESI) 463.2 (M+H); $^1$H NMR (300 MHz, $CDCl_3$) δ 12.19 (s, 1H), 8.59 (dd, 1H), 7.73 (d, 2H), 7.21-7.32 (m, 4H), 6.92 (d, 1H), 6.73 (d, 1H), 6.57 (t, 1H), 6.39 (t, 1H), 2.90-3.11 (m, 6H), 2.78-2.87 (m, 1H), 2.56-2.68 (m, 4H), 2.37 (s, 3H), 2.00-2.08 (m, 1H).

11.2. Synthesis of 1-(4-(4-methylpiperazin-1-yl)-2,3-dihydro-1H-inden-1-yl)-2-oxo-N-(pyridin-4-yl)-1,2-dihydropyridine-3-carboxamide (88)

The title compound was synthesized from appropriate starting materials using the procedures outlined above in Example 11.1., or slightly modified versions thereof. MS (ESI) 430.2 (M+H); ¹H NMR (300 MHz, CDCl₃) δ 12.34 (s, 1H), 8.56 (dd, 1H), 8.50 (d, 2H), 7.65 (d, 2H), 7.19-7.26 (m, 2H), 6.90 (d, 1H), 6.71 (d, 1H), 6.54 (t, 1H), 6.38 (t, 1H), 2.74-3.09 (m, 7H), 2.53-2.67 (m, 4H), 1.95-2.06 (m, 1H).

Example 12

12.1. Synthesis of 1-(4-(4-acetylpiperazin-1-yl)-2,3-dihydro-1H-inden-1-yl)-N-(4-chlorophenyl)-2-oxo-1,2-dihydropyridine-3-carboxamide (89)

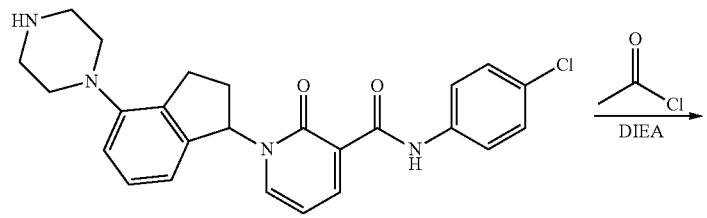

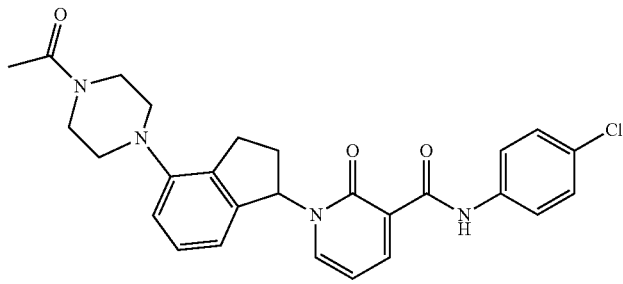

To a solution of N-(4-chlorophenyl)-2-oxo-1-(4-(piperazin-1-yl)-2,3-dihydro-1H-inden-1-yl)-1,2-dihydropyridine-3-carboxamide (40 mg, 1.0 eq.) in 2 ml CH₂Cl₂ was added DIEA (0.04 ml, 2.5 eq.) and acetyl chloride (9.1 mg, 1.3 eq.). The resulting mixture was stirred at rt. for 40 min; then diluted with 30 ml CH₂Cl₂, washed with 10 ml 2N KHSO4, water, and brine. The crude mixture was purified on flash column in silica gel to provide white solid 42 mg (yield 96%) 1-(4-(4-acetylpiperazin-1-yl)-2,3-dihydro-1H-inden-1-yl)-N-(4-chlorophenyl)-2-oxo-1,2-dihydropyridine-3-carboxamide. Retention time (min)=7.179, method [7], MS (ESI) 491.1 (M+H); ¹H NMR (300 MHz, CDCl₃) δ 12.16 (s, 1H), 8.60 (dd, 1H), 7.73 (d, 2H), 7.31 (d, 2H), 7.23-7.28 (m, 2H), 6.90 (d, 1H), 6.78 (d, 1H), 6.61 (m, 1H), 6.40 (t, 1H), 3.70-3.84 (m, 2H), 3.61-3.67 (m, 2H), 2.90-3.12 (m, 6H), 2.81-2.89 (m, 1H), 2.15 (s, 3H), 2.01-2.10 (m, 1H).

12.2. Additional Compounds

The following compounds were synthesized from appropriate starting materials using the procedures outlined above in Example 12.1., or slightly modified versions thereof.

1-(4-(4-acetylpiperazin-1-yl)-2,3-dihydro-1H-inden-1-yl)-2-oxo-N-(pyridin-4-yl)-1,2-dihydropyridine-3-carboxamide (90)

Retention time (min)=1.528, method [7], MS (ESI) 485.2 (M+H); ¹H NMR (300 MHz, CDCl₃) δ 13.24 (s, 1H), 8.58 (dd, 1H), 8.50 (d, 2H), 8.06 (d, 2H), 7.24-7.36 (m, 2H), 6.89 (d, 1H), 6.75 (d, 1H), 6.54 (m, 1H), 6.46 (t, 1H), 3.58-3.84 (m, 4H), 2.93-3.09 (m, 6H), 2.80-2.91 (m, 1H), 2.15 (s, 3H), 1.97-2.08 (m, 1H).

N-(4-chlorophenyl)-1-(4-(4-(methylsulfonyl)piperazin-1-yl)-2,3-dihydro-1H-inden-1-yl)-2-oxo-1,2-dihydropyridine-3-carboxamide (91)

Retention time (min)=8.145, method [7], MS (ESI) 528.1 (M+H); ¹H NMR (300 MHz, DMSO-d6) δ 12.19 (s, 1H), 8.43 (dd, 1H), 7.75 (d, 2H), 7.60 (m, 1H), 7.38 (d, 2H), 7.20 (t, 1H), 6.92 (d, 1H), 6.75 (d, 1H), 6.49-6.58 (m, 2H), 3.24-3.27 (m, 4H), 3.03-3.12 (m, 5H), 2.86-2.96 (m, 4H), 2.60-2.71 (m, 1H), 2.08-2.12 (m, 1H).

Example 13

Synthesis of tert-butyl 2-(2-(2-(2-(4-(1-(3-(4-chlorophenylcarbamoyl)-2-oxopyridin-1(2H)-yl)-2,3-dihydro-1H-inden-4-yl)piperazin-1-yl)-2-oxoethoxy)ethoxy)ethoxy)ethylcarbamate (92)

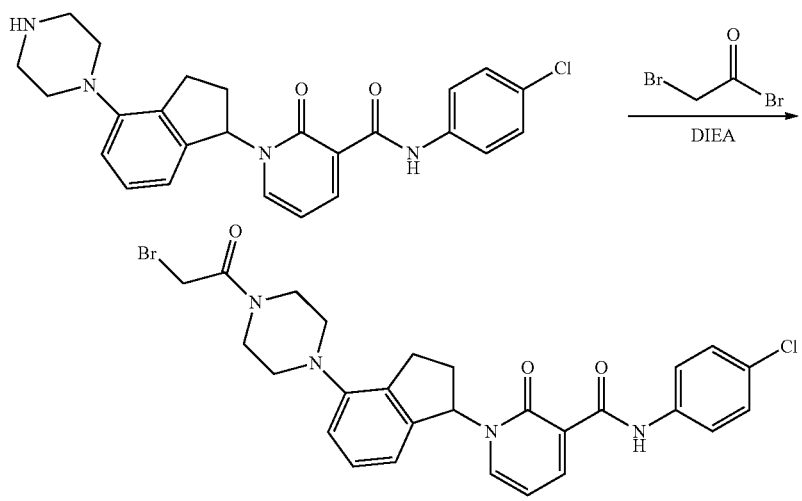

N-(4-chlorophenyl)-2-oxo-1-(4-(piperazin-1-yl)-2,3-dihydro-1H-inden-1-yl)-1,2-dihydropyridine-3-carboxamide (80 mg, 1.0 eq.) and DIEA (58 mg, 2.5 eq.) were dissolved in 3 ml CH$_2$Cl$_2$. The mixture was cooled over an ice-water bath. A solution of 2-bromoacetyl bromide (43.2 mg, 1.2 eq.) in 2 ml CH$_2$Cl$_2$ was added dropwise. The resulting reaction was stirred at 0° C. for 30 mins; then diluted with 30 ml CH$_2$Cl$_2$, washed with 2×15 ml water, 10 ml 2N KHSO4, and brine. The organic phase was dried over sodium sulfate. Removal solvent in vacuo afforded brown solid 90 mg (yield 89%) 1-(4-(4-(2-bromoacetyl)piperazin-1-yl)-2,3-dihydro-1H-inden-1-yl)-N-(4-chlorophenyl)-2-oxo-1,2-dihydropyridine-3-carboxamide which was used without further purification.

NaH (60% dispersion in mineral oil) (12.6 mg, 2.0 eq.) was suspended in 2 ml dry DMF. A solution of tert-butyl 2-(2-(2-hydroxyethoxy)ethoxy)ethylcarbamate (59 mg, 1.5 eq.) in 1 ml DMF was added dropwise at room temperature. The mixture was heated at 60° C. for 5 mins The reaction was cooled to room temperature; then a solution of 1-(4-(4-(2-bromoacetyl)piperazin-1-yl)-2,3-dihydro-1H-inden-1-yl)-N-(4-chlorophenyl)-2-oxo-1,2-dihydropyridine-3-carboxamide (90 mg, 1.0 eq.) in 1 ml DMF was added. The resulting reaction mixture was stirred at rt. for 1 hr. The reaction was diluted with 50 ml ethyl acetate, washed with 3×20 ml water, and brine. The crude mixture was purified on HPLC to provide white solid 53 mg (yield 45%) tert-butyl 2-(2-(2-(2-(4-

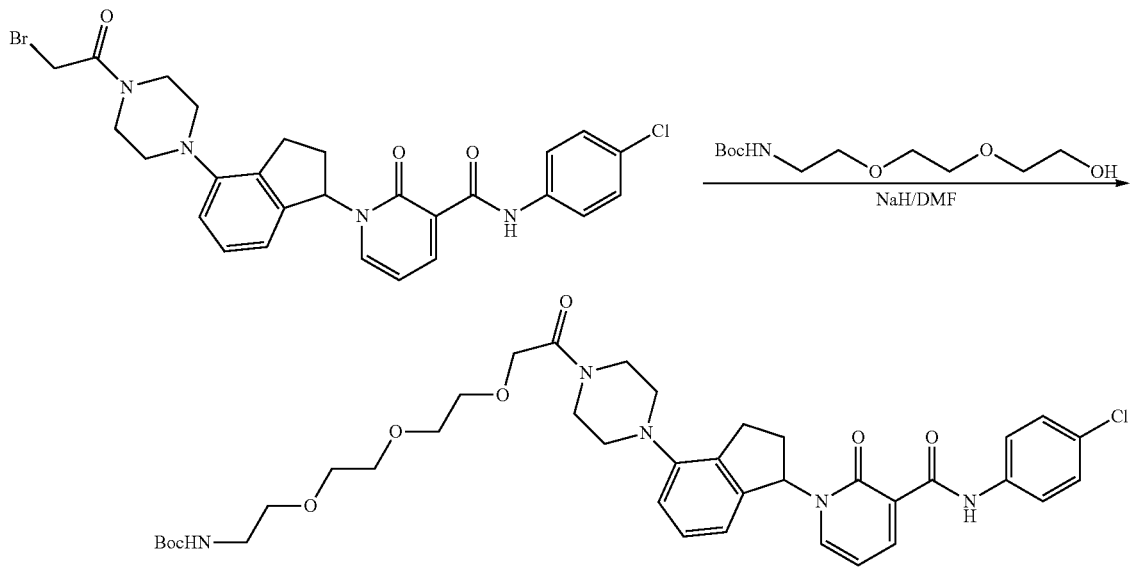

(1-(3-(4-chlorophenylcarbamoyl)-2-oxopyridin-1(2H)-yl)-2,3-dihydro-1H-inden-4-yl)piperazin-1-yl)-2-oxoethoxy)ethoxy)ethylcarbamate. Retention time (min)=8.824, method [7], MS (ESI) 760.3 (M+Na); $^1$H NMR (300 MHz, CDCl$_3$) δ 12.15 (s, 1H), 8.60 (dd, 1H), 7.73 (d, 2H), 7.23-7.33 (m, 4H), 6.89 (d, 1H), 6.78 (d, 1H), 6.60 (m, 1H), 6.41 (t, 1H), 5.04 (m, 1H), 4.27 (s, 2H), 3.60-3.84 (m, 12H), 3.50-3.59 (m, 2H), 3.27-3.32 (m 2H), 2.93-3.09 (m, 6H), 2.80-2.90 (m, 1H), 2.00-2.10 (m, 1H), 1.42 (s, 9H).

Example 14

Synthesis of 1-(4-(4-(2-(2-(2-(2-aminoethoxy)ethoxy)ethoxy)acetyl)piperazin-1-yl)-2,3-dihydro-1H-inden-1-yl)-N-(4-chlorophenyl)-2-oxo-1,2-dihydropyridine-3-carboxamide (93)

2 hrs. The solvent and TFA were removed in vacuo. The residue was dissolved in 25 ml ethyl acetate, washed with 2×10 ml 2 M Na$_2$CO$_3$ and brine. The organic phase was dried over sodium sulfate; then evaporated in vacuo to provide white solid 36 mg (yield 93%) 1-(4-(4-(2-(2-(2-(2-aminoethoxy)ethoxy)ethoxy)acetyl)-piperazin-1-yl)-2,3-dihydro-1H-inden-1-yl)-N-(4-chlorophenyl)-2-oxo-1,2-dihydropyridine-3-carboxamide. Retention time (min)=5.677, method [7], MS (ESI) 639.3 (M+Na); $^1$H NMR (300 MHz, DMSO-d6) δ 12.23 (s, 1H), 8.42 (dd, 1H), 7.73 (d, 2H), 7.59-7.62 (m, 1H), 7.39 (d, 2H), 7.18 (t, 1H), 6.87 (d, 1H), 6.72 (d, 1H), 6.49-6.58 (m, 2H), 4.18 (s, 2H), 3.44-3.56 (m, 6H), 3.29-3.37 (m, 4H), 3.27-3.32 (m 2H), 2.92-3.09 (m, 6H), 2.46-2.70 (m, 3H), 2.05-2.14 (m, 1H).

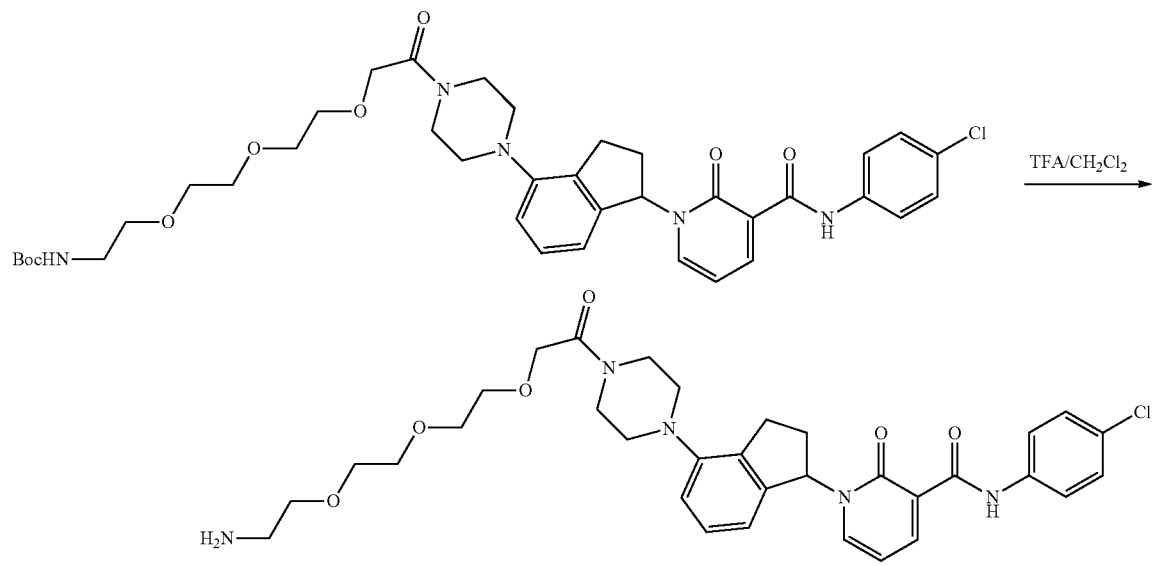

To a solution of tert-butyl 2-(2-(2-(2-(4-(1-(3-(4-chlorophenylcarbamoyl)-2-oxopyridin-1(2H)-yl)-2,3-dihydro-1H-inden-4-yl)piperazin-1-yl)-2-oxoethoxy)ethoxy)-ethoxy)ethylcarbamate (45 mg) in 2 ml CH$_2$Cl$_2$ was added 0.4 ml TFA. The mixture was stirred at room temperature for Example 15

15.1. Synthesis of N-(4'-hydroxybiphenyl-4-yl)-1-(4-methoxy-2,3-dihydro-1H-inden-1-yl)-2-oxo-1,2-dihydropyridine-3-carboxamide (94)

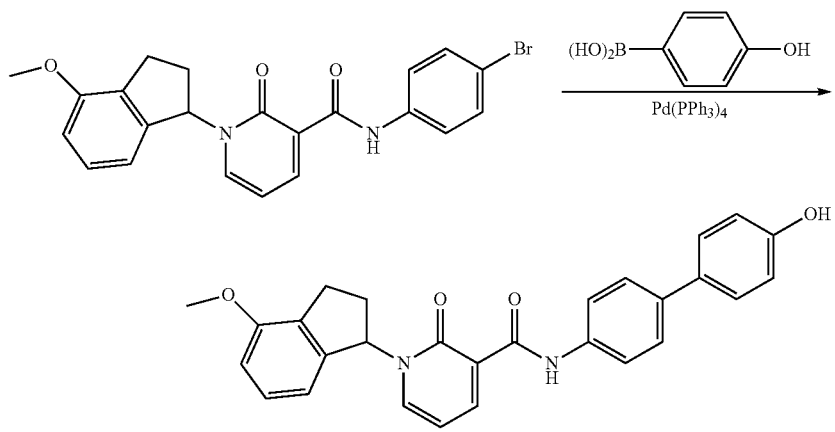

N-(4-bromophenyl)-1-(4-methoxy-2,3-dihydro-1H-inden-1-yl)-2-oxo-1,2-dihydropyridine-3-carboxamide (150 mg, 1.0 eq.), Pd(PPh$_3$)$_4$ (59 mg, 0.15 eq.) and 4-hydroxyphenylboronic acid (61.2 mg, 1.3 eq.) were dissolved in 3 ml DMF. To the solution was added 0.5 ml 2N Na$_2$CO$_3$. The resulting mixture was heated at 100° C. under N$_2$ for 30 mins. The reaction was diluted with 50 ml ethyl acetate, washed with 3×20 ml water and brine. The crude mixture was purified on flash column in silica gel to afford white solid 132 mg (yield 85%) N-(4'-hydroxybiphenyl-4-yl)-1-(4-methoxy-2,3-dihydro-1H-inden-1-yl)-2-oxo-1,2-dihydropyridine-3-carboxamide. Retention time (min)=8.029, method [7], MS (ESI) 453.2 (M+H); $^1$H NMR (300 MHz, CDCl$_3$) δ 12.15 (s, 1H), 8.58 (dd, 1H), 7.80 (d, 2H), 7.44-7.51 (m, 4H), 7.16-7.26 (m, 2H), 6.80-6.87 (m, 3H), 6.70 (d, 1H), 6.60 (m, 1H), 6.36 (t, 1H), 4.89 (s, 3H), 3.86 (s, 3H), 2.89-3.09 (m, 21H), 2.77-2.84 (m, 1H), 1.94-2.05 (m, 1H).

15.2. Additional Compounds

The following compounds were synthesized from appropriate starting materials using the procedures outlined above in Example 15.1., or slightly modified versions thereof.

1-(4-Methoxy-2,3-dihydro-1H-inden-1-yl)-N-(4'-methoxybiphenyl-4-yl)-2-oxo-1,2-dihydropyridine-3-carboxamide (95)

Retention time (min)=10.232, method [7], MS (ESI) 467.2 (M+H); $^1$H NMR (300 MHz, CDCl$_3$) δ 12.12 (s, 1H), 8.58 (dd, 1H), 7.80 (d, 2H), 7.49-7.53 (m, 4H), 7.16-7.26 (m, 2H), 6.92 (m, 2H), 6.82 (d, 1H), 6.70 (d, 1H), 6.60 (m, 1H), 6.36 (t, 1H), 3.86 (s, 3H), 3.81 (s, 3H), 2.91-3.09 (m, 2H), 2.77-2.89 (m, 1H), 1.94-2.05 (m, 1H).

N-(3'-ethoxybiphenyl-4-yl)-1-(4-methoxy-2,3-dihydro-1H-inden-1-yl)-2-oxo-1,2-dihydropyridine-3-carboxamide (96)

Retention time (min)=11.100, method [7], MS (ESI) 481.2 (M+H); $^1$H NMR (300 MHz, CDCl$_3$) δ 12.16 (s, 1H), 8.58 (dd, 1H), 7.82 (d, 2H), 7.55 (d, 2H), 7.06-7.29 (m, 5H), 6.82 (m, 2H), 6.70 (d, 1H), 6.60 (m, 1H), 6.36 (t, 1H), 4.06 (q, 2H), 3.85 (s, 3H), 2.91-3.07 (m, 2H), 2.79-2.89 (m, 1H), 1.96-2.05 (m, 1H), 1.41 (t, 3H).

1-(4-methoxy-2,3-dihydro-1H-inden-1-yl)-N-(2'-methoxybiphenyl-4-yl)-2-oxo-1,2-dihydropyridine-3-carboxamide (97)

Retention time (min)=10.286, method [7], MS (ESI) 467.2 (M+H); $^1$H NMR (300 MHz, CDCl$_3$) δ 12.16 (s, 1H), 8.64 (dd, 1H), 7.85 (d, 2H), 7.56 (d, 2H), 7.22-7.38 (m, 4H), 6.99-7.07 (m, 2H), 6.78 (d, 1H), 6.76 (d, 1H), 6.66 (m, 1H), 6.41 (t, 1H), 3.91 (s, 3H), 3.84 (s, 3H), 2.92-3.15 (m, 2H), 2.83-2.90 (m, 1H), 2.00-2.11 (m, 1H).

N-(4'-aminobiphenyl-4-yl)-1-(4-methoxy-2,3-dihydro-1H-inden-1-yl)-2-oxo-1,2-dihydropyridine-3-carboxamide (98)

Retention time (min)=5.056, method [7], MS (ESI) 452.2 (M+H); $^1$H NMR (300 MHz, CDCl$_3$) δ 12.16 (s, 1H), 8.63 (dd, 1H), 7.83 (d, 2H), 7.55 (d, 2H), 7.44 (d, 2H), 7.21-7.32 (m, 2H), 6.87 (d, 1H), 6.75-6.79 (m, 3H), 6.66 (m, 1H), 6.41 (t, 1H), 4.89 (s, 3H), 3.91 (s, 3H), 3.73 (s, 2H), 2.94-3.13 (m, 2H), 2.82-2.92 (m, 1H), 1.99-2.10 (m, 1H).

Example 16

16.1. Synthesis of N-(4'-(2-(2-(2-aminoethoxy)ethoxy)ethoxy)biphenyl-4-yl)-1-(4-methoxy-2,3-dihydro-1H-inden-1-yl)-2-oxo-1,2-dihydropyridine-3-carboxamide (99)

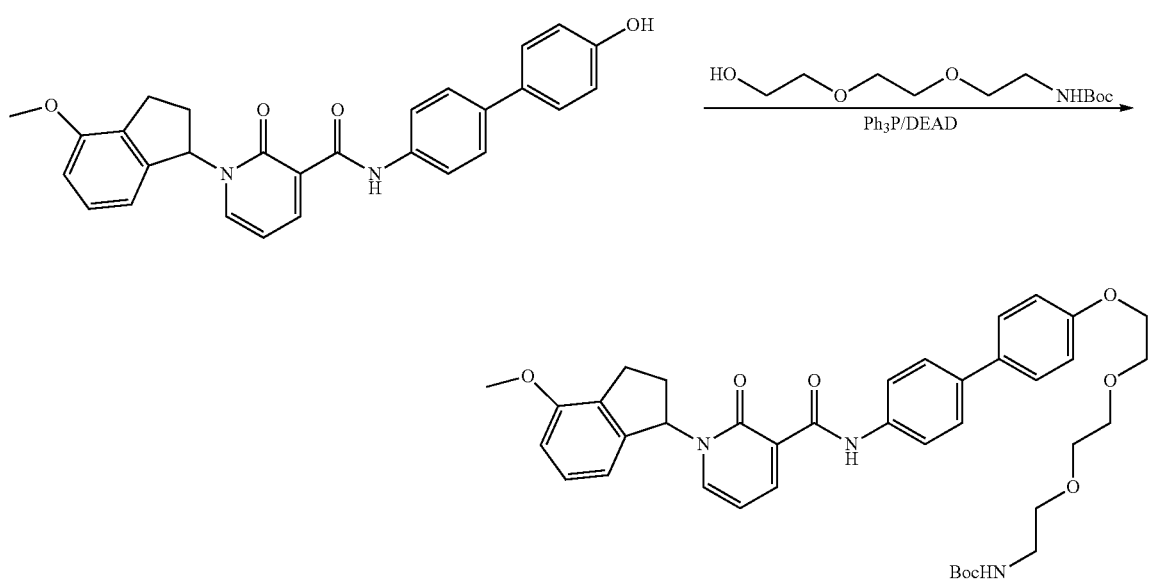

To a solution of N-(4'-hydroxybiphenyl-4-yl)-1-(4-methoxy-2,3-dihydro-1H-inden-1-yl)-2-oxo-1,2-dihydropyridine-3-carboxamide (100 mg, 1.0 eq.) in 4 ml dry THF was added tert-butyl 2-(2-(2-hydroxyethoxy)ethoxy)ethylcarbamate (60.6 mg, 1.1 eq.), Ph₃P (63.8 mg, 1.1 eq.) and DEAD (42.3 mg, 1.1 eq.). The resulting mixture was stirred at rt. for overnight. The solvent was removed in vacuo, the residue mixture was directly purified on flash column in silica gel to provide white solid 50 mg (yield 32%) tert-butyl 2-(2-(2-(4'-(1-(4-methoxy-2,3-dihydro-1H-inden-1-yl)-2-oxo-1,2-dihydropyridine-3-carboxamido)biphenyl-4-yloxy)ethoxy)ethoxy)ethylcarbamate.

N-(3'-(2-(2-(2-aminoethoxy)ethoxy)ethoxy)biphenyl-4-yl)-1-(4-methoxy-2,3-dihydro-1H-inden-1-yl)-2-oxo-1,2-dihydropyridine-3-carboxamide (100)

Retention time (min)=6.291, method [7], MS (ESI) 584.3 (M+H); ¹H NMR (300 MHz, DMSO-d6) δ 12.24 (s, 1H), 8.44 (dd, 1H), 7.78-7.82 (m, 4H), 7.67 (d, 2H), 7.55-7.58 (m, 1H), 7.34 (t, 1H), 6.88-6.95 (m, 2H), 6.71 (d, 1H), 6.52-6.58 (m, 2H), 4.15-4.18 (m, 2H), 3.81 (s, 3H), 3.74-3.77 (m, 2H), 3.57-3.63 (m, 6H), 2.99-3.09 (m, 1H), 2.92-2.95 (m, 2H), 2.81-2.98 (m, 1H), 2.65-2.75 (m, 1H), 2.00-2.12 (m, 1H).

Protocol L

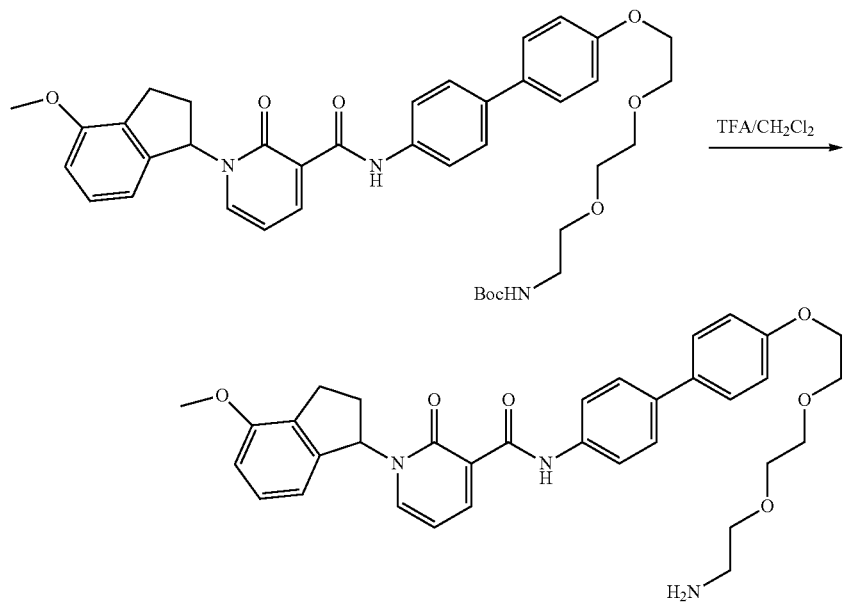

To a solution of tert-butyl 2-(2-(2-(4'-(1-(4-methoxy-2,3-dihydro-1H-inden-1-yl)-2-oxo-1,2-dihydropyridine-3-carboxamido)biphenyl-4-yloxy)ethoxy)ethoxy)ethylcarbamate (50 mg) in 2 ml CH₂Cl₂ was added 0.4 ml TFA. The mixture was stirred at room temperature for 2 hrs. The solvent and TFA were removed in vacuo. The residue was dissolved in 25 ml ethyl acetate, washed with 2×10 ml 2 M Na₂CO₃ and brine. The organic phase was dried over sodium sulfate; then evaporated in vacuo to provide white solid 35 mg (yield 80%) N-(4'-(2-(2-(2-aminoethoxy)ethoxy)ethoxy)biphenyl-4-yl)-1-(4-methoxy-2,3-dihydro-1H-inden-1-yl)-2-oxo-1,2-dihydropyridine-3-carboxamide. Retention time (min)=6.041, method [7], MS (ESI) 584.2 (M+H); ¹H NMR (300 MHz, DMSO-d6) δ 12.21 (s, 1H), 8.44 (dd, 1H), 7.75-7.82 (m, 4H), 7.54-7.62 (m, 5H), 7.23 (t, 1H), 6.92-7.01 (m, 2H), 6.71 (d, 1H), 6.51-6.57 (m, 2H), 4.10-4.13 (m, 2H), 3.81 (s, 3H), 3.73-3.76 (m, 2H), 3.57-3.62 (m, 6H), 2.99-3.09 (m, 1H), 2.80-2.96 (m, 3H), 2.65-2.75 (m, 1H), 2.02-2.10 (m, 1H).

16.2. Additional Compounds

The following compounds were synthesized from appropriate starting materials using the procedures outlined above in Example 16.1., or slightly modified versions thereof.

N-(3'-hydroxybiphenyl-4-yl)-1-(4-methoxy-2,3-dihydro-1H-inden-1-yl)-2-oxo-1,2-dihydropyridine-3-carboxamide (101)

Retention time (min)=8.271, method [7], MS (ESI) 453.2 (M+H); ¹H NMR (300 MHz, DMSO-d6) δ 12.22 (s, 1H), 9.48 (s, 1H), 8.43 (dd, 1H), 7.78 (d, 2H), 7.55-7.60 (m, 3H), 7.19-7.25 (m, 2H), 6.92-7.06 (m, 3H), 6.72 (d, 1H), 6.55 (m, 1H), 3.81 (s, 3H), 2.91-3.09 (m, 1H), 2.71-2.86 (m, 1H), 2.63-2.69 (m, 1H), 2.01-2.12 (m, 1H).

Example 17

Synthesis of tert-butyl 2-(2-(2-(4-(4-(1-(4-methoxy-2,3-dihydro-1H-inden-1-yl)-2-oxo-1,2-dihydropyridine-3-carboxamido)phenoxy)phenoxy)ethoxy)ethoxy)ethylcarbamate (102)

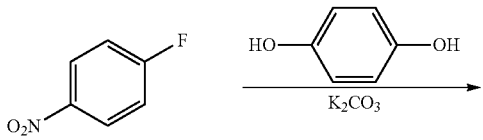

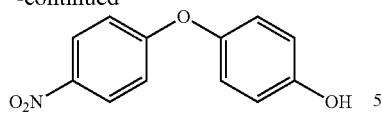

1-Fluoro-4-nitrobenzene (692 mg, 1.0 eq), hydroquinone (540 mg, 1.0 eq) and potassium carbonate (2.03 g, 3.0 eq) were combined in 20 ml dry DMF. The mixture was heated at 120° C. for 4 hrs. The in-organic salt was removed by filtration. The filtrate was diluted with 200 ml ethyl acetate, washed with 3×80 ml water, and brine. The crude mixture was purified on flash column to give brown solid 210 mg (yield 18%) 4-(4-nitrophenoxy)phenol.

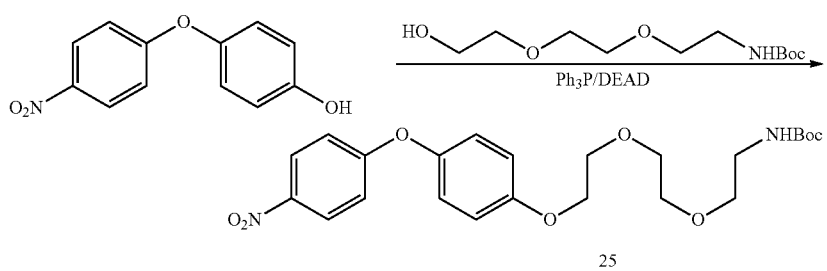

To a solution of 4-(4-nitrophenoxy)phenol (180 mg, 1.0 eq.) in 8 ml dry THF was added tert-butyl 2-(2-(2-hydroxyethoxy)ethoxy)ethylcarbamate (210 mg, 1.1 eq.), Ph₃P (408 mg, 2.0 eq.) and DEAD (271 mg, 2.0 eq.). The resulting mixture was stirred at rt. for overnight. The solvent was removed in vacuo, the residue mixture was directly purified on flash column in silica gel to provide yellow solid 340 mg (yield 94%) tert-butyl 2-(2-(2-(4-(4-nitrophenoxy)phenoxy)ethoxy)ethoxy)ethylcarbamate.

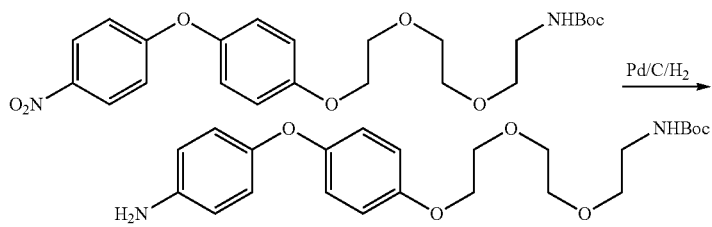

tert-butyl 2-(2-(2-(4-(4-nitrophenoxy)phenoxy)ethoxy)ethoxy)ethylcarbamate (388 mg) was dissolved in 40 ml MeOH, added catalyst (40 mg, 10% Palladium on carbon). The mixture was hydrogenated (50 psi H₂) at ambient temperature for 30 mins The catalyst was removed by filtration. The solvent was evaporated in vacuo to give yellow oil 240 mg (yield 75%) tert-butyl 2-(2-(2-(4-(4-aminophenoxy)phenoxy)-ethoxy)ethylcarbamate.

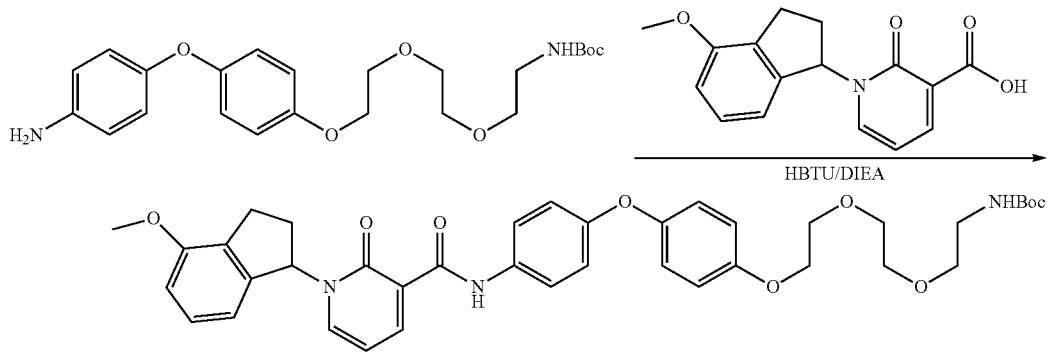

Following Protocol C, 1-(4-methoxy-2,3-dihydro-1H-inden-1-yl)-2-oxo-1,2-dihydropyridine-3-carboxylic acid was converted to tert-butyl 2-(2-(2-(4-(4-(1-(4-methoxy-2,3-dihydro-1H-inden-1-yl)-2-oxo-1,2-dihydropyridine-3-carboxamido)phenoxy)phenoxy)ethoxy)ethoxy)ethylcarbamate. Retention time (min)=10.484, method [7], MS (ESI) 722.3 (M+Na); $^1$H NMR (300 MHz, CDCl$_3$) δ 12.02 (s, 1H), 8.56 (dd, 1H), 7.68 (d, 2H), 7.15-7.25 (m, 2H), 6.70-6.94 (m, 7H), 6.69 (d, 1H), 6.58 (m, 1H), 6.34 (t, 1H), 4.99 (m, 1H), 4.07-4.10 (m, 2H), 3.85 (s, 3H), 3.80-3.84 (m, 2H), 3.67-3.70 (m, 2H), 3.60-3.63 (m, 2H), 3.50-3.53 (m, 2H), 3.26-3.31 (m, 2H), 2.90-3.06 (m, 2H), 2.75-2.88 (m, 1H), 1.93-2.04 (m, 1H), 1.39 (s, 9H).

Example 18

Synthesis of N-(4-(4-(2-(2-(2-aminoethoxy)ethoxy)ethoxy)phenoxy)phenyl)-1-(4-methoxy-2,3-dihydro-1H-inden-1-yl)-2-oxo-1,2-dihydropyridine-3-carboxamide (103)

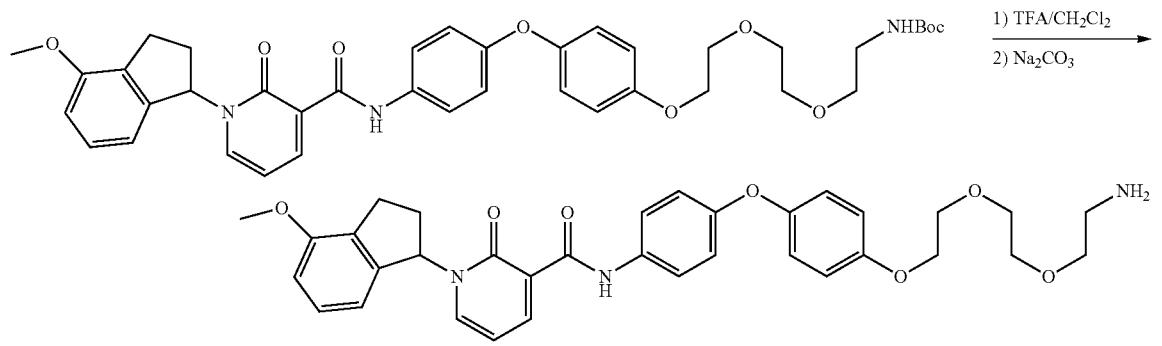

To a solution of tert-butyl 2-(2-(2-(4-(4-(1-(4-methoxy-2,3-dihydro-1H-inden-1-yl)-2-oxo-1,2-dihydropyridine-3-carboxamido) phenoxy)phenoxy)ethoxy)ethoxy)ethylcarbamate (15 mg) in 0.5 ml CH$_2$Cl$_2$ was added 0.1 ml TFA. The mixture was stirred at room temperature for 2 hrs. The solvent and TFA were evaporated in vacuo. The residue was dissolved in 10 ml ethyl acetate, washed with 2×3 ml 2 M Na$_2$CO$_3$ and brine. The organic phase was dried over sodium sulfate; then evaporated in vacuo to provide white solid 9.8 mg (yield 72%) N-(4-(4-(2-(2-(2-aminoethoxy)ethoxy)ethoxy)phenoxy)phenyl)-1-(4-methoxy-2,3-dihydro-1H-inden-1-yl)-2-oxo-1,2-dihydropyridine-3-carboxamide. Retention time (min) =6.236, method [7], MS (ESI) 600.3 (M+H); $^1$H NMR (300 MHz, DMSO-d6) δ 12.11 (s, 1H), 8.41 (dd, 1H), 7.68 (d, 2H), 7.53 (m, 1H), 7.22 (d, 1H), 6.90-6.99 (m, 7H), 6.69 (d, 1H), 6.49-6.56 (m, 2H), 4.04-4.07 (m, 2H), 3.81 (s, 3H), 3.71-3.74 (m, 2H), 3.56-3.62 (m, 6H), 2.98-3.08 (m, 1H), 2.81-2.95 (m, 2H), 2.66-2.79 (m, 1H), 2.62-2.74 (m, 1H), 1.99-2.10 (m, 1H).

Example 19

Synthesis of 2-oxo-1-(4-(pyridin-3-yl)-2,3-dihydro-1H-inden-1-yl)-N-(pyridin-4-yl)-1,2-dihydropyridine-3-carboxamide (104)

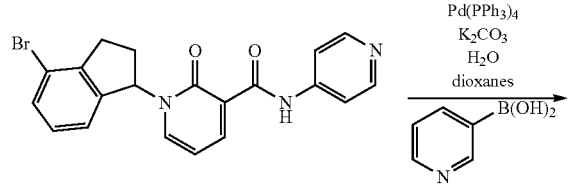

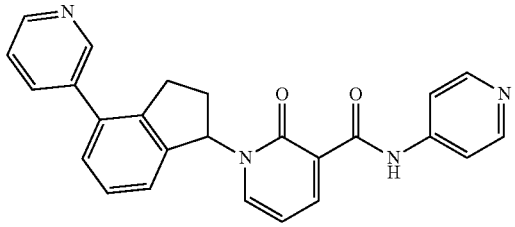

2-oxo-1-(4-(pyridin-3-yl)-2,3-dihydro-1H-inden-1-yl)-N-(pyridin-4-yl)-1,2-dihydropyridine-3-carboxamide was prepared by heating a mixture of 1-(4-bromo-2,3-dihydro-1H-inden-1-yl)-2-oxo-N-(pyridin-4-yl)-1,2-dihydropyridine-3-carboxamide (35.1 mg, 0.0855 mmol, 1.0 eq.), pyridin-3-ylboronic acid (12.8 mg, 0.104 mmol, 1.2 eq.), Pd(PPh$_3$)$_4$ (5.6 mg, 0.0048 mmol, 0.056 eq.), and potassium carbonate (15.1 mg, 0.109 mmol, 1.3 eq.) in 0.80 mL of dioxanes and 0.20 mL of H$_2$O in a microwave at 140° C. for 5 min. The crude material was filtered through celite and the filtrate was purified by reverse phase HPLC using the method of 5-35% ACN/H$_2$O in 40 min The purified material was concentrated and dried under vacuum to give 2-oxo-1-(4-(pyridin-3-yl)-2,3-dihydro-1H-inden-1-yl)-N-(pyridin-4-yl)-1,2-dihydropyridine-3-carboxamide as a clear colorless oil. Retention time (min)=8.051, method [8], MS (ESI) 409.2 (M+H); $^1$H NMR (300 MHz, CDCl$_3$) δ 9.19 (m, 1H), 8.90 (m, 1H), 8.67 (m, 2H), 8.53 (m, 2H), 8.24 (d, J=7.1 Hz, 2H), 8.06 (m, 1H), 7.53 (m, 2H), 7.32 (m, 1H), 6.71 (t, J=7.7 Hz, 1H), 6.62 (t, J=7.1 Hz, 1H), 3.20 (m, 3H), 2.95 (m 1H), 2.19 (m, 1H).

Example 20

Synthesis of 1-(4-nitro-2,3-dihydro-1H-inden-1-yl)-2-oxo-N-(pyridin-4-yl)-1,2-dihydropyridine-3-carboxamide (105)

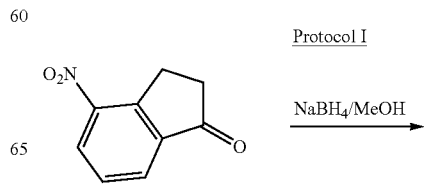

-continued

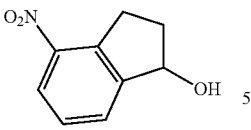

To a mixture of 4-nitro-2,3-dihydro-1H-inden-1-one (8.0 g, 1.0 eq) in MeOH (125 mL) was added NaBH₄ (0.6 eq) in portions, the mixture was stirred at room temperature for 40 minutes. At the end of reaction, the mixture was concentrated and water was added. The solution was extracted with ethyl acetate three times. The combined organic layer was washed with brine and dried over Na₂SO₄, filtrated and evaporated to give 4-nitro-2,3-dihydro-1H-inden-1-one (7.9 g, 98%).

Protocol J

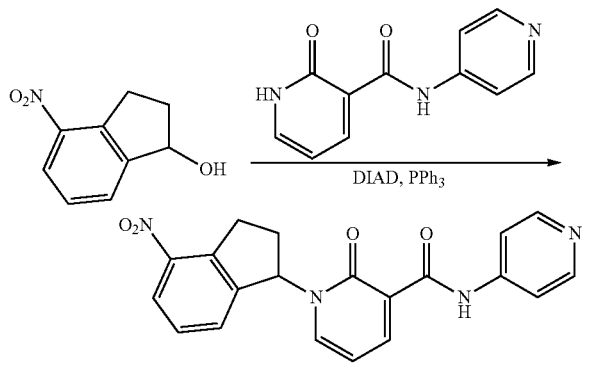

To a mixture of 2-oxo-N-(pyridin-4-yl)-1,2-dihydropyridine-3-carboxamide (8.0 g, 1.0 eq) in dry DMF (30 mL) was added 4-nitro-2,3-dihydro-1H-inden-1-one (1.2 eq) and PPh₃ (3.0 eq), then added DIAD (3.0 eq) under N₂ atmosphere. Then the mixture was stirred at room temperature overnight. At the end of reaction, water was added and extracted with ethyl acetate. The combined organic layer was washed with brine and dried over MgSO₄, filtrated and evaporated to give the crude product, which was purified by Flash Column (PE: EtOAc=1:2), concentrated the crude product, and recrystallized by EtOAc to give 1-(4-nitro-2,3-dihydro-1H-inden-1-yl)-2-oxo-N-(pyridin-4-yl)-1,2-dihydropyridine-3-carboxamide (3.5 g, 21%). MS (ESI) 377.0 (M+H); ¹H NMR (300 MHz, CDCl₃) δ 12.22 (s, 1H), 8.62 (m, 1H), 8.53 (m, 2H), 8.24 (m, 1H), 7.67 (m, 2H), 7.49 (m, 2H), 6.75 (m, 1H), 6.50 (m, 1H), 3.71 (m, 1H), 3.57 (m, 1H), 2.97 (m, 1H), 2.21 (m, 2H).

Example 21

Synthesis of 1-(4-amino-2,3-dihydro-1H-inden-1-yl)-2-oxo-N-(pyridin-4-yl)-1,2-dihydropyridine-3-carboxamide (106)

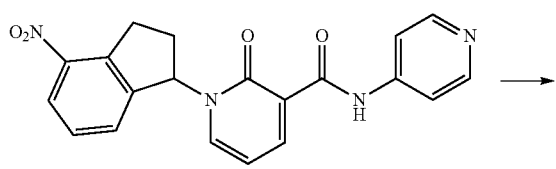

-continued

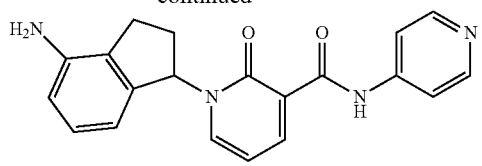

To a mixture of 1-(4-nitro-2,3-dihydro-1H-inden-1-yl)-2-oxo-N-(pyridin-4-yl)-1,2-dihydropyridine-3-carboxamide (3.5 g, 1.0 eq) in EtOH (125 mL) was added SnCl₂*2H₂O (5.0 eq) in portions, the mixture was stirred at 70° C. overnight. At the end of reaction, the mixture was concentrated and ethyl acetate was added. The organic layer was washed with NaHCO₃ aqueous for three times. The combined organic layer was washed with brine and dried over MgSO₄, filtered and evaporated to give the crude product, which was purified by HPLC to afford 1-(4-amino-2,3-dihydro-1H-inden-1-yl)-2-oxo-N-(pyridin-4-yl)-1,2-dihydropyridine-3-carboxamide (3 g, 93%). MS (ESI) 347.0 (M+H); 1H NMR (300 MHz, DMSO-d6) δ12.44 (s, 1H), 8.49 (d, J=3.0 Hz, 2H), 8.46 (d, J=4.2 Hz, 1H), 7.72 (d, J=3.0 Hz, 2H), 7.57 (d, J=4.2 Hz, 1H), 6.96 (t, J=4.5 Hz, 1H), 6.57-6.61 (m, 2H), 6.45 (t, J=4.2 Hz, 1H), 6.31 (d, J=4.2 Hz, 1H), 5.19 (s, 2H), 2.85-2.90 (m, 1H), 2.65-2.75 (m, 2H), 2.00-2.05 (m, 1H).

Example 22

Synthesis of 1-(4-cyano-2,3-dihydro-1H-inden-1-yl)-2-oxo-N-(pyridin-4-yl)-1,2-dihydropyridine-3-carboxamide (107)

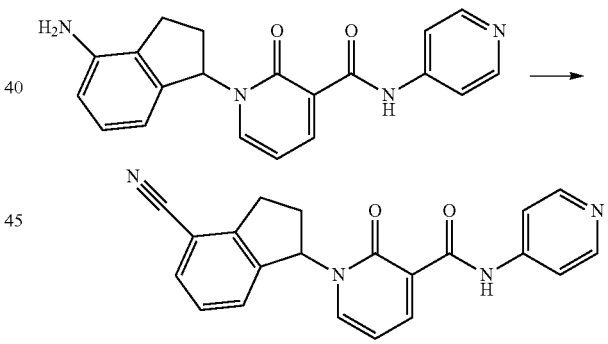

To a mixture of 1-(4-amino-2,3-dihydro-1H-inden-1-yl)-2-oxo-N-(pyridin-4-yl)-1,2-dihydropyridine-3-carboxamide (200 mg, 1.0 eq) in H₂O (4 mL) and conc. HCl (0.5 mL) was dropped the materials of NaNO₂ (1.1 eq) in 1 mL of H₂O at 0° C., the mixture was stirred at room temperature for 30 minutes. Then this mixture was added to another flask contained CuCN (9.0 eq), KCN (8.8 eq) and 2 mL H₂O at 0° C., maintained stiffing for 5 h. At the end of reaction, FeSO4 aqueous was added to the mixture, filtrated and washed the solid substance with DMSO, evaporated the filtrate to give the crude product, which was purified by HPLC to afford 1-(4-cyano-2,3-dihydro-1H-inden-1-yl)-2-oxo-N-(pyridin-4-yl)-1,2-dihydropyridine-3-carboxamide (20 mg, 10%). MS (ESI) 357.0 (M+H); 1H NMR (300 MHz, DMSO-d6) δ 12.31 (s, 1H), 8.48 (br, 1H), 8.47 (d, J=4.5 Hz, 2H), 7.83 (d, J=4.5 Hz, 1H), 7.79 (bd, 1H), 7.72 (bs, 2H), 7.52 (d, J=4.5 Hz, 1H), 7.45

(t, J=4.5 Hz, 1H), 6.61 (m, 2H), 3.3 (overlap with DMSO-d6, 1H), 3.10-3.25 (m, 1H), 2.70-2.80 (m, 1H), 2.20-2.27 (m, 1H).

Example 23

Synthesis of 1-(4-chloro-2,3-dihydro-1H-inden-1-yl)-2-oxo-N-(pyridin-4-yl)-1,2-dihydropyridine-3-carboxamide (108)

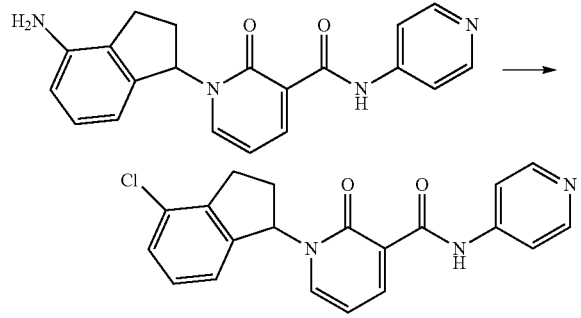

To a mixture of 1-(4-amino-2,3-dihydro-1H-inden-1-yl)-2-oxo-N-(pyridin-4-yl)-1,2-dihydropyridine-3-carboxamide (600 mg, 1.0 eq) in H$_2$O (4 mL) and conc. HCl (2 mL) was added dropwise NaNO$_2$ (1.1 eq) in H$_2$O (1 mL) at 0° C., the mixture was stirred at room temperature for 30 minutes. Then this mixture was added to another flask containing CuCl (1.5 eq), 2 mL H$_2$O and 1 mL aqueous HCl at 0° C., the mixture was stirred for 5 h. At the end of reaction, saturated Na$_2$CO$_3$ aqueous was added to adjust to pH 12. The aqueous solution was extracted with ethyl acetate three times. The combined organic layer was washed with brine and dried over MgSO$_4$, evaporated the filtrate to give the crude product, which was purified by Flash Column (DCM:MeOH=30:1) to afford 1-(4-chloro-2,3-dihydro-1H-inden-1-yl)-2-oxo-N-(pyridin-4-yl)-1,2-dihydropyridine-3-carboxamide (350 mg, 55%). MS (ESI) 366.0 (M+H); $^1$H NMR (300 MHz, CDCl$_3$) δ 12.31 (s, 1H), 8.61 (bd, 1H), 8.53 (bs, 2H), 7.69 (bs, 2H), 7.38 (bd, 1H), 7.26 (bm, 2H), 7.03 (d, J=6.0 Hz, 2H), 6.69 (bs, 1H), 6.46 (bs, 1H), 3.05-3.25 (bm, 2H), 2.91 (bd, 1H), 2.08 (bd, 1H).

Example 24

Synthesis of 1-(4-(methylamino)-2,3-dihydro-1H-inden-1-yl)-2-oxo-N-(pyridin-4-yl)-1,2-dihydropyridine-3-carboxamide (109) and 1-(4-(dimethylamino)-2,3-dihydro-1H-inden-1-yl)-2-oxo-N-(pyridin-4-yl)-1,2-dihydropyridine-3-carboxamide (110)

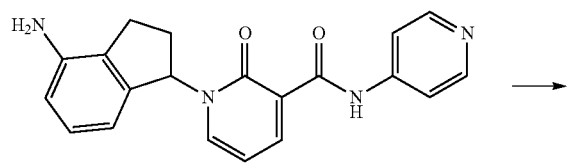

-continued

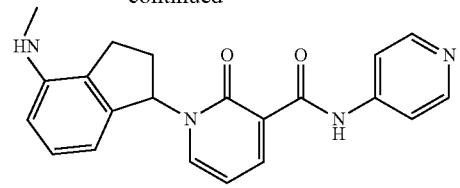

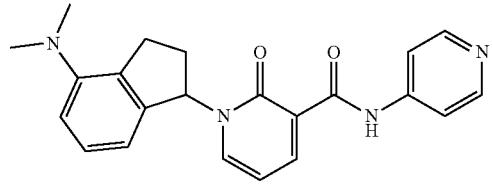

To a mixture of 1-(4-amino-2,3-dihydro-1H-inden-1-yl)-2-oxo-N-(pyridin-4-yl)-1,2-dihydropyridine-3-carboxamide (400 mg, 1.0 eq) in DCM (12 mL) and 2 mL of acetic acid was added Na(OAc)$_3$BH (3.0 eq) in portions and polymeric formaldehyde (10 eq), the mixture was stirred at room temperature overnight. At the end of reaction, the mixture was concentrated and water was added then extracted with ethyl acetate. The combined organic layer was washed with brine and dried over MgSO$_4$, filtrated and evaporated to give the crude product, which was purified by HPLC to afford 1-(4-(methylamino)-2,3-dihydro-1H-inden-1-yl)-2-oxo-N-(pyridin-4-yl)-1,2-dihydropyridine-3-carboxamide (100 mg, 24%) and 1-(4-(dimethylamino)-2,3-dihydro-1H-inden-1-yl)-2-oxo-N-(pyridin-4-yl)-1,2-dihydropyridine-3-carboxamide (85 mg, 20%).

( ): MS (ESI) 361.0 (M+H); $^1$H NMR (300 MHz, CDCl$_3$) δ 12.43 (s, 1H), 8.58 (d, J=5.4 Hz, 1H), 8.53 (d, J=3.6 Hz, 2H), 7.71 (d, J=3.6 Hz, 2H), 7.28 (overlap with CDCl$_3$, 1H), 7.23 (t, J=6.0 Hz, 1H), 6.61 (d, J=6.0 Hz, 1H), 6.56 (t, J=4.8 Hz, 1H), 6.50 (d, J=6.0 Hz, 1H), 6.40 (t, J=5.4 Hz, 1H), 2.95 (s, 3H), 2.75-2.90 (m, 3H), 2.00-2.05 (m, 1H).

( ): MS (ESI) 375.0 (M+H); $^1$H NMR (300 MHz, CDCl$_3$) δ 12.43 (s, 1H), 8.60 (dd, J=1.2 Hz, 4.2 Hz, 1H), 8.53 (d, J=3.3 Hz, 2H), 7.71 (d, J=3.3 Hz, 2H), 7.31 (dd, J=1.2 Hz, 4.2 Hz, 1H), 7.23 (t, J=4.7 Hz, 1H), 6.88 (d, J=4.7 Hz, 1H), 6.68 (d, J=4.7 Hz, 1H), 6.57 (t, J=4.2 Hz, 1H), 6.43 (t, J=4.2 Hz, 1H), 3.00-3.10 (m, 2H), 2.92 (s, 6H), 2.75-2.90 (m, 1H), 2.00-2.05 (m, 1H).

Example 25

Synthesis 1-(4-acetamido-2,3-dihydro-1H-inden-1-yl)-2-oxo-N-(pyridin-4-yl)-1,2-dihydropyridine-3-carboxamide (111)

To a mixture of 1-(4-amino-2,3-dihydro-1H-inden-1-yl)-2-oxo-N-(pyridin-4-yl)-1,2-dihydropyridine-3-carboxamide (140 mg, 1.0 eq) in DCM (8 mL) was added acetyl chloride (1.5 eq) and Et$_3$N (2.0 eq), the mixture was stirred at room temperature overnight. At the end of reaction, the mixture was concentrated and water was added then extracted with ethyl acetate. The combined organic layer was washed with brine and dried over MgSO$_4$, filtrated and evaporated until the aim product precipitated, filtrated and washed with some DCM to afford 1-(4-acetamido-2,3-dihydro-1H-inden-1-yl)-2-oxo-N-(pyridin-4-yl)-1,2-dihydropyridine-3-carboxamide (90 mg, 59%). MS (ESI) 389.1 (M+H); $^1$H NMR (300 MHz, DMSO-d6) δ 13.06 (s, 1H), 9.56 (s, 1H), 8.77 (d, J=3.9 Hz, 2H), 8.51 (d, J=4.2 Hz, 1H), 8.27 (d, J=3.9 Hz, 2H), 7.72 (m, 2H), 7.23 (t, J=4.5 Hz, 1H), 6.90 (d, J=4.5 Hz, 1H), 6.55 (t, J=4.2 Hz, 1H), 6.57 (t, J=4.2 Hz, 1H), 3.05-3.15 (m, 1H), 2.90-3.05 (m, 1H), 2.60-2.75 (m, 1H), 2.05-2.15 (m, 1H), 2.11 (s, 3H).

Example 26

Synthesis 1-(4-methyl-2,3-dihydro-1H-inden-1-yl)-2-oxo-N-(pyridin-4-yl)-1,2-dihydropyridine-3-carboxamide (112)

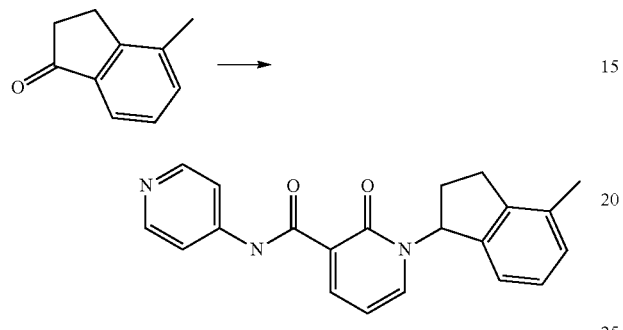

Following protocol I and J, 4-methyl-2,3-dihydro-1H-inden-1-one was converted to 1-(4-methyl-2,3-dihydro-1H-inden-1-yl)-2-oxo-N-(pyridin-4-yl)-1,2-dihydropyridine-3-carboxamide. MS (ESI) 346.0 (M+H); 1H NMR (300 MHz, DMSO-d6) δ13.01 (s, 1H), 8.73 (d, J=3.6 Hz, 2H), 8.50 (d, J=3.9 Hz, 1H), 8.19 (d, J=3.6 Hz, 2H), 7.68 (d, J=3.9 Hz, 1H), 7.18 (d, J=2.6 Hz, 2H), 6.97 (t, J=2.6 Hz, 1H), 6.64 (t, J=3.9 Hz, 1H), 6.55 (t, J=4.2 Hz, 1H), 3.07-3.25 (m, 1H), 2.85-3.00 (m, 1H), 2.65-2.75 (m, 1H), 2.31 (s, 3H), 2.05-2.15 (m, 1H).

Example 26

Synthesis of 2-oxo-1-(4-phenyl-2,3-dihydro-1H-inden-1-yl)-N-(pyridin-4-yl)-1,2-dihydropyridine-3-carboxamide (113)

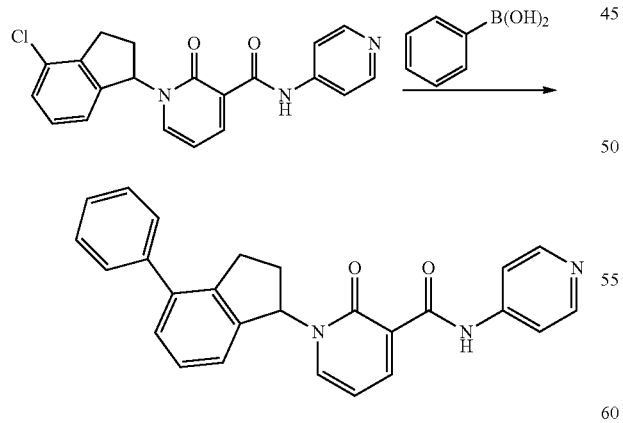

To a mixture of 1-(4-chloro-2,3-dihydro-1H-inden-1-yl)-2-oxo-N-(pyridin-4-yl)-1,2-dihydropyridine-3-carboxamide (200 mg, 1.0 eq) in DME (4 mL) was added phenylboronic acid (3.5 eq), Pd(PPh3)2Cl2 (0.2 eq) and aqueous Na2CO3 (2M, 2 mL). The mixture was stirred at 120° C. for 30 mins by microwave. At the end of reaction 50 mL of H2O was added and extracted with ethyl acetate. The combined organic layer was washed with brine and dried over MgSO4, evaporated the filtrate to give the crude product, which was purified by HPLC to afford 2-oxo-1-(4-phenyl-2,3-dihydro-1H-inden-1-yl)-N-(pyridin-4-yl)-1,2-dihydropyridine-3-carboxamide (21 mg, 10%). MS (ESI) 408.0 (M+H); 1H NMR (300 MHz, DMSO-d6) δ12.93 (s, 1H), 8.71 (br, 2H), 8.53 (d, J=3.9 Hz, 1H), 8.15 (d, J=3.3 Hz, 2H), 7.84 (d, J=3.9 Hz, 1H), 7.57 (d, J=4.5 Hz, 2H), 7.50 (t, J=4.5 Hz, 2H), 7.37-7.43 (m, 3H), 7.17 (d, J=4.5 Hz, 1H), 6.61-6.69 (m, 2H), 3.15-3.25 (m, 1H), 3.05-3.15 (m, 1H), 2.60-2.75 (m, 1H), 2.50 (s, 6H), 2.10-2.15 (m, 1H).

Example 27

Synthesis of 1-(4-(methylcarbamoyl)-2,3-dihydro-1H-inden-1-yl)-2-oxo-N-(pyridin-4-yl)-1,2-dihydropyridine-3-carboxamide (114)

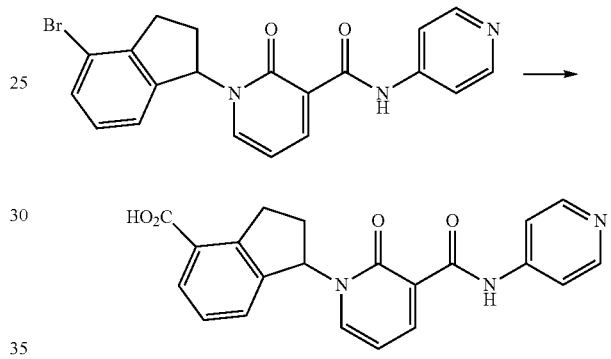

To a mixture of 1-(4-bromo-2,3-dihydro-1H-inden-1-yl)-2-oxo-N-(pyridin-4-yl)-1,2-dihydropyridine-3-carboxamide (250 mg, 1.0 eq) in t-BuOH (15 mL) and DMSO (4 mL) was added the materials of Pd(OAc)2 (0.15 eq), dppp (0.15 eq) and Et3N (2.25 eq), the mixture was stirred at 95° C. for 18 hours under CO (5.0 atmosphere pressure) in a high pressure vessel. At the end of reaction, the solvent was evaporated to give the crude product, which was purified by HPLC to afford 1-(2-oxo-3-(pyridin-4-ylcarbamoyl)pyridin-1(2H)-yl)-2,3-dihydro-1H-indene-4-carboxylic acid (90 mg, 39%).

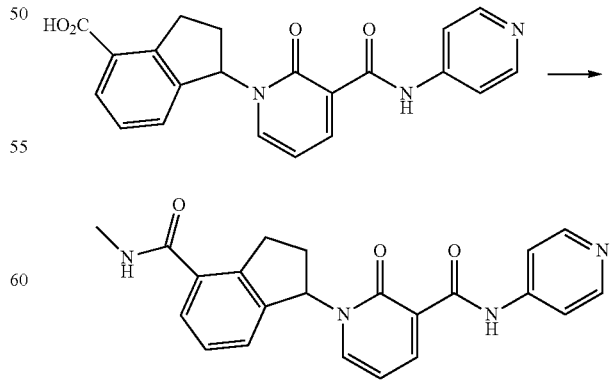

To a mixture of 1-(2-oxo-3-(pyridin-4-ylcarbamoyl)pyridin-1(2H)-yl)-2,3-dihydro-1H-indene-4-carboxylic acid (45 mg, 1.0 eq) in DCM (4 mL) was added EDC.HCl (1.5 eq), HOBt (1.5 eq), Et₃N (3.0 eq) and MeNH2.HCl (1.1 eq) The mixture was stirred at room temperature overnight. Water was added and the mixture was extracted with DCM. The combined organic layer was washed with brine and dried over MgSO₄, evaporated the filtrate to give the crude product, which was purified by HPLC to afford 1-(4-(methylcarbamoyl)-2,3-dihydro-1H-inden-1-yl)-2-oxo-N-(pyridin-4-yl)-1,2-dihydropyridine-3-carboxamide (18 mg, 39%). 389.2 (M+H); ¹H NMR (300 MHz, DMSO-d6) δ 12.97 (s, 1H), 8.73 (d, J=3.6 Hz, 2H), 8.51 (dd, J=1.2 Hz, 4.2 Hz, 1H), 8.31 (d, J=2.8 Hz, 1H), 8.20 (d, J=3.6 Hz, 2H), 7.74 (d, J=4.2 Hz, 1H), 7.60 (d, J=4.2 Hz, 1H), 7.35 (t, J=4.2 Hz, 1H), 7.27 (d, J=4.2 Hz, 2H), 6.65 (t, J=4.2 Hz, 1H), 6.55 (t, J=4.2 Hz, 1H), 3.37 (overlap with DMSO-d6, 2H), 2.60-2.75 (m, 1H), 2.05-2.15 (m, 1H).

Example 28

28.1. Synthesis of N-(4-bromophenyl)-1-(4-hydroxy-2,3-dihydro-1H-inden-1-yl)-2-oxo-1,2-dihydropyridine-3-carboxamide (115)

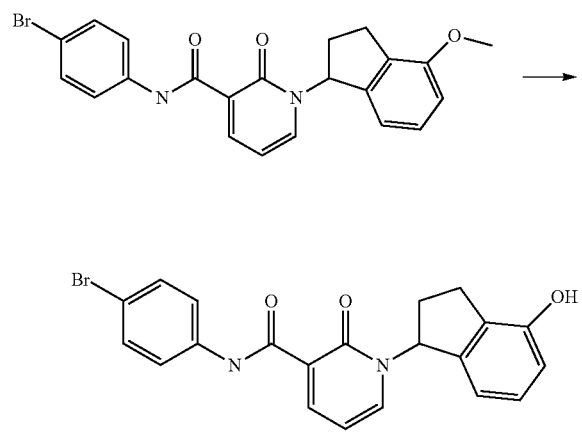

To a solution of N-(4-bromophenyl)-1-(4-methoxy-2,3-dihydro-1H-inden-1-yl)-2-oxo-1,2-dihydropyridine-3-carboxamide (0.4 g, 0.91 mmol) in Ch2Cl2 (2 mL) at 0 C was added BBr3 (1M in CH₂Cl₂, 9 mL). The reaction was stirred at 0° C. for 1 hr. It was poured into sat. aqueous NaHCO₃ (50 mL). The mixture was extracted with EtOAc (3×50 mL). The combined organic layers were dried and concentrated to a solid. The solid was washed with MeOH and CH₂Cl₂ to afford a white solid. It was further purified by prep. HPLC to afford N-(4-bromophenyl)-1-(4-hydroxy-2,3-dihydro-1H-inden-1-yl)-2-oxo-1,2-dihydropyridine-3-carboxamide (120 mg, 31%). Retention time (min)=7.127, method [7], MS (ESI) 425.0 (M+H); ¹H NMR (300 MHz, CDCl₃) δ 12.19 (s, 1H), 8.61 (dd, J=2.1 Hz, 7.0 Hz, 1H), 7.68 (d, J=9.0 Hz, 2H), 7.47 (d, J=9.0 Hz, 2H), 7.15-7.30 (overlap with CDCl₃, 2H), 6.81 (d, J=7.8 Hz, 1H), 6.72 (d, J=7.2 Hz, 1H), 6.60 (dd, J=5.4 Hz, 7.2 Hz, 1H), 6.41 (t, J=7.0 Hz, 1H), 5.0 (br, 1H), 2.80-3.10 (m, 3H), 1.98-2.15 (m, 1H).

28.2. Synthesis of N-(biphenyl-4-yl)-1-(4-hydroxy-2,3-dihydro-1H-inden-1-yl)-2-oxo-1,2-dihydropyridine-3-carboxamide (116)

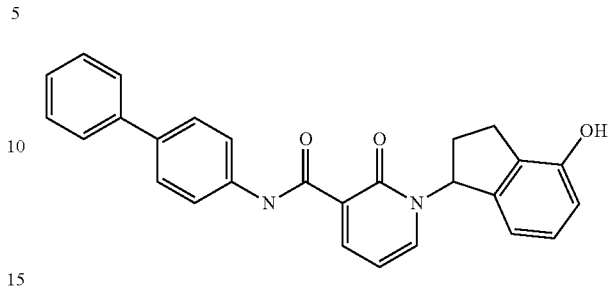

The title compound was synthesized from appropriate starting materials using the procedures outlined above in Example 28.1., or slightly modified versions thereof. Retention time (min)=8.181, method [7], MS (ESI) 423.1 (M+H); ¹H NMR (300 MHz, CDCl₃) δ 12.30 (s, 1H), 8.65 (dd, J=2.1 Hz, 6.9 Hz, 1H), 7.88 (m, 2H), 7.63 (m, 4H), 7.48 (m, 2H), 7.36 (m, 1H), 7.26 (dd, J=2.1 Hz, 6.9 Hz, 1H), 7.18 (t, J=7.8 Hz, 1H), 6.89 (d, J=7.8 Hz, 1H), 6.72 (d, J=7.8 Hz, 1H), 6.64 (dd, J=5.4 Hz, 8.1 Hz, 1H), 6.42 (t, J=6.9 Hz, 1H), 2.80-3.20 (m, 3H), 2.00-2.15 (m, 1H).

Example 29

29.1. Synthesis of N-(4-bromophenyl)-1-(4-(2-hydroxyethoxy)-2,3-dihydro-1H-inden-1-yl)-2-oxo-1,2-dihydropyridine-3-carboxamide (117)

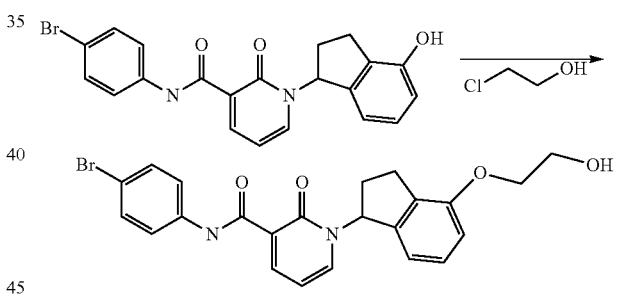

To a solution of N-(4-bromophenyl)-1-(4-hydroxy-2,3-dihydro-1H-inden-1-yl)-2-oxo-1,2-dihydropyridine-3-carboxamide (30 mg, 0.071 mmol) in DMF (0.2 mL) was added K₂CO₃ (30 mg, 0.22 mmol) and 2-chloroethanol (9.3 uL, 0.14 mmol). The reaction mixture was heated at 70 C overnight. It was filtered and purified by prep HPLC to afford N-(4-bromophenyl)-1-(4-(2-hydroxyethoxy)-2,3-dihydro-1H-inden-1-yl)-2-oxo-1,2-dihydropyridine-3-carboxamide (20 mg, 60%). Retention time (min)=7.588, method [7], MS (ESI) 469.1 (M+H); ¹H NMR (300 MHz, CDCl₃) δ 12.20 (s, 1H), 8.57 (dd, J=2.1 Hz, 6.9 Hz, 1H), 7.65 (d, J=9.0 Hz, 2H), 7.44 (d, J=9.0 Hz, 2H), 7.15-7.30 (overlap with CDCl₃, 2H), 6.83 (d, J=8.1 Hz, 1H), 6.73 (d, J=7.5 Hz, 1H), 6.58 (dd, J=5.4 Hz, 8.4 Hz, 1H), 6.39 (t, J=6.9 Hz, 1H), 4.14 (m, 2H), 4.00 (m, 2H), 2.78-3.15 (m, 3H), 1.90-2.10 (m, 1H).

29.2. Additional Compounds

The following compounds were synthesized from appropriate starting materials using the procedures outlined above in Example 29.1., or slightly modified versions thereof.

N-(4-bromophenyl)-1-(4-(2-(2-(2-hydroxyethoxy)ethoxy)ethoxy)-2,3-dihydro-1H-inden-1-yl)-2-oxo-1,2-dihydropyridine-3-carboxamide (118)

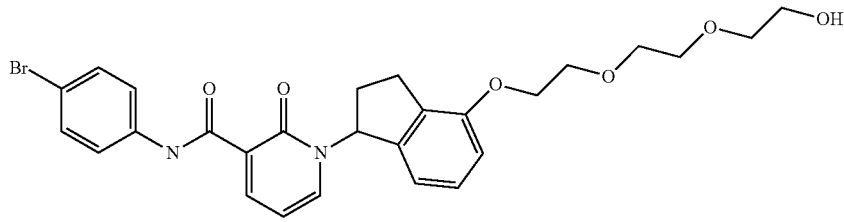 [SMILES: O=C(Nc1ccc(Br)cc1)c1cccn(C2CCc3c(OCCOCCOCCO)cccc32)c1=O]

Retention time (min)=7.579, method [7], MS (ESI) 557.1 (M+H); ¹H NMR (300 MHz, CDCl₃) δ 12.22 (s, 1H), 8.60 (dd, J=1.8 Hz, 7.2 Hz, 1H), 7.71 (d, J=9.0 Hz, 2H), 7.48 (d, J=9.0 Hz, 2H), 7.20-7.30 (overlap with CDCl₃, 2H), 6.86 (d, J=8.1 Hz, 1H), 6.75 (d, J=7.5 Hz, 1H), 6.62 (dd, J=5.7 Hz, 7.8 Hz, 1H), 6.42 (t, J=7.2 Hz, 1H), 4.23 (m, 2H), 3.93 (dd, J=4.2 Hz, 8.4 Hz, 2H), 3.60-3.90 (m, 9H), 2.78-3.20 (m, 3H), 1.90-2.10 (m, 1H).

N-(biphenyl-4-yl)-1-(4-(2-(2-(2-hydroxyethoxy)ethoxy)ethoxy)-2,3-dihydro-1H-inden-1-yl)-2-oxo-1,2-dihydropyridine-3-carboxamide (119)

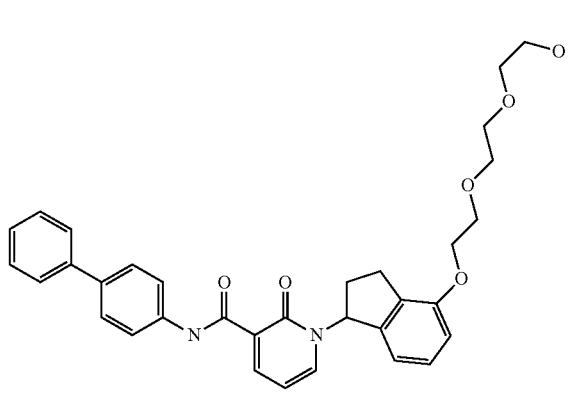 [SMILES: O=C(Nc1ccc(-c2ccccc2)cc1)c1cccn(C2CCc3c(OCCOCCOCCO)cccc32)c1=O]

Retention time (min)=8.387, method [7], MS (ESI) 555.3 (M+H); ¹H NMR (300 MHz, CDCl₃) δ 12.18 (s, 1H), 8.59 (dd, J=2.1 Hz, 7.2 Hz, 1H), 7.85 (m, 2H), 7.58 (m, 4H), 7.41 (m, 2H), 7.17-7.33 (overlap with CDCl₃, 3H), 6.82 (d, J=7.8 Hz, 1H), 6.72 (d, J=7.8 Hz, 1H), 6.61 (dd, J=5.7 Hz, 7.8 Hz, 1H), 6.38 (t, J=7.2 Hz, 1H), 4.17-4.23 (m, 2H), 3.89 (m, 2H), 3.66-3.78 (m, 6H), 3.58-3.65 (m, 2H), 2.78-3.16 (m, 3H), 1.95-2.08 (m, 1H).

Example 30

Synthesis of tert-butyl 2-(2-(2-(1-(3-(biphenyl-4-ylcarbamoyl)-2-oxopyridin-1(2H)-yl)-2,3-dihydro-1H-inden-4-yloxy)ethoxy)ethoxy)ethylcarbamate (120)

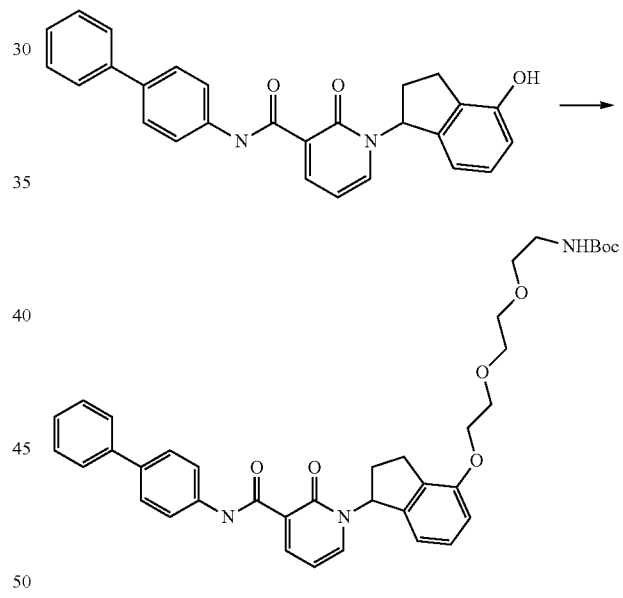

Following Protocol K, N-(biphenyl-4-yl)-1-(4-hydroxy-2,3-dihydro-1H-inden-1-yl)-2-oxo-1,2-dihydropyridine-3-carboxamide was converted to tert-butyl 2-(2-(2-(1-(3-(biphenyl-4-ylcarbamoyl)-2-oxopyridin-1(2H)-yl)-2,3-dihydro-1H-inden-4-yloxy)ethoxy)ethoxy)ethylcarbamate. Retention time (min)=10.622, method [7], MS (ESI) 676.4 (M+Na); ¹H NMR (300 MHz, CDCl₃) δ 12.33 (s, 1H), 8.64 (dd, J=2.1 Hz, 7.2 Hz, 1H), 7.86 (m, 2H), 7.64 (m, 4H), 7.47 (m, 2H), 7.20-7.41 (overlap with CDCl₃, 3H), 6.87 (d, J=8.1 Hz, 1H), 6.77 (d, J=7.5 Hz, 1H), 6.64 (dd, J=5.4 Hz, 8.1 Hz, 1H), 6.45 (t, J=7.2 Hz, 1H), 4.20-4.30 (m, 2H), 3.94 (t, J=5.1 Hz, 2H), 3.89 (m, 2H), 3.66-3.78 (m, 6H), 3.58-3.65 (m, 2H), 2.78-3.16 (m, 3H), 1.95-2.08 (m, 1H), 1.79 (s, 9H).

Example 31

Synthesis of 1-(4-(2-(2-(2-aminoethoxy)ethoxy)ethoxy)-2,3-dihydro-1H-inden-1-yl)-N-(biphenyl-4-yl)-2-oxo-1,2-dihydropyridine-3-carboxamide trifluoroacetate (121)

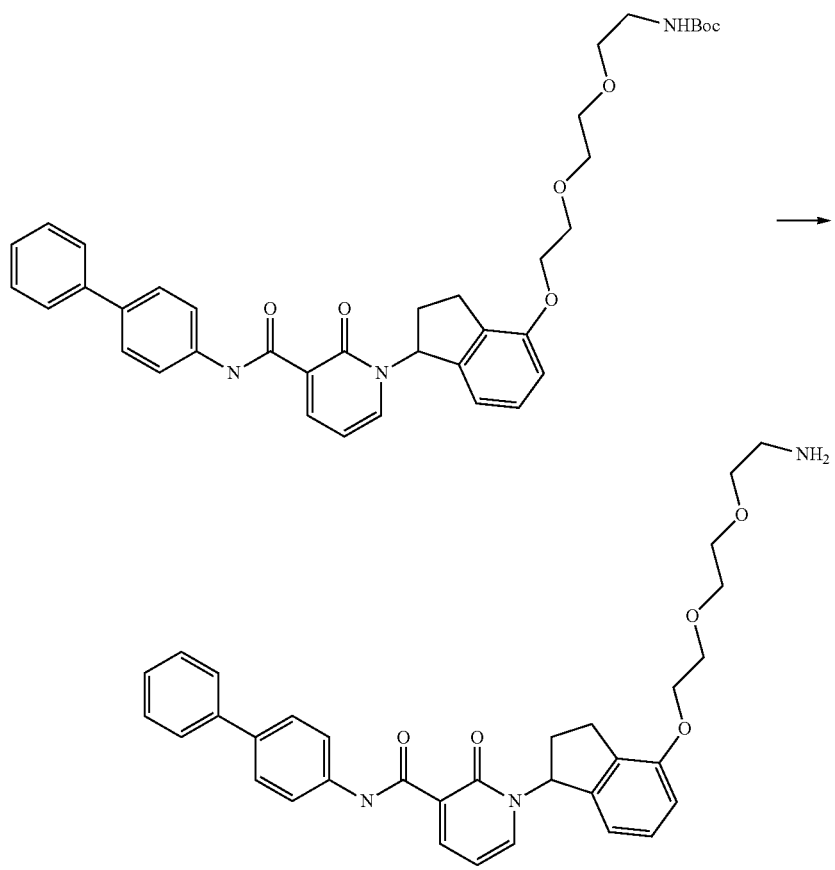

Following Protocol L, tert-butyl 2-(2-(2-(1-(3-(biphenyl-4-ylcarbamoyl)-2-oxopyridin-1(2H)-yl)-2,3-dihydro-1H-inden-4-yloxy)ethoxy)ethoxy)ethylcarbamate was converted to 1-(4-(2-(2-(2-aminoethoxy)ethoxy)ethoxy)-2,3-dihydro-1H-inden-1-yl)-N-(biphenyl-4-yl)-2-oxo-1,2-dihydropyridine-3-carboxamide trifluoroacetate. Retention time (min) =7.005, method [7], MS (ESI) 554.3 (M+H); $^1$H NMR (300 MHz, CDCl$_3$) δ 12.23 (s, 1H), 8.58 (dd, J=1.5 Hz, 8.4 Hz, 1H), 7.86 (d, J=8.2 Hz, 2H), 7.59 (m, 4H), 7.41 (t, J=7.5 Hz, 2H), 7.18-7.33 (overlap with CDCl$_3$, 3H), 6.80 (d, J=8.1 Hz, 1H), 6.72 (d, J=7.8 Hz, 1H), 6.58 (dd, J=6.6 Hz, 9.6 Hz, 1H), 6.40 (t, J=8.4 Hz, 1H), 4.18 (br, 2H), 3.60-3.95 (br, 11H), 3.19 (br, 2H), 2.75-3.15 (m, 3H), 1.95-2.08 (m, 1H).

Example 32

In Vitro α4β7 Integrin Adhesion Assay (8866 Cell Adhesion to MadCAM-Fc)

Compounds of the present invention were tested for their ability to compete with a natural ligand (MadCAM) for binding to α$_4$β$_7$ integrin (i.e., block MadCAM-α4/β7 integrin interactions) using the following cell-based assay.

Materials
H/S++ buffer: 140 mM NaCl, 20 mM HEPES, 1 mM CaCl$_2$, 1 mM MgCl$_2$)
Assay buffer: H/S++ buffer with 0.3% BSA
8866 media recipe (1 Liter): RPMI 1640 Medium (Gibco) (880 ml), 10% FBS from (100 ml), Penn/Strep (media aliquots) (10 ml), L-Glutamine (media aliquots) (10 ml)

A. Cell Preparation, Cell Harvest and Labeling 8866 cells were split from a carrying flask the day before the assay and incubated in 8866 media at 37° C. and 5% CO$_2$.

Harvest six flasks of 8866 cells into two 500 ml conical tubes. Spin down for 5 minutes at 1000 rpm. Aspirate the supernatants and re-suspend the cells in assay buffer. Wash the cells with 50 ml of assay buffer, gently mix by pipetting up and down several times, transfer to 50 ml tube to be centrifuged again for 5 minutes at 1000 rpm.

Aspirate the wash and re-suspend the cells in 16 ml of assay buffer. Mix gently with pipette (carefully w/o bubbles) and then add 16 µl of Calcein AM (1:1000 10 mg/ml; Invitrogen). Invert gently several times and then incubate with agitation for 30 min at RT while covering the tube with foil (calcein AM is light sensitive). After incubation, add assay buffer to 50 ml, mix well and count the cells. After counting, spin down the cells at 1000 rpm and re-suspend at 2.5×10$^6$ cells/ml in assay buffer.

B. MadCAM Plate Coating

Prepare Mouse ascites anti Hu Fc (Sigma 1-6260) at 1:300. Add 180 µl of stock into 54 ml of H/S$^{++}$ buffer. Add 100 µl/well to 96-well ELISA plate (Costar 3590) and incubate at RT for 1 hour.

Aspirate the plate, blot, and block the plate with 100 µl/well assay buffer at RT for 1 hour.

Prepare MadCAM solution at 0.15 µg/ml—add 14.7 µl of MadCAM-1/Fc stock at 0.55 mg/ml into 54 ml of PBS$^{++}$.

Aspirate the plates, wash 3 times with 150 µl/well assay buffer, add 100 µl/well of respective MadCAM-1/Fc to the plates and incubate overnight at 4° C.

Wash the MadCAM-Fc coated plates 3 times with 150 µl/well of assay buffer. Leave the last wash in until ready to add cells/compounds to MadCAM-Fc plates.

C. Preparation of Compound Solutions (a) Reference Compound (ELAN 91852-8)

Prepare 604.08 µM by adding 42.3 µL of 10 mM (DMSO) stock into 0.7 mL of media. Add this compound to A1-A3 of 100% plates and use the Hamilton program "α4β7 1:3" to dilute compound 1 to 3.

(b) Test Compounds

For a 10 µM starting concentration, dilute 15 µL of compound with 285 µL of DMSO. Transfer into triplicates of row A of 100% plates and dilute 1 to 3 using the Hamilton. For 100 µM starting conc., dilute 105 µL compound with 105 µL of DMSO and add triplicates to 100% plates to be diluted 1:3.

Use the Multimek program "147tranf" to transfer 147 µl of assay buffer to each well (w/exception of row H) of the 2% plates. Then use the multimek program "3 µltrans" to transfer 3 µl of compound from the 100% plates to add to the 147 µl of buffer in the 2% plates. Keep all compound plates on shaker when not in use.

D. Preparation of 21/6—Positive Control

Prepare 21/6 at a working conc. of 20 µg/ml for a final conc. of 10 µg/ml. Add 20 µg/ml solution of 21/6 to wells H4-H12 of all the 2% plates.

E. Assay

Bring the cells in the deep well, the compounds in the 2% plates, and empty 1% plates to the multimek. Transfer 70 µl/well of cells from deep well plate to 1% plates followed by adding 70 µl/well of the respective compounds from 2% plates to 1% plates. (No cells or compounds in H1-H3). Incubate cells+compounds for 30 min. at RT.

Then transfer 100 µl/well from 1% plates to MadCAM-Fc plates. Mix well and consistently in order to have enough cells in the wells. Incubate for another 30 min at RT.

Carefully wash the plates 4 times with 100 µl/well. Aspirate wells H1-H3 after plate is ready and add 50 µl media+50 µl 2× cells=total input.

Read the plates using Cytoflour (Excitation=485, Emission=530, and Gain=47).

Example 33

In Vitro Biological Evaluation (SRU MadCAM Assay)

Compounds of the present invention were tested for their ability to compete with a natural ligand (MadCAM) for binding to α$_4$β$_7$ integrin using the following assay. The SRU Bind platform is a label free assay platform that consists of three parts: (1) a plate-based optical biosensor (2) the Bind Reader, and (3) a software analysis packet. This system offers advantages over manual methods in terms of increased throughput, greater sensitivity, and lower assay to assay variability. Specifically, this assay measures adhesion of 8866 cells endogenously expressing a4b7 to immobilized recombinant and soluble MadCAM, which was expressed as a fusion protein with a human IgGFc tail.

The SRU Bind cell adhesion assay is a two-day assay. On the first day, the 384-well SRU Bind biosensor plate was hydrated for 15 minutes, washed with Hepes buffer pH 7.4 containing 100 mM NaCl and then incubated with a monoclonal antibody to human Fc (Sigma I-6260 1:500 dilution in Hepes pH 7.4 buffer) for 60 minutes at room temperature. The plate was then blocked with 4% BSA in 20 mM Hepes buffer pH 7.4, for one hour and then incubated overnight with 0.15 µg/ml of recombinant MadCAM at 4° C. On the second day, test compounds were serially diluted 1:2 in DMSO (200× final concentration) for a 10-point dose response curve. Compounds were then diluted 50× in 20 mM Hepes buffer pH 7.4 containing 1 mM MgCl$_2$, 1 mM CaCl$_2$, 140 mM NaCl, and 0.3% BSA (Buffer A) using a Multimek liquid handler. 8866 cells grown in 500 ml conical tubes were harvested (4×-final) in Buffer A and were incubated with the test compounds (1:1) for thirty minutes at room temperature. The biosensor assay plate was washed with Buffer A containing 1% DMSO leaving 25 µl in-wells and a baseline measurement was taken. 25 µl of 8866 cells that had been incubated with compound were then transferred to the SRU Bind assay plate (50000 cells/well final at a 1% DMSO final concentration) and the extent of cell adhesion was measured at 45 minutes. The ability of compounds to block a4b7-mediated 8866 cell adhesion was then quantified and plotted using Excel-fit.

Example 34

Cell Adhesion Assay

Compounds of this invention can be tested for their ability to inhibit cellular adhesion. Using RPMI-8866 cells, adhesion to recombinant, immobilized soluble MadCAM-1 can be measured. This assay is described by Tidswell et al., *J. Immunol.* (1997) 159(3):1497-1505.

Example 35

Soluble MadCAM-1 FACS Assay

This assay measures the interaction of recombinant soluble MadCAM-1 with RPMI-8866 cells in suspension. Recombinant soluble MadCAM-1 ("rsMadCAM-1") was expressed as a fusion protein with a human IgG Fc tail (Tidswell et al., *J. Immunol.* (1997) 159(3):1497-1505). Soluble MadCAM-1 was mixed with RPMI-8866 cells in the presence and absence of test compounds. 1 mM MnCl$_2$ was included in the assay buffer to increase the activity of α$_4$β$_7$ integrin and to promote its interaction with the MadCAM-1 construct. After 30 minutes at room temperature, the cells were washed with buffer containing 1 mM MnCl$_2$, and were exposed to a fluorescently labeled antibody against the Fc tail of the MadCAM-1 fusion protein in the presence of 1 mM MnCl$_2$, for 30 minutes at 4° C. The cells were washed, re-suspended in MnCl$_2$ containing buffer and examined by FACS analysis. An identical assay can be performed to measure the interaction of recombinant soluble VCAM-1 with cells that express α$_4$β$_1$, such as the Jurkat T cell line.

Example 35

Cell Free ELISA Assay

This assay measures the interaction of solubilized integrin with MadCAM-1 immobilized on a plastic surface. RPMI- 8866 cells were lysed with a detergent to solubilize the $\alpha_4\beta_7$ integrin. An antibody against $\beta_7$ integrin (2G3) was added to the lysate. See Tidswell et al. *J. Immunol.* (1997) 159(3): 1497-1505. This antibody serves two purposes. First, it is a tag by which $\alpha_4\beta_7$ integrin can be detected in the assay and, second, 2G3 is an antibody that stabilizes a ligand occupied conformation of $\beta_7$ integrin and promotes $\beta_7$ integrin-dependent interactions. Cell lysate, 2G3, and test compound were added to microtiter wells coated with MadCAM-1. The mixture was incubated for 30 minutes at room temperature. The plate was washed, blocked with 1% BSA, and exposed to HRP-conjugated goat anti-mouse Ig, which recognizes 2G3 associated with MadCAM-bound $\alpha_4\beta_7$ integrin. After 30 minutes at room temperature, the wells were washed and exposed to a substrate for HRP to quantify the amount of $\alpha_4\beta_7$ integrin bound to MadCAM-1.

Example 36

FACS Assay for Receptor Occupancy

This assay measures the interaction of antibody 2G3 with RPMI-8866 cells or with lymphocytes. The antibody recognizes a ligand-occupied epitope of either rat or human $\beta_7$ integrin. Increasing concentrations of small molecule ligand induce the 2G3 epitope on $\beta_7$ integrin and will allow higher levels of antibody binding to the surface of the cells. The concentration of ligand required for receptor occupancy is directly related to the ligand's affinity for $\alpha_4\beta_7$ integrin. A similar assay has been described for examining the interaction of ligands with $\alpha_4\beta_1$ integrin, which utilizes an analogous antibody against a ligand occupied epitope of $\beta_1$ integrin (antibody 15/7; Yednock et al. (1995) *JBC* 270:28740-50). The $\beta_1$ integrin assay relies on cells that express $\alpha_4\beta_1$ integrin, rather than $\alpha_4\beta_7$ integrin (such as Jurkat cells). In both assays, the appropriate cells are mixed with either 2G3 or 15/7 in the presence of the small molecule ligand. The cells are incubated at room temperature for 30 minutes and washed to remove unbound antibody. The cells are exposed to a fluorescently-labeled antibody against mouse IgG, which detects cell-associated 2G3 or 15/7 and the cells are examined by FACS analysis.

Example 37

Ex Vivo Cell Adhesion Assay

This assay measures the adhesion of lymphocytes or RPMI-8866 cells to high endothelial venules exposed in tissue sections of Peyer's Patches (lymphoid tissue associated with the intestine). These vessels express high levels of Mad-CAM-1. This assay is described by Yednock et al., *JCB* (1987) 104:725-731.

Example 38

In Vivo Migration Assay

Migration of $In^{111}$-labeled or fluorescently-labeled lymphocytes to Peyer's Patches in vivo. In this assay, lymphocytes are isolated from one group of animals and are labeled with a radioactive or fluorescent tracer. The cells are injected intravenously into a second group of animals. After 1 to 24 hours, the localization of the labeled cells to different tissues can be monitored by either determining the number of radioactive counts associated with different tissues in a gamma counter, or by isolating lymphocytes from the tissue and determining the number of cells that carry a fluorescent tag (determined by FACS analysis). This type of assay is described by Rosen et al., *J. Immunol.* 1989, 142:1895-1902.

Example 39

In Vivo Biological Evaluation (Asthma Models)

Inflammatory conditions mediated by $\alpha_4\beta_1$ integrin include, for example, eosinophil influx, airway hyper-responsiveness and occlusion that occurs with chronic asthma. The following describes animal models of asthma that are used to study the in vivo effects of the compounds of this invention for use in treating asthma.

39.1. Rat Asthma Model (E2)

Following the procedures described by Chapman, et al., Am J. Resp. Crit. Care Med., 153-4, A219 (1996) and Chapman, et al., Am. J. Resp. Crit. Care Med. 155:4, A881 (1997), both of which are incorporated by reference in their entirety.

Ovalbumin (OA; 10 µg/mL) is mixed with aluminum hydroxide (10 mg/mL) and injected (i.p.) in Brown Norway rats on day 0. Injections of OA, together with adjuvant, are repeated on days 7 and 14. On day 21, sensitized animals are restrained in plastic tubes and exposed (60 minutes) to an aerosol of OA (10 mg/kg) in a nose-only exposure system Animals are sacrificed 72 hours later with pentobarbital (250 mg/kg, i.p.). The lungs are lavaged via a tracheal cannula using 3 aliquots (4 mL) of Hank's solution (HBSS×10, 100 ml; EDTA 100 mM, 100 mL; HEPES 1 M, 25 mL; made up to 1 L with $H_2O$); recovered cells are pooled and the total volume of recovered fluid adjusted to 12 mL by addition of Hank's solution. Total cells are counted (Sysmex microcell counter F-500, TOA Medical Electronics Otd., Japan) and smears are made by diluting recovered fluid (to approximately $10^6$ cells/mL) and pipetting an aliquot (100 µl) into a centrifuge (Cytospin, Shandon, U.K.). Smears are air dried, fixed using a solution of fast green in methanol (2 mg/mL) for 5 seconds and stained with eosin G (5 seconds) and thiazine (5 seconds) (Diff-Quick, Browne Ltd. U.K.) in order to differentiate eosinophils, neutrophils, macrophages and lymphocytes. A total of 500 cells per smear are counted by light microscopy under oil immersion (×100). Compounds of this invention can be formulated into a 0.5% carboxymethylcellulose and 2% Tween 80 suspension and administered orally to rats which had been sensitized to the allergen, ovalbumin Compounds which inhibited allergen-induced leukocyte accumulation in the airways of actively sensitized Brown Norway rats are considered to be active in this model.

39.2. Mouse Asthma Model (E3)

Compounds are also evaluated in a mouse model of acute pulmonary inflammation following the procedures described by, Kung, et al., Am J. Respir. Cell Mol. Biol., 13:360-365, (1995) and Schneider, et al., (1999). Am J. Respir. Cell Mol. Biol. 20:448-457, (1999), which are each incorporated by reference in their entirety. Female Black/6 mice (8-12 weeks of age) are sensitized on day 1 by an intraperitoneal injection of 0.2 mL ova/alum mixture containing 20 µg of ova (Grade 4, Sigma) and 2 mg inject Alum (Pierce). A booster injection is administered on day 14. Mice are challenged on days 28 and 29 with aerosolized 1% ova (in 0.9% saline) for 20 minutes. Mice are euthanized and bronchaveolar lavage samples (3 mL) are collected on day 30, 48 hours post first challenge. Eosinophils are quantified by a FACS/FITC staining method.

Compounds of this invention are formulated into a 0.5% carboxymethylcellulose and 2% Tween 80 suspension and administered orally to mice which had been sensitized to the allergen, ovalbumin Compounds which inhibited allergen-induced leucocyte accumulation in the airways of actively sensitized C57BL/6 mice are considered to be active in this model.

39.3. Sheep Asthma Model (E4)

This model employs the procedures described by Abraham, et al., J. Clin, Invest, 93:776-787 (1994) and Abraham, et al., Am J. Respir. Crit. Care Med., 156:696-703 (1997), both of which are incorporated by reference in their entirety. Compounds of this invention are evaluated by intravenous (saline aqueous solution), oral (2% Tween 80, 0.5% carboxymethylcellulose), and aerosol administration to sheep which are hypersensitive to *Ascaris suum* antigen. Compounds which decrease the early antigen-induced bronchial response and/or block the late-phase airway response, e.g. have a protective effect against antigen-induced late responses and airway hyper-responsiveness ("AHR"), are considered to be active in this model.

Allergic sheep which are shown to develop both early and late bronchial responses to inhaled *Ascaris suum* antigen are used to study the airway effects of the candidate compounds. Following topical anesthesia of the nasal passages with 2% lidocaine, a balloon catheter is advanced through one nostril into the lower esophagus. The animals are then incubated with a cuffed endotracheal tube through the other nostril with a flexible fiberoptic bronchoscope as a guide.

Pleural pressure is estimated according to Abraham (1994). Aerosols (see formulation below) are generated using a disposable medical nebulizer that provided an aerosol with a mass median aerodynamic diameter of 3.2 μm as determined with an Andersen cascade impactor. The nebulizer is connected to a dosimeter system consisting of a solenoid valve and a source of compressed air (20 psi). The output of the nebulizer is directed into a plastic T-piece, one end of which is connected to the inspiratory port of a piston respirator. The solenoid valve is activated for 1 second at the beginning of the inspiratory cycle of the respirator. Aerosols are delivered at VT of 500 mL and a rate of 20 breaths/minute. A 0.5% sodium bicarbonate solution only is used as a control.

To assess bronchial responsiveness, cumulative concentration-response curves to carbachol is generated according to Abraham (1994). Bronchial biopsies are taken prior to and following the initiation of treatment and 24 hours after antigen challenge. Bronchial biopsies are preformed according to Abraham (1994).

An in vitro adhesion study of alveolar macrophages can also be performed according to Abraham (1994), and a percentage of adherent cells can be calculated.

Aerosol Formulation

A solution of compound n 0.5% sodium bicarbonate/saline (w/v) at a concentration of 30.0 mg/mL is prepared using the following procedure:

A. Preparation of 0.5% Sodium Bicarbonate/Saline Stock Solution: 100.0 mL

| Ingredient | Gram/100.0 mL | Final Concentration |
|---|---|---|
| Sodium Bicarbonate | 0.5 g | 0.5% |
| Saline | q.s. ad 100.0 mL | q.s. ad 100% |

Procedure:
1. Add 0.5 g sodium bicarbonate into a 100 mL volumetric flask.
2. Add approximately 90.0 mL saline and sonicate until dissolved.
3. Q.S. to 100.0 mL with saline and mix thoroughly.

B. Preparation of 30.0 mg/mL Compound: 10.0 mL

| Ingredient | Gram/10.0 mL | Final Concentration |
|---|---|---|
| Compound | 0.300 g | 30.0 mg/mL |
| 0.5% Sodium Bicarbonate/Saline Stock Solution | q.s. ad 10.0 mL | q.s ad 100% |

Procedure:
1. Add 0.300 g of the compound into a 10.0 mL volumetric flask.
2. Add approximately 9.7 mL of 0.5% sodium bicarbonate/saline stock solution.
3. Sonicate until the compound is completely dissolved.
4. Q.S. to 10.0 mL with 0.5% sodium bicarbonate/saline stock solution and mix thoroughly.

Example 40

In Vivo Biological Evaluation (Arthritis)

40.1. Adjuvant-Induced Arthritis in Rats

Adjuvant induced arthritis ("AIA") is an animal model useful in the study of rheumatoid arthritis ("RA"), which is induced by injecting *M. tuberculosis* in the base of the tail of Lewis rats. Between 10 and 15 days following injection, animals develop a severe, progressive arthritis.

The compounds of the invention can be tested for their ability to alter hind paw swelling and bone damage resulting from adjuvant induced edema in rats. To quantitate the inhibition of hind paw swelling resulting from AIA, two phases of inflammation have been defined: (1) the primary and secondary injected hind paw, and (2) the secondary non-injected hind paw, which generally begins developing about eleven days from the induction of inflammation in the injected paw. Reduction of the latter type of inflammation is an indication of immunosuppressive activity. CF Chang, *Arth. Rheum.*, 20, 1135-1141 (1977).

Using an animal model of RA, such as AIA, enables one to study the cellular events involved in the early stages of the disease. CD44 expression on macrophages and lymphocytes is up regulated during the early development of adjuvant arthritis, whereas LFA 1 expression is up regulated later in the development of the disease. Understanding the interactions between adhesion molecules and endothelium at the earliest stages of adjuvant arthritis could lead to significant advances in the methods used in the treatment of RA.

40.2. Collagen Induced Arthritis in Rats

Compounds of the invention can be tested in this animal model by measuring the inhibition of inflammation, cartilage destruction and bone resorption that occurs in developing type II collagen arthritis in rats.

Animals: 54 Female Lewis rats (Harlan), weighing 125-150 g on arrival. (inject 50 with collagen to get 50 responders on days 10, 11, 12 for 6 groups of 10). The animals (10/group for arthritis, 4/group for normal control), housed 4-5/cage, were acclimated for 4-8 days. The animals were dosed at po3 mg/kg bid, po10 mg/kg bid, and po30 mg/kg bid.

Materials: Agents or drugs in vehicle, Type II collagen, Freund's incomplete adjuvant, methotrexate (Sigma), compounds of the invention.

General Study Design

Dosing was initiated on day minus 1. The acclimated animals were anesthetized with isoflurane and given collagen injections (D0). On day 6 they were anesthetized again for the second collagen injection. Collagen was prepared by making a 4 mg/mL solution in 0.01N acetic acid. Equal volumes of collagen and Freund's incomplete adjuvant, were emulsified by hand mixing until a bead of this material held its form when placed in water. Each animal received 300 μL of the mixture each time spread over 3 sites on back. Calipering of normal (pre-disease) right and left ankle joints were done on day 9. On days 10-12, onset of arthritis occurred.

Rats were weighed on days (-) 1, 6, 9, 10, 11, 12, 13, 14, 15, 16, 17, 18, 19, and 20 of the study and caliper measurements of ankles taken every day beginning on day 9. Final body weights were taken on day 20. After final body weight measurement, animals were anesthetized for terminal plasma collection and then euthanized.

Both hind paws and knees were removed. Hind paws were weighed, placed (with knees) in formalin and then processed for microscopy.

Processing of Joints

Following 1-2 days in fixative and then 4-5 days in decalcifier, the ankle joints were cut in half longitudinally, knees were cut in half in the frontal plane, processed, embedded, sectioned and stained with toluidine blue.

Certain compounds of the invention exhibited significant inhibition compared to controls receiving no treatment of ankle inflammation and ankle histopathology at doses tested (3.0 mg/kg, 10.0 mg/kg and 30.0 mg/kg).

Example 41

In Vivo Biological Evaluation (Colitis)

Induction of Colitis in HLA-B27 Rats

The efficacy of the compounds of the present invention in reversing colitis was determined in HLA-B27 transgenic rats. HLA-B27 transgenic rats have been utilized as an animal model of Inflammatory Bowel Disease which mimics Crohn's Disease in humans. The rats overexpress the human MHC class I HLA-B27 heavy chain and beta-2 microglobulin proteins, which induces a variety of autoimmune diseases that include inflammation of the colon.

The therapeutic effect of the compounds of this invention in resolving colitis was evaluated in HLA-B27 transgenic rats. Diseased rats were dosed subcutaneously with 100 mg/kg of a selected compound of this invention twice a day for 16 days. Animal samples dosed with 100 mg/kg of the compound of this invention showed clinical and histological resolution of colitis and mimicked similar efficacy with the positive control group treated with anti-alpha4 antibody GG5/3.

Disease Activity Index (DAI) scores indicated overall improved scores for rats dosed with 100 mg/kg of certain compounds of this invention and 10 mg/kg of GG5/3 (positive control) than rats dosed with vehicle. Fecal consistency and FOB scores for rats dosed with the compound and GG5/3 were statistically different from the vehicle group.

Induction of Colitis

20 HLA-B27 (6-9 weeks old) transgenic rats were ordered from Taconic. Rats acclimated in animal facility for 10 weeks. Animal bedding was mixed from different cages once a week to control for a "dirty" environmental flora. Certain compounds of the invention inhibit kainic acid-induced phospho-cJun upregulation in Mice.

What is claimed is:

1. A compound having a structure according to Formula (Ia):

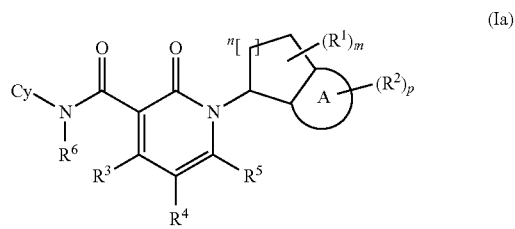

or a salt or solvate or single stereoisomer or mixture of stereoisomers thereof, wherein m is an integer selected from 0 to 4;

n is an integer selected from 0 to 3;

p is an integer selected from 0 to 4;

ring A is a member selected from substituted or unsubstituted aryl and substituted or unsubstituted heteroaryl;

Cy is a member selected from substituted or unsubstituted $(C_3-C_{10})$cycloalkyl, substituted or unsubstituted 3- to 10-membered heterocycloalkyl, substituted or unsubstituted aryl and substituted or unsubstituted heteroaryl;

each $R^1$ and each $R^2$ is a member independently selected from H, substituted or unsubstituted $(C_1-C_{10})$alkyl, substituted or unsubstituted 2- to 10-membered heteroalkyl, substituted or unsubstituted $(C_3-C_{10})$cycloalkyl, substituted or unsubstituted 3- to 10-membered heterocycloalkyl, substituted or unsubstituted aryl, substituted or unsubstituted heteroaryl, nitro, CN, halogen, $OR^{12}$, $SR^{12}$, $NR^{12}R^{13}$, $C(O)R^{14}$, $C(O)NR^{12}R^{13}$, $OC(O)NR^{12}R^{13}$, $C(O)OR^{12}$, $NR^{15}C(O)R^{14}$, $NR^{15}C(O)OR^{12}$, $NR^{15}C(O)NR^{12}R^{13}$, $NR^{15}C(S)NR^{12}R^{13}$, $NR^{15}S(O)_2R^{14}$, $S(O)_2NR^{12}R^{13}$ and $S(O)_zR^{14}$, wherein z is 1 or 2;

$R^{12}$, $R^{13}$ and $R^{15}$ are members independently selected from H, acyl, substituted or unsubstituted $(C_1-C_{10})$alkyl, substituted or unsubstituted 2- to 10-membered heteroalkyl, substituted or unsubstituted aryl, substituted or unsubstituted heteroaryl, substituted or unsubstituted $(C_3-C_{10})$cycloalkyl, substituted or unsubstituted 3- to 10-membered heterocycloalkyl; and $R^{14}$ is a member independently selected from substituted or unsubstituted $(C_1-C_{10})$alkyl, substituted or unsubstituted 2- to 10-membered heteroalkyl, substituted or unsubstituted aryl, substituted or unsubstituted heteroaryl, substituted or unsubstituted $(C_3-C_{10})$cycloalkyl, substituted or unsubstituted 3- to 10-membered heterocycloalkyl, wherein $R^{12}$ and $R^{13}$, together with the nitrogen atoms to which they are attached, are optionally joined to form a 4- to 7-membered ring, and wherein two adjacent $R^1$, together with the atoms to which they are attached, are optionally joined to form a 5- to 7-membered ring, and wherein two adjacent $R^2$, together with the atoms to which they are attached, are optionally joined to form a 5- to 7-membered ring;

$R^3$, $R^4$ and $R^5$ are members independently selected from H, substituted or unsubstituted $(C_1-C_4)$alkyl, halogen and CN; and $R^6$ is a member selected from H and substituted or unsubstituted $(C_1-C_4)$alkyl.

2. The compound of claim 1, wherein ring A is a member selected from phenyl and thiophene.

3. The compound of claim 1, wherein $R^3$, $R^4$ and $R^5$ are each independently selected from H and F.

4. The compound of claim 1, wherein n is 1.

5. The compound of claim 1, wherein $R^6$ is H.

6. The compound of claim 1, wherein the compound has a structure according to Formula (IVa):

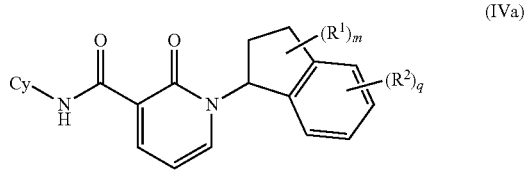

(IVa)

or a salt or solvate thereof, wherein q is an integer selected from 0 to 4; and

Cy, $R^1$, $R^2$ and m are defined as in claim 1.

7. The compound of claim 1, wherein the compound has a structure according to Formula (IVb) or Formula (IVc):

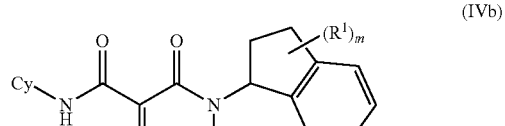

(IVb)

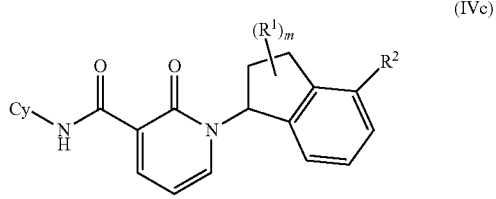

(IVc)

or a salt or solvate thereof, wherein Cy, $R^1$, $R^2$ and m are defined as in claim 1.

8. The compound of claim 1, wherein Cy is a member selected from substituted or unsubstituted phenyl and substituted or unsubstituted pyridyl.

9. The compound of claim 1, wherein the compound has a structure according to Formula (XII):

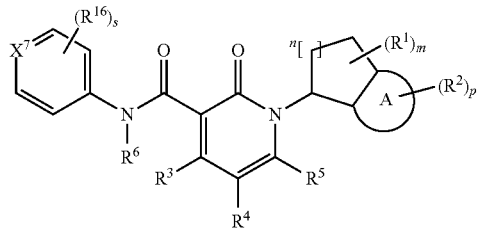

(XII)

or a salt or solvate thereof, wherein ring A, $R^1$, $R^2$, $R^3$, $R^4$, $R^5$, $R^6$, m, n and p are defined as in claim 1;

s is an integer selected from 0 to 4;

$X^7$ is a member selected from $CR^{16}$ and N;

each $R^{16}$ is a member independently selected from H, substituted or unsubstituted $(C_1-C_{10})$alkyl, substituted or unsubstituted 2- to 10-membered heteroalkyl, substituted or unsubstituted $(C_3-C_{10})$cycloalkyl, substituted or unsubstituted 3- to 10-membered heterocycloalkyl, substituted or unsubstituted aryl, substituted or unsubstituted heteroaryl, CN, halogen, $OR^{17}$, $SR^{17}$, $NR^{17}R^{18}$, $C(O)R^{19}$, $C(O)NR^{17}R^{18}$, $OC(O)NR^{17}R^{18}$, $C(O)OR^{17}$, $NR^{20}C(O)R^{19}$, $NR^{20}C(O)OR^{17}$, $NR^{20}C(O)NR^{17}R^{18}$, $NR^{20}C(S)NR^{17}R^{18}$, $NR^{20}S(O)_2R^{19}$, $S(O)_2NR^{17}R^{18}$ and $S(O)_zR^{19}$, wherein z is 1 or 2;

$R^{17}$, $R^{18}$ and $R^{20}$ are members independently selected from H, substituted or unsubstituted $C_1-C_{10}$ alkyl, substituted or unsubstituted 2- to 10-membered heteroalkyl, substituted or unsubstituted $C_3-C_{10}$ cycloalkyl, substituted or unsubstituted 3- to 10-membered heterocycloalkyl, substituted or unsubstituted aryl, and substituted or unsubstituted heteroaryl, wherein $R^{17}$ and $R^{18}$, together with the nitrogen atom to which they are attached, are optionally joined to form a 5- to 7-membered ring; and $R^{19}$ is a member independently selected from substituted or unsubstituted $C_1-C_{10}$ alkyl, substituted or unsubstituted 2- to 10-membered heteroalkyl, substituted or unsubstituted $C_3-C_{10}$ cycloalkyl, substituted or unsubstituted 3- to 10-membered heterocycloalkyl, substituted or unsubstituted aryl, and substituted or unsubstituted heteroaryl, wherein two adjacent $R^{16}$, together with the atoms to which they are attached, are optionally joined to form a 5- to 7-membered ring.

10. The compound of claim 9, wherein $R^6$ is H.

11. The compound of claim 9, wherein $R^3$, $R^4$ and $R^5$ are each independently selected from H and F.

12. The compound of claim 9, wherein n is 1.

13. The compound of claim 9, wherein ring A is a member selected from phenyl and thiophene.

14. The compound of claim 9, wherein the compound has a structure according to Formula (XIIb):

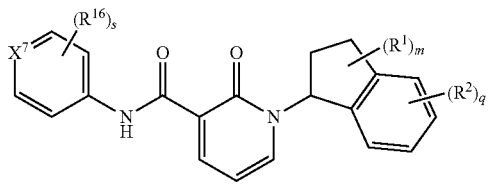

(XIIb)

or a salt or solvate thereof, wherein $X^7$, $R^1$, $R^2$, $R^{16}$, m, and s are defined as in claim 9 and wherein q is an integer selected from 0 to 4.

15. The compound of claim 9, wherein $R^{16}$ is a member selected from substituted or unsubstituted phenyl, halogen and $OR^{17}$, wherein $R^{17}$ is defined as in claim 9.

16. The compound of claim 9, wherein the compound has a structure according to Formula (XIIc) or Formula (XIId):

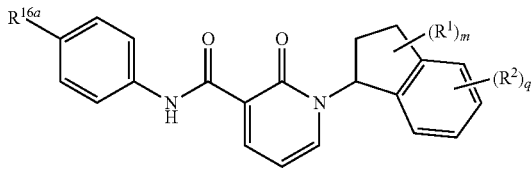

(XIIc)

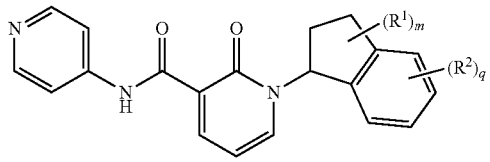

(XIId)

or a salt or solvate thereof, wherein $R^1$, $R^2$, and m are defined as in claim 9;

q is an integer selected from 0 to 4; and $R^{16a}$ is a member selected from halogen, substituted or unsubstituted phenyl and substituted or unsubstituted phenyloxy.

17. The compound according to claim 1 or 9, wherein each $R^1$ is a member independently selected from H, $(C_1-C_4)$alkyl, CN and halogen.

18. The compound of claim 1 or 9, wherein each $R^2$ is a member selected from H, substituted or unsubstituted phenyl, $NR^{12}R^{13}$, substituted or unsubstituted pyridyl, substituted or unsubstituted cyclopropyl, $OR^{12}$, $SR^{12}$, halogen and CN.

19. A compound selected from the group consisting of:
(R)-1-(2,3-dihydro-1H-inden-1-yl)-2-oxo-N-(pyridin-4-yl)-1,2-dihydropyridine-3-carboxamide;
1-(2,3-Dihydro-1H-inden-1-yl)-2-oxo-N-(pyridin-4-yl)-1,2-dihydropyridine-3-carboxamide;
N-(4-Chlorophenyl)-1-(2,3-dihydro-1H-inden-1-yl)-2-oxo-1,2-dihydropyridine-3-carboxamide;
(S)-1-(2,3-Dihydro-1H-inden-1-yl)-2-oxo-N-(pyridin-4-yl)-1,2-dihydropyridine-3-carboxamide;
(S)—N-(4-Chlorophenyl)-1-(2,3-dihydro-1H-inden-1-yl)-2-oxo-1,2-dihydropyridine-3-carboxamide;
(R)—N-(4-Chlorophenyl)-1-(2,3-dihydro-1H-inden-1-yl)-2-oxo-1,2-dihydropyridine-3-carboxamide;
N-(4-Chlorophenyl)-1-((1S,2R)-2-hydroxy-2,3-dihydro-1H-inden-1-yl)-2-oxo-1,2-dihydropyridine-3-carboxamide;
1-((1S,2R)-2-Hydroxy-2,3-dihydro-1H-inden-1-yl)-2-oxo-N-(pyridin-4-yl)-1,2-dihydropyridine-3-carboxamide;
N-(4-Chlorophenyl)-1-((1R,2S)-2-hydroxy-2,3-dihydro-1H-inden-1-yl)-2-oxo-1,2-dihydropyridine-3-carboxamide;
1-((1R,2S)-2-Hydroxy-2,3-dihydro-1H-inden-1-yl)-2-oxo-N-(pyridin-4-yl)-1,2-dihydropyridine-3-carboxamide;
N-(4-chlorophenyl)-1-(4-methoxy-2,3-dihydro-1H-inden-1-yl)-2-oxo-1,2-dihydropyridine-3-carboxamide;
1-(6-Methoxy-2,3-dihydro-1H-inden-1-yl)-2-oxo-N-(pyridin-4-yl)-1,2-dihydropyridine-3-carboxamide;
N-(4-chlorophenyl)-1-(6-methoxy-2,3-dihydro-1H-inden-1-yl)-2-oxo-1,2-dihydropyridine-3-carboxamide;
N-(4-chlorophenyl)-1-(5-methoxy-2,3-dihydro-1H-inden-1-yl)-2-oxo-1,2-dihydropyridine-3-carboxamide;
1-(6-methoxy-2,3-dihydro-1H-inden-1-yl)-2-oxo-N-(pyridin-4-yl)-1,2-dihydropyridine-3-carboxamide;
1-(6-bromo-2,3-dihydro-1H-inden-1-yl)-N-(4-chlorophenyl)-2-oxo-1,2-dihydropyridine-3-carboxamide;
1-(6-bromo-2,3-dihydro-1H-inden-1-yl)-2-oxo-N-(pyridin-4-yl)-1,2-dihydropyridine-3-carboxamide;
1-(4-methoxy-2,3-dihydro-1H-inden-1-yl)-2-oxo-N-(pyridin-4-yl)-1,2-dihydropyridine-3-carboxamide;
1-(7-methoxy-2,3-dihydro-1H-inden-1-yl)-2-oxo-N-(pyridin-4-yl)-1,2-dihydropyridine-3-carboxamide;
N-(7-chlorophenyl)-1-(4-methoxy-2,3-dihydro-1H-inden-1-yl)-2-oxo-1,2-dihydropyridine-3-carboxamide;
N-(4-chlorophenyl)-1-(3-methyl-2,3-dihydro-1H-inden-1-yl)-2-oxo-1,2-dihydropyridine-3-carboxamide;
1-(3-methyl-2,3-dihydro-1H-inden-1-yl)-2-oxo-N-(pyridin-4-yl)-1,2-dihydropyridine-3-carboxamide;
1-(4-bromo-2,3-dihydro-1H-inden-1-yl)-2-oxo-N-(pyridin-4-yl)-1,2-dihydropyridine-3-carboxamide;
1-(4-bromo-2,3-dihydro-1H-inden-1-yl)-N-(4-chlorophenyl)-2-oxo-1,2-dihydropyridine-3-carboxamide;
1-(4-methoxy-2,3-dihydro-1H-inden-1-yl)-2-oxo-N-(pyridin-4-yl)-1,2-dihydropyridine-3-carboxamide;
1-(4-methoxy-2,3-dihydro-1H-inden-1-yl)-2-oxo-N-(pyridin-4-yl)-1,2-dihydropyridine-3-carboxamide;
N-(biphenyl-4-yl)-1-(4-methoxy-2,3-dihydro-1H-inden-1-yl)-2-oxo-1,2-dihydropyridine-3-carboxamide;
1-(4-methoxy-2,3-dihydro-1H-inden-1-yl)-2-oxo-N-(4-phenoxyphenyl)-1,2-dihydropyridine-3-carboxamide;
N-(4-bromophenyl)-1-(4-methoxy-2,3-dihydro-1H-inden-1-yl)-2-oxo-1,2-dihydropyridine-3-carboxamide;
1-(4-isopropoxy-2,3-dihydro-1H-inden-1-yl)-2-oxo-N-(pyridin-4-yl)-1,2-dihydropyridine-3-carboxamide;
N-(4-chlorophenyl)-1-(4-isopropoxy-2,3-dihydro-1H-inden-1-yl)-2-oxo-1,2-dihydropyridine-3-carboxamide;
1-(4-methoxy-2,3-dihydro-1H-inden-1-yl)-2-oxo-N-(4-phenoxyphenyl)-1,2-dihydropyridine-3-carboxamide;
1-(4-methoxy-2,3-dihydro-1H-inden-1-yl)-2-oxo-N-(4-phenoxyphenyl)-1,2-dihydropyridine-3-carboxamide;
N-(biphenyl-4-yl)-1-(4-methoxy-2,3-dihydro-1H-inden-1-yl)-2-oxo-1,2-dihydropyridine-3-carboxamide;
N-(biphenyl-4-yl)-1-(4-methoxy-2,3-dihydro-1H-inden-1-yl)-2-oxo-1,2-dihydropyridine-3-carboxamide;
1-(4-bromo-2,3-dihydro-1H-inden-1-yl)-2-oxo-N-(pyridin-4-yl)-1,2-dihydropyridine-3-carboxamide;
1-(4-bromo-2,3-dihydro-1H-inden-1-yl)-2-oxo-N-(pyridin-4-yl)-1,2-dihydropyridine-3-carboxamide;
1-(4-methoxy-2,3-dihydro-1H-inden-1-yl)-2-oxo-N-(4-(trifluoromethoxy)phenyl)-1,2-dihydropyridine-3-carboxamide;

N-cyclohexyl-1-(4-methoxy-2,3-dihydro-1H-inden-1-yl)-2-oxo-1,2-dihydropyridine-3-carboxamide;
N-(4-fluorophenyl)-1-(4-methoxy-2,3-dihydro-1H-inden-1-yl)-2-oxo-1,2-dihydropyridine-3-carboxamide;
N-(4-iodophenyl)-1-(4-methoxy-2,3-dihydro-1H-inden-1-yl)-2-oxo-1,2-dihydropyridine-3-carboxamide;
1-(4-methoxy-2,3-dihydro-1H-inden-1-yl)-2-oxo-N-phenyl-1,2-dihydropyridine-3-carboxamide;
N-(4,4-difluorocyclohexyl)-1-(4-methoxy-2,3-dihydro-1H-inden-1-yl)-2-oxo-1,2-dihydropyridine-3-carboxamide;
N-(3,4-difluorophenyl)-1-(4-methoxy-2,3-dihydro-1H-inden-1-yl)-2-oxo-1,2-dihydropyridine-3-carboxamide;
1-(4-methoxy-2,3-dihydro-1H-inden-1-yl)-N-(4-(4-methoxyphenoxy)phenyl)-2-oxo-1,2-dihydropyridine-3-carboxamide;
1-(4-cyclopropyl-2,3-dihydro-1H-inden-1-yl)-2-oxo-N-(pyridin-4-yl)-1,2-dihydropyridine-3-carboxamide;
N-(4-chlorophenyl)-1-(4-cyclopropyl-2,3-dihydro-1H-inden-1-yl)-2-oxo-1,2-dihydropyridine-3-carboxamide;
1-(7,8-dihydro-6H-indeno[5,4-d][1,3]dioxol-6-yl)-2-oxo-N-(pyridin-4-yl)-1,2-dihydropyridine-3-carboxamide;
N-(4-chlorophenyl)-1-(7,8-dihydro-6H-indeno[5,4-d][1,3]dioxol-6-yl)-2-oxo-1,2-dihydropyridine-3-carboxamide;
N-(4-chlorophenyl)-2-oxo-1-(4-(trifluoromethoxy)-2,3-dihydro-1H-inden-1-yl)-1,2-dihydropyridine-3-carboxamide;
2-oxo-N-(pyridin-4-yl)-1-(4-(trifluoromethoxy)-2,3-dihydro-1H-inden-1-yl)-1,2-dihydropyridine-3-carboxamide;
1-(4-(methylthio)-2,3-dihydro-1H-inden-1-yl)-2-oxo-N-(pyridin-4-yl)-1,2-dihydropyridine-3-carboxamide;
tert-butyl 4-(1-(2-oxo-3-(pyridin-4-ylcarbamoyl)pyridin-1(2H)-yl)-2,3-dihydro-1H-inden-4-yl)piperazine-1-carboxylate;
tert-butyl 4-(1-(3-(4-chlorophenylcarbamoyl)-2-oxopyridin-1(2H)-yl)-2,3-dihydro-1H-inden-4-yl)piperazine-1-carboxylate;
1-(4-morpholino-2,3-dihydro-1H-inden-1-yl)-2-oxo-N-(pyridin-4-yl)-1,2-dihydropyridine-3-carboxamide;
N-(4-chlorophenyl)-1-(4-morpholino-2,3-dihydro-1H-inden-1-yl)-2-oxo-1,2-dihydropyridine-3-carboxamide;
1-(4-morpholino-2,3-dihydro-1H-inden-1-yl)-2-oxo-N-(4-phenoxyphenyl)-1,2-dihydropyridine-3-carboxamide;
N-(4-fluorophenyl)-1-(4-morpholino-2,3-dihydro-1H-inden-1-yl)-2-oxo-1,2-dihydropyridine-3-carboxamide;
N-(4-bromophenyl)-1-(4-morpholino-2,3-dihydro-1H-inden-1-yl)-2-oxo-1,2-dihydropyridine-3-carboxamide;
N-cyclohexyl-1-(4-morpholino-2,3-dihydro-1H-inden-1-yl)-2-oxo-1,2-dihydropyridine-3-carboxamide;
N-(4-iodophenyl)-1-(4-morpholino-2,3-dihydro-1H-inden-1-yl)-2-oxo-1,2-dihydropyridine-3-carboxamide;
1-(4-morpholino-2,3-dihydro-1H-inden-1-yl)-2-oxo-N-p-tolyl-1,2-dihydropyridine-3-carboxamide;
1-(4-morpholino-2,3-dihydro-1H-inden-1-yl)-2-oxo-N-phenyl-1,2-dihydropyridine-3-carboxamide;
1-(4-morpholino-2,3-dihydro-1H-inden-1-yl)-2-oxo-N-phenyl-1,2-dihydropyridine-3-carboxamide;
N-(4,4-difluorocyclohexyl)-1-(4-morpholino-2,3-dihydro-1H-inden-1-yl)-2-oxo-1,2-dihydropyridine-3-carboxamide;
N-(4-methoxyphenyl)-1-(4-morpholino-2,3-dihydro-1H-inden-1-yl)-2-oxo-1,2-dihydropyridine-3-carboxamide;
N-(4-(difluoromethoxy)phenyl)-1-(4-morpholino-2,3-dihydro-1H-inden-1-yl)-2-oxo-1,2-dihydropyridine-3-carboxamide;
1-(4-morpholino-2,3-dihydro-1H-inden-1-yl)-2-oxo-N-(4-(trifluoromethoxy)phenyl)-1,2-dihydropyridine-3-carboxamide;
1-(4-morpholino-2,3-dihydro-1H-inden-1-yl)-2-oxo-N-(4-(trifluoromethyl)phenyl)-1,2-dihydropyridine-3-carboxamide;
N-(4-cyanophenyl)-1-(4-morpholino-2,3-dihydro-1H-inden-1-yl)-2-oxo-1,2-dihydropyridine-3-carboxamide;
1-(4-(4-hydroxypiperidin-1-yl)-2,3-dihydro-1H-inden-1-yl)-2-oxo-N-(pyridin-4-yl)-1,2-dihydropyridine-3-carboxamide;
N-(4-chlorophenyl)-1-(4-(4-hydroxypiperidin-1-yl)-2,3-dihydro-1H-inden-1-yl)-2-oxo-1,2-dihydropyridine-3-carboxamide;
N-(4-(4-methoxyphenylamino)phenyl)-1-(4-morpholino-2,3-dihydro-1H-inden-1-yl)-2-oxo-1,2-dihydropyridine-3-carboxamide;
N-(3,4-difluorophenyl)-1-(4-morpholino-2,3-dihydro-1H-inden-1-yl)-2-oxo-1,2-dihydropyridine-3-carboxamide;
tert-butyl 4-(1-(3-(4-fluorophenylcarbamoyl)-2-oxopyridin-1(2H)-yl)-2,3-dihydro-1H-inden-4-yl)piperazine-1-carboxylate;
tert-butyl 4-(1-(3-(4-chlorophenylcarbamoyl)-2-oxopyridin-1(2H)-yl)-2,3-dihydro-1H-inden-4-yl)piperazine-1-carboxylate;
N-(4-(dimethylamino)phenyl)-1-(4-morpholino-2,3-dihydro-1H-inden-1-yl)-2-oxo-1,2-dihydropyridine-3-carboxamide;
1-(4-(cyclopropylamino)-2,3-dihydro-1H-inden-1-yl)-2-oxo-N-(pyridin-4-yl)-1,2-dihydropyridine-3-carboxamide;
N-(4-chlorophenyl)-1-(4-(methylsulfonyl)-2,3-dihydro-1H-inden-1-yl)-2-oxo-1,2-dihydropyridine-3-carboxamide;
1-(4-(methylsulfonyl)-2,3-dihydro-1H-inden-1-yl)-2-oxo-N-(pyridin-4-yl)-1,2-dihydropyridine-3-carboxamide;
N-(4-chlorophenyl)-2-oxo-1-(4-(piperazin-1-yl)-2,3-dihydro-1H-inden-1-yl)-1,2-dihydropyridine-3-carboxamide;
2-oxo-1-(4-(piperazin-1-yl)-2,3-dihydro-1H-inden-1-yl)-N-(pyridin-4-yl)-1,2-dihydropyridine-3-carboxamide;
N-(4-fluorophenyl)-2-oxo-1-(4-(piperazin-1-yl)-2,3-dihydro-1H-inden-1-yl)-1,2-dihydropyridine-3-carboxamide;
N-(4-bromophenyl)-2-oxo-1-(4-(piperazin-1-yl)-2,3-dihydro-1H-inden-1-yl)-1,2-dihydropyridine-3-carboxamide;
N-(4-chlorophenyl)-1-(4-(4-(2-hydroxyethyl)piperazin-1-yl)-2,3-dihydro-1H-inden-1-yl)-2-oxo-1,2-dihydropyridine-3-carboxamide;
N-(4-chlorophenyl)-1-(4-(4-(2-(2-(2-hydroxyethoxy)ethoxy)ethyl)piperazin-1-yl)-2,3-dihydro-1H-inden-1-yl)-2-oxo-1,2-dihydropyridine-3-carboxamide;
N-(4-chlorophenyl)-1-(4-(4-methylpiperazin-1-yl)-2,3-dihydro-1H-inden-1-yl)-2-oxo-1,2-dihydropyridine-3-carboxamide;
1-(4-(4-methylpiperazin-1-yl)-2,3-dihydro-1H-inden-1-yl)-2-oxo-N-(pyridin-4-yl)-1,2-dihydropyridine-3-carboxamide;
1-(4-(4-acetylpiperazin-1-yl)-2,3-dihydro-1H-inden-1-yl)-N-(4-chlorophenyl)-2-oxo-1,2-dihydropyridine-3-carboxamide;

1-(4-(4-acetylpiperazin-1-yl)-2,3-dihydro-1H-inden-1-yl)-2-oxo-N-(pyridin-4-yl)-1,2-dihydropyridine-3-carboxamide;

N-(4-chlorophenyl)-1-(4-(4-(methylsulfonyl)piperazin-1-yl)-2,3-dihydro-1H-inden-1-yl)-2-oxo-1,2-dihydropyridine-3-carboxamide;

tert-butyl 2-(2-(2-(2-(4-(1-(3-(4-chlorophenyl carbamoyl)-2-oxopyridin-1(2H)-yl)-2,3-dihydro-1H-inden-4-yl)piperazin-1-yl)-2-oxoethoxy)ethoxy)ethoxy)ethylcarbamate;

1-(4-(4-(2-(2-(2-(2-aminoethoxy)ethoxy)ethoxy)acetyl)piperazin-1-yl)-2,3-dihydro-1H-inden-1-yl)-N-(4-chlorophenyl)-2-oxo-1,2-dihydropyridine-3-carboxamide;

N-(4'-hydroxybiphenyl-4-yl)-1-(4-methoxy-2,3-dihydro-1H-inden-1-yl)-2-oxo-1,2-dihydropyridine-3-carboxamide;

1-(4-Methoxy-2,3-dihydro-1H-inden-1-yl)-N-(4'-methoxybiphenyl-4-yl)-2-oxo-1,2-dihydropyridine-3-carboxamide;

N-(3'-ethoxybiphenyl-4-yl)-1-(4-methoxy-2,3-dihydro-1H-inden-1-yl)-2-oxo-1,2-dihydropyridine-3-carboxamide;

1-(4-methoxy-2,3-dihydro-1H-inden-1-yl)-N-(2'-methoxybiphenyl-4-yl)-2-oxo-1,2-dihydropyridine-3-carboxamide;

N-(4'-aminobiphenyl-4-yl)-1-(4-methoxy-2,3-dihydro-1H-inden-1-yl)-2-oxo-1,2-dihydropyridine-3-carboxamide;

N-(4'-(2-(2-(2-aminoethoxy)ethoxy)ethoxy)biphenyl-4-yl)-1-(4-methoxy-2,3-dihydro-1H-inden-1-yl)-2-oxo-1,2-dihydropyridine-3-carboxamide;

N-(3'-(2-(2-(2-aminoethoxy)ethoxy)ethoxy)biphenyl-4-yl)-1-(4-methoxy-2,3-dihydro-1H-inden-1-yl)-2-oxo-1,2-dihydropyridine-3-carboxamide;

N-(3'-hydroxybiphenyl-4-yl)-1-(4-methoxy-2,3-dihydro-1H-inden-1-yl)-2-oxo-1,2-dihydropyridine-3-carboxamide;

tert-butyl 2-(2-(2-(4-(4-(1-(4-methoxy-2,3-dihydro-1H-inden-1-yl)-2-oxo-1,2-dihydropyridine-3-carboxamido)phenoxy)phenoxy)ethoxy)ethoxy)-ethylcarbamate;

N-(4-(4-(2-(2-(2-aminoethoxy)ethoxy)ethoxy)phenoxy)phenyl)-1-(4-methoxy-2,3-dihydro-1H-inden-1-yl)-2-oxo-1,2-dihydropyridine-3-carboxamide;

2-oxo-1-(4-(pyridin-3-yl)-2,3-dihydro-1H-inden-1-yl)-N-(pyridin-4-yl)-1,2-dihydropyridine-3-carboxamide;

1-(4-nitro-2,3-dihydro-1H-inden-1-yl)-2-oxo-N-(pyridin-4-yl)-1,2-dihydropyridine-3-carboxamide;

1-(4-amino-2,3-dihydro-1H-inden-1-yl)-2-oxo-N-(pyridin-4-yl)-1,2-dihydropyridine-3-carboxamide;

1-(4-cyano-2,3-dihydro-1H-inden-1-yl)-2-oxo-N-(pyridin-4-yl)-1,2-dihydropyridine-3-carboxamide;

1-(4-chloro-2,3-dihydro-1H-inden-1-yl)-2-oxo-N-(pyridin-4-yl)-1,2-dihydropyridine-3-carboxamide;

1-(4-(methylamino)-2,3-dihydro-1H-inden-1-yl)-2-oxo-N-(pyridin-4-yl)-1,2-dihydropyridine-3-carboxamide;

1-(4-(dimethylamino)-2,3-dihydro-1H-inden-1-yl)-2-oxo-N-(pyridin-4-yl)-1,2-dihydropyridine-3-carboxamide;

1-(4-acetamido-2,3-dihydro-1H-inden-1-yl)-2-oxo-N-(pyridin-4-yl)-1,2-dihydropyridine-3-carboxamide;

1-(4-methyl-2,3-dihydro-1H-inden-1-yl)-2-oxo-N-(pyridin-4-yl)-1,2-dihydropyridine-3-carboxamide;

2-oxo-1-(4-phenyl-2,3-dihydro-1H-inden-1-yl)-N-(pyridin-4-yl)-1,2-dihydropyridine-3-carboxamide;

1-(4-(methylcarbamoyl)-2,3-dihydro-1H-inden-1-yl)-2-oxo-N-(pyridin-4-yl)-1,2-dihydropyridine-3-carboxamide;

N-(4-bromophenyl)-1-(4-hydroxy-2,3-dihydro-1H-inden-1-yl)-2-oxo-1,2-dihydropyridine-3-carboxamide;

N-(biphenyl-4-yl)-1-(4-hydroxy-2,3-dihydro-1H-inden-1-yl)-2-oxo-1,2-dihydropyridine-3-carboxamide;

N-(4-bromophenyl)-1-(4-(2-hydroxyethoxy)-2,3-dihydro-1H-inden-1-yl)-2-oxo-1,2-dihydropyridine-3-carboxamide;

N-(4-bromophenyl)-1-(4-(2-(2-(2-hydroxyethoxy)ethoxy)ethoxy)-2,3-dihydro-1H-inden-1-yl)-2-oxo-1,2-dihydropyridine-3-carboxamide;

N-(biphenyl-4-yl)-1-(4-(2-(2-(2-hydroxyethoxy)ethoxy)ethoxy)-2,3-dihydro-1H-inden-1-yl)-2-oxo-1,2-dihydropyridine-3-carboxamide;

tert-butyl 2-(2-(2-(1-(3-(biphenyl-4-ylcarbamoyl)-2-oxopyridin-1(2H)-yl)-2,3-dihydro-1H-inden-4-yloxy)ethoxy)ethoxy)ethylcarbamate; and 1-(4-(2-(2-(2-aminoethoxy)ethoxy)ethoxy)-2,3-dihydro-1H-inden-1-yl)-N-(biphenyl-4-yl)-2-oxo-1,2-dihydropyridine-3-carboxamide trifluoroacetate;

or a salt or a solvate thereof.

20. A pharmaceutical composition comprising a compound according to claim 1 or 19 and a pharmaceutically acceptable carrier.

21. A method of treating an inflammatory disease comprising administering to a mammalian subject in need thereof a pharmaceutically effective-amount of a compound according to claim 1 or 19, wherein the inflammatory disease is selected from the group consisting of asthma, inflammatory bowel disease, ulcerative colitis, Crohn's disease, multiple sclerosis, rheumatoid arthritis, tumor metastasis, graft versus host disease, and organ or tissue rejection.

22. The method of claim 21, wherein said inflammatory disease is a member selected from Crohn's disease and ulcerative colitis.

23. An in vitro assay for measuring binding of an α4β1 or α4β7 integrin to an integrin ligand, wherein the assay comprises:
    (i) binding the ligand to a surface;
    (ii) contacting the ligand with a cell expressing the integrin, in the presence of a compound of claim 1 or 19; and
    (iii) measuring the amount of cells bound to the surface.

24. The assay according to claim 23, wherein the integrin ligand is a member selected from fibronectin (FN), VCAM-1, osteopontin and MadCAM.

25. An in vitro assay for measuring binding of the compound to an α4β1 or α4β7 integrin in the presence of a candidate molecule, wherein the assay comprises incubating the test molecule in the presence of a compound of claim 1 or 19 labeled with a radioactive, colorimetric or fluorescent label, and measuring the amount of the labeled compound for binding to the integrin.

26. An in vitro assay for identifying a candidate molecule capable of binding to α4β1 or α4β7 integrin, wherein the assay comprises incubating the candidate molecule in the presence of a compound of claim 1 or 19 labeled with a radioactive, colorimetric or fluorescent label, and measuring the amount of the labeled compound for binding to the integrin, and wherein the candidate molecule is identified as capable of binding to the integrin if it exhibits a binding activity of an $IC_{50}$ of not more than 10 μM in the assay.

27. The method of claim 21, further comprising a pharmaceutically acceptable carrier.

* * * * *